(12) United States Patent
Coon et al.

(10) Patent No.: US 11,147,441 B2
(45) Date of Patent: Oct. 19, 2021

(54) PHYSICAL ASSESSMENT DEVICE

(71) Applicant: Welch Allyn, Inc., Skaneateles Falls, NY (US)

(72) Inventors: Kenneth V. Coon, Jordan, NY (US); Paul DeLucia, Baldwinsville, NY (US); David M. Babson, Warners, NY (US); Richard H. Weitzel, Beaverton, OR (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 299 days.

(21) Appl. No.: 16/248,482

(22) Filed: Jan. 15, 2019

(65) Prior Publication Data
US 2019/0216307 A1    Jul. 18, 2019

Related U.S. Application Data

(63) Continuation-in-part of application No. 29/676,212, filed on Jan. 9, 2019, now Pat. No. Des. 905,239, and
(Continued)

(51) Int. Cl.
*A61B 1/227*    (2006.01)
*A61B 3/12*     (2006.01)
(Continued)

(52) U.S. Cl.
CPC .......... *A61B 1/227* (2013.01); *A61B 1/00006* (2013.01); *A61B 1/00032* (2013.01);
(Continued)

(58) Field of Classification Search
CPC ............ A61B 1/00006; A61B 1/00025; A61B 1/00027; A61B 1/00032; A61B 1/00105;
(Continued)

(56) References Cited

U.S. PATENT DOCUMENTS 3,586,424 A    6/1971   Schenk et al.
3,614,214 A    10/1971  Cornsweet et al.
(Continued)

FOREIGN PATENT DOCUMENTS

CN    103082999 A    5/2013
CN    103118585 A    5/2013
(Continued)

OTHER PUBLICATIONS

International Preliminary Report on Patentability for PCT/US2019/013775; dated Nov. 19, 2019; 7 pages.
(Continued)

*Primary Examiner* — Zade Coley
(74) *Attorney, Agent, or Firm* — Barclay Damon LLP

(57) ABSTRACT

An instrument head is provided for attachment to a plurality of instrument handles having different power profiles. The instrument head contains an illumination assembly including at least one LED as well as a drive circuit for detecting a power profile of an attached instrument handle and converting variable voltages received from the attached instrument handle to a constant current for powering the at least one LED based on the power profile. Accordingly, the instrument head enables use with a plurality of instrument handles, including those originally configured for use only with incandescent light sources.

11 Claims, 124 Drawing Sheets

Related U.S. Application Data a continuation-in-part of application No. 29/676,213, filed on Jan. 9, 2019, now Pat. No. Des. 905,240.

(60) Provisional application No. 62/617,929, filed on Jan. 16, 2018.

(51) Int. Cl.
*A61B 1/00* (2006.01)
*A61B 3/00* (2006.01)

(52) U.S. Cl.
CPC ...... *A61B 1/00052* (2013.01); *A61B 1/00105* (2013.01); *A61B 1/00108* (2013.01); *A61B 1/00124* (2013.01); *A61B 1/00128* (2013.01); *A61B 1/00195* (2013.01); *A61B 3/0091* (2013.01); *A61B 3/12* (2013.01); *A61B 3/1208* (2013.01)

(58) Field of Classification Search
CPC ....... A61B 1/00108; A61B 1/06; A61B 1/227; A61B 3/0008; A61B 3/12; A61B 3/1208; A61B 2017/0046; A61B 90/30; A61B 2090/308
See application file for complete search history.

(56) References Cited

U.S. PATENT DOCUMENTS

| | | |
|---|---|---|
| 3,638,641 A | 2/1972 | Abromavage et al. |
| 3,675,641 A | 7/1972 | Fiore |
| 3,698,099 A | 10/1972 | Matsura |
| 3,698,387 A | 10/1972 | Moore et al. |
| 3,840,004 A | 10/1974 | Heine |
| 3,893,447 A | 7/1975 | Hochheimer et al. |
| 3,914,032 A | 10/1975 | Takano et al. |
| 3,978,850 A | 9/1976 | Moore et al. |
| 4,132,466 A | 1/1979 | Matsumura |
| 4,252,420 A | 2/1981 | Kohayakawa |
| 4,265,518 A | 5/1981 | Matsumura |
| 4,366,811 A | 1/1983 | Riester |
| 4,439,024 A | 3/1984 | Ito |
| 4,442,736 A | 4/1984 | True et al. |
| 4,526,449 A | 7/1985 | Newman et al. |
| 4,564,273 A | 1/1986 | Iba et al. |
| 4,567,881 A | 2/1986 | Heller |
| 4,662,360 A | 5/1987 | O'Hara et al. |
| 4,679,919 A | 7/1987 | Itoh et al. |
| 4,682,866 A | 7/1987 | Volk |
| 4,721,378 A | 1/1988 | Volk |
| 4,785,796 A | 11/1988 | Mattson |
| 4,856,872 A | 8/1989 | Spitznas et al. |
| 4,997,419 A | 3/1991 | Lakatos et al. |
| 5,070,883 A | 12/1991 | Kasahara |
| 5,093,719 A | 3/1992 | Prescott |
| 5,139,936 A | 8/1992 | Botstein et al. |
| 5,255,025 A | 10/1993 | Volk |
| 5,363,839 A | 11/1994 | Lankford |
| 5,390,663 A | 2/1995 | Schaefer |
| 5,424,789 A | 6/1995 | Volk |
| 5,579,063 A | 11/1996 | Magnante et al. |
| 5,624,453 A | 4/1997 | Ahmed |
| 5,658,235 A | 8/1997 | Priest et al. |
| 5,713,047 A | 1/1998 | Kohayakawa |
| 5,720,756 A | 2/1998 | Green et al. |
| 5,722,762 A | 3/1998 | Soll |
| 5,751,395 A | 5/1998 | Thall |
| 5,795,067 A | 8/1998 | Fraden et al. |
| 5,842,971 A | 12/1998 | Yoon |
| 5,880,813 A | 3/1999 | Thall |
| 5,919,130 A | 7/1999 | Monroe et al. |
| 5,982,255 A | 11/1999 | Melville et al. |
| 6,019,721 A | 2/2000 | Holmes et al. |
| 6,053,875 A | 4/2000 | Rosenbaum et al. |
| 6,065,837 A | 5/2000 | Goldfain et al. |
| 6,099,537 A | 8/2000 | Sugai et al. |
| 6,106,457 A | 8/2000 | Perkins et al. |
| 6,129,661 A | 10/2000 | Iafrati et al. |
| 6,142,934 A | 11/2000 | Lagerway et al. |
| 6,147,705 A | 11/2000 | Krauter et al. |
| 6,190,310 B1 | 2/2001 | Cook |
| 6,213,938 B1 | 4/2001 | Cook |
| 6,254,271 B1 | 7/2001 | Lin |
| 6,273,565 B1 | 8/2001 | Matsumoto |
| 6,331,156 B1 | 12/2001 | Haefele et al. |
| 6,359,677 B2 | 3/2002 | Itoh et al. |
| 6,383,133 B1 | 5/2002 | Jones |
| 6,425,857 B1 | 7/2002 | Rudischhauser et al. |
| 6,450,970 B1 | 9/2002 | Mahler et al. |
| 6,475,138 B1 | 11/2002 | Schechter et al. |
| 6,511,420 B1 | 1/2003 | Farrell et al. |
| 6,537,208 B1 | 3/2003 | Konno |
| 6,554,765 B1 | 4/2003 | Yarush et al. |
| 6,569,090 B1 | 5/2003 | Mezzoli et al. |
| 6,692,431 B2 | 2/2004 | Kazakevich |
| 6,705,726 B2 | 3/2004 | Tanassi et al. |
| 6,968,127 B2 | 11/2005 | Nanjyo |
| 7,029,439 B2 | 4/2006 | Roberts et al. |
| 7,048,379 B2 | 5/2006 | Miller et al. |
| 7,177,088 B2 | 2/2007 | Hirata |
| 7,224,822 B2 | 5/2007 | Heacock |
| 7,276,025 B2 * | 10/2007 | Roberts ............... A61B 1/227 315/312 |
| 7,290,882 B2 | 11/2007 | Collins et al. |
| 7,354,399 B2 | 4/2008 | Strom et al. |
| 7,364,297 B2 | 4/2008 | Goldfain et al. |
| 7,399,275 B2 | 7/2008 | Goldfain et al. |
| 7,448,753 B1 | 11/2008 | Chinnock |
| 7,583,035 B2 | 9/2009 | Shteynberg et al. |
| 7,597,443 B2 | 10/2009 | Fujii et al. |
| 7,677,730 B2 | 3/2010 | Shimizu |
| 7,744,219 B2 | 6/2010 | Davis |
| 7,762,950 B2 | 7/2010 | Hirata |
| 7,803,110 B2 | 9/2010 | Goldfain et al. |
| 7,854,510 B2 | 12/2010 | Verdooner et al. |
| 7,901,353 B2 | 3/2011 | Vayser et al. |
| 8,043,211 B2 | 10/2011 | Hirata |
| 8,066,634 B2 | 11/2011 | Andreassen et al. |
| 8,100,826 B2 | 1/2012 | MacKinnon et al. |
| 8,109,981 B2 | 2/2012 | Gertner et al. |
| 8,152,718 B2 | 4/2012 | Cheng |
| 8,159,153 B2 | 4/2012 | Hum |
| D659,840 S | 5/2012 | Cheng et al. |
| 8,197,403 B2 | 6/2012 | Strom et al. |
| 8,210,680 B2 | 7/2012 | Tanguay, Jr. et al. |
| 8,231,522 B2 | 7/2012 | Endo et al. |
| 8,459,794 B2 | 6/2013 | Juhasz et al. |
| 8,550,626 B2 | 10/2013 | Griggio et al. |
| 8,602,971 B2 | 12/2013 | Farr |
| 8,684,526 B2 | 4/2014 | Neal |
| 8,816,604 B2 | 8/2014 | Carli |
| 8,890,489 B2 | 11/2014 | Wood |
| 8,944,596 B2 | 2/2015 | Wood et al. |
| 9,001,326 B2 | 4/2015 | Goldfain |
| 9,022,566 B2 | 5/2015 | Utagawa |
| 9,153,994 B2 | 10/2015 | Wood et al. |
| 9,191,562 B1 | 11/2015 | Schorr, II |
| 9,289,122 B2 | 3/2016 | Chinnock et al. |
| 9,392,933 B2 | 7/2016 | Bedard et al. |
| 9,392,938 B2 | 7/2016 | Cheng et al. |
| 9,411,215 B2 | 8/2016 | Hunt |
| 9,445,713 B2 | 9/2016 | Douglas et al. |
| 9,516,711 B2 | 12/2016 | Weil et al. |
| 9,532,708 B2 | 1/2017 | Juhasz et al. |
| 9,596,987 B2 | 3/2017 | Fujino et al. |
| 9,655,517 B2 | 5/2017 | Su et al. |
| 9,795,293 B2 | 10/2017 | Howes |
| 9,826,894 B2 * | 11/2017 | Masaki ............... A61B 1/00009 |
| 9,833,133 B2 * | 12/2017 | Stone .................. F21V 23/005 |
| 9,904,013 B2 | 2/2018 | Schultheis et al. |
| 9,931,021 B2 | 4/2018 | Ruppersberg et al. |
| 2001/0014112 A1 | 8/2001 | Yamaka |
| 2002/0085616 A1 | 7/2002 | Yu |
| 2002/0143239 A1 | 10/2002 | Henzler |

(56) References Cited

U.S. PATENT DOCUMENTS

| | | |
|---|---|---|
| 2002/0188177 A1 | 12/2002 | Miyanaga |
| 2002/0193665 A1 | 12/2002 | Jones |
| 2003/0063386 A1 | 4/2003 | Slawson et al. |
| 2003/0187331 A1 | 10/2003 | Faludi et al. |
| 2004/0174498 A1 | 9/2004 | Zorn et al. |
| 2004/0186352 A1 | 9/2004 | Roberts et al. |
| 2005/0027168 A1 | 2/2005 | Strom et al. |
| 2005/0027169 A1 | 2/2005 | Goldfain et al. |
| 2005/0043588 A1 | 2/2005 | Tsai |
| 2005/0043591 A1 | 2/2005 | Witte |
| 2005/0110949 A1 | 5/2005 | Goldfain et al. |
| 2006/0020176 A1 | 1/2006 | Berall |
| 2006/0159155 A1 | 7/2006 | Lantz et al. |
| 2006/0183977 A1 | 8/2006 | Ishigami et al. |
| 2007/0219417 A1 | 9/2007 | Roberts et al. |
| 2007/0255108 A1 | 11/2007 | Schmitz |
| 2008/0051637 A1 | 2/2008 | Andreassen et al. |
| 2008/0079897 A1 | 4/2008 | Goldfain et al. |
| 2008/0309876 A1 | 12/2008 | Massie |
| 2009/0287192 A1 | 11/2009 | Vivenzio et al. |
| 2010/0081875 A1 | 4/2010 | Fowler et al. |
| 2010/0317924 A1 | 12/2010 | Sisko et al. |
| 2011/0060184 A1 | 3/2011 | Rothberg et al. |
| 2011/0234977 A1 | 9/2011 | Verdooner |
| 2012/0209074 A1 | 8/2012 | Titus |
| 2012/0229617 A1 | 9/2012 | Yates et al. |
| 2012/0320340 A1 | 12/2012 | Coleman, III |
| 2013/0083183 A1 | 4/2013 | Cheng et al. |
| 2013/0128223 A1 | 5/2013 | Wood et al. |
| 2013/0150675 A1 | 6/2013 | Folley |
| 2013/0178707 A1 | 7/2013 | Kwong |
| 2013/0208241 A1 | 8/2013 | Lawson et al. |
| 2013/0267783 A1 | 10/2013 | Davis et al. |
| 2013/0300919 A1 | 11/2013 | Fletcher et al. |
| 2014/0051923 A1 | 2/2014 | Mirza et al. |
| 2014/0146288 A1 | 5/2014 | Anand et al. |
| 2014/0213936 A1* | 7/2014 | Monovoukas ....... A61B 5/1075 600/587 |
| 2015/0103317 A1 | 4/2015 | Goldfain et al. |
| 2015/0126810 A1 | 5/2015 | Wood et al. |
| 2015/0223678 A1 | 8/2015 | Goldfain et al. |
| 2015/0342458 A1 | 12/2015 | Watanabe et al. |
| 2015/0374208 A1 | 12/2015 | Ruppersberg et al. |
| 2016/0051142 A1 | 2/2016 | Howes |
| 2016/0073875 A1 | 3/2016 | Goldfain et al. |
| 2016/0128555 A1 | 5/2016 | McMahon et al. |
| 2016/0262611 A1 | 9/2016 | Rotenstreich |
| 2016/0296112 A1 | 10/2016 | Fletcher et al. |
| 2016/0367134 A1 | 12/2016 | Su |
| 2017/0006683 A1 | 1/2017 | Shiyu et al. |
| 2017/0119237 A1 | 5/2017 | Bedard et al. |
| 2017/0123131 A1 | 5/2017 | Root et al. |
| 2017/0215719 A1 | 8/2017 | Goldfain et al. |
| 2017/0239012 A1 | 8/2017 | Wood et al. |
| 2017/0280524 A1 | 9/2017 | West |
| 2017/0303857 A1 | 10/2017 | Perkins et al. |
| 2018/0000336 A1 | 1/2018 | Gilad-Gilor et al. |
| 2018/0049637 A1 | 2/2018 | González Márquez et al. |
| 2018/0084996 A1 | 3/2018 | Su et al. |
| 2018/0116509 A1 | 5/2018 | Myung et al. |
| 2018/0125345 A1 | 5/2018 | Rebella et al. |
| 2018/0153399 A1 | 6/2018 | Fink et al. |
| 2018/0153402 A1 | 6/2018 | Saidman et al. |
| 2018/0303329 A1 | 10/2018 | Goldfain et al. |

FOREIGN PATENT DOCUMENTS

| | | |
|---|---|---|
| CN | 103687532 A | 3/2014 |
| DE | 197 44 131 A1 | 4/1998 |
| DE | 10 2007 036 683 B4 | 10/2017 |
| EP | 1 152 687 B1 | 9/2004 |
| EP | 2 473 092 | 3/2011 |
| JP | 2007-115594 A | 5/2007 |
| JP | 2012-119541 A | 6/2012 |
| SU | 501374 | 10/1976 |
| TW | 201216916 A1 | 5/2012 |
| TW | 201229557 A1 | 7/2012 |
| WO | WO 99/42760 | 8/1999 |
| WO | WO 02/056756 A2 | 7/2002 |
| WO | WO 2005/020804 A1 | 3/2005 |
| WO | WO 2005/044098 A1 | 5/2005 |
| WO | WO 2005/053519 A1 | 6/2005 |
| WO | WO 2006/131770 A2 | 12/2006 |
| WO | WO 2007/026158 A1 | 3/2007 |
| WO | WO 2011/042722 A1 | 4/2011 |
| WO | WO 2011/047214 A2 | 4/2011 |
| WO | WO 2011/050496 A1 | 5/2011 |
| WO | WO 2015/049404 A1 | 4/2015 |
| WO | WO 2016/193998 A2 | 12/2016 |
| WO | WO 2016/193998 A3 | 12/2016 |
| WO | WO 2017/195223 A1 | 11/2017 |
| WO | WO 2017/201584 A1 | 11/2017 |
| WO | WO 2018/013923 A1 | 1/2018 |
| WO | WO 2018/043657 A1 | 3/2018 |
| WO | WO 2018/049480 A1 | 3/2018 |
| WO | WO 2018/069346 A1 | 4/2018 |

OTHER PUBLICATIONS

Australian Examination Report for AU 2001263366; dated Dec. 9, 2004; 2 pages.

Australian Examination Report for AU 2001263366; dated Dec. 19, 2005; 2 pages.

Australian Examination Report for AU 2012335072; dated May 24, 2016; 2 pages.

European Search Report for EP 08 798 437.3; dated Oct. 27, 2010; 7 pages.

European Examination Report for EP 12 791 644.3; dated Apr. 24, 2018; 3 pages.

European Office Action for EP 15 771 386.8; dated Aug. 3, 2018; 2 pages.

European Office Action for EP 15 771 386.8; dated Mar. 20, 2019; 3 pages.

International Preliminary Report on Patentability and Written Opinion for PCT/US2015/050165; dated Mar. 21, 2017; 8 pages.

International Search Report and Written Opinion for PCT/US2007/065367; dated Jun. 3, 2008; 9 pages.

International Search Report for PCT/US2008/073956; dated Mar. 10, 2009; 2 pages.

International Search Report and Written Opinion for PCT/US2012/064510; dated Apr. 29, 2013; 16 pages.

International Search Report and Written Opinion for PCT/US2017/029322; dated Oct. 17, 2017; 18 pages.

International Search Report and Written Opinion for PCT/US2019/013775; dated Mar. 28, 2019; 13 pages.

Invitation to Pay Additional Fees, and Where Applicable, Protest Fee; dated Dec. 2, 2015; 6 pages.

Japanese Notice of Grounds for Rejection for JP 2000-583418; dated Jan. 31, 2006; 3 pages.

U.S. Appl. No. 29/207,233, filed Jun. 10, 2004; Roberts et al.; 7 pages.

Large Field of View, Modular, Stabilized, Adaptive-Optics-Based Scanning Laser Ophthalmoscope; Stephen A. Burns, Remy Tumbar and Ann E. Elsner; http://www.ncbi.nlm.nih.gov/pmc/articles/PMC2443858/pdf/nihms21600; Published in May 2007; 24 pages.

Adaptive Optics Scanning Laser Ophthalmoscope With Integrated Wide-Field Retinal Imaging and Tracking; R. Daniel Ferguson, Zhangyi Zhong, Daniel X. Hammer, Mircea Mujat, Ankit H. Patel, Cong Deng, Weiyao Zou and Stephen A. Burns; http://www.ncbi.nlm.nih.gov/pmc/articles/PMC3071649/pdf/nihms-250025; Published in Nov. 2010; 27 pages.

Medimaging Integrated Solution Inc.; http://www.miis.com.tw/?option=product&language=zh-tw&mod=5, accessed Apr. 18, 2013; 11 pages.

Digital Hand-held Diagnostic Set, Medimaging Integrated Solution, Inc.; 3 pages.

(56) References Cited

OTHER PUBLICATIONS

Rudolf Riester GmbH—medical diagnostic instruments, Source: http://www.riester.de/Home.1+B6Jkw9MSZMPTA_.0.html, Date Accessed: Sep. 14, 2012; 2 pages.

Parnes et al. (1996); Advances in the Development of the Interferometric Otoscope; The Laryngoscope, 106: 263-267; 5 pages.

Nishikawa, et al. (2011); A Novel Colonoscope with High Color-Rendering White Light-Emitting Diodes, 73: 598-602; 5 pages.

Rajewski (2012); An Optical Engineering Feat from the Kitchen; Cummings School of Veterinary Medicine at Tufts University; 2 pages.

All-N1 Video Otoscope (MD Scope); Source: http://www.jedmed.com/products/all-n1-video-otoscope; Date Accessed: Oct. 25, 2011; 2 pages.

Dreher, Andreas W.; Field Portable Digital Ophthalmoscope/Fundus Camera; Laser Diagnostic Technologies, Inc.; Jun. 1997; 26 pages.

Smithwick et al.; Non-Paraxial Design for a Transportable Digital Retinal Imager; http://www.opticsinfobase.org/abstract.cfm?uri=FiO-2004-FWM5; 1 page.

Optomap Panoramic200; http://www.joneseyecenters.com/index.cfm/technology/optomap; Date Accessed: Feb. 27, 2013; 3 pages.

\* cited by examiner

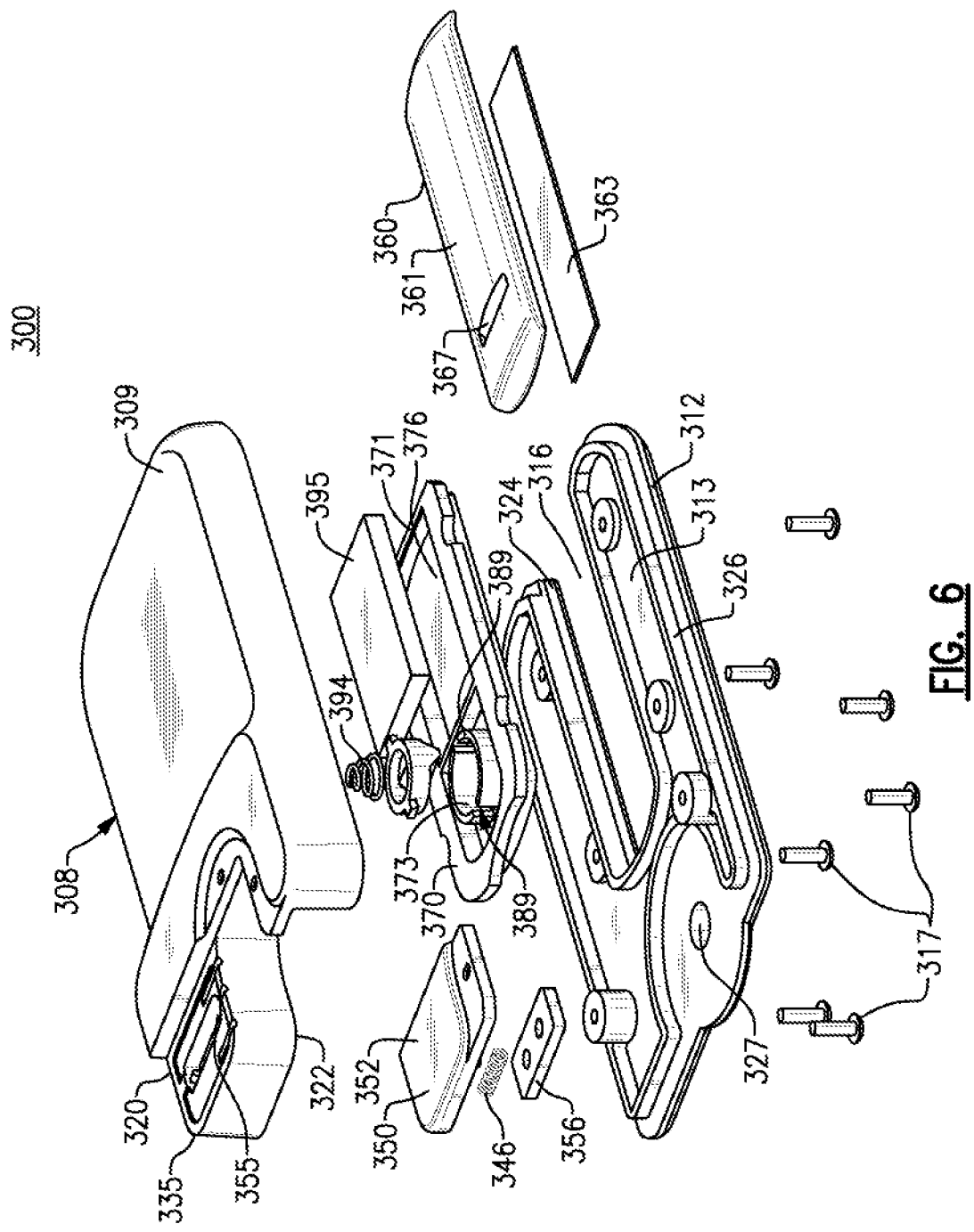

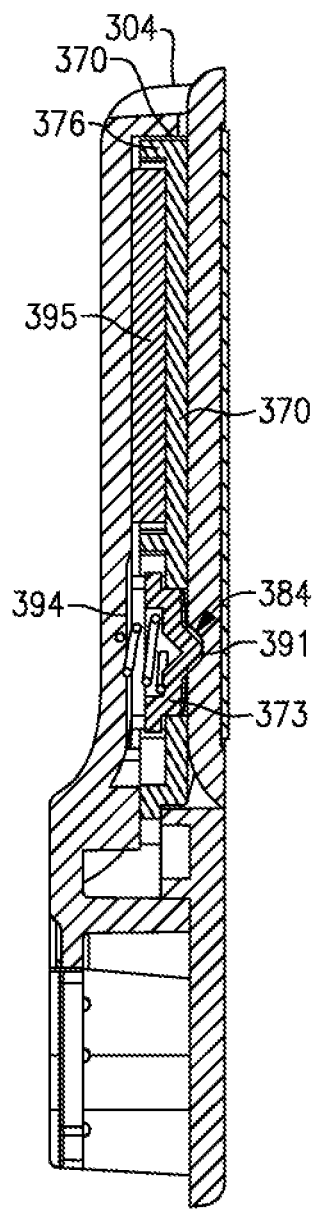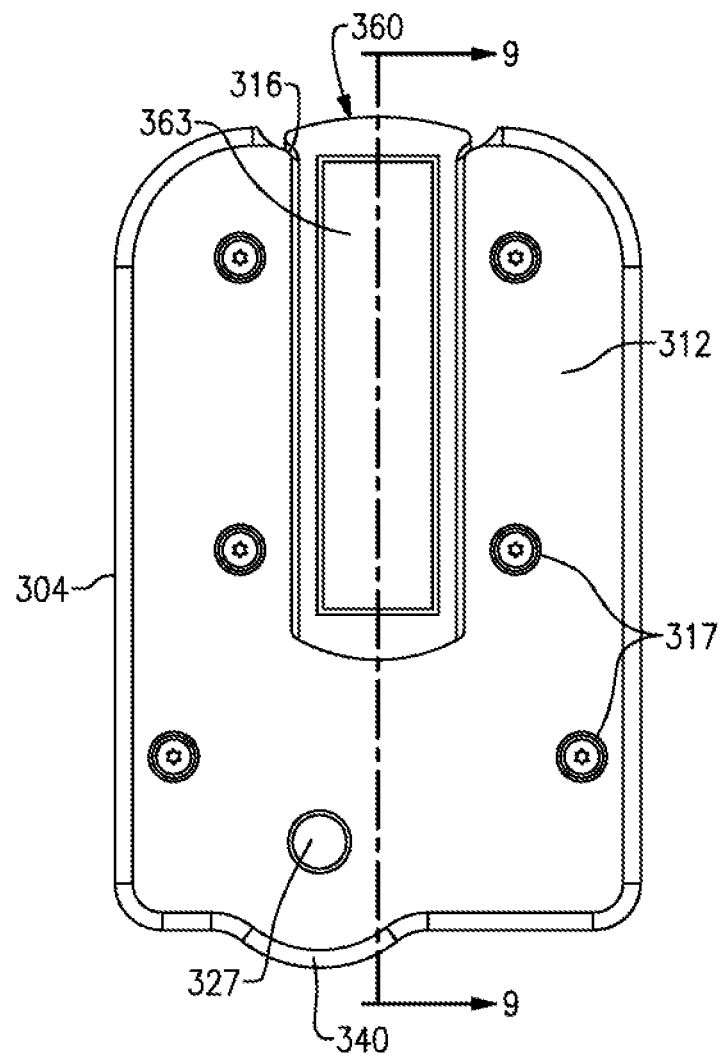
FIG. 9(a)
FIG. 9(b)

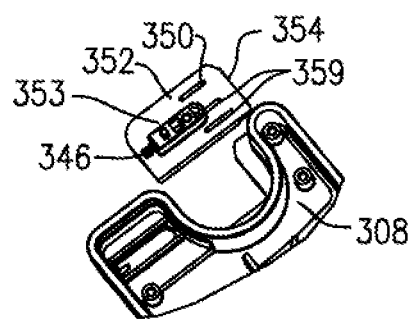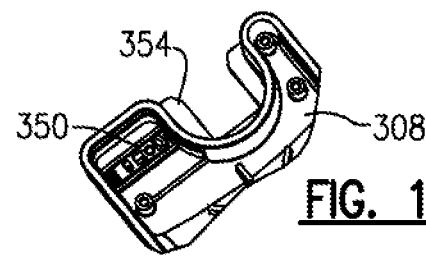
FIG. 10(a)
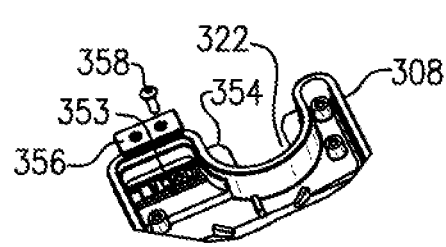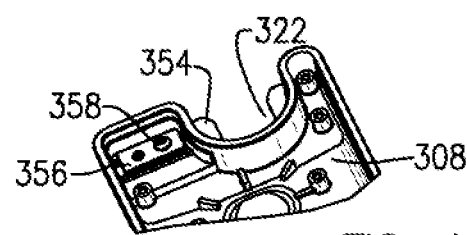
FIG. 10(b)
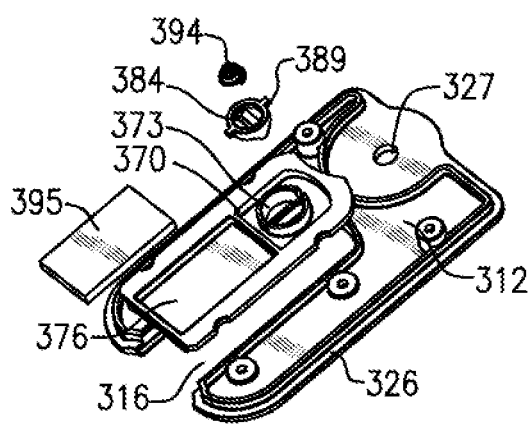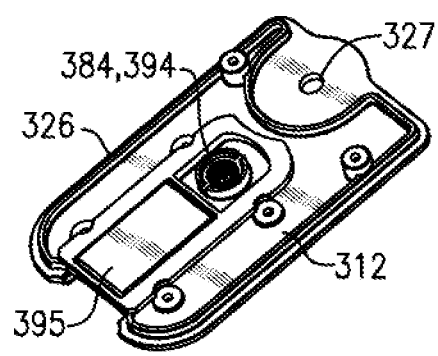
FIG. 10(c)

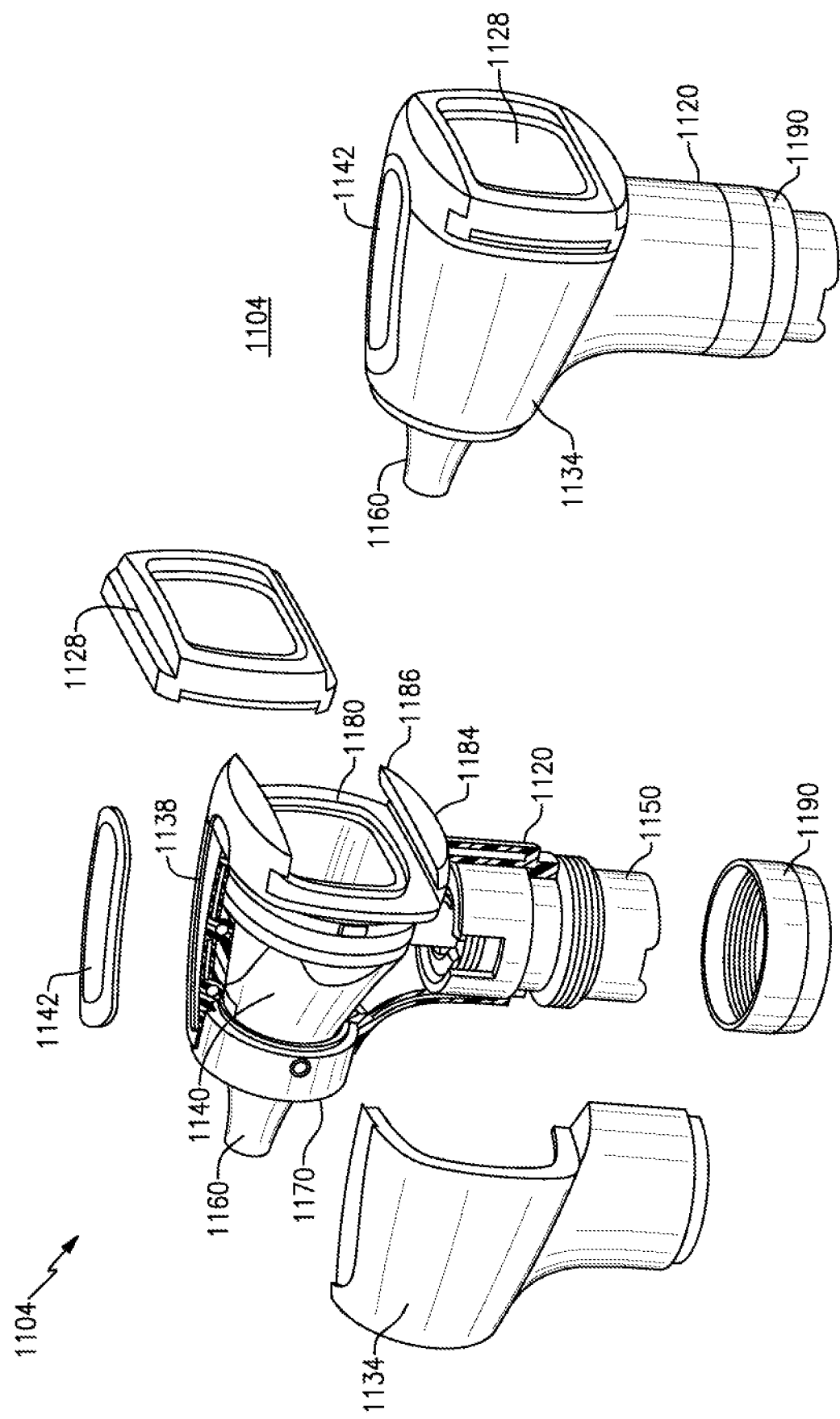

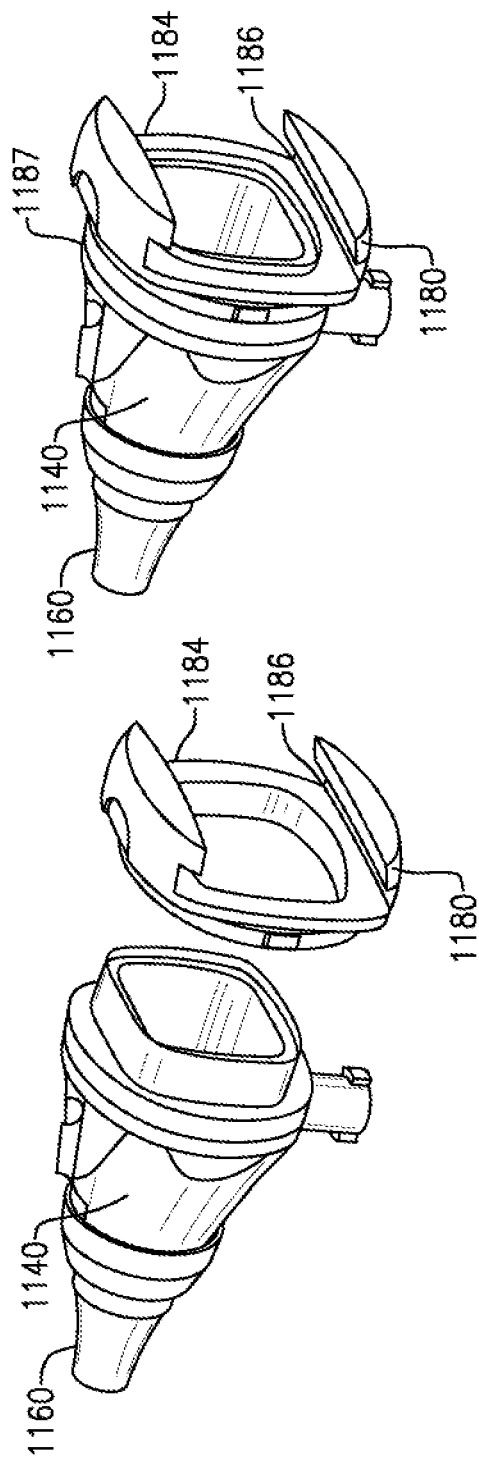

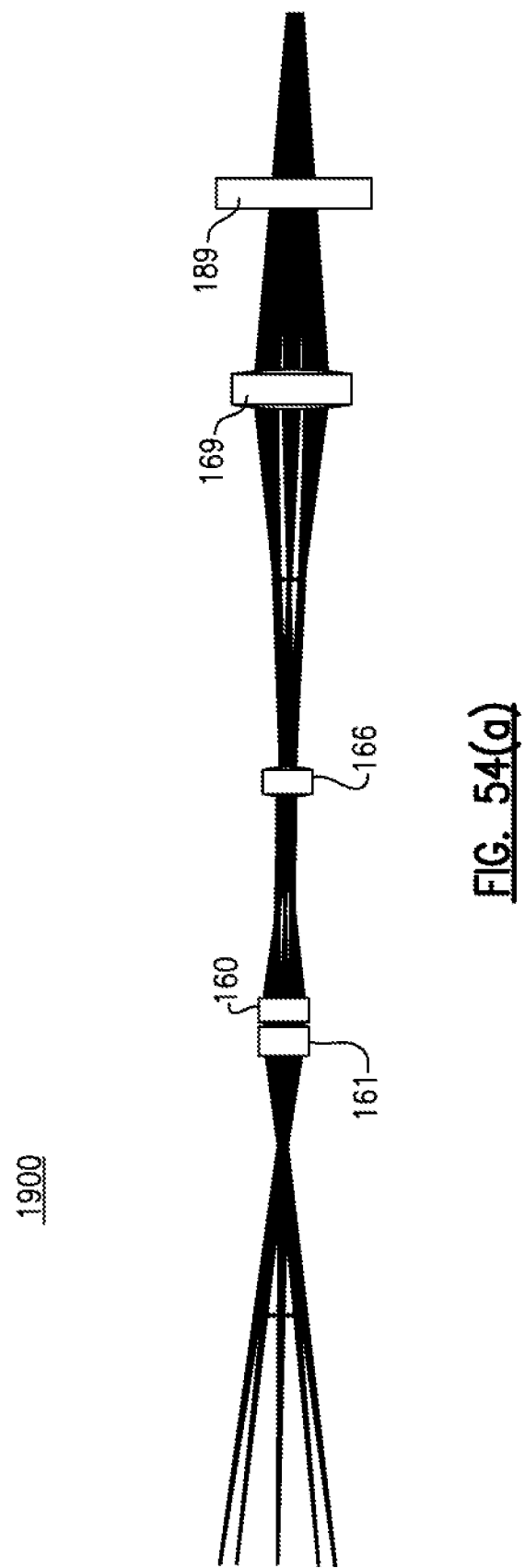

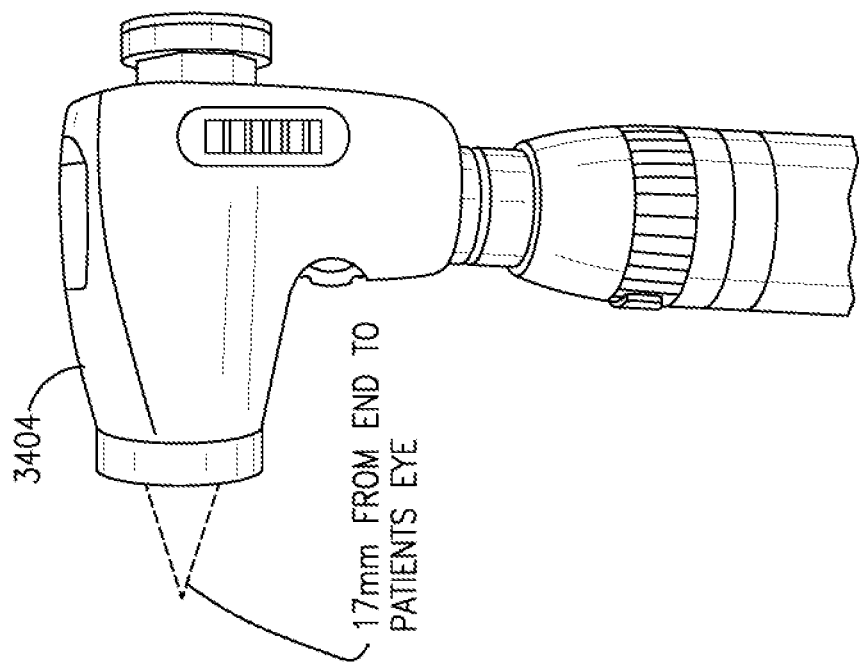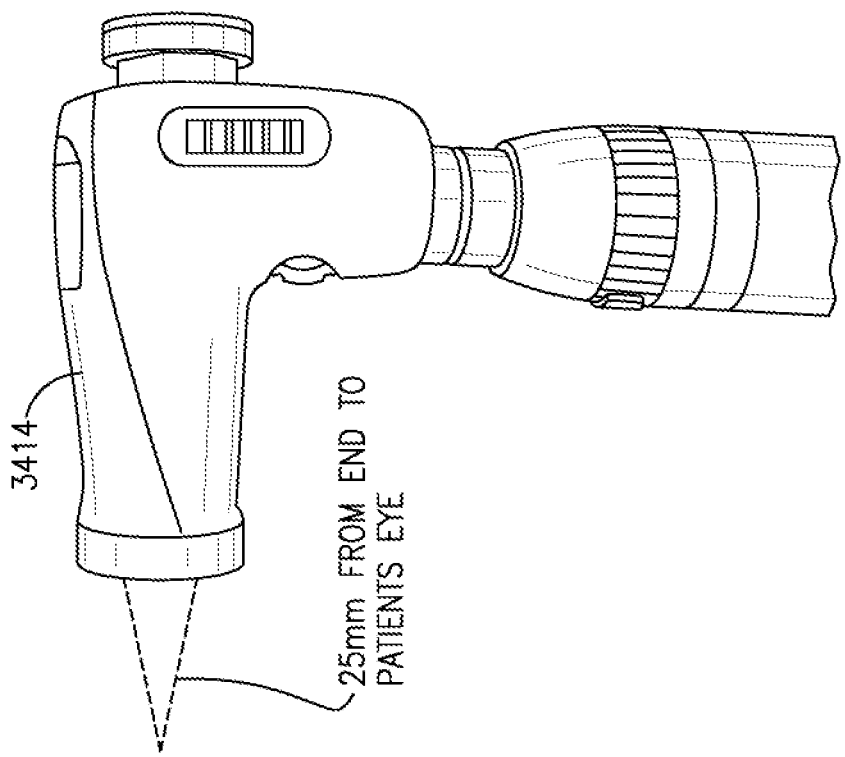
FIG. 74

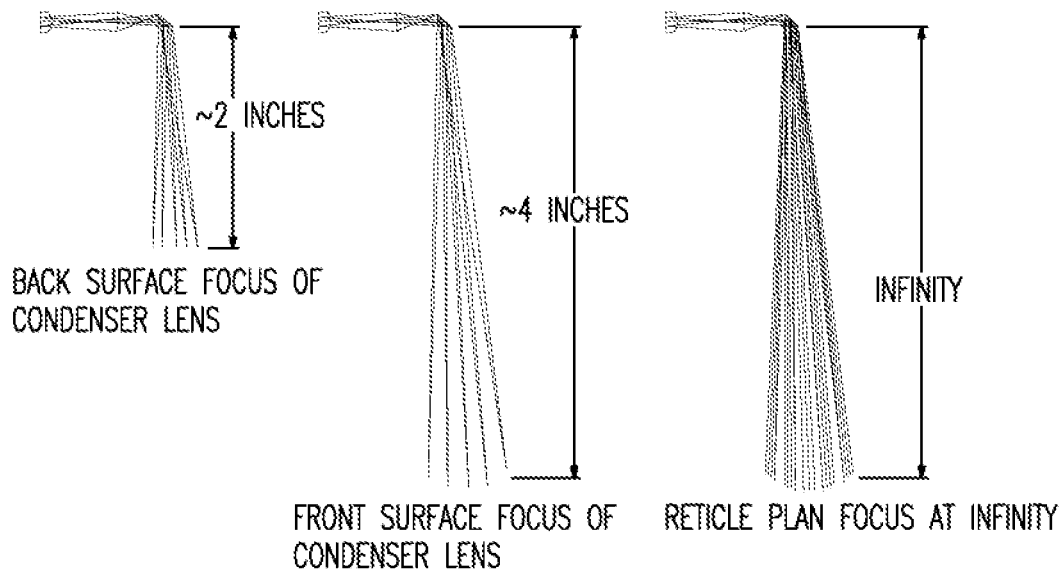
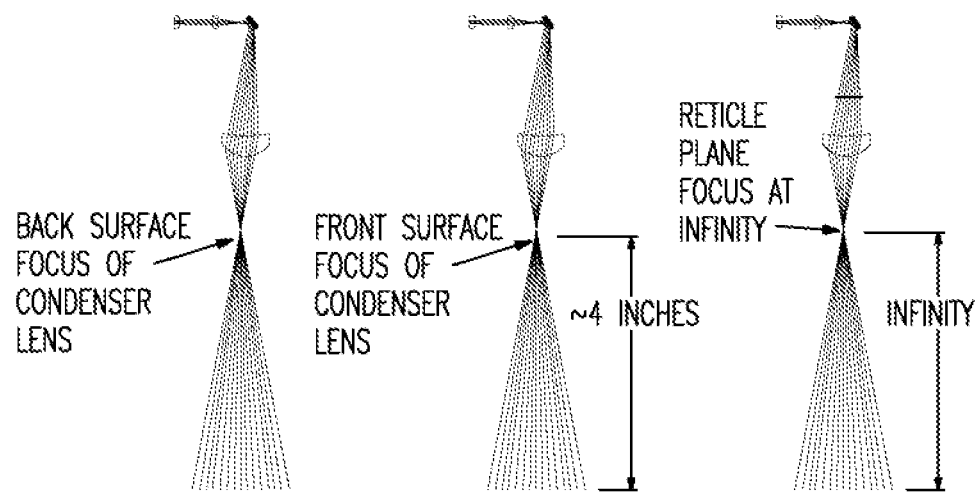
FIG. 75

# PHYSICAL ASSESSMENT DEVICE

CROSS REFERENCE TO RELATED APPLICATION

This application is herein filed under relevant portions of 35 U.S.C. § 111 and 37 CFR §§ 1.51 and 1.53 and claims priority under relevant portions of 35 U.S.C. § 120 to U.S. Patent Application Ser. No. 62/617,929, entitled: Physical Assessment Device, filed Jan. 16, 2018. This application further claims domestic priority to U.S. patent application Ser. No. 29/676,212, entitled: Medical Device, filed Jan. 9, 2019, which claims priority to U.S. patent application Ser. No. 29/654,308, filed Jun. 22, 2018, and U.S. patent application Ser. No. 29/676,213, entitled: Medical Device, filed Jan. 9, 2019, which claims priority to U.S. patent application Ser. No. 29/650,401, filed Jun. 6, 2018. Each of the above-noted applications are incorporated by reference in their entirety.

TECHNICAL FIELD

This application is generally directed to the field of diagnostic medicine and more specifically to an improved physical assessment device, (e.g., an otoscope or ophthalmoscope), which is configured for performing diagnostic patient examinations.

BACKGROUND

Physical assessment devices are well known in the field of diagnostic medicine for examining patients as part of wellness visits and/or routine examinations. These devices include, among others, otoscopes for diagnosing conditions of the ear, ophthalmoscopes for diagnosing conditions associated with the eye of a patient, and dermatoscopes for examining the skin of a patient. Each of these physical assessment devices typically includes an instrument head that is releasably attached to the upper end of an instrument handle, the latter containing a set of batteries, enabling the devices to be compact and capable of being handled with one hand. The instrument head can retain optics that enable an image of a medical target (e.g., ear, eye) to be viewed by a caregiver through an eyepiece, or alternatively the image of the medical target can be transmitted to an electronic imager associated with the physical assessment device. Suitable illumination of the medical target of interest is provided by a resident light source, such as an incandescent lamp.

There is a general need in the field of diagnostic medicine to improve physical assessment devices, such those described above.

BRIEF DESCRIPTION

According to one aspect, there is provided an instrument head for attachment to a plurality of instrument handles having different power profiles. The instrument head includes an illumination assembly including at least one LED, and a drive circuit for detecting a power profile of an attached instrument handle and converting variable voltages received from the attached instrument handle to a constant current for powering the at least one LED based on the power profile.

The drive circuit outputs a pulse width modulation (PWM) of the constant current to illuminate the at least one LED, wherein dimming of the at least one LED is achieved by varying a duty cycle of the PWM of the constant current responsive to changes in the variable voltages received from the attached instrument handle.

In one version, the drive circuit outputs the pulse width modulation (PWM) of the constant current to power the at least one LED at a given illumination level when connected to either a first of the plurality of instrument handles with a first power profile and first variable voltages or a second of the plurality of instrument handles with a second power profile and second variable voltages, wherein the first and second power profiles are different power profiles.

According to another version, the drive circuit comprises a buck/boost circuit that outputs a constant voltage notwithstanding an input voltage from the instrument handle being above or below the constant voltage.

The drive circuit can comprise a rectifier including field effect transistors (FETs) for converting an alternating current input from the instrument handle to a direct current for powering the at least one LED.

In at least one version, the drive circuit includes a controller, wherein the controller detects a polarity of the instrument handle attached to the instrument head. The controller can detect a vibration or idle state of the instrument head and responsive thereto can powers up or power down the instrument head. In at least one version, the controller uses a lookup table to determine the power profile of the attached instrument handle based on power up signals received when attached.

According to a preferred embodiment, the instrument head is part of a physical assessment device. More specifically, the physical assessment device is an otoscope or an ophthalmoscope in which at least one of the instrument handles used with the instrument head are typically configured only for use with an incandescent light source.

According to another aspect, there is provided a physical assessment device including an instrument head that is attached to an instrument handle, in which the instrument head has a distal end and an opposing proximal end. An illumination assembly disposed within the instrument head includes at least one LED as a light source. An optical assembly is also disposed within the instrument head and includes a plurality of optical components aligned along an imaging axis. An accessory attached to the distal end of the instrument head acts as an interface to a patient for purposes of examination in which the optical assembly creates an entrance pupil that is sufficiently distal from a distalmost optical element of the imaging assembly such that the attached accessory is not in the field of view of the optical assembly.

In at least one version, the attached accessory is a speculum tip and the physical assessment device is an otoscope in which the speculum tip is cropped from a resulting image of the ear canal of a patient due to the location of the distal entrance pupil. The optical assembly permits the entire tympanic membrane to be viewed all at once in the field of view.

The instrument head can include a pair of mating housing sections defining an interior of the instrument head, an innerformer disposed within the interior, and a sealing member attached to the innerformer to permit insufflation of a patient. According to at least one version, the sealing member is elastomeric and attached to a proximal end of the innerformer. Advantageously, the sealing member further provides an antifogging measure relative to at least one optical component of the optical assembly.

According to yet another aspect, an illumination assembly includes an LED attached to a circuit board, and a component that centers and aligns the LED in relation to a defined illumination axis. The centering and aligning component can include a domed surface configured to receive and collimate the light from the LED.

According to one version, the centering and aligning component comprises an annular ring that centers the domed surface relative to the LED and in which the domed surface is a condensing lens. Advantageously, the annular ring can include according to at least one version, an outer threaded portion that provides a dirt and debris barrier to the LED.

The illumination assembly can be used in a physical assessment device which is at least one of an otoscope or an ophthalmoscope. Preferably, the instrument head is attachable to an instrument handle having at least contained power source for energizing the LED. According to one version, the instrument head is attachable to one of a disparate number of instrument handles, including instrument handles configured to power illumination assemblies having an incandescent bulb as a light source. The circuit board can include circuitry configured to permit any of the disparate instrument handles to be attached to the instrument head and energize the LED without flickering thereof.

According to yet another aspect, there is provided a physical assessment device that includes an instrument head having a distal end, an opposing proximal end and an interior. An optical assembly is disposed within the instrument head, including a plurality of optical components disposed along an optical axis. In addition, an adapter interface member is disposed at the proximal end of the instrument head. The adapter interface member enables the attachment of a smart device to be attached and aligned with the optical axis.

In at least one version, a smart device adapter is releasably engageable with the adapter interface member, the smart device adapter having a surface sized and configured for receiving a smart device.

According to at least one embodiment, the adapter interface member includes a distal portion, a proximal portion and a recess between the distal and proximal portions. At least one optical component of the optical assembly can be retained in the adapter interface member.

In at least one version, the smart device adapter includes a device engagement portion made up of a plurality of engagement surfaces that are engageable with the recess of the adapter interface member. The recess of the adapter interface member can include a plurality of machined flats that are engageable with the engagement surfaces of the smart device adapter. According to at least one version, the smart device adapter includes a slot which includes the device engagement portion. The device engagement portion can include three engagement surfaces including two parallel engagement surfaces with a defined spacing therebetween and a third engagement surface orthogonal to the two parallel engagement surfaces, the engagement surfaces forming an open-ended clevis. According to at least one embodiment, one of the two parallel engagement surfaces is part of a slider member that biases the engagement surface into the adapter slot.

The distal portion of the adapter interface member can include a plurality of axial openings in which each of the axial openings retains a ball or similar feature that is biased into the recess and configured to axially engage the smart device adapter when attached. The machined flats of the recess of the adapter interface member further enables the smart device adapter and an attached smart device to be selectively placed in multiple orientations about the optical axis of the physical assessment device.

According to at least one version, the smart device adapter includes a slot sized and configured to receive a device engagement member. According to certain embodiments, the device engagement member includes an adhesive strip on one side that enables attachment to a smart device and an opposing side of the device engagement member includes a transverse groove.

The smart device adapter can include a detent member that is engageable with the transverse groove of the device engagement member when attached through the slot. In at least one embodiment, the detent member is disposed within a detent cover supported within the slot of the smart device adapter wherein the detent member is biased by a spring which is supported by the detent cover.

A strip of insulating material supported on an interior surface of the supported detent cover is configured to provide resistance to the device engagement member, when the latter is attached to the smart device adapter via the slot. The smart device adapter includes an opening at the device engagement portion that is aligned with the optical axis of the optical assembly when attached to the physical assessment device.

According to another aspect, there is provided a smart device adapter for a physical assessment device. The adapter includes an adapter housing, including a proximal surface that is sized and shaped to support a smart device, as well as a device engagement portion, the latter being sized and configured to releasably engage a physical assessment device. A smart device engagement member having at least one feature enables releasable attachment to a smart device.

According to one version, the device engagement portion includes an arm extending from the adapter housing that is suitably shaped and configured to engage the lower end of an instrument head of the physical assessment device. The arm may include a ring-shaped engagement portion that is sized to engage over the lower end of the instrument head, the arm being made from an elastomeric material. In at least one version, the device engagement portion includes a C-shaped engagement feature at a lower end of the adapter housing that is sized and shaped to snap fittingly engage a cylindrical handle of the physical assessment device.

According to another version, the device engagement portion is configured to engage an adapter interface member at the proximal end of the physical assessment device. The adapter can include a detent member that is engageable with the smart device engagement member when the smart device engagement member is attached to the adapter housing via a slot. The detent member is supported by a detent cover and biased outward into the slot by a spring supported by the detent cover.

According to yet another aspect, there is provided a smart device adapter for a physical assessment device that includes a pair of housing sections defining an interior, a device engagement portion sized and configured to releasably engage the proximal end of a physical assessment device, and a smart device engagement member configured to releasably engage a slot of one of the housing sections and having at least one feature that enables releasable attachment to a smart device.

In at least one embodiment, one of the housing portions includes a slot that is sized and configured to receive the smart device engagement member.

The adapter can include a detent member extending through the slot and engageable with the smart device engagement member. According to at least one version, one side of the smart device engagement member includes an adhesive strip on one side that is engageable with a smart device. A transverse groove on an opposing side is engageable with the detent member when the smart device engagement member is attached to the slot of the adapter.

The detent member is supported within a detent cover within the interior of the adapter housing, the detent member being biased outward into the slot by a spring. According to at least one version, the device engagement portion includes a plurality of engagement surfaces formed in a slotted configuration that enables releasable attachment to the adapter interface member of a physical assessment device. One of the engagement surfaces can be biased inwardly relative to the slotted configuration of the device engagement portion and in which the biased engagement surface is an edge surface of a slider member whose position relative to the slotted configuration is biased by a spring.

The smart device adapter also includes an opening formed in the adapter housing that is aligned with the optics of an attached smart device.

According to yet another aspect, there is provided an ophthalmic device that includes an instrument head including a distal end and an opposing proximal end. An illumination assembly is disposed within the instrument head including at least one light source for illuminating a medical target of interest and a pair of fixation lights disposed in spaced relation at the distal end of the instrument head.

In at least one embodiment, a plurality of optical fibers extend from the at least one light source to the fixation lights. An optical assembly includes an objective lens disposed at the distal end of the instrument head, in which the fixation lights are distally disposed in relation to the objective lens.

According to a preferred embodiment, the at least one light source is an LED in which the fixation lights include polarizer windows that are disposed in spaced relation. The ophthalmic device can further receive an elastomeric eye cup at its distal end adjacent the fixation lights.

According to yet another aspect, there is provided a physical assessment device comprising an instrument head having a distal end, an opposing proximal end and an interior. An illumination assembly is disposed within the instrument head and includes at least one light source and a plurality of components aligned along a defined illumination axis The illumination assembly further includes a mirror to direct light from the at least one light source and at least one feature for enabling adjustment of the mirror.

According to at least one embodiment, the physical assessment device comprises a mirror support mount that retains the mirror. An adjustment member is accessible through the housing of the instrument head preferably during manufacture that engages the mirror mount to adjust the position of the mirror relative to the illumination axis.

According to at least one version, the light source is an LED, wherein the illumination assembly further includes a condensing lens disposed above the LED. The condensing lens is disposed in a component having a feature that aligns and centers the condensing lens with the LED along the illumination axis. According to at least one version, the condensing lens is formed as a molded domed section or surface on the aligning and centering component.

One advantage realized by the herein described physical assessment device is that a smart device, such as a smart phone, can be mechanically and optically coupled to a device, such as an otoscope or ophthalmoscope, which is typically only configured for optical viewing by a caregiver.

Another advantage is that a plurality of accessories, such as speculum tip elements having different engagement features, can be releasably and interchangeably attached to an otoscope made in accordance with at least one embodiment.

Still another advantage is that according to at least one embodiment, a smart device can be attached to an existing physical assessment device without modification such that the optical axis of the attached smart device is aligned with the optical axis of the physical assessment device.

Yet another advantage is that an instrument head made in accordance with the invention can be interchangeably attached to a plurality of instrument handles in which the instrument head is configured to detect the attached handle and suitably adjust a retained light source.

Still another advantage realized is that the optical system of the physical assessment device enables the attachment of an accessory, such as a speculum tip without the accessory being part of the field of view of an intended medical target.

These and other features and advantages will be apparent from the following Detailed Description, which should be read in conjunction with the accompanying drawings.

BRIEF DESCRIPTION OF THE DRAWINGS

FIG. 1(*b*) is a front perspective view of the physical assessment device of FIG. 1(*a*);

FIG. 2(*b*) is a side view taken in section, of the instrument head of FIGS. 1(*a*)-2(*a*);

FIG. 2(*c*) is a rear facing view of the instrument head of FIGS. 1(*a*)-2(*b*);

FIG. 2(*d*) is a rear perspective view of the instrument head of FIGS. 1(*a*)-2(*c*);

FIG. 2(*e*) is a another rear perspective view of the instrument head of FIGS. 1(*a*)-2(*d*);

FIG. 2(*f*) is a side perspective view of the instrument head of FIGS. 1(*a*)-2(*e*);

FIG. 2(*g*) is another side perspective view of the instrument head of FIGS. 1(*a*)-2(*f*);

FIG. 2(*h*) is a bottom plan view of the instrument head of FIGS. 1(*a*)-2(*g*);

FIG. 2(*i*) is a top plan view of the instrument head of FIGS. 1(*a*)-2(*h*);

FIG. 2(*j*) is a left side elevation view of the instrument head of FIGS. 1(*a*)-2(*i*);

FIG. 2(*k*) is a right side elevation view of the instrument head of FIGS. 1(*a*)-2(*j*);

FIG. 5(*b*) is a side view, taken in section, of the instrument head of FIG. 5(*a*);

FIGS. 6 and 7 are exploded assembly views of a smart device adapter made in accordance with an exemplary embodiment;

FIG. 8(*b*) is a sectioned view of the adapter taken through line 8-8 of FIG. 8(*a*);

FIG. 9(*a*) is a rear facing view of the smart device adapter of FIGS. 8(*a*) and 8(*b*);

FIG. 9(*b*) is a side sectioned view of the smart device adapter taken through section lines 9-9 of FIG. 9(*a*);

FIG. 11(l) is another bottom view of the smart device adapter of FIGS. 6-11(k);

FIGS. 25(a), 25(c) and 25(d) are partial assembly views and FIG. 25(b) is an assembled view of the instrument head of FIGS. 21 and 23;

FIG. 54(a) presents an optical layout of the physical assessment device of FIG. 13(b);

FIG. 74 illustrates physical assessment devices having the optical assemblies illustrated in FIG. 73;

FIG. 75 illustrates various ray traces of an illumination assembly according to an embodiment as compared to an existing illumination assembly;

FIG. 84 illustrates an electrical circuit in accordance with another embodiment enabling an instrument handle to be charged using a charging base or via USB;

Figure 85:
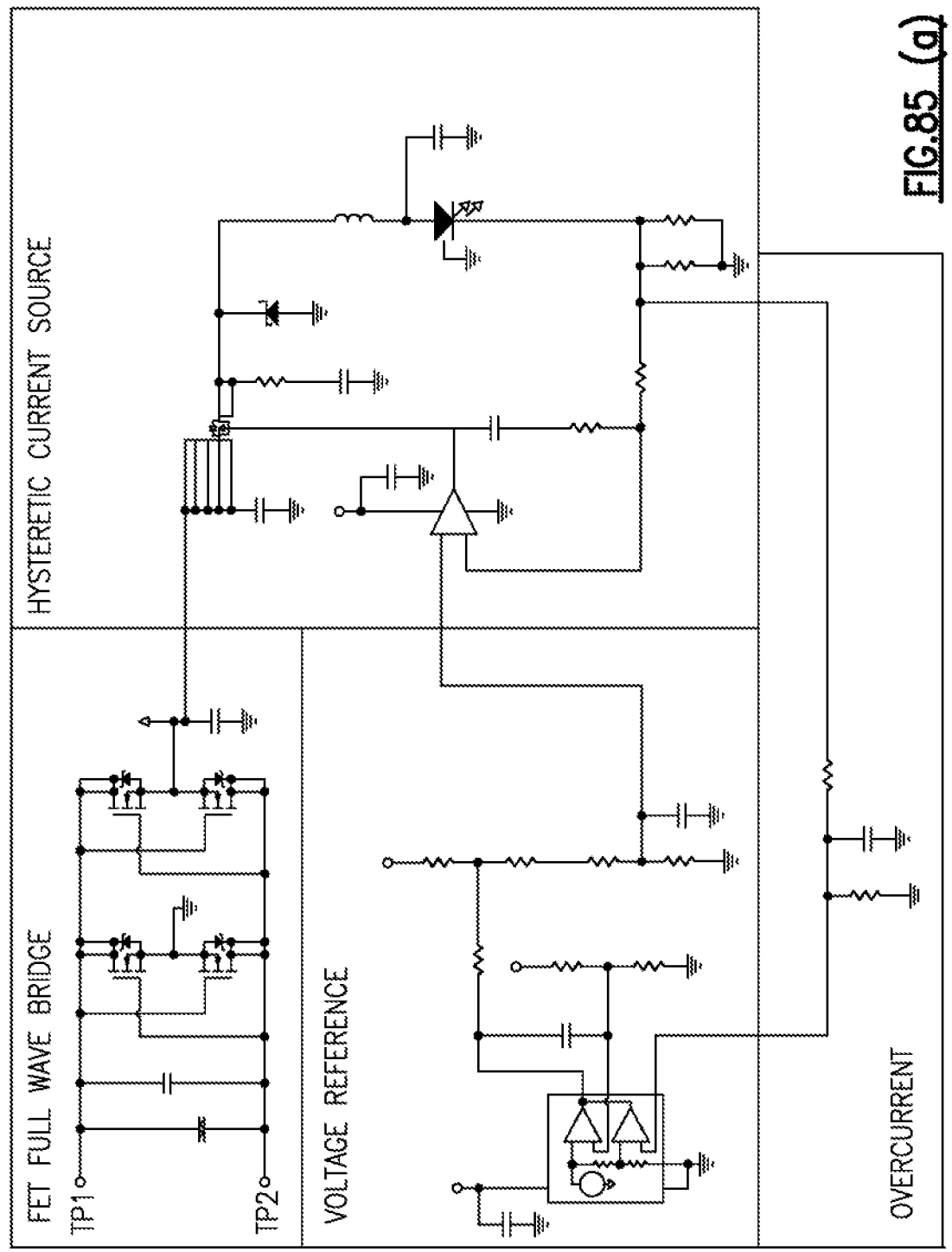
Figure 85:
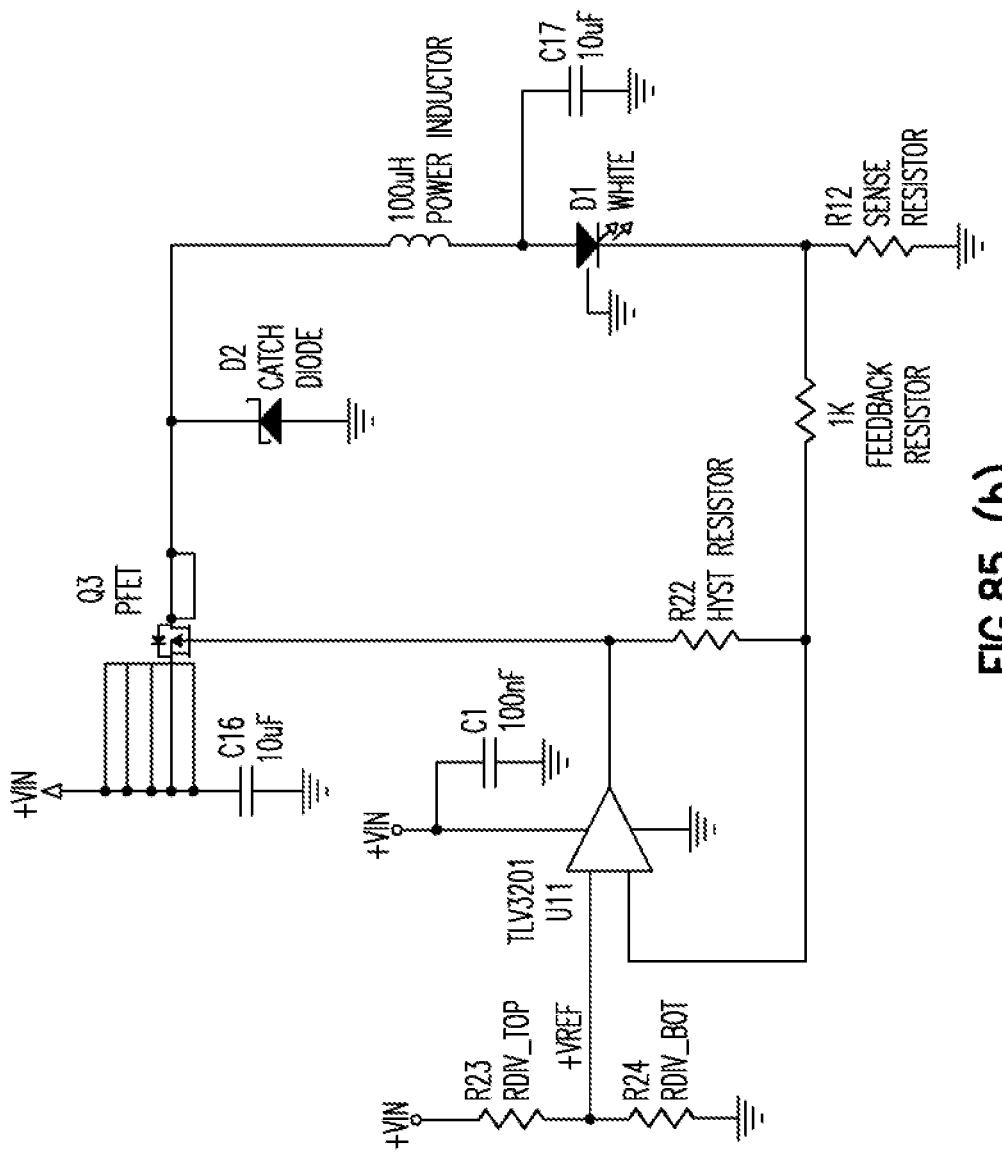
Figure 86:
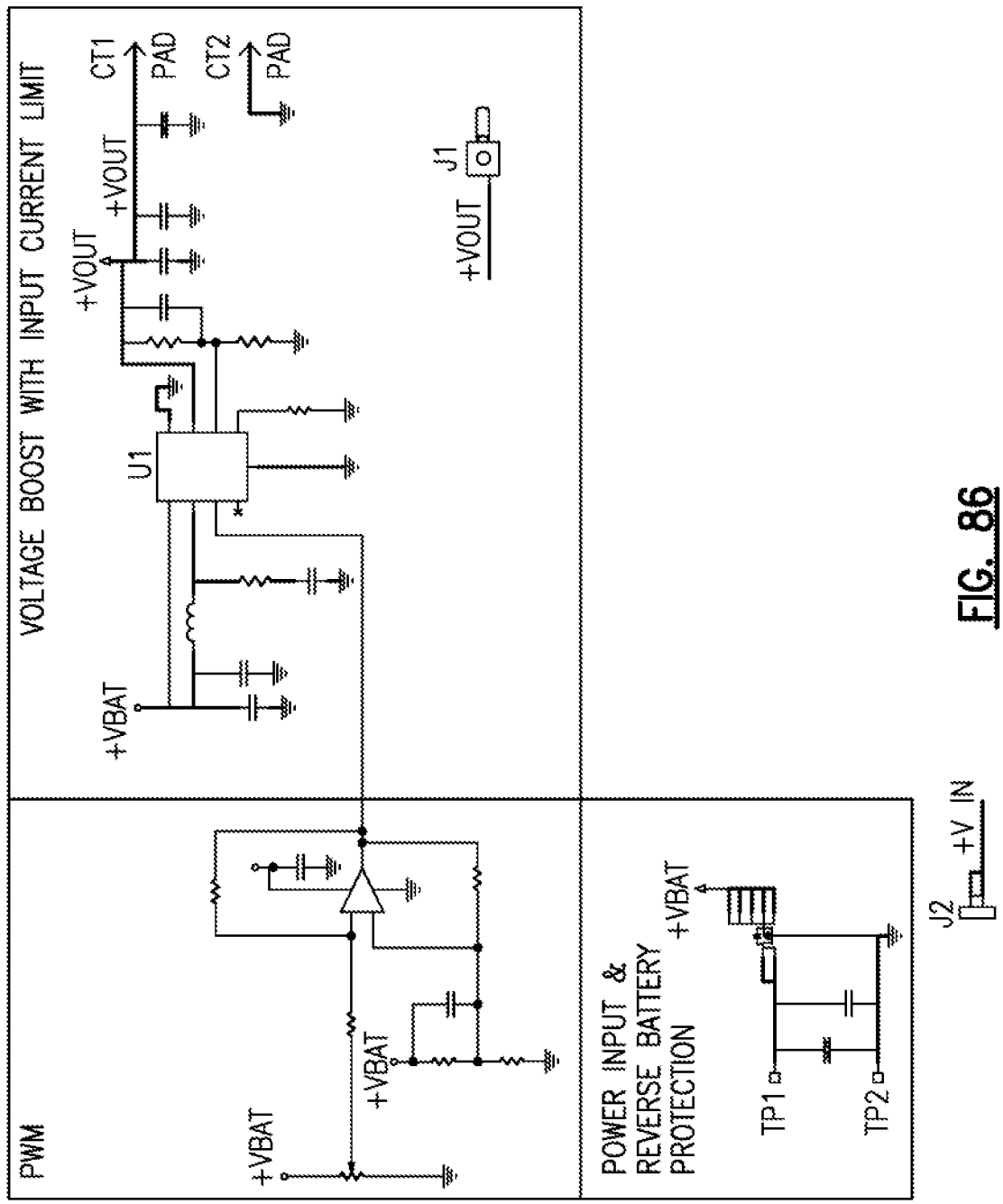

FIGS. 85(a) and 85(b) are diagrams of circuits that will drive both an LED and halogen based lamp from a single varying power source and maintain loop stability so that there is no risk of blinking LEDs; and FIG. 86 is a schematic diagram of a voltage boost circuit made in accordance with an embodiment.

DETAILED DESCRIPTION

The following relates to various embodiments of physical assessment devices that are typically used for examining a patient, and more specifically otoscopes typically used for examining the ears of a patient and ophthalmoscopes typically used for examining the eyes of a patient. It will be readily apparent to the reader from the description that follows that a number of the herein described features can be incorporated into physical assessment devices other than those being described. In addition, a number of the inventive features described are not confined to any specific embodiment and are equally applicable to other described embodiments/devices. In addition, a number of terms are used throughout the following description for purposes of providing a suitable frame of reference in regard to the accompanying drawings. These terms, which include "first", "second", "upper", "lower", "left", "right", "above", "below", "distal", "proximal", "interior", "exterior", "internal" and "external", among others, are not intended to limit any of the described inventive aspects, except where so specifically and conspicuously indicated. In addition and for purposes of clarity, like reference numerals are used throughout the discussion of each of the various embodiments.

In addition, the drawings provided are intended to show salient features of the herein described physical assessment devices. The drawings, however, are not intended to provide scalar relationships between any of the various depicted components unless specified to the contrary.

Otoscope

Figure 1A:
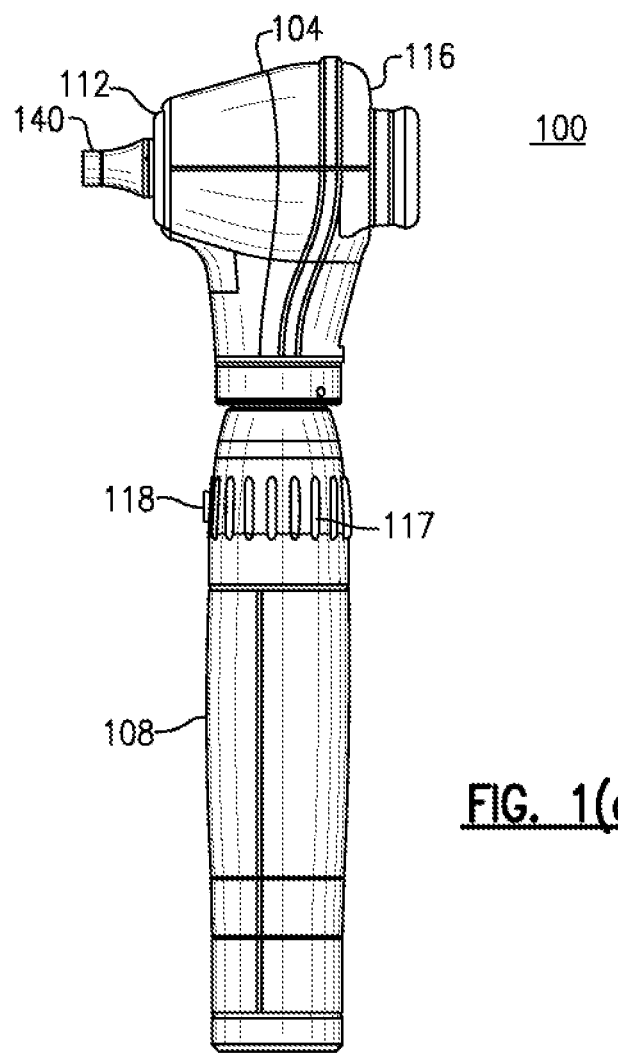
FIG. 1(*a*) is a side elevational view of a physical assessment device made in accordance with an embodiment.
Figure 1B:
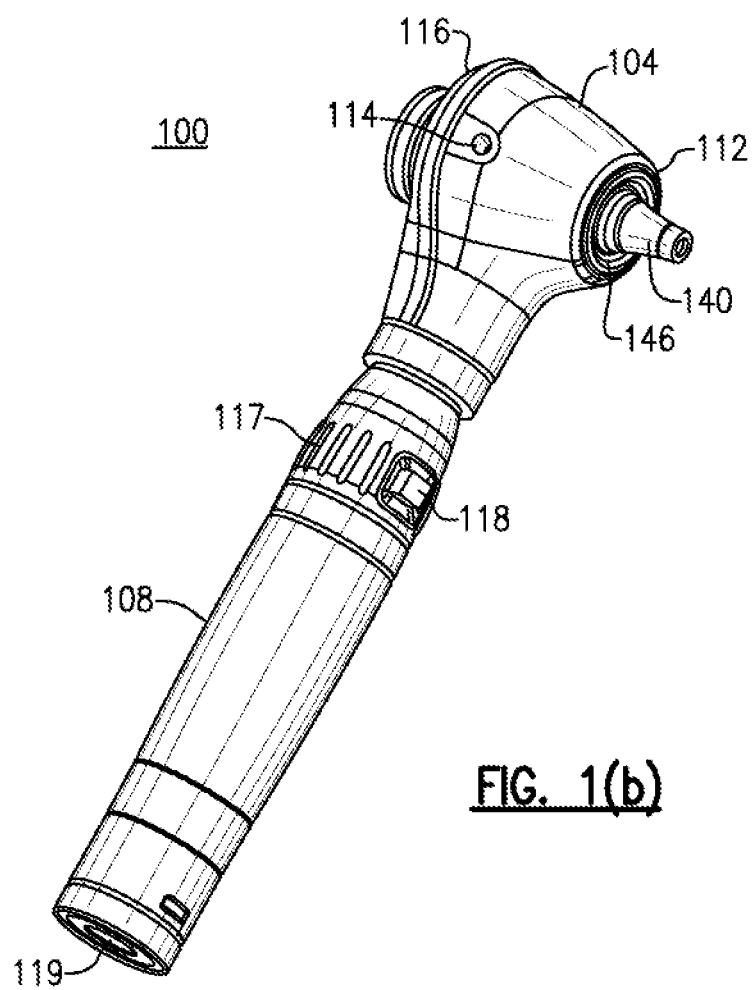

A first physical assessment device (otoscope) is described. FIGS. 1(a) and 1(b) depict a side view and a front perspective view of the physical assessment device, respectively, which according to this embodiment is an otoscope 100. The otoscope 100 is designed primarily for performing diagnostic examinations of the ear of a patient, although the herein described physical assessment device 100 can also be used for examining other anatomical cavities (i.e., the nose, throat) of a patient. The otoscope 100 is defined by an instrument head 104 that is releasably attached to the upper end of an instrument handle or handle portion 108. The instrument handle 108 is sized and shaped to permit the otoscope 100 to be handheld and is further configured to retain at least one battery (not shown in these views) for powering a light source (not shown) contained in the instrument head 104. The contained light source is energized by an on-off button 118 disposed on the exterior of the handle portion 108, wherein the illumination output of the contained light source can be controlled using a rheostat 117, the latter including a twistable portion formed on the handle portion 108. The contained battery can preferably be recharged via a charging port 119, which is provided in the bottom end of the handle portion 108.

Figure 2A:
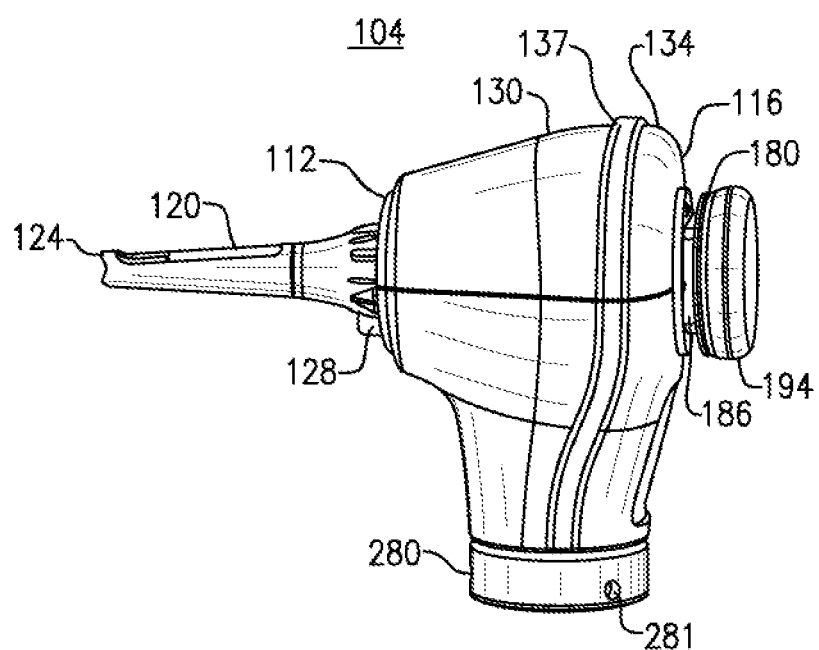
FIG. 2(*a*) is a side elevational view of the instrument head of the physical assessment device of FIGS. 1(*a*) and 1(*b*)

As shown in FIG. 2(a), the instrument head 104 according to this embodiment is defined by a body or housing having a distal or patient end 112 and an opposing proximal or caregiver end 116. A hollow speculum tip element 120 is releasably attached to the distal end 112 of the instrument head 104, the speculum tip element 120 being designed and shaped to fit a predetermined distance into the ear canal while the proximal end 116 of the instrument head 104 includes an adapter interface member 180.

The interior of the instrument head 104 is essentially hollow and sized and configured to retain a plurality of components. With reference to FIGS. 2(a)-2(k) and 3 and according to this exemplary embodiment, the instrument head 104 includes a pair of mated housing sections; specifically a front housing section 130 and a rear housing section 134. Each housing section 130, 134 is a shell-like member made from a structural material, such as a moldable plastic. Each of the housing sections 130, 134 are mated to one another according to this embodiment using fasteners 136, FIG. 3, to define an interior cavity. Alternatively, the housing sections 130, 134 can also be secured by welding, such as ultrasonic welding or other suitable means. As discussed in greater detail in a later portion of this description, the lower ends 131, 135 of each of the housing sections 130, 134 are retained at the bottom of the instrument head 104 using a securing ring 280. According to this embodiment, a peripheral bumper 137 is disposed between the front and rear housing sections 130, 134. An innerformer 138 disposed within the interior of the front housing section 130 includes a conical distal portion 139, as well as a lower portion 141. The innerformer 138 is essentially hollow and defines an interior cavity of the instrument head 104 to enable insufflation via a port connector (not shown) extending outwardly to a corresponding access opening 114, FIG. 1(b), formed in the front housing section 130.

With reference to FIGS. 2(b)-4, the herein described otoscope 100 retains an optical assembly that includes a hollow lens tube 152 containing a plurality of optical components is supported within the interior of the instrument head 104 and more specifically within the innerformer 138. The lens tube 152 is defined by opposing distal and proximal ends 154, 156, respectively. An objective lens 160 is fitted within the distal end 154 of the lens tube 152 adjacent an optical window 161 that covers the distal end 154 of the lens tube 152. A cylindrical hollow spacer 163 is provided proximally of the objective lens 160 along with a relay lens 166, each of the spacer 163 and relay lens 166 being disposed within an intermediate axial portion 155 of the lens tube 152. The diameter of the lens tube 152 further widens at its proximal end 156, which retains an imaging lens 169 disposed in relation to a field stop 170 with a coiled spring 172 being disposed therebetween. A threaded retaining cap 175 at the proximal end 156 of the lens tube 152 maintains pressure against the imaging lens 169. In addition, a field stop 164 is disposed within the lens tube 152 between the window 161 and objective lens 160 to reduce light scatter and an aperture plate 167 is disposed within the lens tube 152 proximal to the relay lens 166.

Figure 2B:
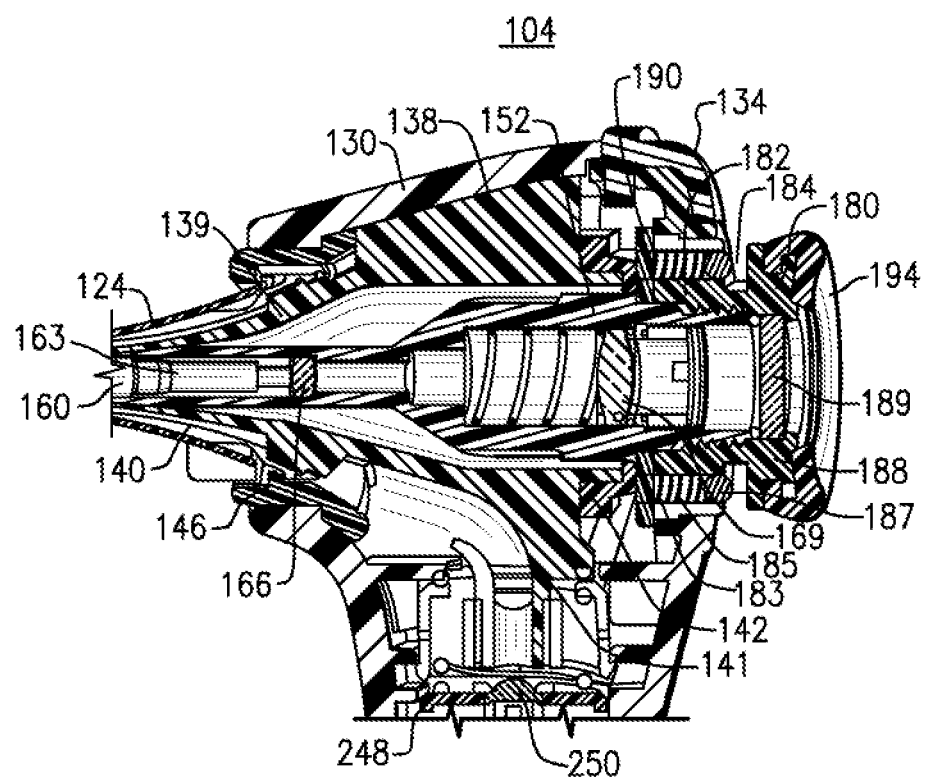
Figure 2C:
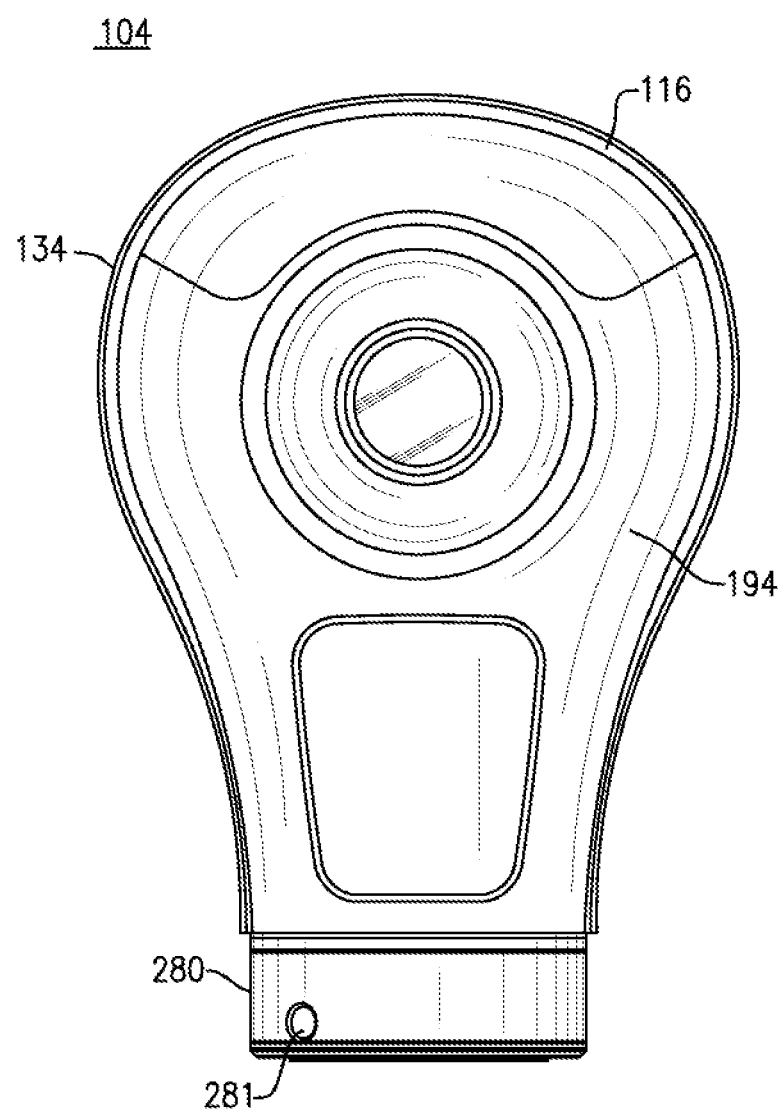
Figure 2D:
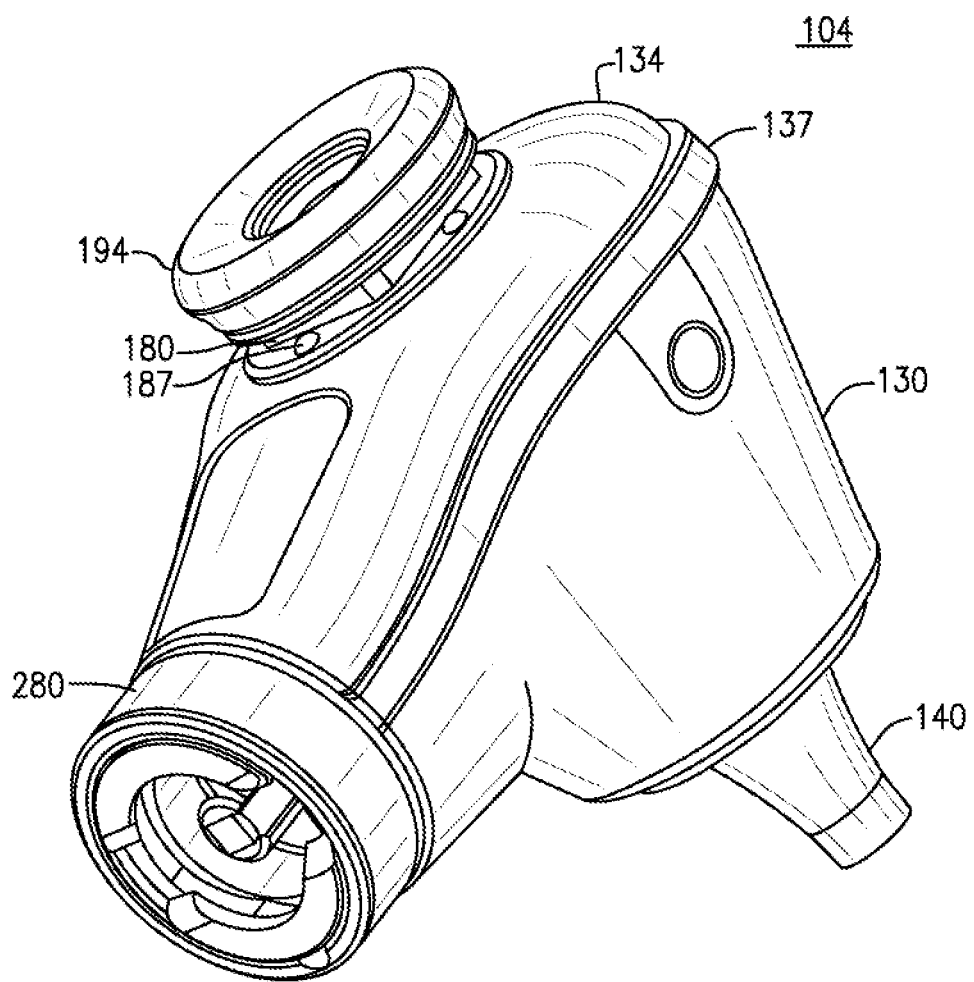
Figure 2E:
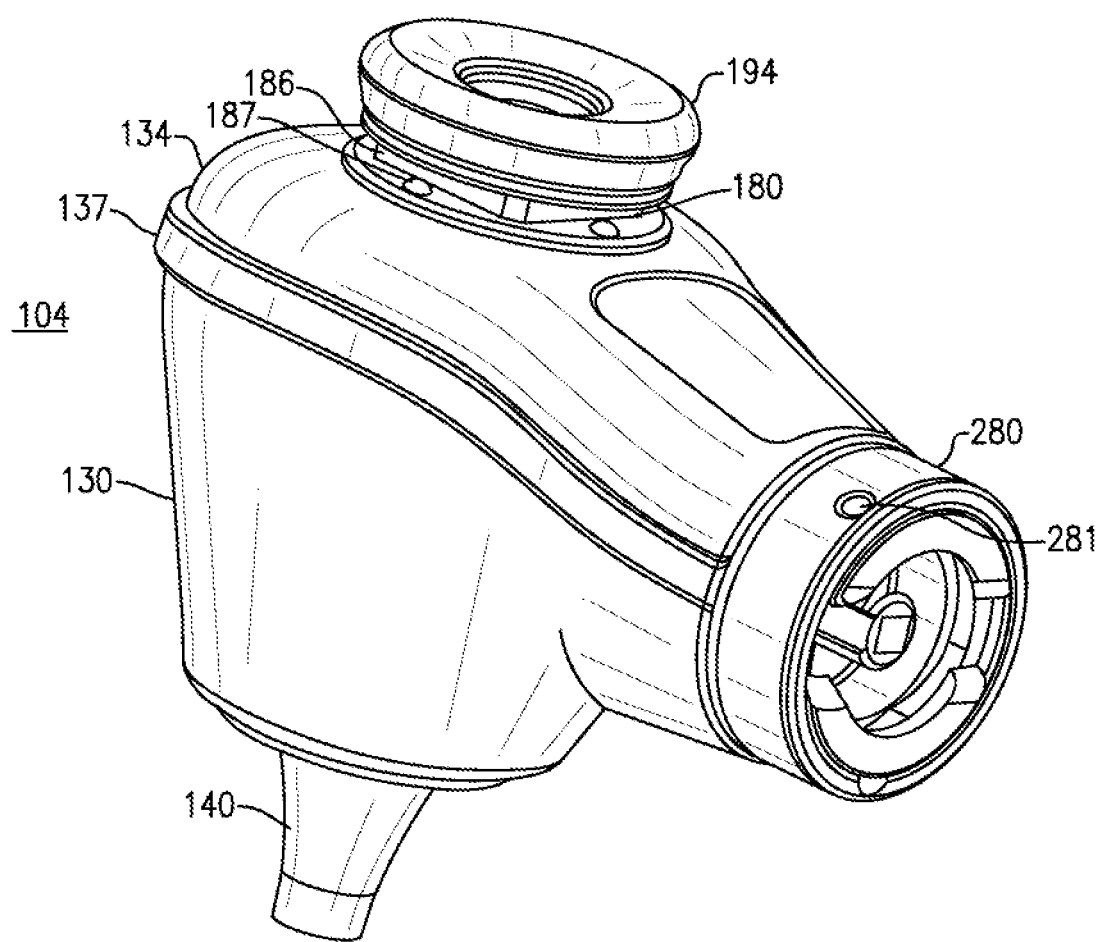
Figure 2F:
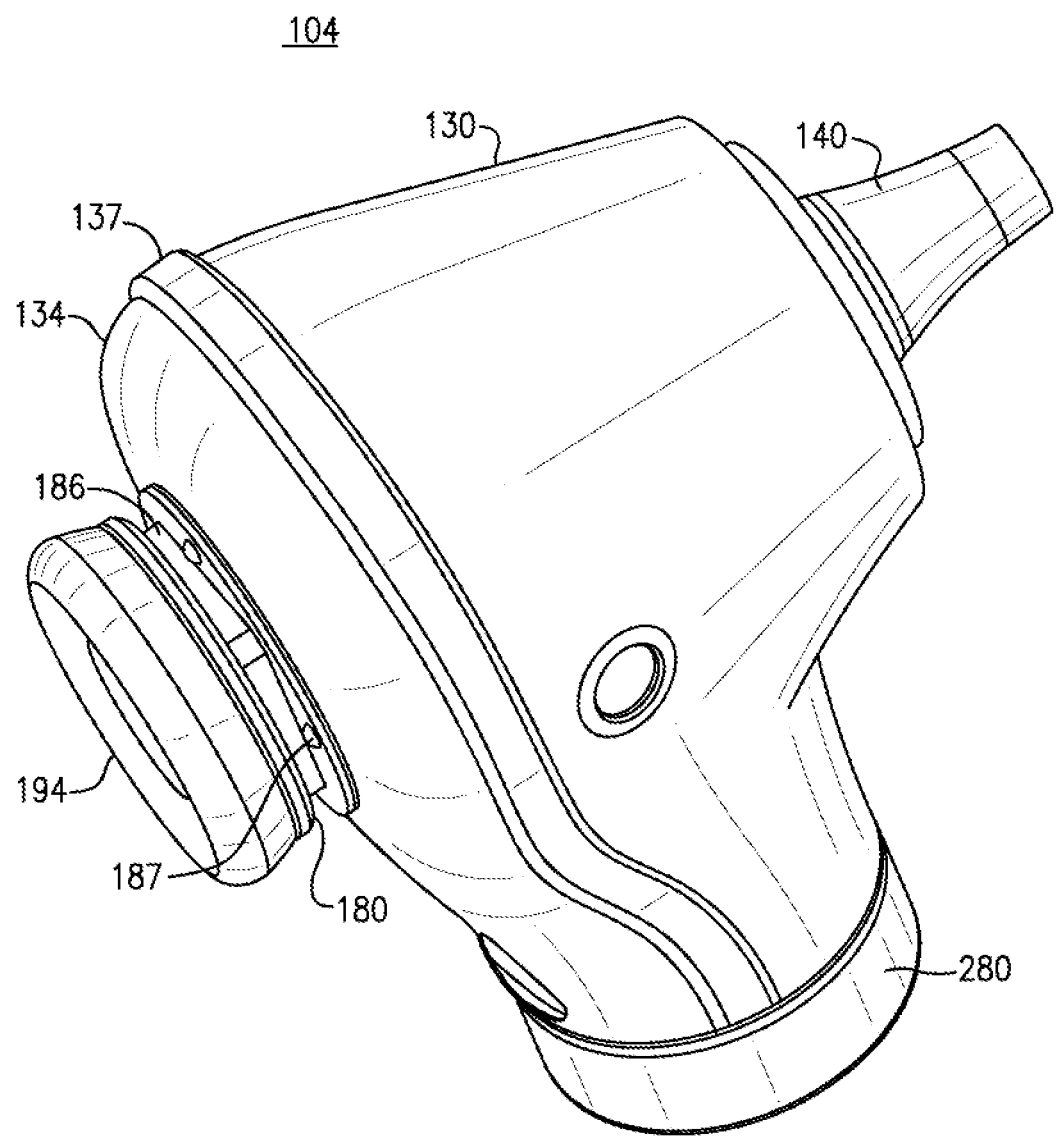
Figure 2G:
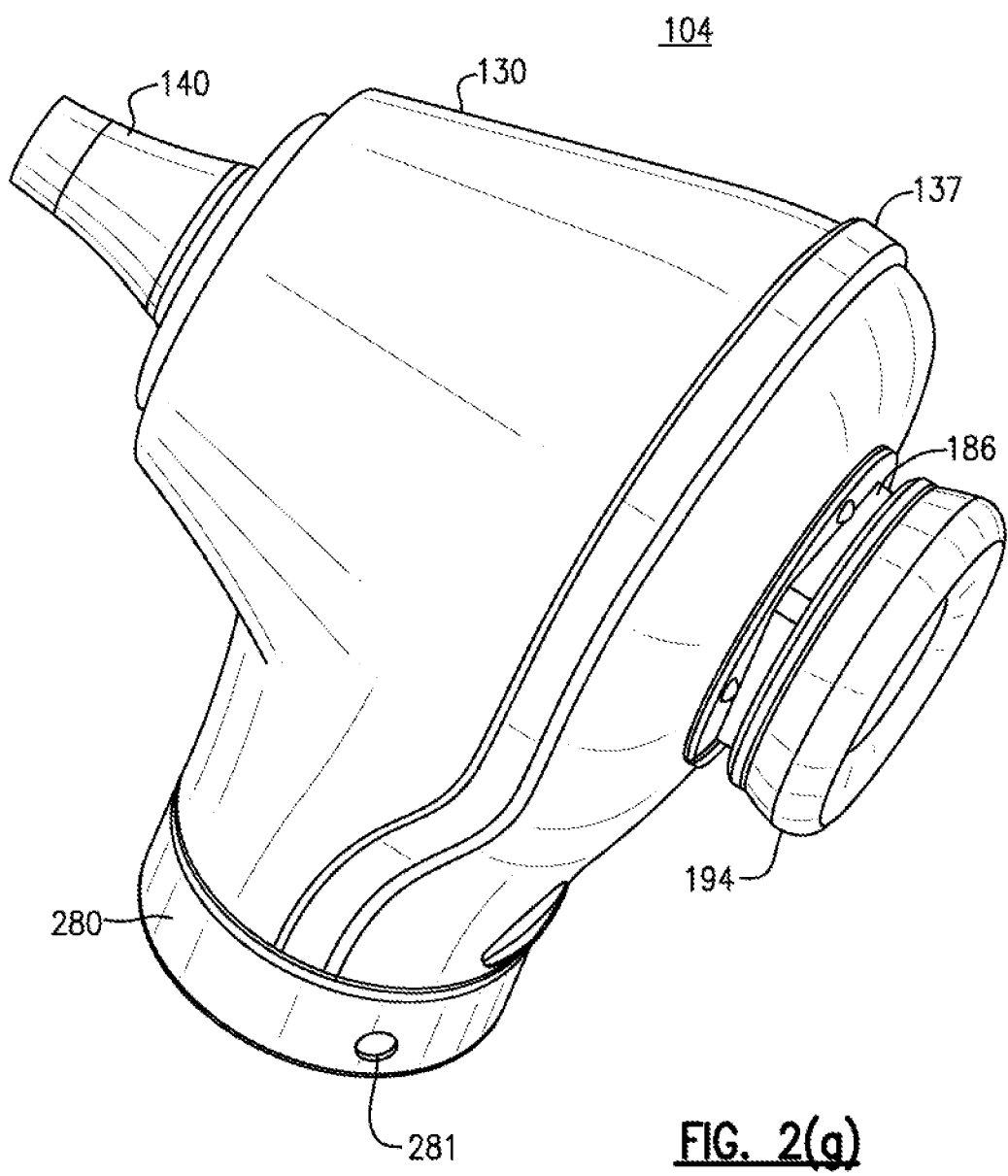
Figure 2H:
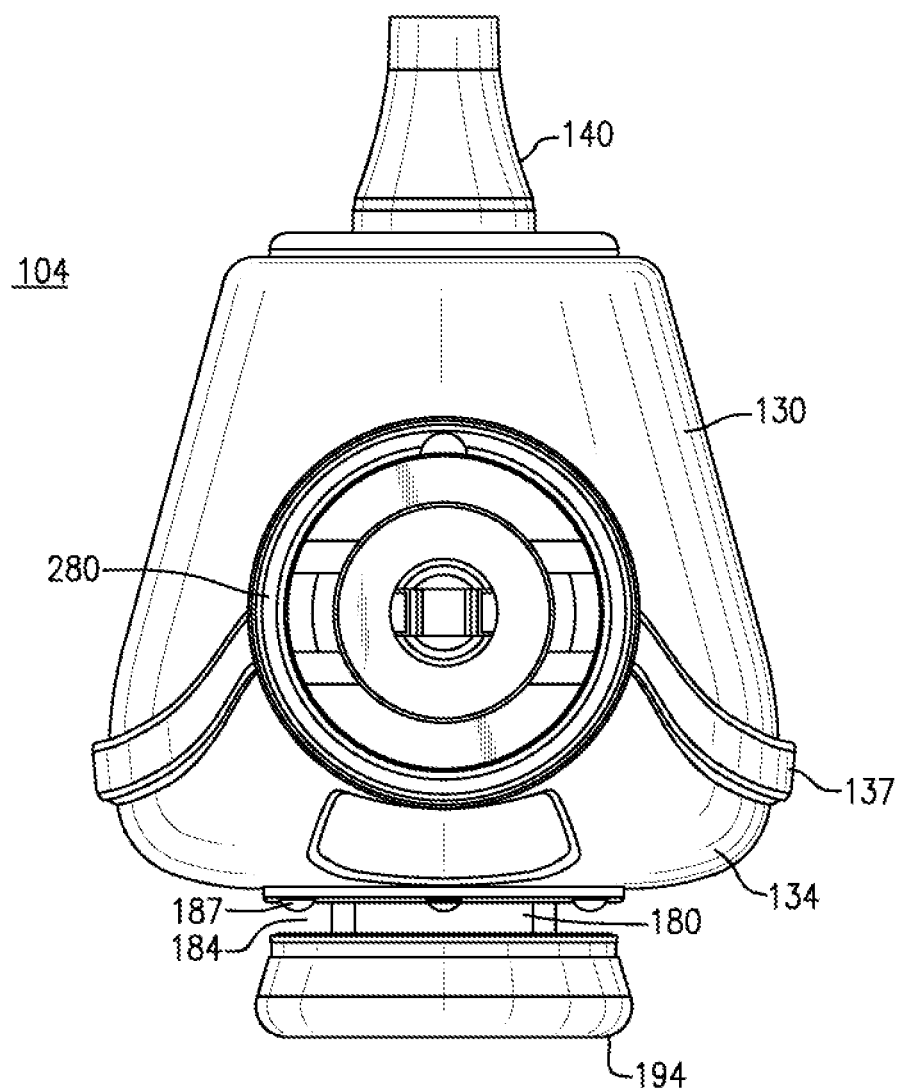
Figure 2I:
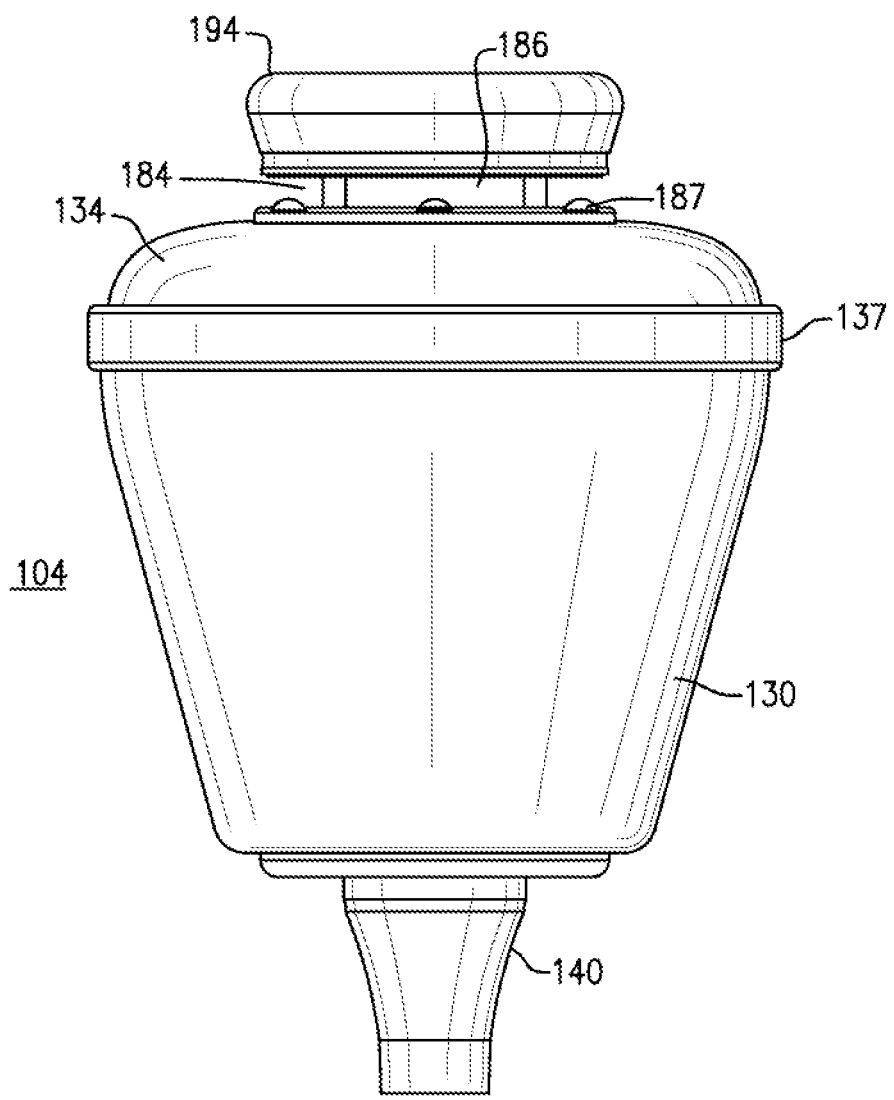
Figure 2J:
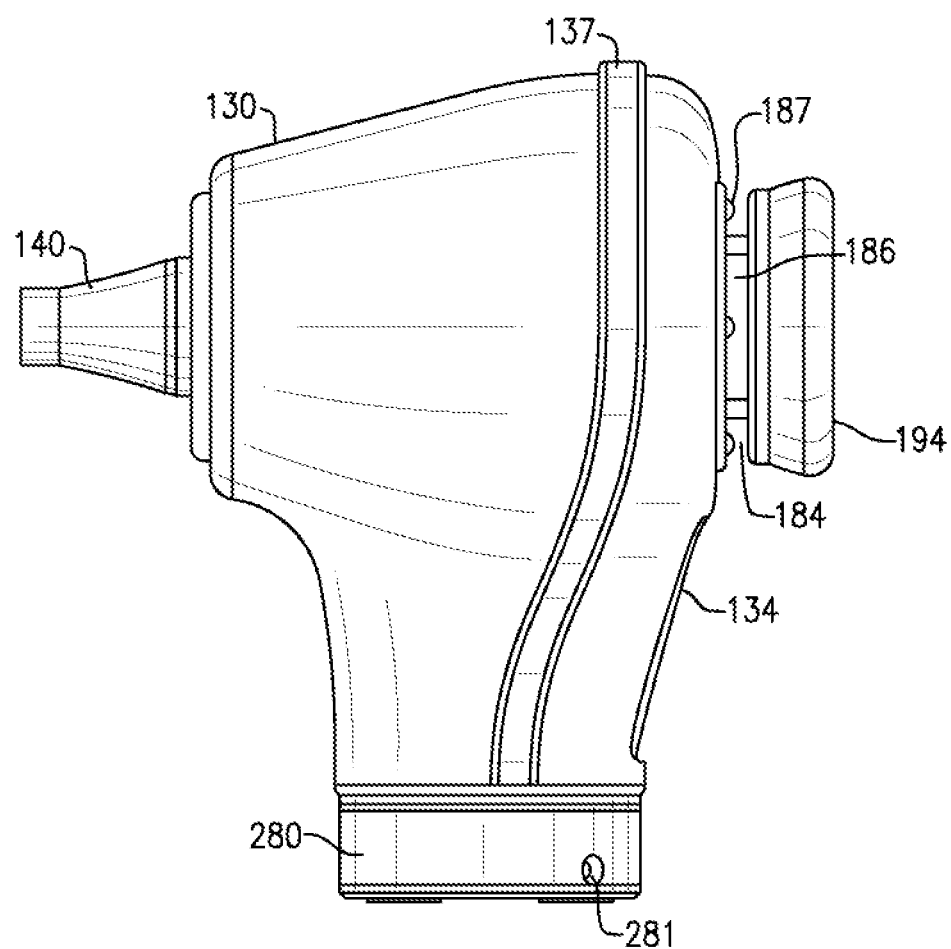
Figure 2K:
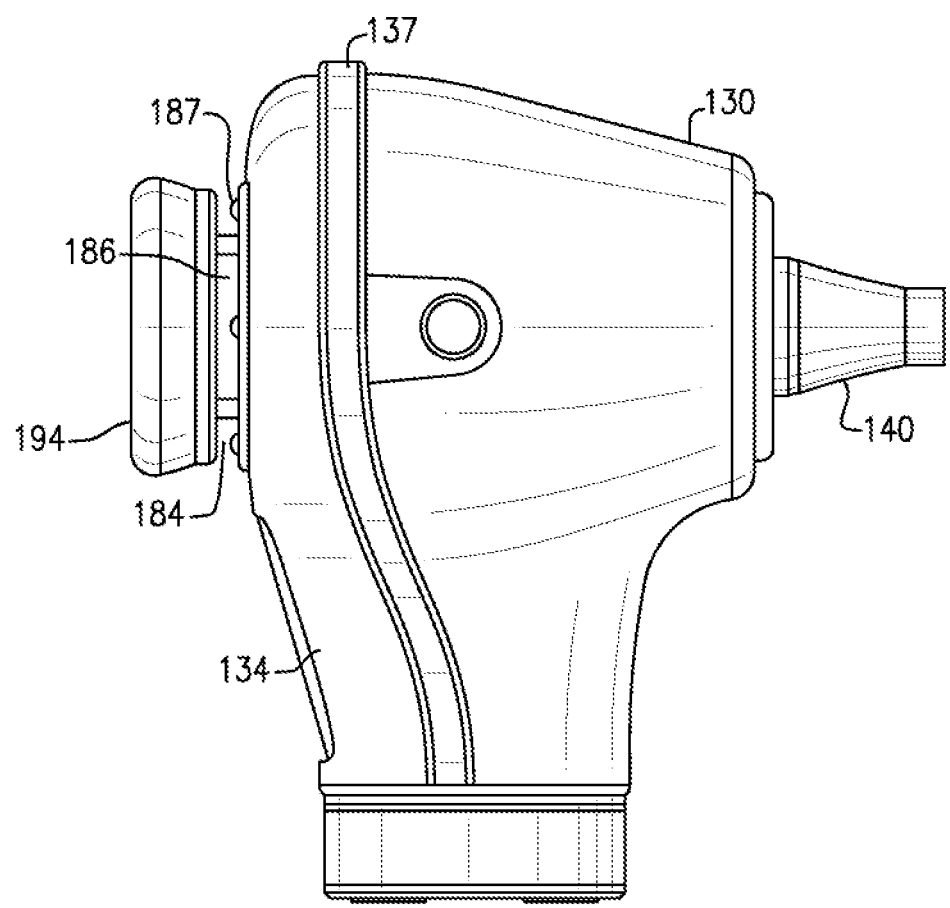
Figure 3:
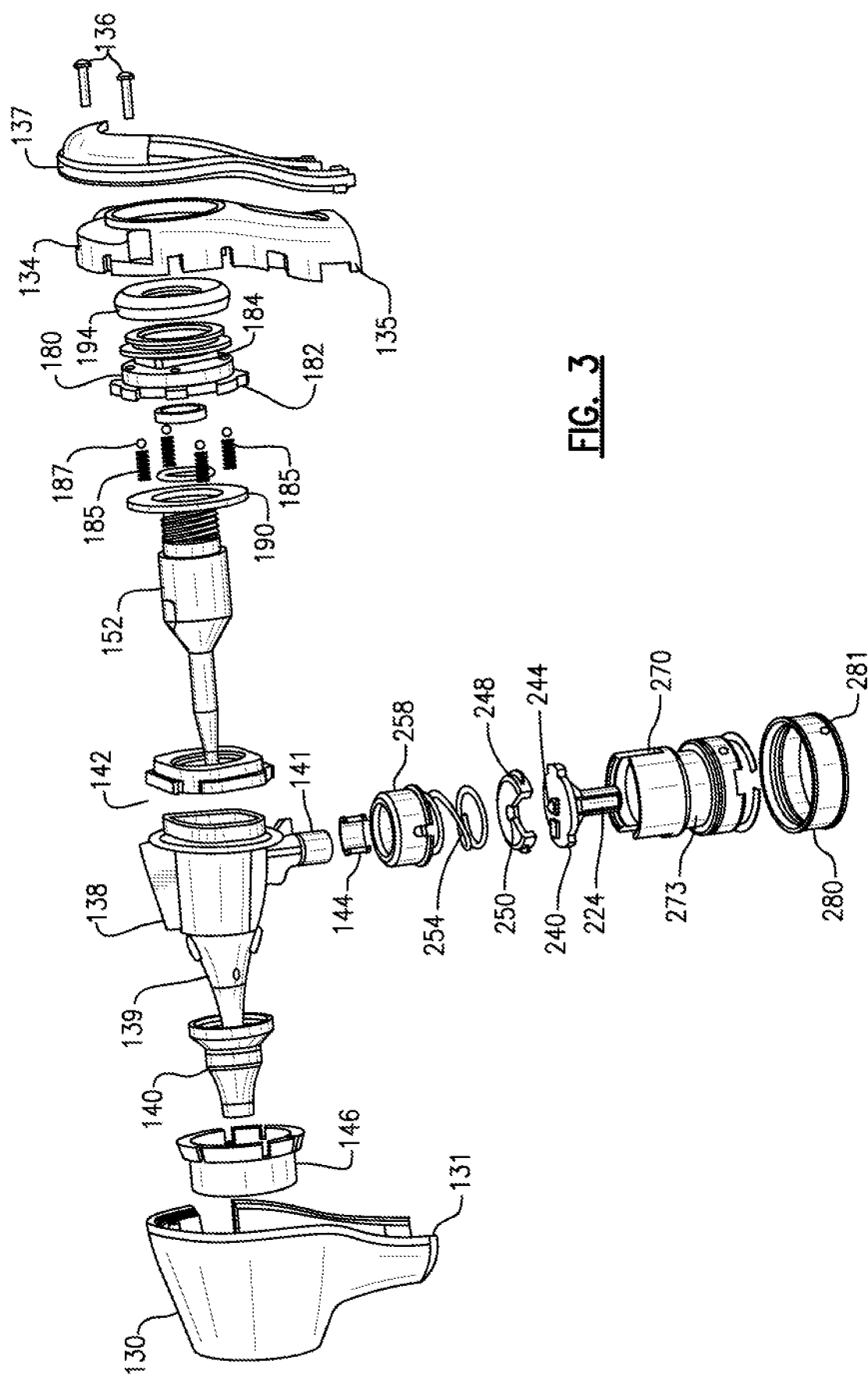
FIG. 3 is an exploded assembly view of the instrument head shown in FIG. 1(*a*)-FIG. 2(*k*)
Figure 4:
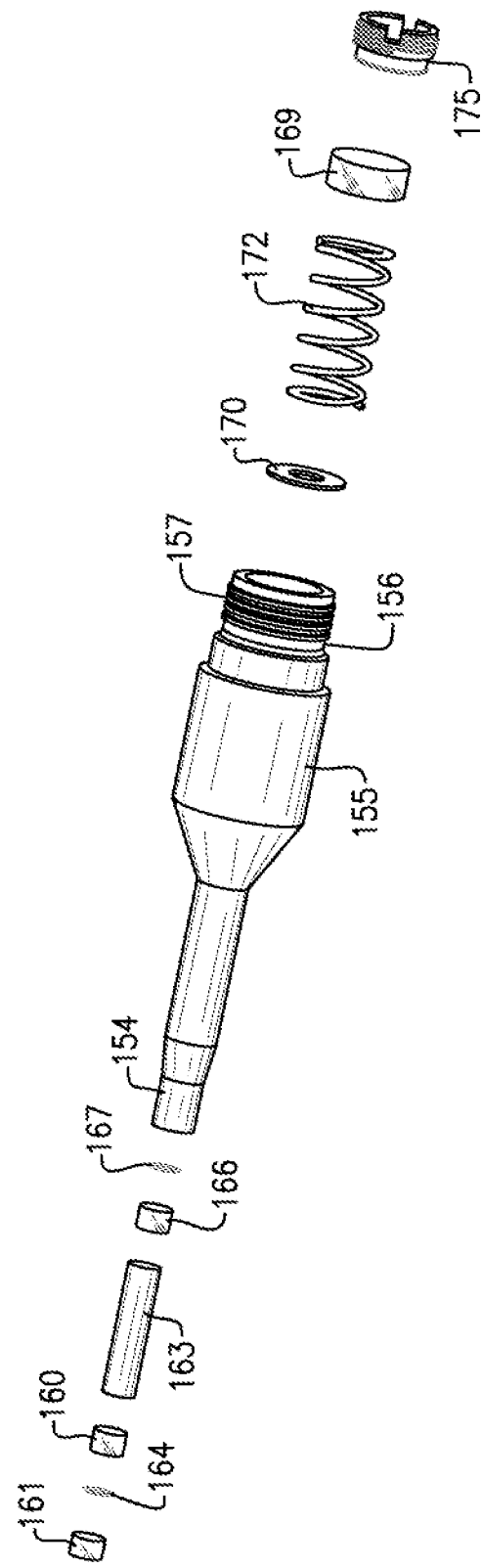
FIG. 4 is an exploded view of a lens tube fitted within the instrument head of FIG. 1(*a*)-FIG. 3.

As shown in FIGS. 2(b), 3 and 4, the proximal threaded portion 157 of the hollow lens tube 152 engages a set of corresponding internal threads formed on a distal portion of the adapter interface member 180. The adapter interface member 180 is a substantially cylindrical section according to this embodiment having its distal portion 182 extending into the proximal end 116 of the instrument head 104 and further including an outwardly extending proximal portion 188. A recess 184 defined between the distal and proximal portions 182, 188 of the adapter interface member 180 is sized and configured to receive a smart device adapter 300, partially shown in FIG. 5. The recess 184, is substantially annular with the inclusion of a series of machined flats 186, FIG. 2(a) and FIGS. 2(d)-2(k). According to this embodiment, four (4) flats 186 are provided, although the specific number can be suitably varied. Further details relating to the smart device adapter 300 are described in greater detail in a subsequent section of this application.

When assembled, the distal end 154 of the hollow lens tube 152 is positioned at the distal end 112 of the instrument head 104 with the opposing proximal end 156 of the lens tube 152 extending from an opening formed in the innerformer 138. The adapter interface member 180 is threadingly engaged with the proximal end 156 of the hollow lens tube 152 and extends outwardly from an opening formed in the rear housing section 134 of the instrument head 104.

A series of circumferentially spaced axial openings 183 are provided within the distal portion 182 of the adapter interface member 180. Each axial opening 183, which extends into the defined recess 184, receives a coiled compression spring 185 as well as a ball 187, the latter extending partially into the recess 184 to provide positive engagement with a smart device adapter 300, when the latter is attached. An intermediate plate 190 is positioned onto the exterior of the proximal end 156 of the lens tube 152 distally relative to the threaded portion of the lens tube 152 and in contact with a sealing member 142. According to this embodiment, the adapter interface member 180 is further defined by an interior that includes an optical window 189 secured within the outwardly extending proximal portion 188. A brow rest or cap 194 covers the extending proximal portion 188 of the adapter interface member 180.

The sealing member 142 is made from an elastomeric material and disposed at the proximal end of the innerformer 138 on a formed annular shoulder. When assembled, the sealing member 142 is further engaged against the intermediate plate 190 and the adapter interface member 180 to provide adequate sealing within the innerformer 138 to enable insufflation of a patient.

With further reference to FIGS. 2(*b*) and 3, the distal end 154 of the hollow lens tube 152 extends through the distal insertion portion 140 such that the optical window 161 and adjacent objective lens 160 are disposed at the distal end 154 of the distal insertion portion 140. As previously discussed, a speculum tip element 120 is releasably attached to the distal end 112 of the instrument head 104. According to this embodiment, the speculum tip element 120 is a hollow member made from a lightweight molded plastic material defined by a truncated frusto-conical shape having a distal tip opening 124 and an opposing proximal tip opening 128. The exterior surface of the speculum tip element 120 at its proximal end includes at least one engagement feature that enables the speculum tip element 120 to be releasably attached to the distal end 112 of the instrument head 104. According to this specific version, a total of three (3) engagement features are provided, each engagement feature including a ramped surface having a series of closely spaced engagement teeth.

The speculum tip element 120 is disposed in overlaying relation onto a distal insertion portion 140, the latter being defined by a substantially conical surface that is disposed in overlaying relation onto the conical distal portion 139 of the innerformer 138. According to this exemplary amendment, the innerformer 138 can include at least one exterior feature shaped and configured for engaging and retaining the distal insertion portion 140. The speculum tip element 120 is releasably secured to a distal ring member 146, the latter being disposed within the distal end of the front housing section 130 with the distal insertion portion 140 extending distally outward of the distal ring member 146.

The distal ring member 146, which is disposed relative to the front housing section 130 includes a number of engagement features that are configured to permit releasable attachment of the speculum tip element 120. More specifically, the distal ring member 146 includes a plurality of ramped surfaces formed at circumferentially spaced locations, each ramped surface being shaped and configured to engage the exterior engagement features of the speculum tip member 120. According to this embodiment, the distal ring member 146 is configured to receive one of a plurality of speculum tip elements 120, including those having instrumentation, each tip element 120 having exterior engagement features that engage with the ramped surfaces of the distal ring member 146.

The speculum tip element 120 is mounted onto the distal insertion portion 140 with the exterior engagement features of the speculum tip element 120 being engaged by the ramped surfaces provided on the distal ring member 146. The speculum tip element 120 is secured and released by means of an appropriate twisting motion. As noted and when attached, the speculum tip element 120 is designed to be fitted up to a predetermined distance into the ear canal of the patient.

The foregoing components combine to define the optical assembly for the herein described otoscope 100. As described in later portions of this application, a smart device adapter can be attached to the adapter interface member 180 to enable a smart device (e.g., a smart phone) to be attached to the instrument head 104 and enable images of the ear canal and more specifically the tympanic membrane to be captured.

Figure 5A:
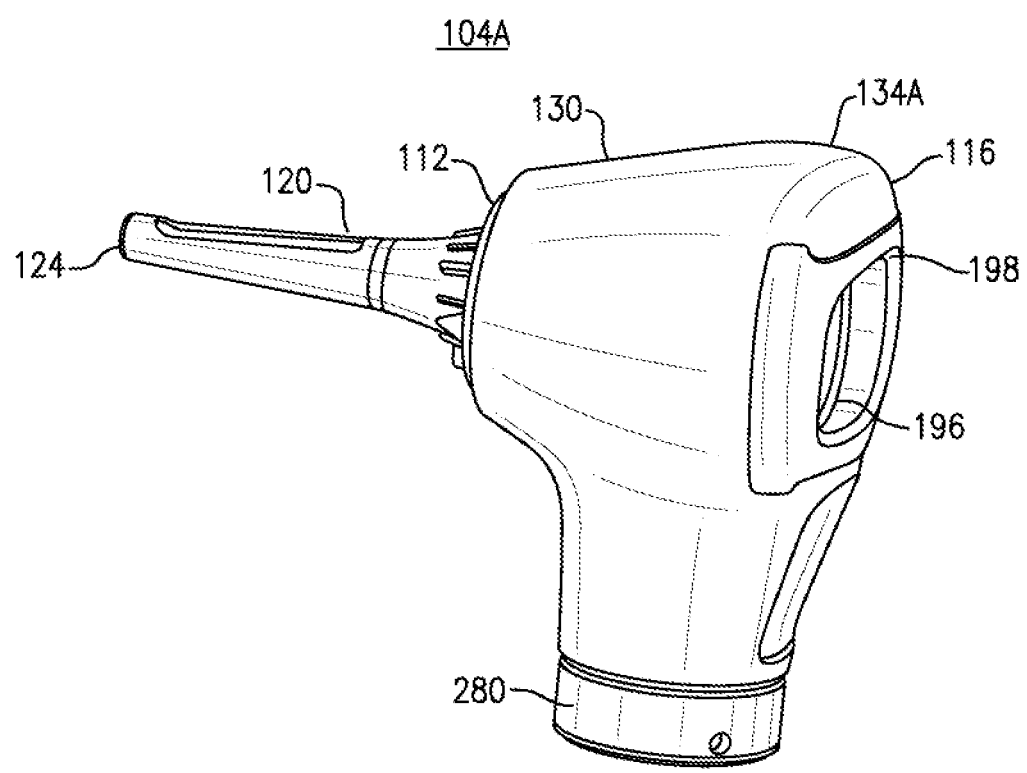
FIG. 5(*a*) is a side perspective view of an instrument head in accordance with an alternative embodiment.
Figure 5B:
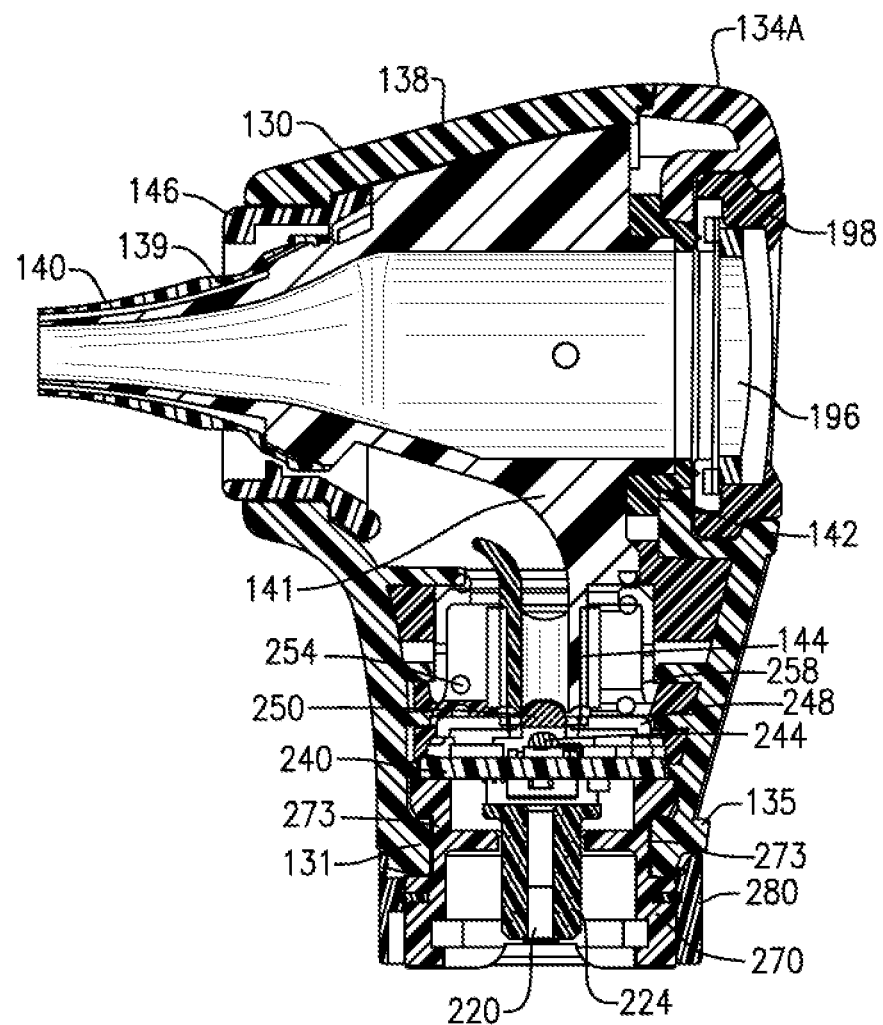

An alternative version of an otoscopic instrument head 104A is shown in FIGS. 5(*a*) and 5(*b*). Similar parts are labeled with the same reference numerals for the sake of clarity. This instrument head 104A according to this embodiment includes the front housing portion 130, a rear housing portion 134A and an innerformer 138, as well as a distal insertion member 140, distal ring member 146 and sealing member 142. However, this specific instrument version does not include a lens tube or an adapter interface member. In lieu of these components, the instrument head 104A includes an eyepiece window 196 that is provided at the proximal end 116 within a cover portion 198 disposed within the rear housing portion 134A. The eyepiece window 196 may or may not be configured to provide optical power (magnification) for enhanced viewing of the medical target.

With reference to FIGS. 2(*b*), 3 and 5(*b*), the lower portion of each of the herein described instrument heads 104, 104A retains an illumination assembly. According to this version, the light source of the illumination assembly is an LED 244, which is disposed upon the upper surface of a printed circuit board 240. The circuit board 240 is electrically coupled to a downwardly depending electrical contact 220, the latter being retained within an insulator member 224 biased by a spring 254, which is disposed within a lens retainer 248 provided above the circuit board 240, along with a condensing lens 250. The opposite end of the electrical contact 220 extends from an opening formed in the insulator member 224 and a handle stud base member 270. The securing ring 280 is secured over the lower end of the handle stud base member 270. The handle stud base member 270 includes an intermediate recessed portion 273 that is sized to retain the lower ends 131, 135 of the front and rear housing sections 130, 134, 134A of the instrument head 104, which is engaged by the securing ring 280. According to at least one version, the securing ring 280 can include a locking element, such as, for example, a pin (not shown) that is insertable through a transverse opening 281 formed in the securing ring 280.

The circuit board 240 is retained upon an upper shoulder of the handle stud base member 270 according to this embodiment. The condensing lens 250 is integrally molded as a domed section into the lens retainer 248 that is disposed above the LED 244 and circuit board 240. According to this version, the lens retainer 248 is made from a moldable plastic. One end of the biasing spring 254 acts upon a surface of the lens retainer 248, allowing the LED 244 and condensing lens 250 to be aligned and suitably positioned relative to the lower portion 141 of the innerformer 138 and more specifically a sleeve 144 that retains the polished end of a set of optical fibers (not shown). The optical fibers are advanced upwardly within the innerformer 138 and extend as a ringlet (not shown) that is provided in an annular spacing between the distal insertion portion 140 and the conical distal section 139 of the innerformer 138 in order to emit light toward the target of interest.

In operation, the contained LED 244 is engaged electrically via the contact 220, as biased by the retained spring 254. Upon energization of the LED 244 by the on/off switch 118, FIG. 1(*a*) provided on the handle portion 108, FIG.

1(a), illumination from the LED 244 is directed through the condensing lens 250 with the collimated light being directed to the polished proximal end of the optical fibers (not shown) at a lower end of the innerformer 138. As noted, the optical fibers (not shown) are directed through the innerformer 138 with the distal ends of the optical fibers being arranged in a ring-like configuration at the distal end opening of the distal insertion portion 140 and about the periphery of the hollow lens tube 152.

Smart Device Adapter

As shown in FIGS. 6-13(*b*), a smart device adapter 300 in accordance with an exemplary embodiment is described. The smart device adapter 300 is releasably attachable to the proximal end 116, FIG. 1(*a*), of a suitably configured physical assessment device, such as the previously described otoscope 100, FIG. 1(*a*). The smart device adapter 300 according to this exemplary embodiment is defined by an housing or body 304 having a pair of housing sections, namely a front housing section 308 and a rear housing section 312, which when assembled combine to create an interior that is suitably sized and shaped to retain a plurality of components. Each of the components of the smart device adapter 300 according to this embodiment are manufactured from a moldable plastic, although other suitable materials can be used.

The front housing section 308 of the smart device adapter 300 is defined by a lower portion 320, which includes a semicircular slot 322 provided at one end. The semicircular slot 322 extends entirely through the thickness of the front housing section 308 with the exception of a device engagement section 328, which is most clearly depicted in FIG. 8(*a*), as well as FIGS. 11(*e*), 11(*i*) and 11(*j*).

The device engagement portion 328 is defined by a pair of device engagement surfaces 330, 332, each of which extend inwardly relative to the formed slot 322 and adjacent a front facing surface 309 of the front housing section 308. These engagement surfaces 330, 332 are orthogonal to one another and have a defined thickness.

Figure 8A:
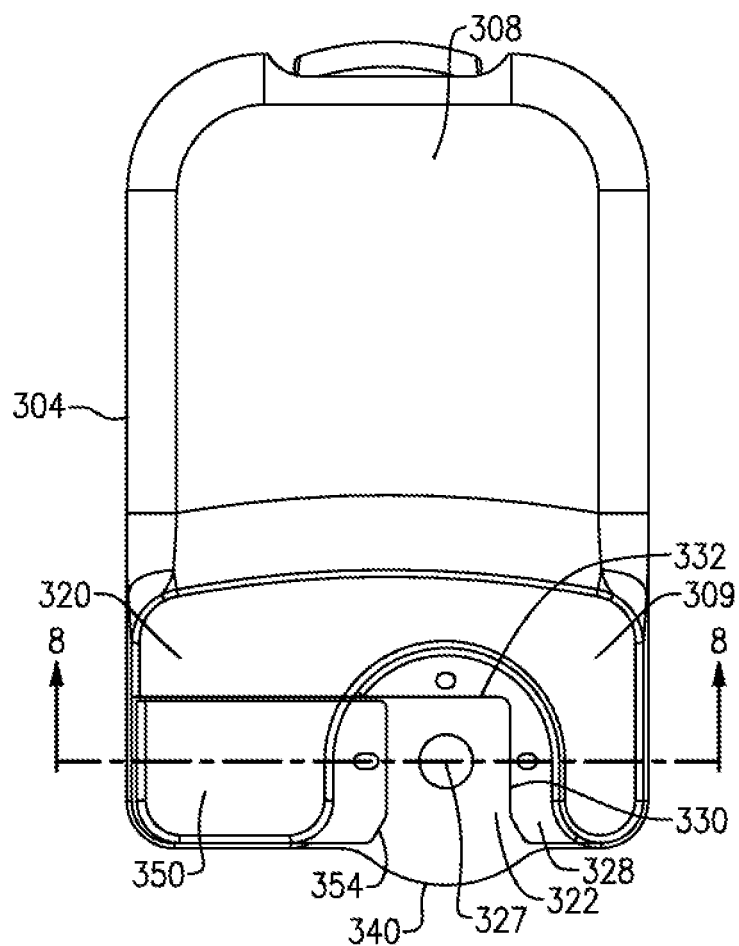
FIG. 8(*a*) is a front facing view of the smart device adapter of FIGS. 6 and 7.
Figure 8B:
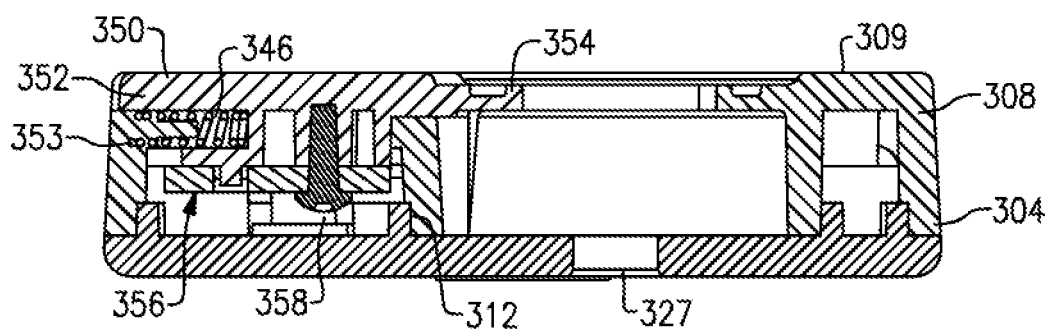

The front facing surface 309 of the front housing section 308 further includes a recess 335, FIG. 6, adjacent the defined semicircular slot 322 on one side of the slot 322 opposite one of the engagement surfaces 330. The recess 335 is sized and configured to receive a slider member 350, which is secured by a slider retainer 356. According to this embodiment, the slider member 350 is defined by an upper plate 352 having an edge surface 354, as well as a lower portion 353. The slider retainer 356 is attached to the lower portion 353 of the slider member 350 using at least one fastener 358, as well as engagement between a downwardly extending tab of the lower portion 353 of the slider member 350 and a corresponding slot formed in an upper surface of the slider retainer 356. When positioned within the recess 335, the edge surface 354 of the slider member 350 is positioned at the same plane as the two device engagement surfaces 330, 332, thereby forming a third device engagement surface. As shown in FIG. 8(*b*), a compression spring 346 is provided within a lateral cavity formed in the lower portion 353 of the slider member 350 that engages a spring pin provided on the front housing portion 308, laterally biasing the slider member 350 and more specifically the edge surface 354 inwardly relative to the formed slot 322. To facilitate movement, the underside of the upper plate 352 of the slider member 350 includes a set of rails 359 that are configured to slide within corresponding tracks 355 formed in the front housing portion 308.

Figure 7:
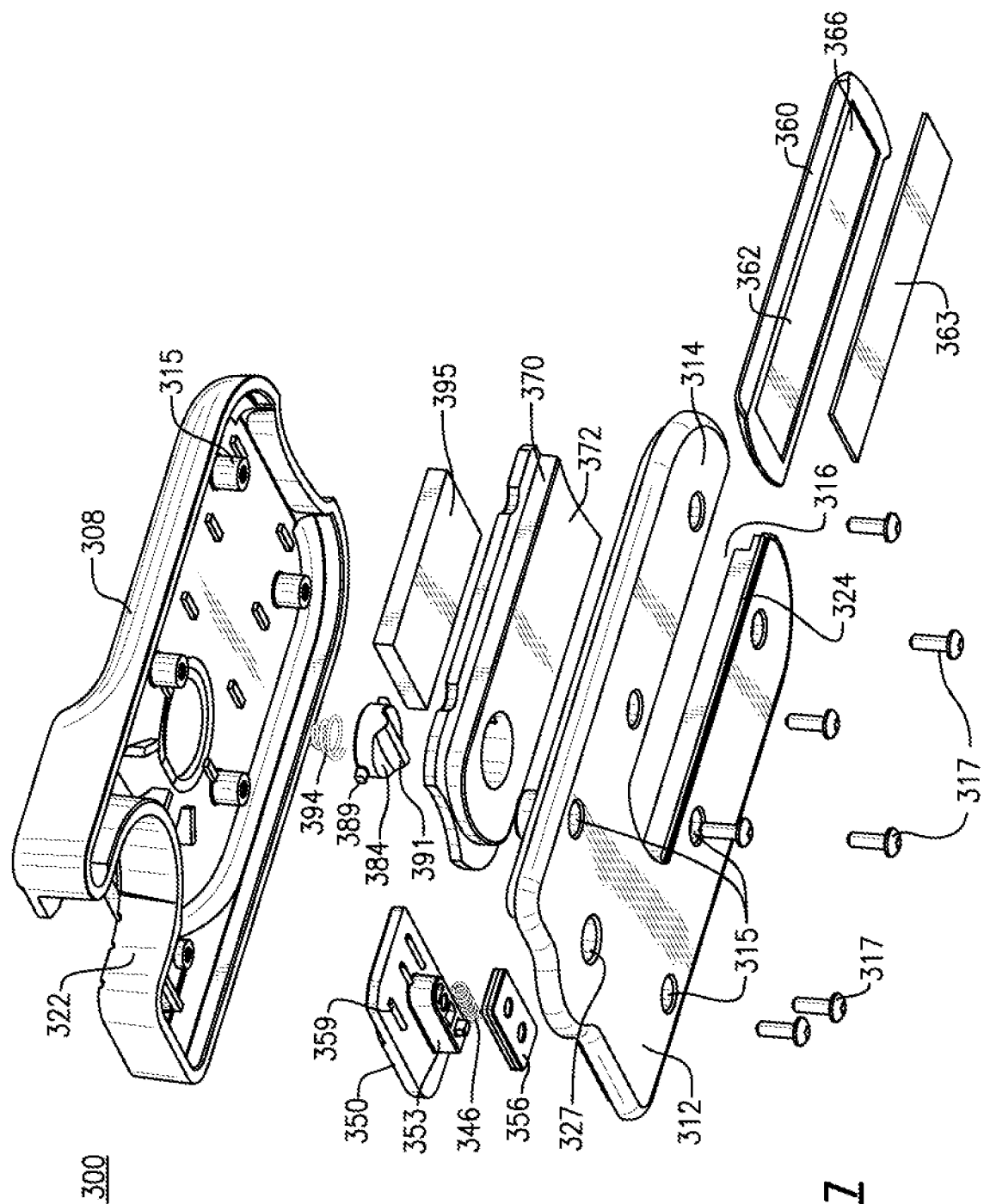

With reference to FIGS. 6, 7, 11(*b*) and 11(*f*), the rear housing section 312 of the smart device adapter 300 includes respective interior and exterior surfaces 313, 314. A slot 316 is formed at a lower end of the rear housing section 312. The slot 316 is further defined by an interior ridge 324. A peripheral border 326 formed on the interior surface 313 extends around the formed slot 316, as well as the entire perimeter of the rear housing section 312. As discussed herein, the portion of the peripheral border 326 about the slot 316 and the interior ridge 324 are sized and configured to support a detent cover 370, as well as a device engagement member 360. The peripheral border 326 includes a semicircular section at the lower end of the rear housing section 312 that corresponds to the semicircular slot 322 formed in the front housing section 308 of the herein described adapter 300. A through opening 327 is also formed at the lower end of the rear housing section 308 as part of a protruding portion 340.

According to this embodiment, the detent cover 370 is an elongate member having a front facing surface 371 and opposing rear facing surface 372 that is sized and configured to be fitted within the formed slot 316 of the rear housing portion 312. A molded projecting portion 373 is provided on the front facing surface 371 of the detent cover 370 that is sized to accommodate a detent member 384, as well as a detent spring 394. The molded projecting portion 373 is circular in configuration according to this exemplary embodiment and includes a pair of diametrically spaced slots 375 that are sized to engage ears 389 formed on the detent member 384 to insure a predetermined placement within the projecting portion 373. It will be readily apparent that the molded projecting portion 373 can assume other suitable configurations. The projecting portion 373 is further defined by a through opening extending entirely through the thickness of the detent cover 370, the opening enabling access to a projecting detent 391.

Adjacent the molded projecting portion 373 on the front facing surface 371 of the detent cover 370 is a formed recess 376 that is sized and configured to receive a strip of insulating material 395. According to this embodiment, the strip of insulating material 395 is made from an open-celled foam material such as poron, although other similar materials can be utilized.

The device engagement member 360 is attachable to the rear housing section 312 of the smart device adapter 300 and more specifically is attachable to the formed slot 316. According to this embodiment, the device engagement member 360 is elongate and defined by opposing planar front and rear facing sides 361, 362, respectively. The rear facing side or surface 362 of the device engagement member 360 receives an adhesive strip 363, which can be fitted thereto. According to one version and with reference to FIGS. 6, 7 and 12(*a*)-12(*h*), the rear facing surface 362 of the device engagement member 360 is defined by a recess 366 sized to accommodate the adhesive strip 363 and position it in a predetermined location and orientation. According to another version, the adhesive strip can be removed and relocated anywhere on the rear facing side 362. The front facing side 361 of the device engagement member 360 includes a groove 367 which is formed transversely relative to the major dimension of the member 360 and adjacent one end.

An exemplary assembly flow is provided in FIGS. 10(*a*)-10(*e*). First and with reference to FIG. 10(*a*), the slider member 350 is attached to the front housing section 308 and fitted within the formed recess 335 with the lower portion 353 of the slider member 350 extending through an access slot provided in the front facing surface 309. The compression spring 346 is engaged within the lateral slot formed in the lower portion 353 of the slider member 350 wherein one end of the compression spring 346 is engaged with a spring pin (shown in FIG. 10(a)). As shown in FIG. 10(b), the slider retainer 384 is then attached to the slider member 350 through the access slot by engaging the tab of the lower portion 353 with the corresponding slot formed in the upper surface of the slider retainer 356 and inserting the fastener 358 to secure the slider retainer 356 and the slider member 350 within the recess 335 of the front housing portion 308.

As shown in FIG. 10(c), the strip of insulating material 395 is added to the recess 376 formed in the rear housing section 312 and the detent member 384 and detent spring 394 is placed within the projecting enclosure 373 of the detent cover 370, aligning the ears 389 of the detent member 384 with the corresponding spaced slots 375 formed on the projecting enclosure 373. Once the foregoing components are in place, the detent cover 370 is placed onto the interior side of the rear housing section 312 and more specifically, the slot 316 with a bordering edge of the detent cover 370 being placed on the peripheral border 326.

Figure 10D:
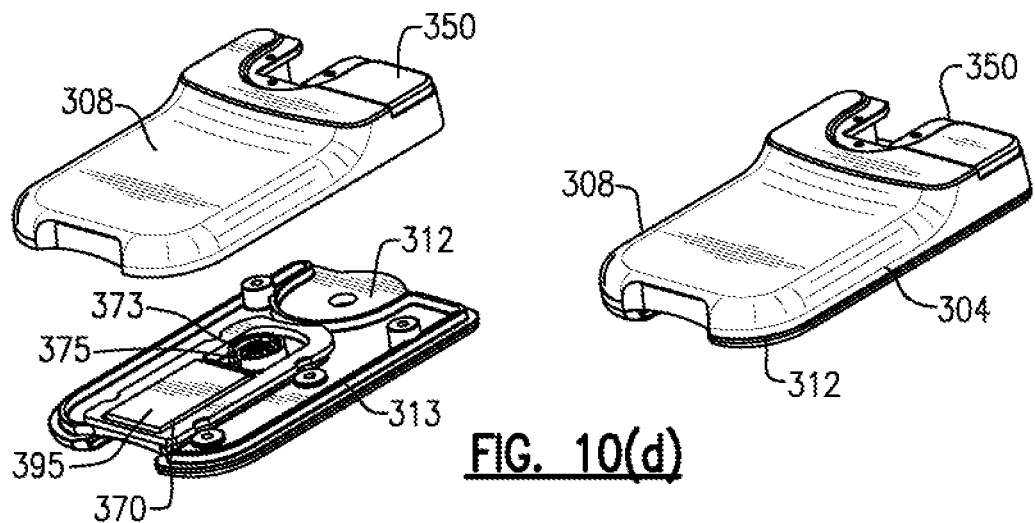
FIGS. 10(*a*)-10(*e*) are views depicting a sequential assembly flow of the smart device adapter of FIGS. 6-9(*b*)

As shown in FIG. 10(d), the front housing section 308 having the assembled slider member 350 and slider retainer 356 is then aligned with and attached to the rear housing section 312 having the assembled detent cover 370, detent member 384 and detent spring 394, as well as the strip of insulating material 395.

Figure 10E:
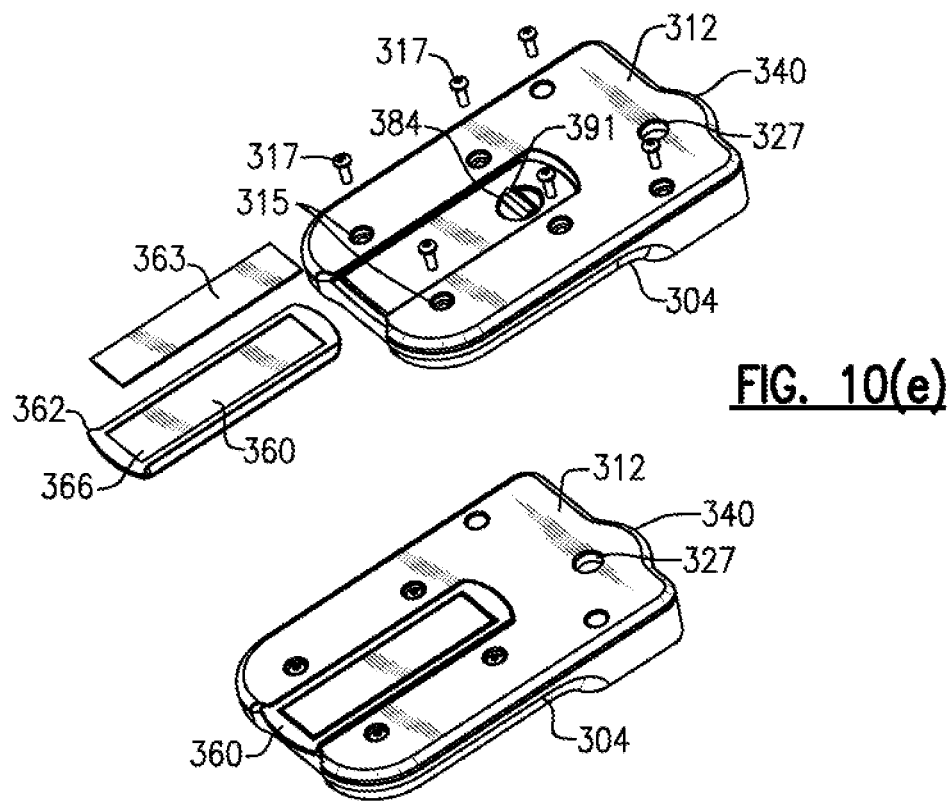

Finally and as shown in FIG. 10(e), the rear housing section 312 and the front housing section 308 are secured using a series of threaded fasteners 317 through a series of mounting holes 315 provided in each of the rear housing portion 312 and front housing portion 308 of the smart device adapter 300. When assembled, the detent cover 370 is sandwiched within the interior of the smart device adapter 300 along with the detent member 384, the detent spring 394 and the strip of insulating material 395, and with the slider member 350 also attached as shown.

The device engagement member 360 can then be slidingly attached to the slot 316. With reference to FIGS. 9(a), 9(b), 11(a), 11(b) and 11(k), the detent member 384 is retained in the interior of the adapter 300 within the detent cover 370. The detent member 384 according to this embodiment includes a projecting detent 391 that is sized and shaped to engage the transverse groove 367 formed on the front surface 361 of the device engagement member 360 when the device engagement member 360 is attached by sliding the device engagement member 360 within the open end of the formed slot 316.

Figure 11A:
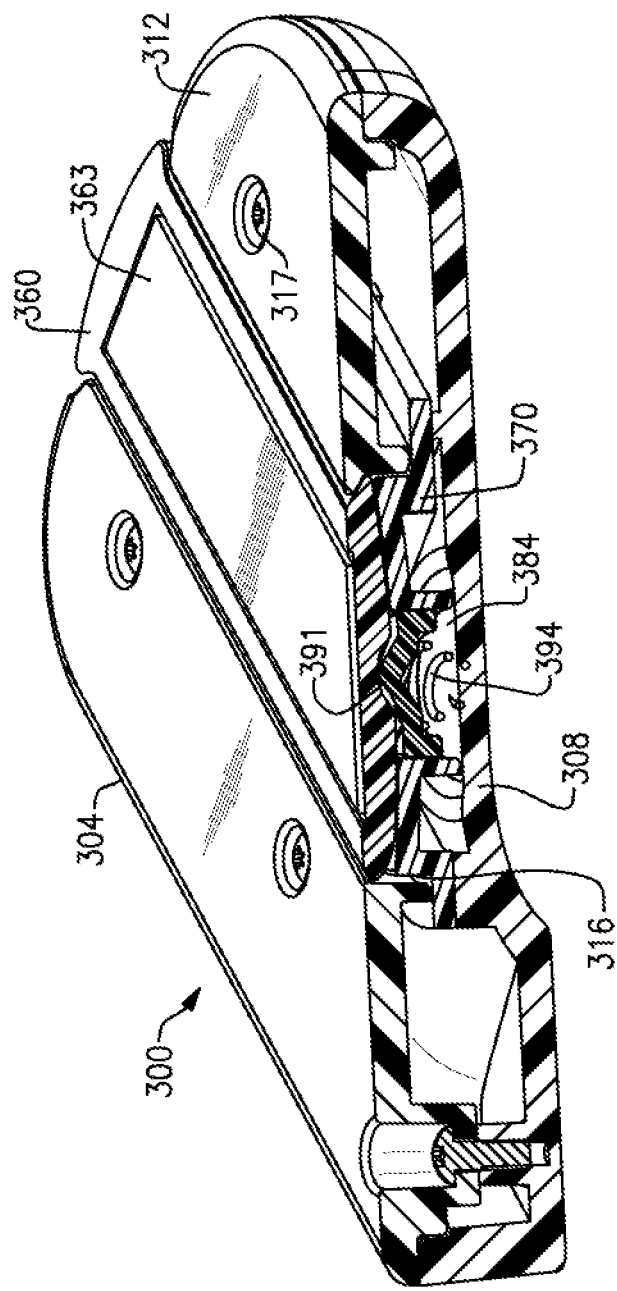
FIG. 11(a) is a partially broken away view of a smart device adapter having an attached device engagement member.
Figure 11B:
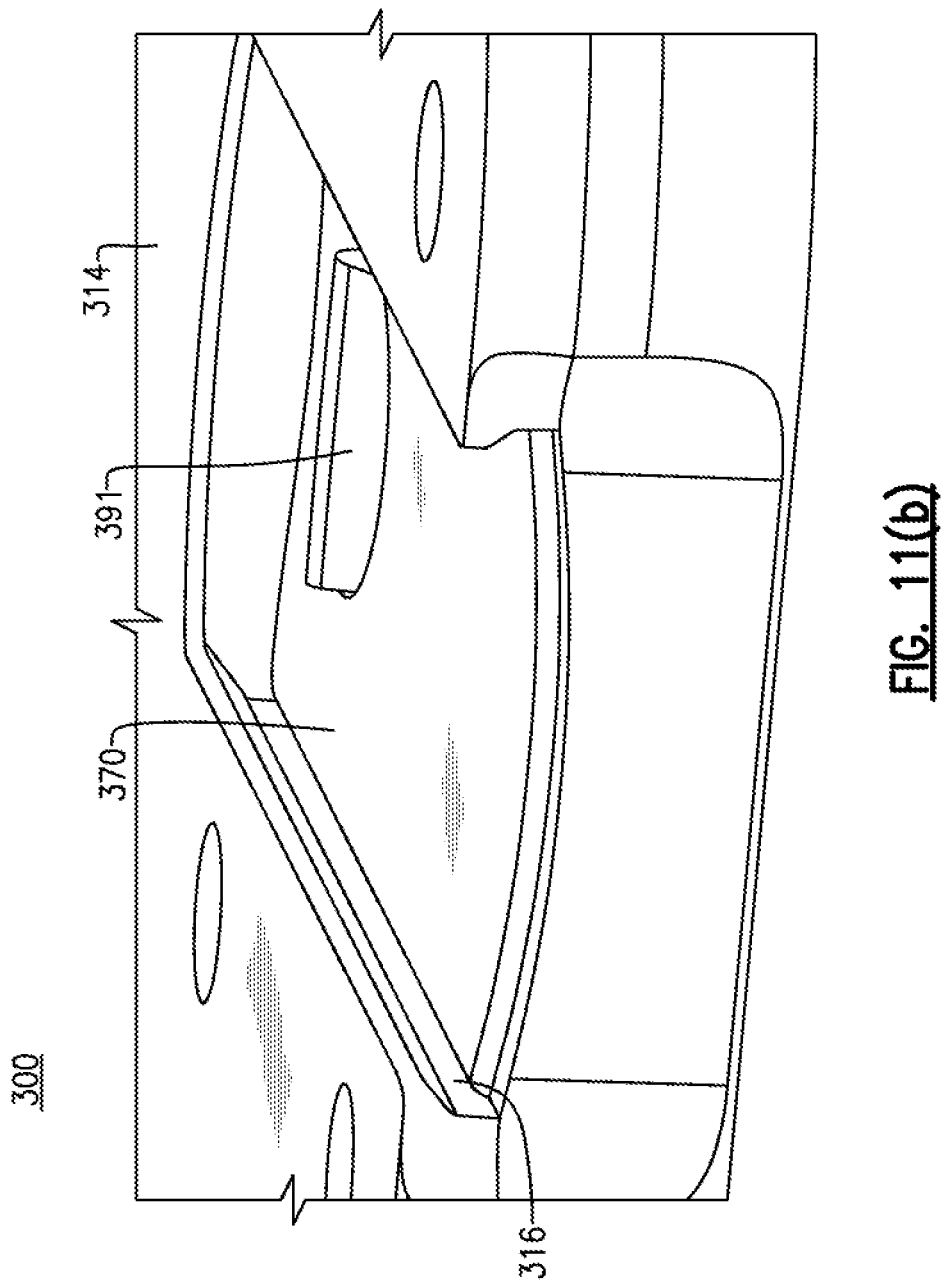
FIG. 11(b) is a partial rear perspective view of the smart device adapter of FIGS. 6-11(a)
Figure 11C:
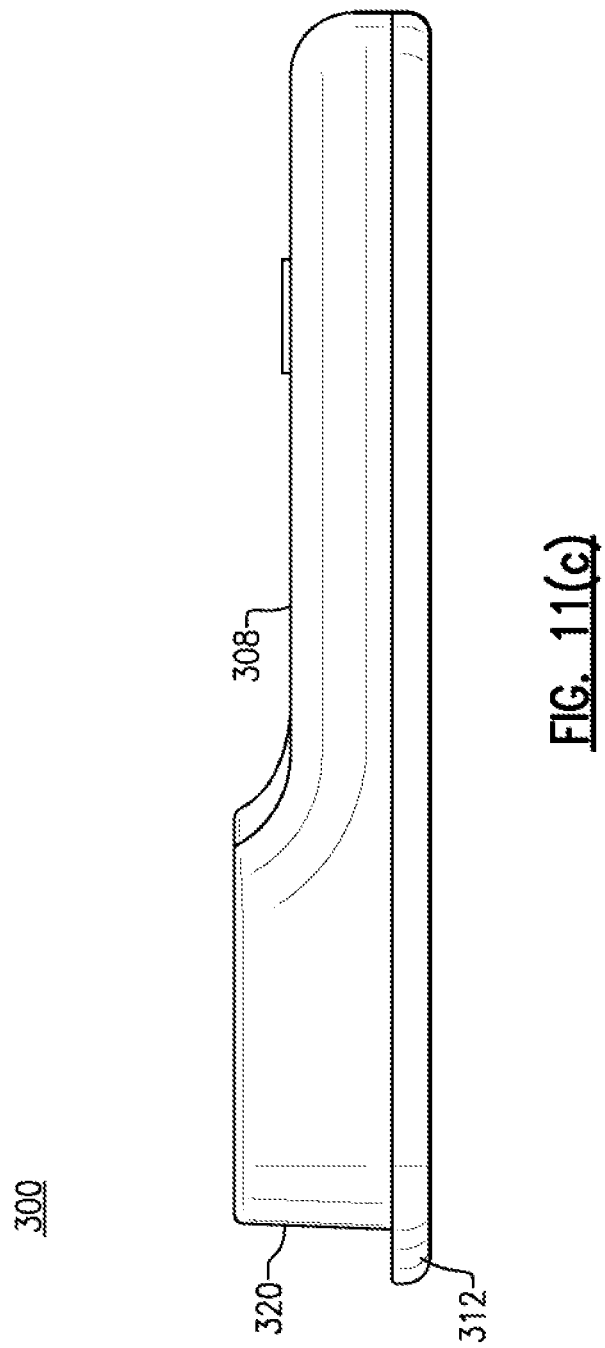
FIG. 11(c) is a left side elevation view of the smart device adapter of FIGS. 6-11(b)
Figure 11D:
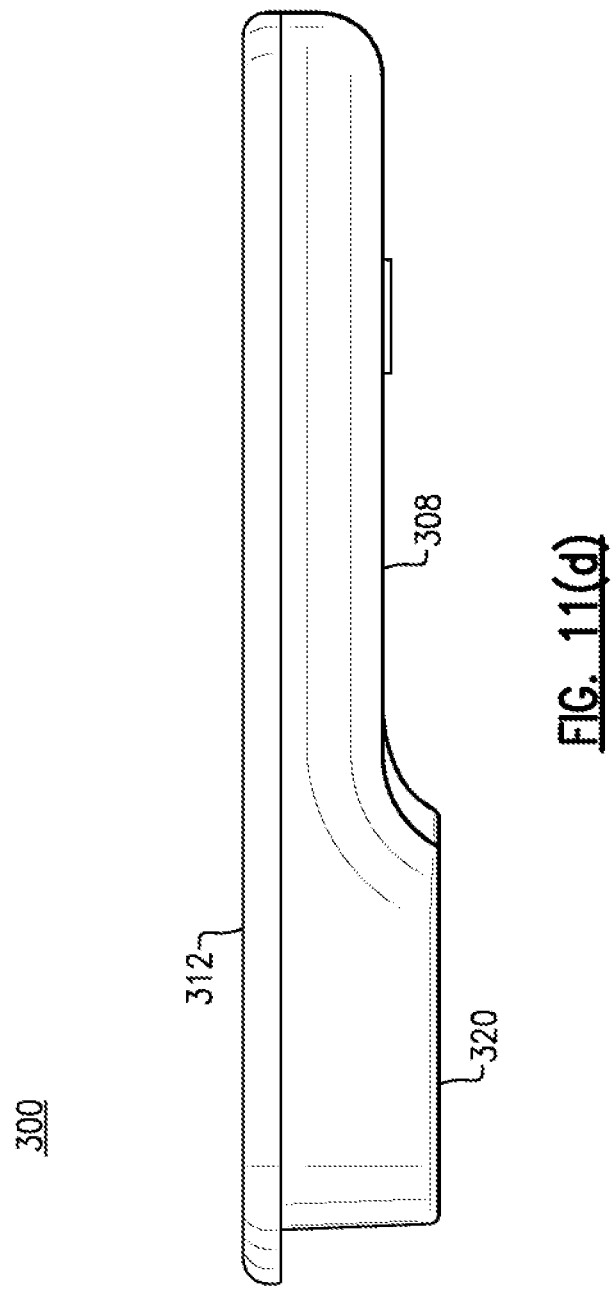
FIG. 11(d) is a right side elevation view of the smart device adapter of FIGS. 6-11(c)
Figure 11E:
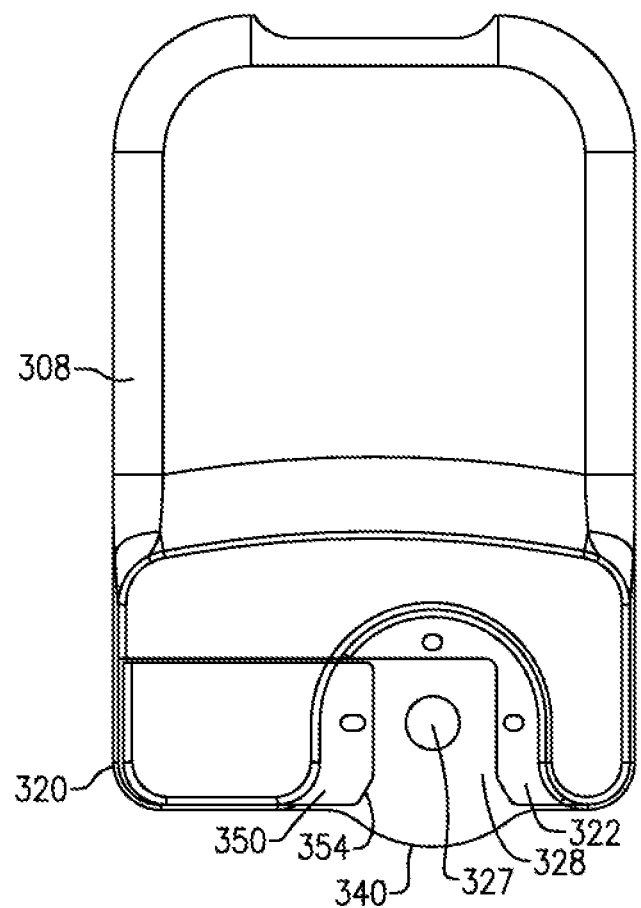
FIG. 11(e) is a front view of the smart device adapter of FIGS. 6-11(d)
Figure 11F:
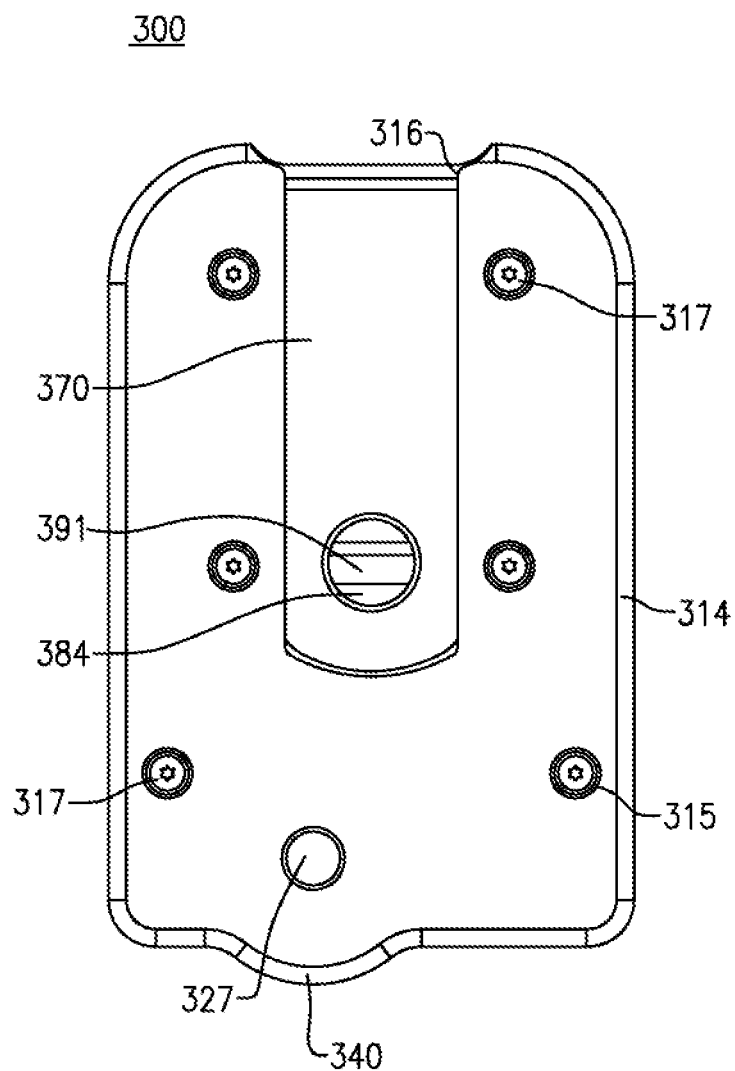
FIG. 11(f) is a rear view of the smart device adapter of FIGS. 6-11(e)
Figure 11G:
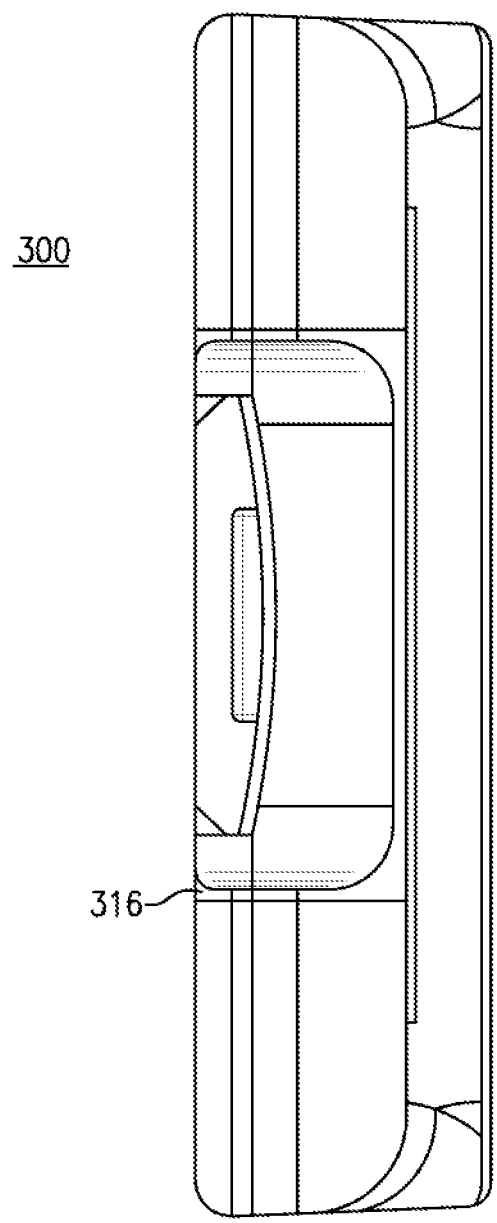
FIG. 11(g) is a top plan view of the smart device adapter of FIGS. 6-11(f)
Figure 11H:
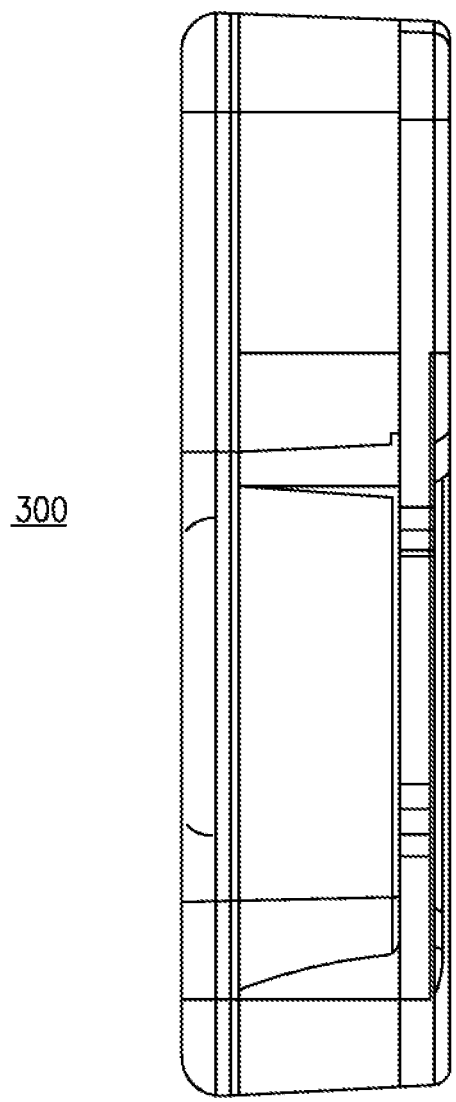
FIG. 11(h) is a bottom plan view of the smart device adapter of FIGS. 6-11(g)
Figure 11I:
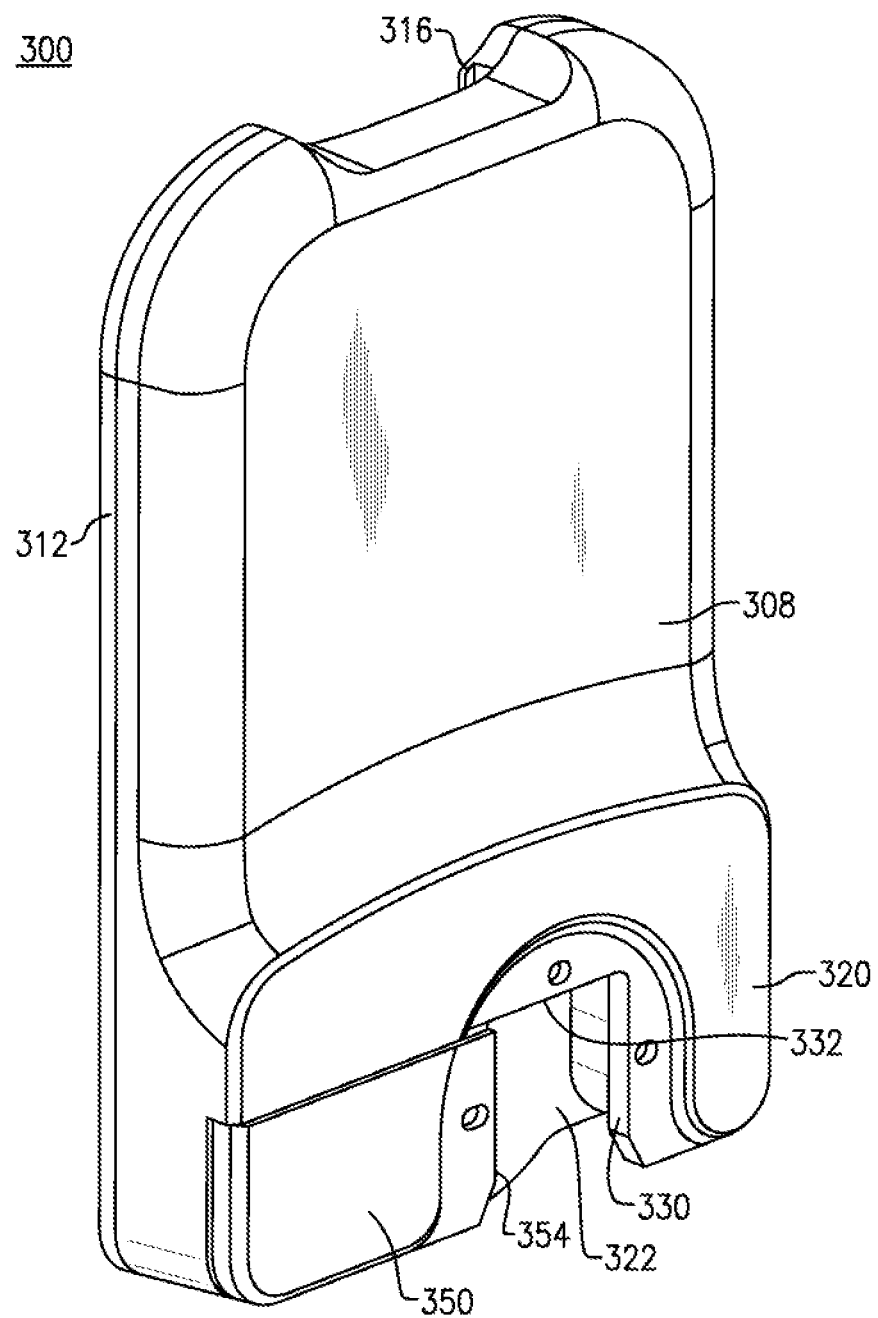
FIG. 11(i) is a front perspective view of the smart device adapter of FIGS. 6-11(h)
Figure 11J:
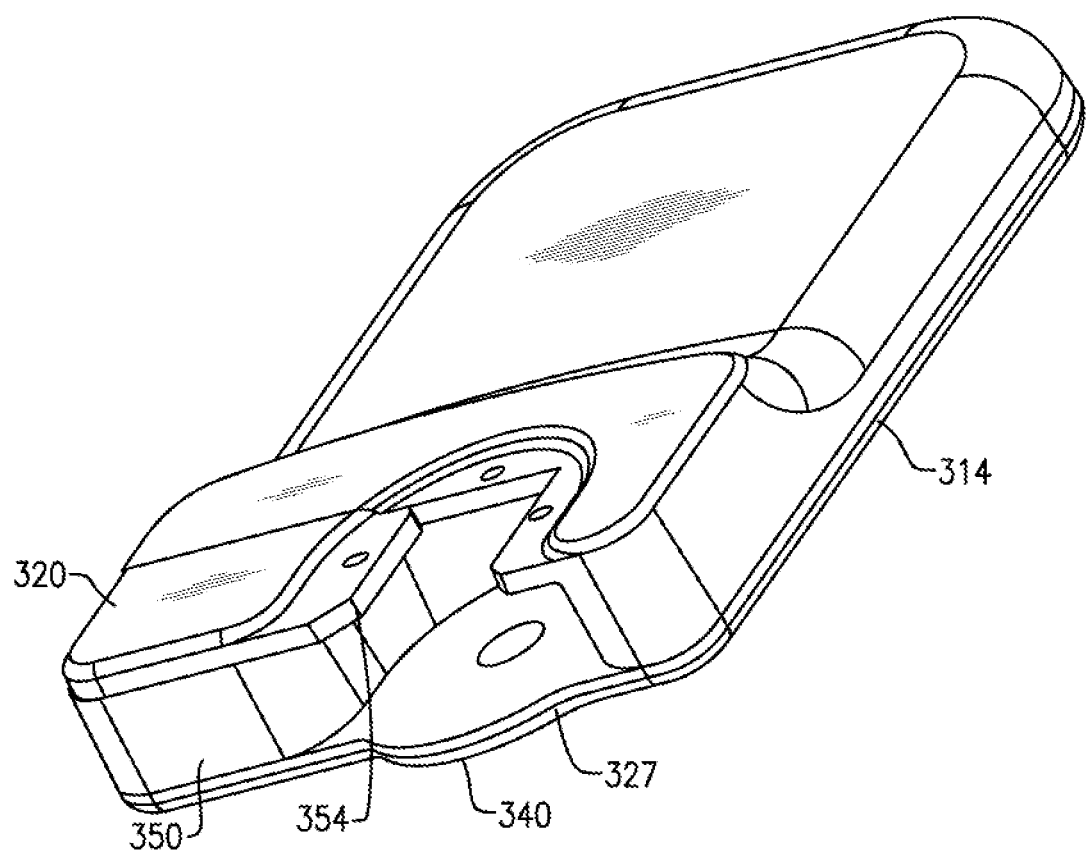
FIG. 11(j) is a bottom perspective view of the smart device adapter of FIGS. 6-11(i)
Figure 11K:
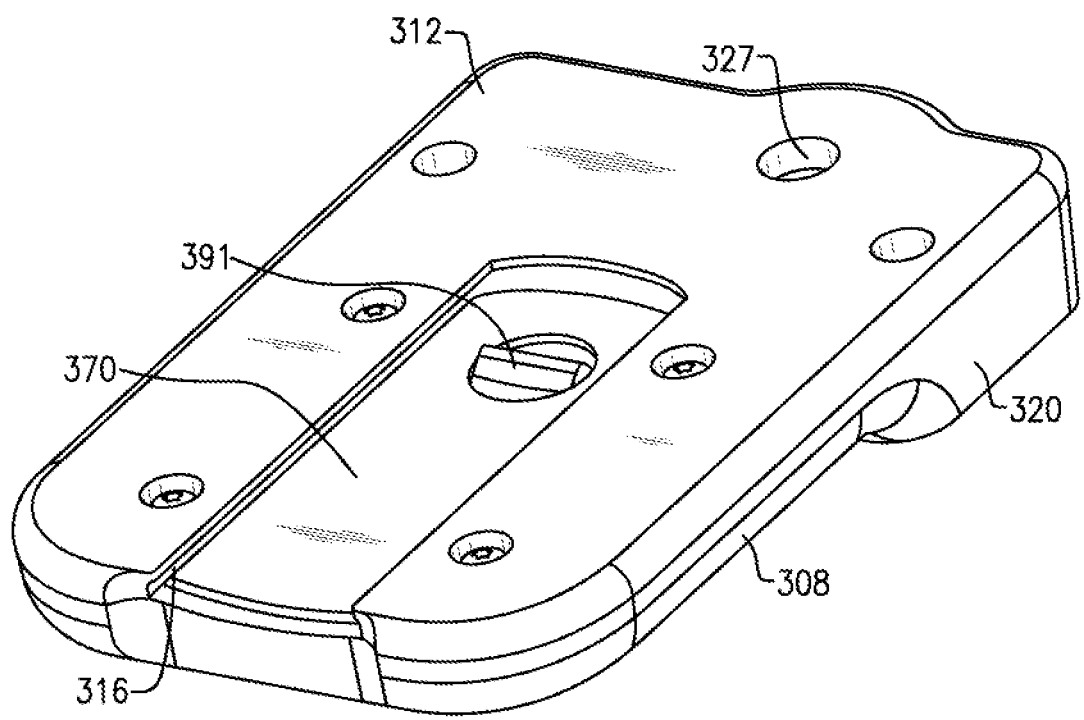
FIG. 11(k) is a rear perspective view of the smart device adapter of FIGS. 6-11(j)
Figure 11I:
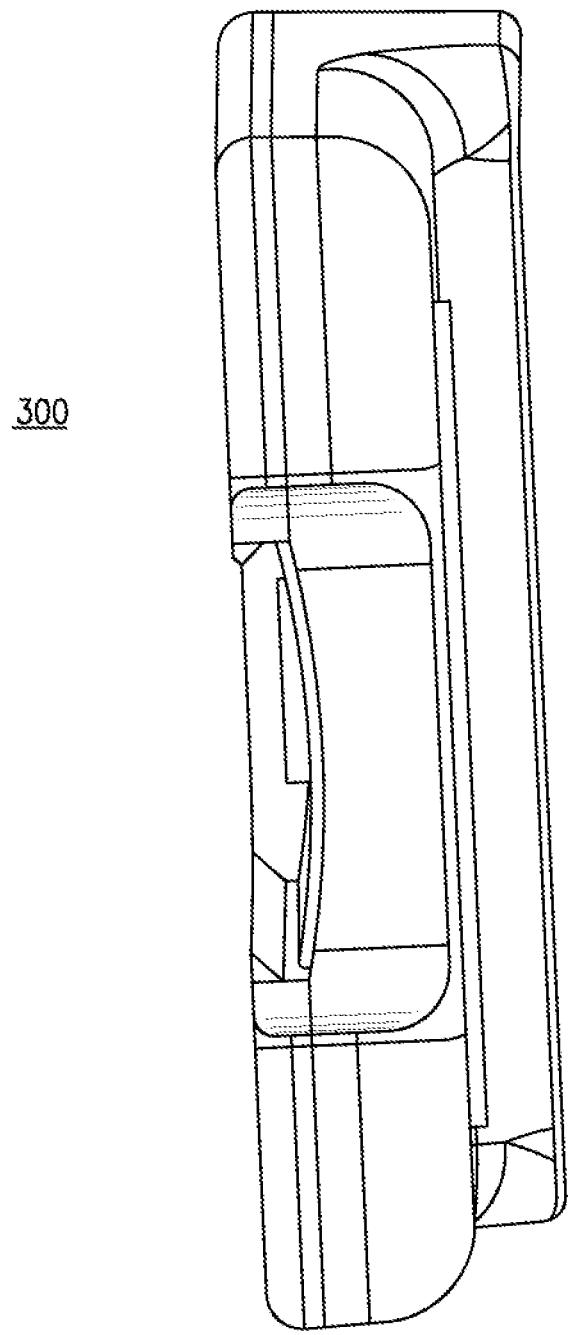
Figure 12A:
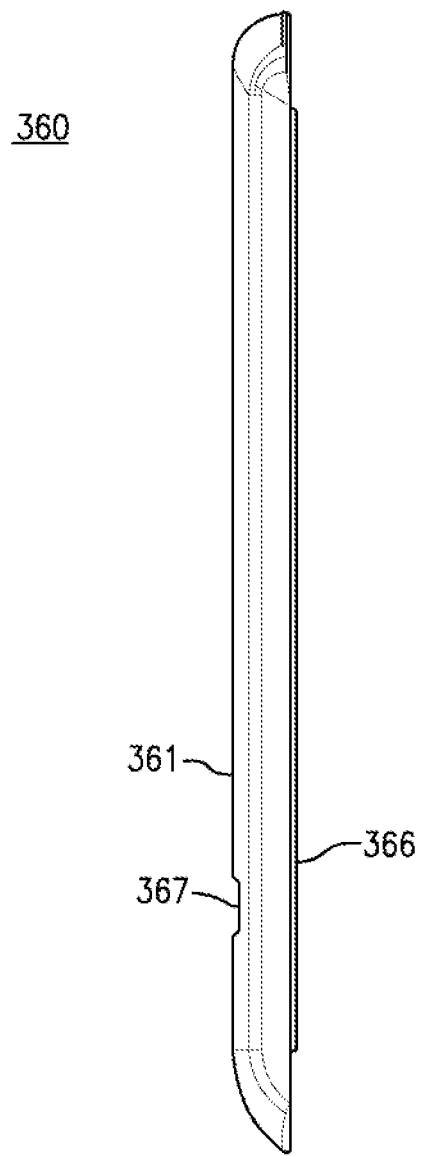
FIG. 12(a) is a left side view of a device engagement member in accordance with an embodiment.
Figure 12B:
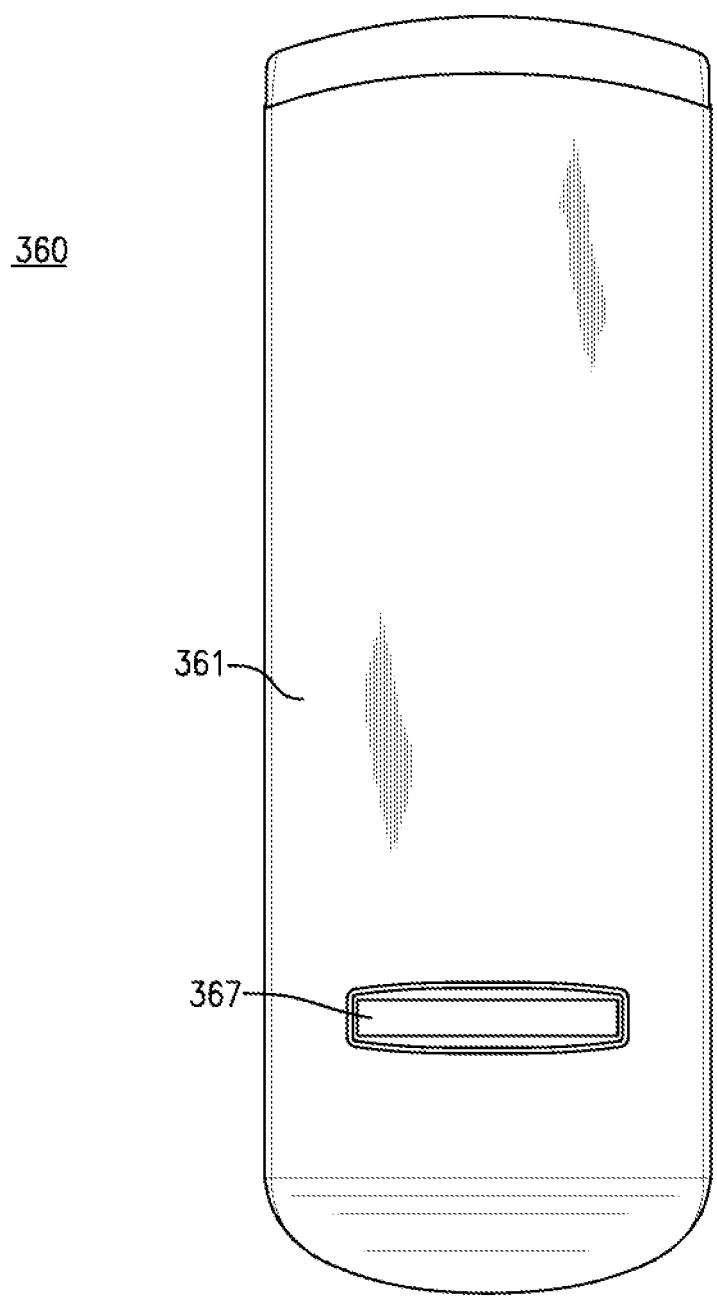
FIG. 12(b) is a front view of the device engagement member of FIG. 12(a)
Figure 12C:
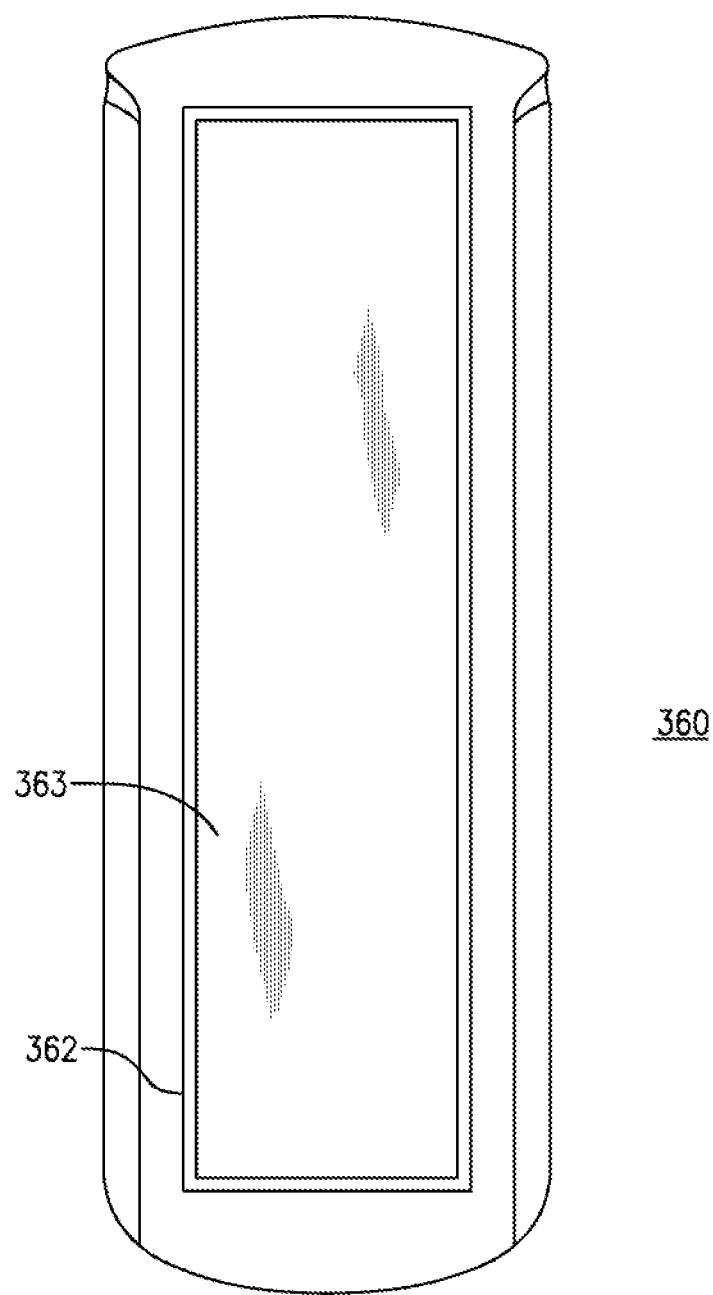
FIG. 12(c) is a rear facing view of the device engagement member of FIGS. 12(a) and 12(b)
Figure 12D:
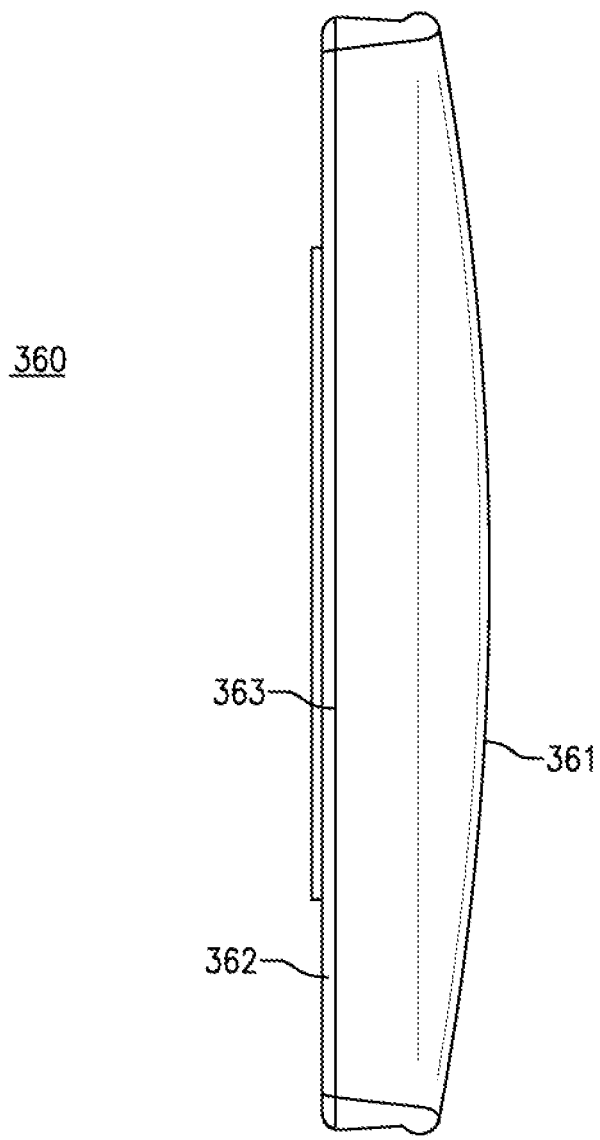
FIG. 12(d) is a top plan view of the device engagement member of FIGS. 12(a)-12(c)
Figure 12E:
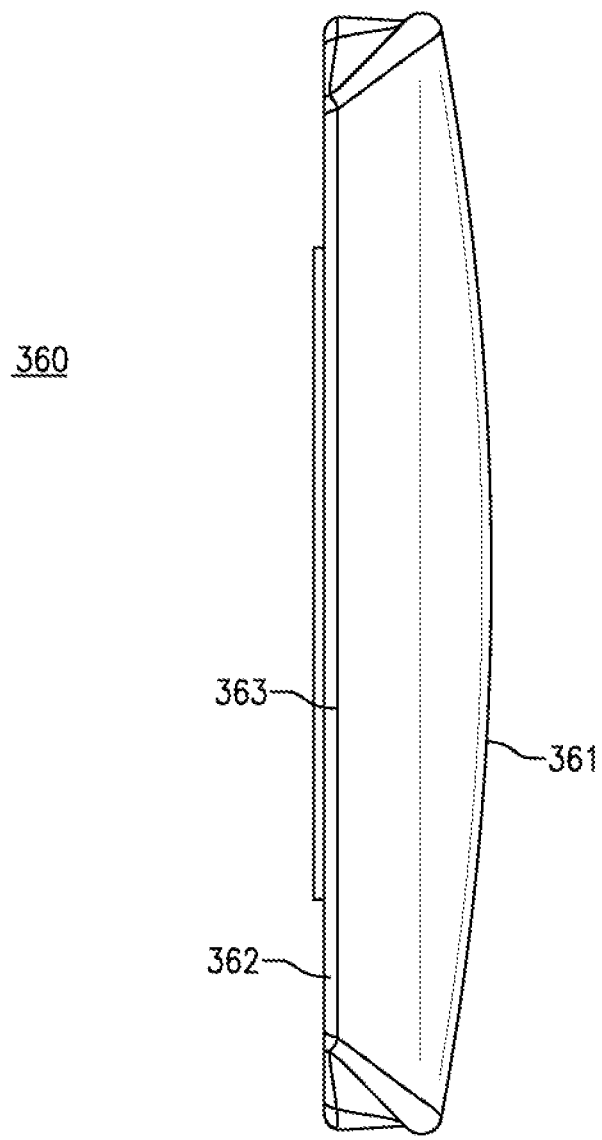
FIG. 12(e) is a bottom view of the device engagement member of FIGS. 12(a)-12(d)
Figure 12F:
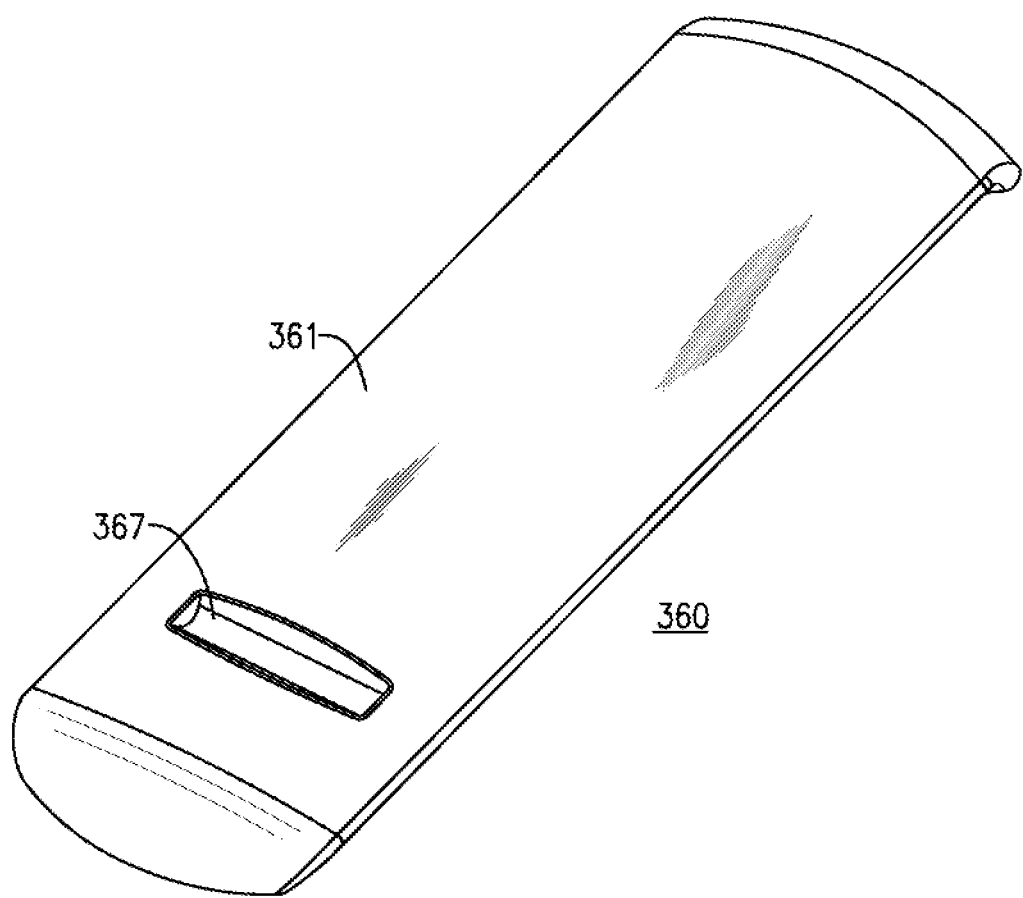
FIG. 12(f) is a front perspective view of the device engagement member of FIGS. 12(a)-12(e)
Figure 12G:
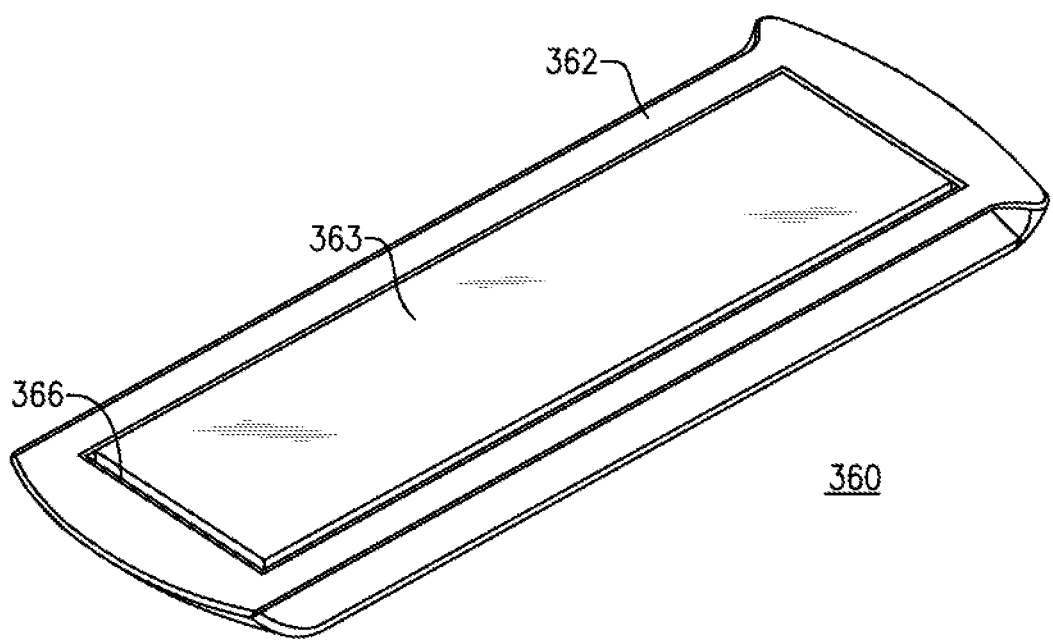
FIG. 12(g) is a rear perspective view of the device engagement member of FIGS. 12(a)-12(f)
Figure 12H:
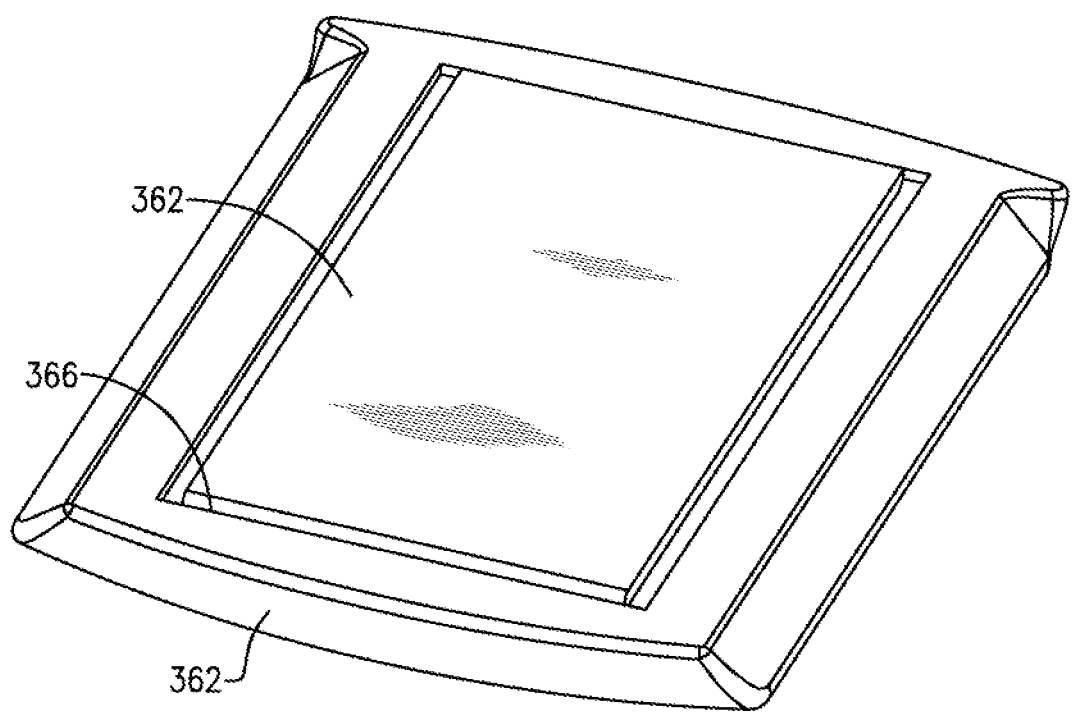
FIG. 12(h) is another rear perspective view of the device engagement member of FIGS. 12(a)-12(g)

As shown in FIGS. 9(a), 9(b) and 11(a) and as the device engagement member 360 is engaged within the slot 316 of the rear housing section 312, the bias of the detent spring 394 enables the detent member 384 to be moved slightly forward relative to the transverse groove 367 formed in the device engagement member 360 to provide greater retention when the device engagement member 360 is attached to the adapter 300. The strip or pad of insulating material 395 eliminates rattle and provides a defined drag when a user slides the device engagement member 360 in the defined slot 316. The device engagement member 360 is slid an appropriate distance within the slot 316 until the front surface of the device engagement member 360 engages the spring loaded detent member 384. Preferably, there is a slight mismatch created between the projecting detent 391 and the transverse groove 367 formed in the device engagement member 360 that biases the device engagement member 360 forward. Additional views of the front and rear interfacing portions of the smart device adapter 300 illustrating each of the foregoing features are depicted in FIGS. 11(a)-11(l).

In operation, the device engagement member 360 can first be attached to a smart device using a fixture (not shown) to a facing surface of a smart device. The device engagement member 360 is preferably located on the smart device (e.g., smart phone) in a position that enables the optical axis of the smart device to be aligned with the optical axis of the physical assessment device when the smart device is attached. The through opening 327 of the rear housing section 312 is aligned with the optical axis of the smart device when the device engagement member 360 is attached to the smart device. When attached, the protruding portion 340 formed on the rear housing portion 312 of the adapter 300 minimizes the intrusion of ambient (room) light into the system.

Figure 13A:
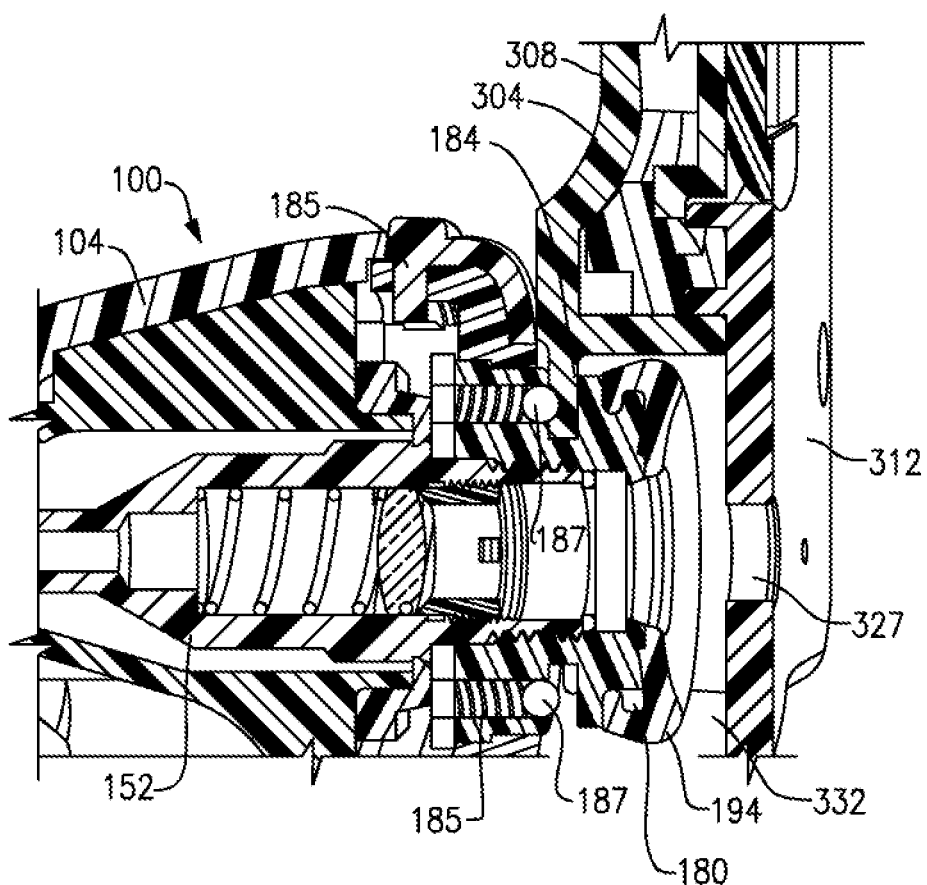
FIG. 13(a) is a partial side view, taken in section, of the smart device adapter of FIGS. 6-11(l) and device engagement member of FIGS. 12(a)-12(h), as assembled to the physical assessment device of FIGS. 1(a)-5.

With reference to FIG. 13(a), the smart device adapter 300 is attachable to the proximal end 116 of the physical assessment device 100 by aligning the device engagement portion 328 of the adapter 300 with the recess 184 of the adapter interface member 180. The three engagement surfaces 330, 332 and 354 have a thickness that enables a fit within the recess 184 of the adapter interface member 180. Moreover, the configuration of the three (3) device engagement surfaces 330, 332 and 354 of the smart device adapter 300, including their length and relative spacing enables releasable attachment of the smart device adapter 300 relative to the recess 184 of the adapter interface member 180, and more specifically the machined flats 186. The slot 322 of the front housing section 308 of the adapter 300 is sufficiently wide so as to accommodate the proximal section 188 of the adapter interface member 180, including the brow rest 194.

As noted, the engagement surface 354 is biased due to the spring loaded slider member providing consistent peripheral contact of the engagement surfaces 330, 332 and 354 with the machined flats 186. In addition, the axial openings of the adapter interface member and more specifically the spring loaded balls 187 of the adapter interface member 180 against the intermediate plate 190, further bias the attached smart device adapter 300 in the direction of the optical axis of the physical assessment device 100 and provide a stable mounted platform for purposes of conducting an examination.

For purposes of positioning, the smart device adapter 300 (and attached smart device (not shown) can be placed in one of four (4) different positions, each position clocked about 90 degrees about the optical axis of the physical assessment device 100. According to this embodiment, the smart device adapter 300 is removed from the physical assessment device 100 and rotated before reengaging the slots of the adapter 300 with the machined flats 186 of the adapter interface member 180. This adjustment can be made either with or without a smart phone being attached to the smart device adapter 300. It will be understood, for example, that the number of machined flats can be suitably varied in order to provide a suitable number of mounting positions.

According to another embodiment, the herein described adapter can be fitted to a physical assessment device, such as an otoscope or ophthalmoscope, without prior optical alignment using a calibration device. Instead of attaching the device engagement member 360 adhesively or otherwise to the smart device following calibration, the device engagement member 360 is initially attached to the smart device adapter 300 by sliding the device engagement member 360 into the slot 316 provided on the rear housing portion of the adapter 300 until there is an audible or other indication that the device engagement member 360 has been placed at a predetermined position. In at least one version, an audible click or other indication, detent is provided to the user. The adhesive layer 363 of the device engagement member 360 is then removed to enable the device engagement member 360 to be attached to a facing surface of the smart device, wherein visual alignment by the user aligns the through opening 327 in the adapter 300 with the optical axis of the attached smart device. The two components can then be assembled by pressing the adhesive surface 363 of the device engagement member 360 against the front facing side of the smart device. To remove the smart device from the adapter 300, the smart device can be pulled from the device engagement member 360. This technique permits a varied number of differently sized smart devices to be releasable fitted to a common smart device adapter 300.

Figure 13B:
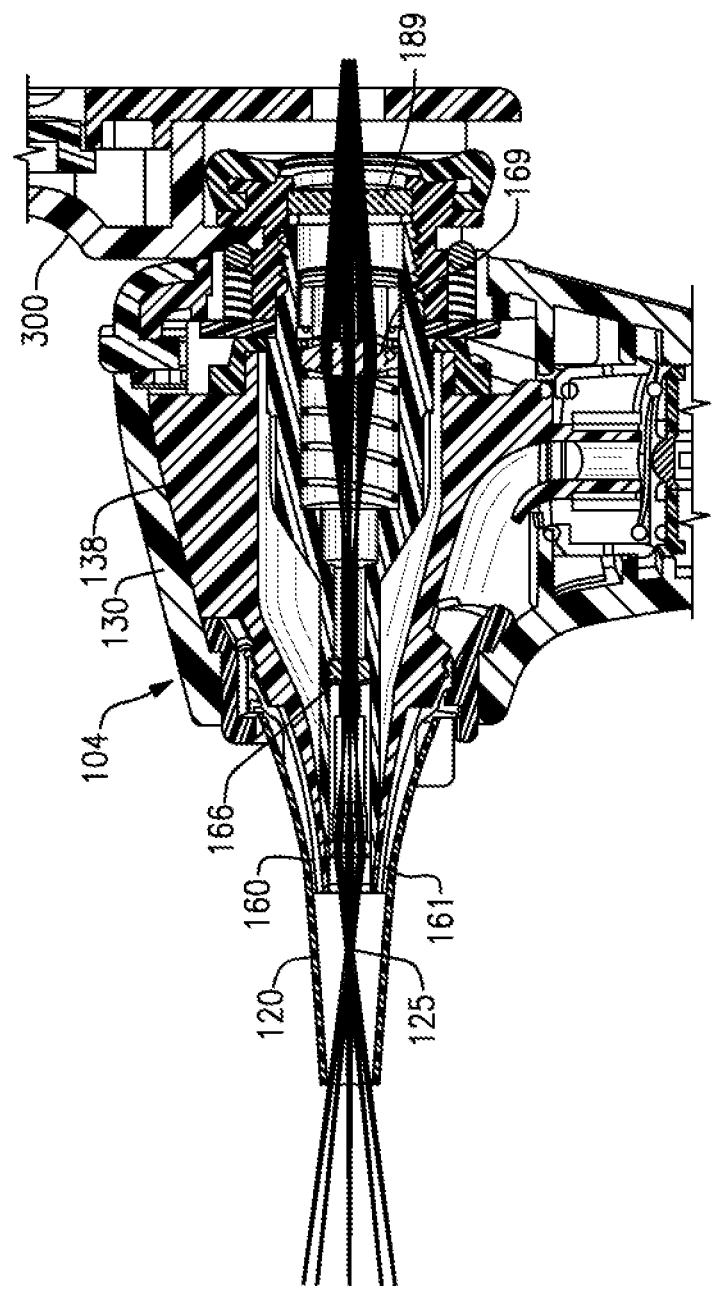
FIG. 13(b) is the side sectioned view of the instrument head of FIGS. 2(b)-2(k), smart device adapter of FIGS. 6-11(l) and device engagement member of FIGS. 12(a)-12(h), further depicting a ray trace of the optical system or assembly including a distal entrance pupil produced by the optical system.

As shown by the ray trace depicted in FIG. 13(b) for the physical assessment device 100 including instrument head 104 and attached smart device adapter 300, the optical assembly of the herein described otoscope 100 creates a virtual distal entrance pupil 125 within the attached speculum tip element 120, FIG. 2(a). The position of the formed entrance pupil according to this embodiment is well distal of the optical window and objective lens. The entrance pupil is positioned such that the attached speculum tip element 120 is not "seen"; that is, the rays of light reflected from the medical target pass sufficiently within the tip opening of the speculum tip element 120, FIG. 2(a), while still enabling a large field of view, permitting the entire tympanic membrane to be viewed all at once. As shown, the light reflected from the medical target is directed along a defined optical axis to the optics of an attached smart device, not shown. The advantageous effect of the entrance pupil is further illustrated in FIGS. 54(a) and 55.

Figure 14:
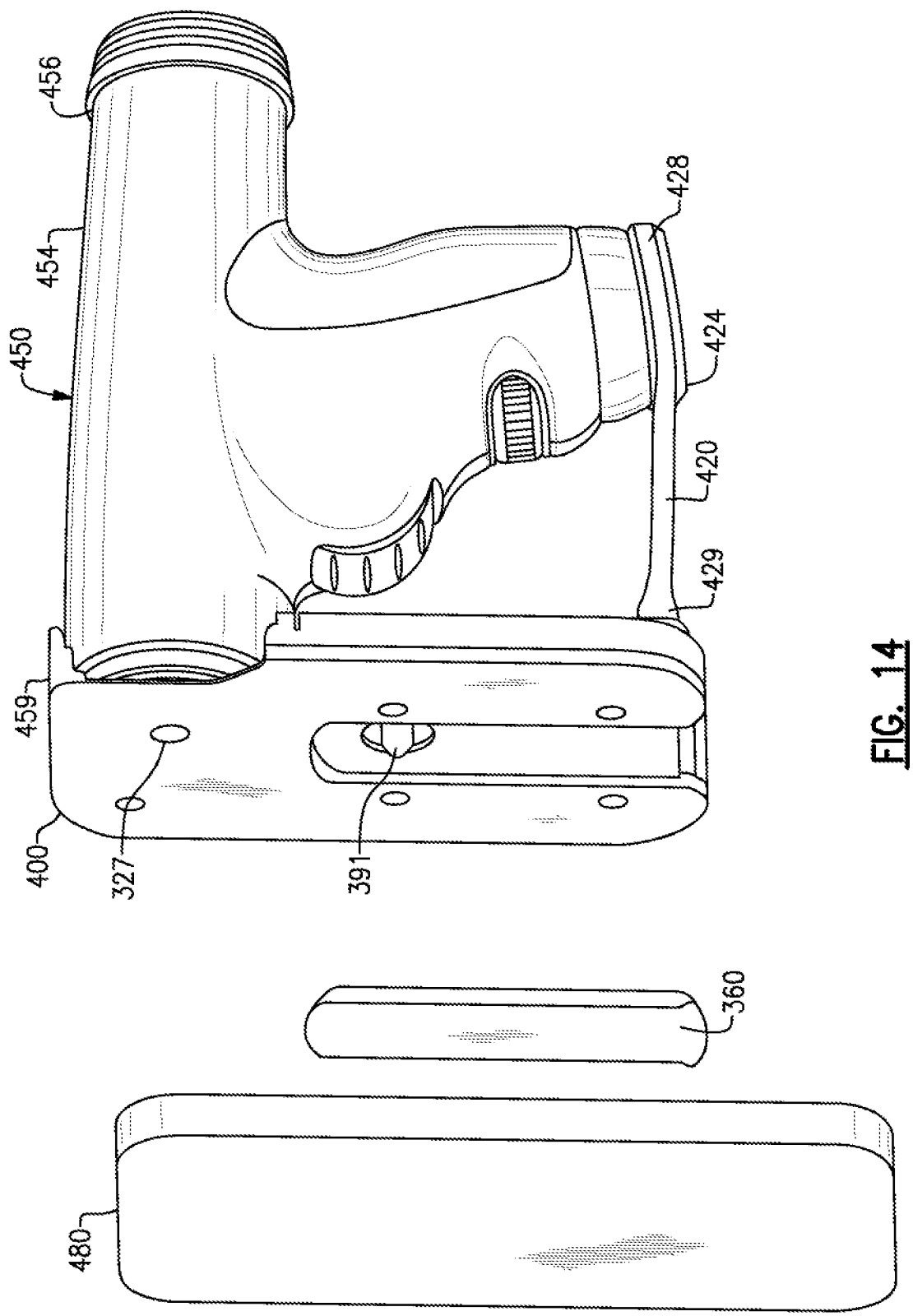
FIG. 14 is a partially assembled rear perspective view of a known physical assessment device having a smart device adapter made in accordance with another embodiment.
Figure 15:
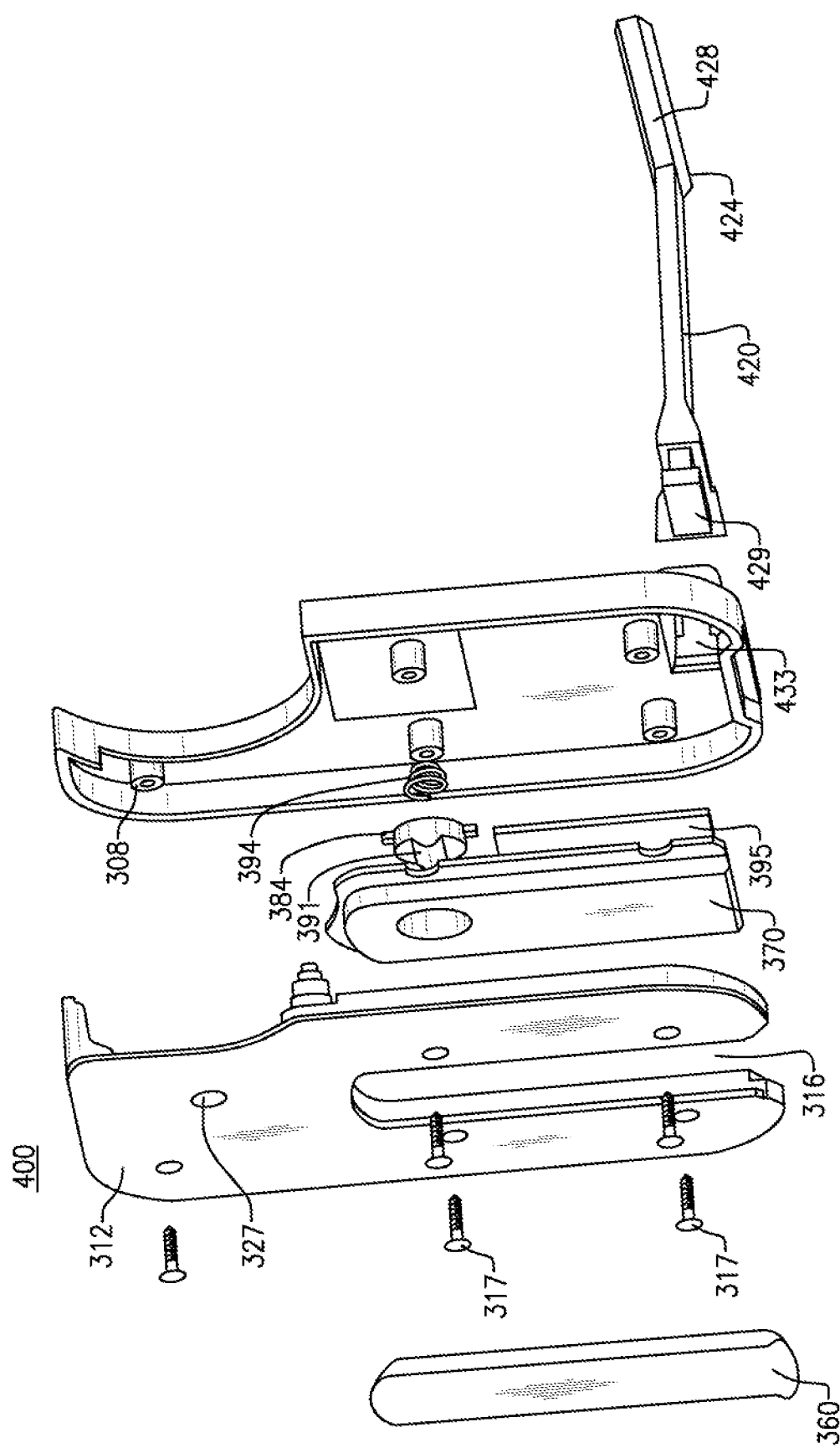
FIG. 15 is an exploded assembly view of the smart device adapter of FIG. 14.
Figure 16:
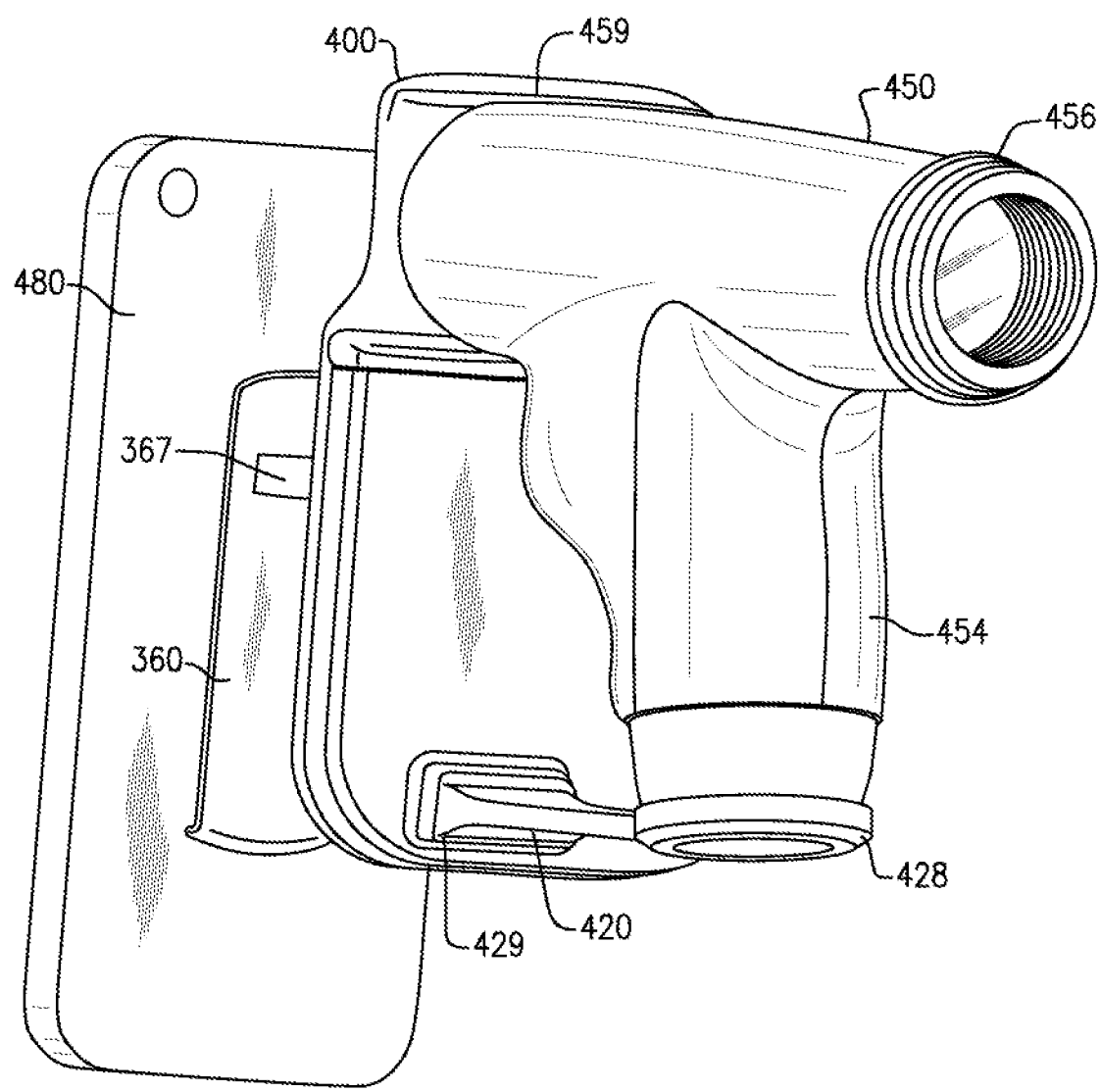
FIG. 16 is a front perspective view of the physical assessment device of FIG. 14 as assembled with the smart device adapter of FIG. 15 prior to a smart device being releasably attached.
Figure 17:
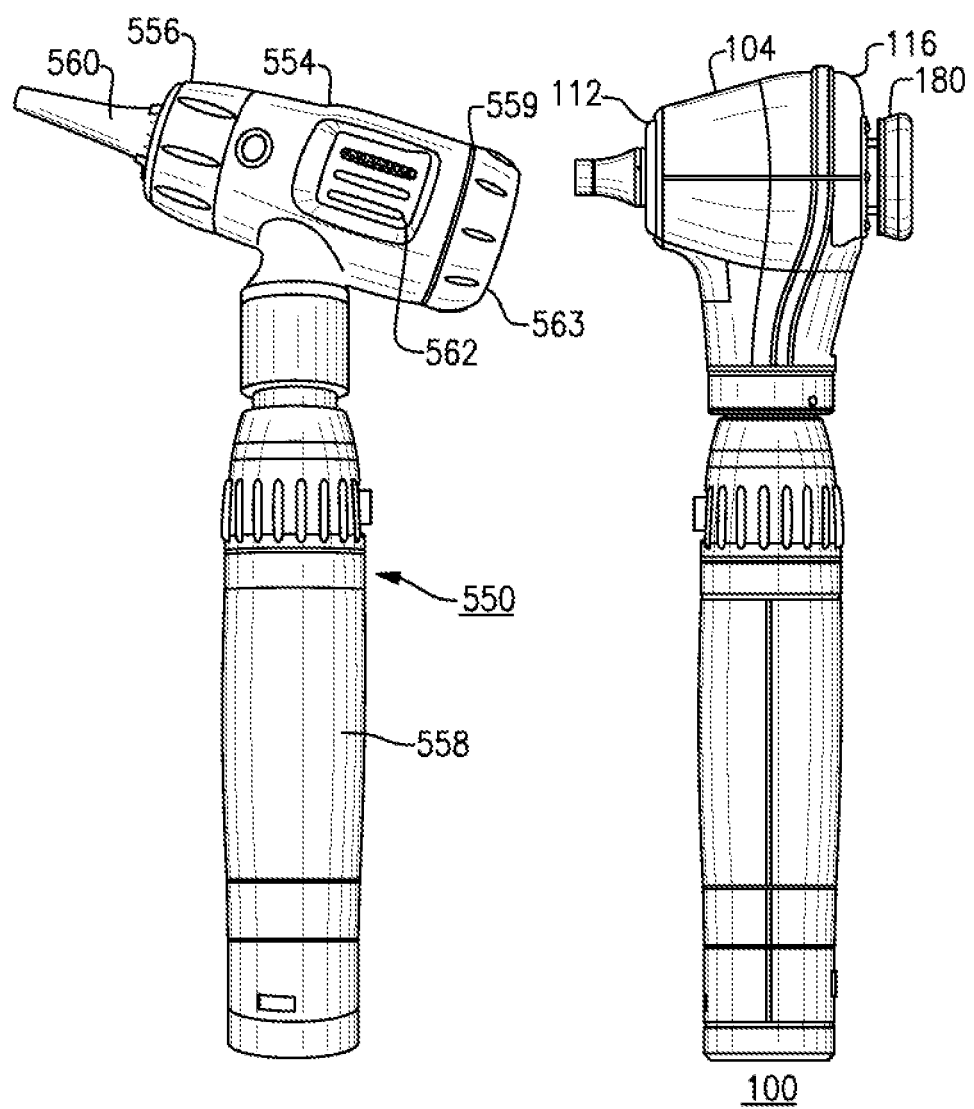
FIG. 17 depicts a prior art physical assessment device (on the left) with the physical assessment device of FIGS. 1-5(b) as shown in side by side relation.

With reference to FIGS. 14-16, a variation of the smart device adapter 400 is described for use on another physical assessment device 450. Similar parts are labeled with the same reference numerals for the sake of clarity. According to this embodiment, the physical assessment device 450 is a Pan Optic™ Ophthalmoscope sold commercially by Welch Allyn, Inc. of Skaneateles Falls, N.Y. The ophthalmoscope 450 is defined by an instrument head 454 that can be releasably attached to a handle portion (not shown). The instrument head 454 includes a distal (patient) end 456 and an opposing proximal (caregiver) end 459. An optical system (not shown) within the instrument head 454 is configured to enable examinations of the eye of a patient, along with a contained illumination system (not shown) that includes at least one light source to illuminate the eye being examined.

According to this embodiment, aspects of the smart device adapter 400 are structurally and functionally similar to the version previously described in FIGS. 6-13(a), including a pair of housing portions 308, 312 that retain a detent cover 370 as well as a detent member 384, the latter being biased by a contained detent spring 394. The rear housing portion 312 includes a slot 316 that is configured to receive the detent cover 370, as well as a device engagement member 360 that is slidably engaged with the slot 316 formed on the adapter 400 and including a transverse groove 367 that engages the detent member 384. The housing portions 308, 312 are secured to one another using a set of fasteners 317, The adapter 400 further includes a through opening 327 that is aligned with the optical axis of the physical assessment device 450 when the adapter 400 (and smart device 480) are attached, as shown in FIG. 16.

The smart device adapter 400 according to this embodiment further includes a flexible arm 420 having a distal end 424 that includes a ring-shaped portion 428. The ring-shaped portion 428 is sized to enable it to be disposed over the downwardly extending portion 458 of the instrument head 454. The proximal end 429 of the flexible arm 420 can be releasably attached to the front housing section 308 of the smart device adapter 400. According to this version, the front housing section 308 includes an opening 433 that is sized to receive the proximal end 429 of the flexible arm 420.

With reference to FIGS. 17-20, a smart device adapter made in accordance with another exemplary embodiment is herein described. First and referring to FIG. 17, a known physical assessment device 500 and the otoscope 100, FIG. 1(a), are shown in side by side relation. As previously discussed, the otoscope 100 includes an adapter interface member 180 at its proximal end 116 that enables a smart device adapter 300, FIG. 6, to be releasably attached. The known assessment device 500, which is a Macroview™ otoscope, commercially sold by Welch Allyn, Inc. of Skaneateles Falls, N.Y., can also be configured with an adapter to enable a smart device to be attached. The known device is defined by an instrument head 554 that includes a distal (patient) end 556 and an opposing (caregiver) end 559, wherein the instrument head 554 is attached to the upper end of a handle portion 558. A speculum tip element 560 is attached to the distal end 556 of the instrument head 554. An optical and an illumination assembly (not shown) are contained within the instrument 550, including an eyepiece 563 provided at the proximal end 558 and a focusing wheel 562 intermediately provided on the exterior of the instrument head 554 that enables relative movement of at least one contained optical element (not shown).

Figure 18:
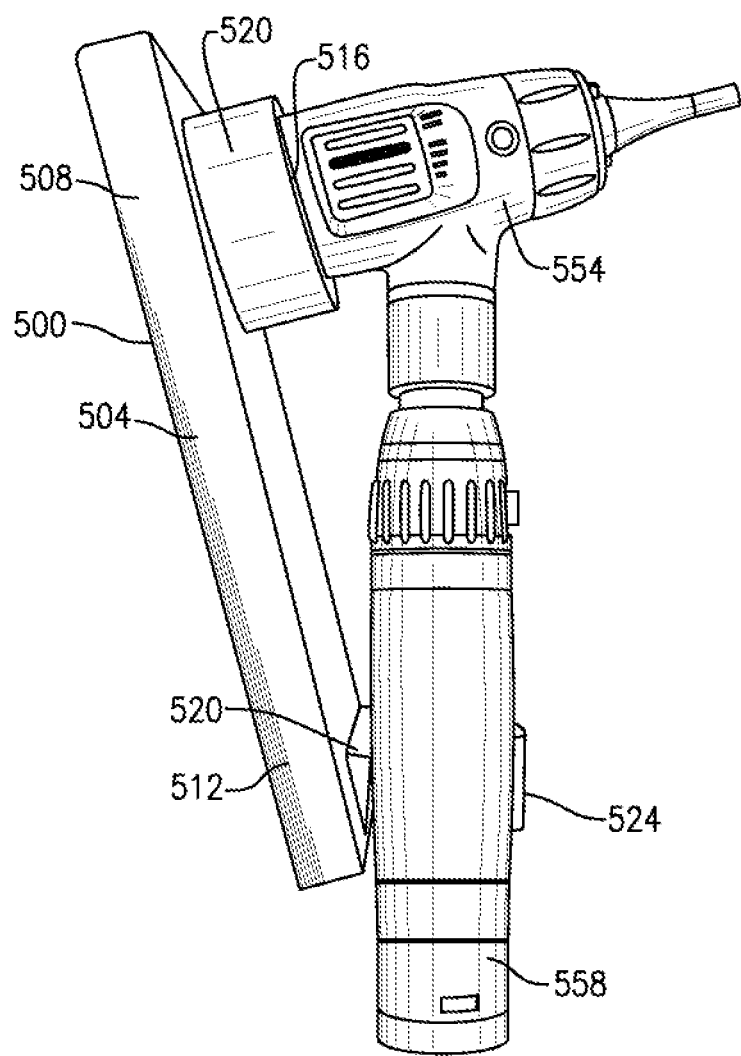
FIG. 18 is a side perspective view of the prior art physical assessment device having an attached smart device adapter, which is made in accordance with another embodiment.
Figure 19:
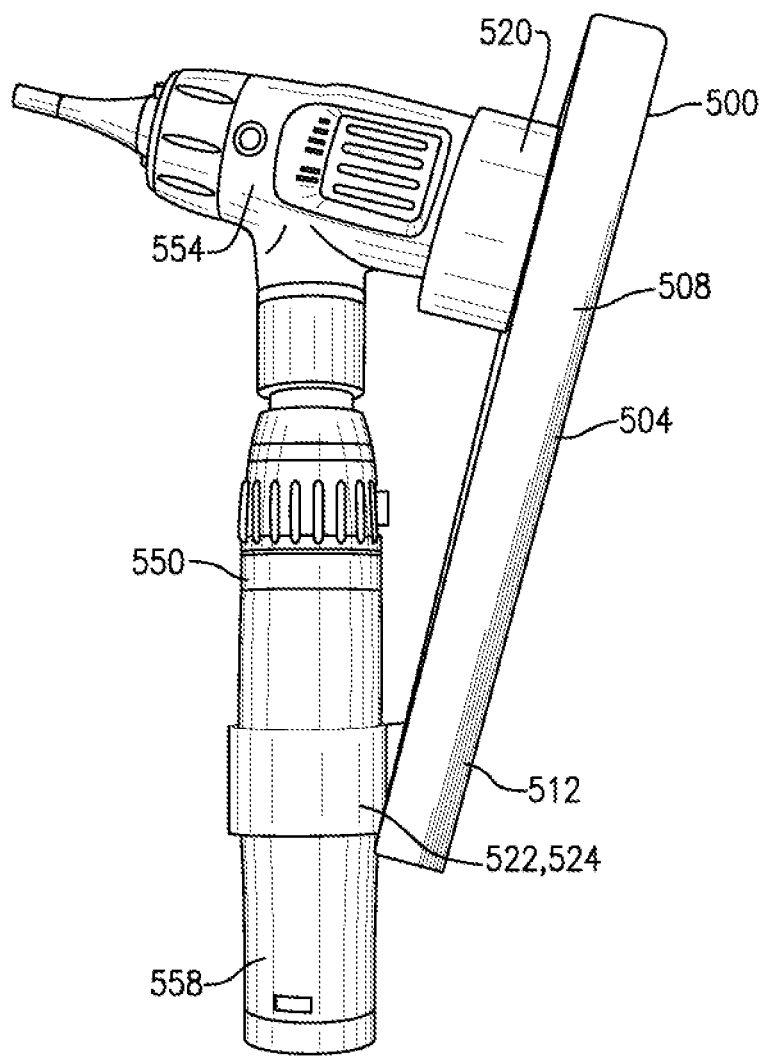
FIG. 19 is another perspective view of the prior art physical assessment device and smart device adapter of FIG. 18.
Figure 20:
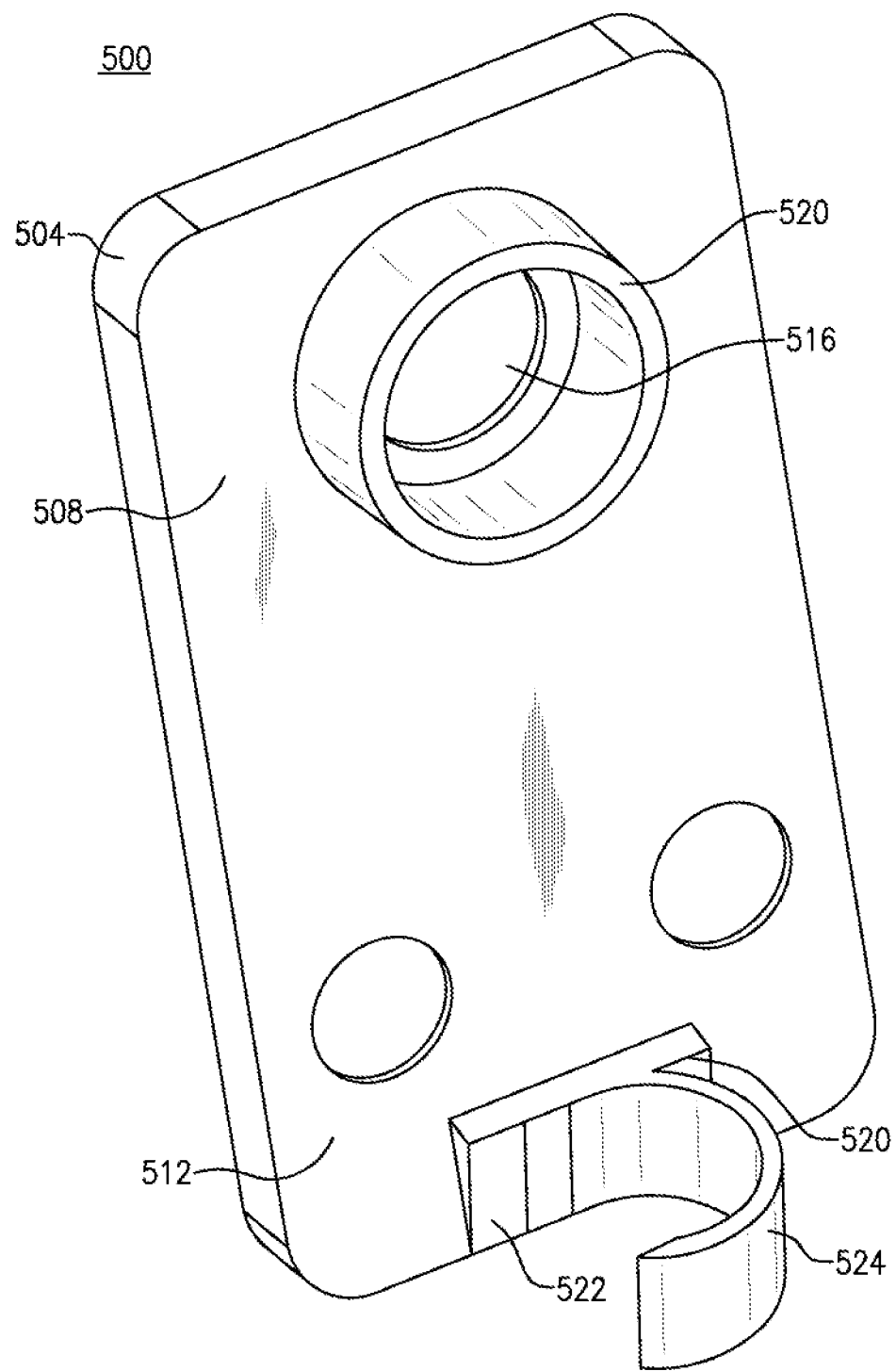
FIG. 20 is a front perspective view of the smart device adapter of FIGS. 18 and 19.

With reference to FIGS. 18-20, a smart device adapter 500 according to this embodiment includes a support or base plate 504 having an upper portion 508 and an opposing lower portion 512. The support plate 508 can be made from a durable molded plastic, although other structural materials can be suitably utilized. The upper portion 508 includes a through opening 516, as well as a hollow cylindrically shaped projection 520 that is aligned with the through opening 516. The hollow projection 520 extends distally from the upper portion 508 and is defined by a cavity that is sized and configured to be fitted over the proximal end 558 and more specifically the eyepiece 563 of the known physical assessment device 550. A flexible engagement portion 522 formed at the lower portion 512 of the base plate 504 is defined by a C-shaped engagement end 524. This engagement end 524 is sized and configured to releasably engage the cylindrical handle portion 558 of the known physical assessment device 500. Though the known physical assessment device 550 is an otoscope, it will be readily apparent to those in the field that other handheld medical diagnostic devices can be similarly configured for attachment.

With further reference to FIGS. 18-20 and in terms of attachment, the projecting cylindrical portion 520 is first fitted onto the proximal end 558 of the physical assessment device 550. This fit still enables the caregiver to access the focusing mechanism 562 of the physical assessment device 550. The smart device adapter 500 is then rotated until the open end of the C-shaped engagement feature 524 is aligned with the handle portion 558, permitting the C-shaped engagement feature 524 to be clamped onto the handle 558. The C-shaped engagement portion 556 is angled relative to the base plate 504 to account for the angled configuration of the instrument head 554 of the otoscope 550.

A smart device such as a smart phone (not shown) can be attached to the proximal side of the support plate 504 in a manner similar to those previously described. Advantageously, the herein described adapter 500 can be attached to a physical assessment device in a matter of seconds, thereby converting the physical assessment device from an optical to a digital physical assessment device without requiring any modification to the device. Once attached, the smart device permits users to use the physical assessment device 550 to take pictures and video and then seamlessly transfer the images or video to a digital medical record or other digital storage medium used in an office or hospital.

Variations—Otoscope

Figure 21:
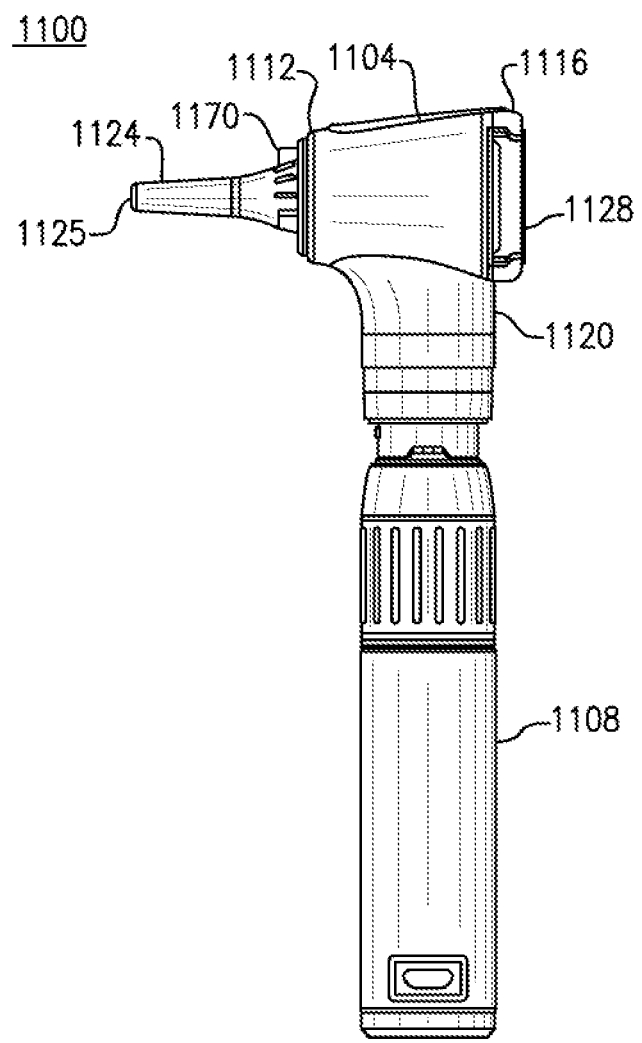
FIG. 21 is a perspective view of a physical assessment device made in accordance with another embodiment.
Figure 23:
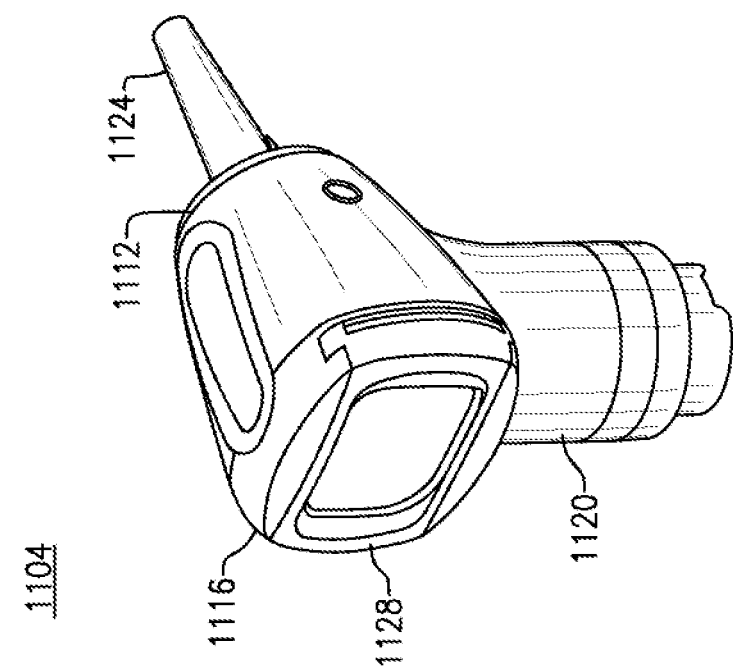
FIG. 23 is a rear perspective view of the instrument head of the physical assessment device of FIG. 21.

An otoscope 1100 made in accordance with another exemplary embodiment is depicted in FIGS. 21 and 23. According to this embodiment, the instrument head 1104 of the otoscope 1100 is defined by a distal end 1112, an opposing proximal end 1116 and a downwardly extending portion 1120 attached to the handle 1108, the latter being shown only in FIG. 21. A disposable hollow speculum tip element 1124 is releasably attached to the distal end 1112 of the instrument head 1104 and more specifically to a tip retaining member 1170, while an optical window 1128 is provided at the proximal end 1116. In use, the speculum tip 1124 is shaped and configured to be inserted a predetermined distance into the ear of the patient and the optical window 1128 enables viewing of a medical target of interest (e.g., the tympanic membrane) through the open distal opening 1125 of the speculum tip 1124.

Figure 22:
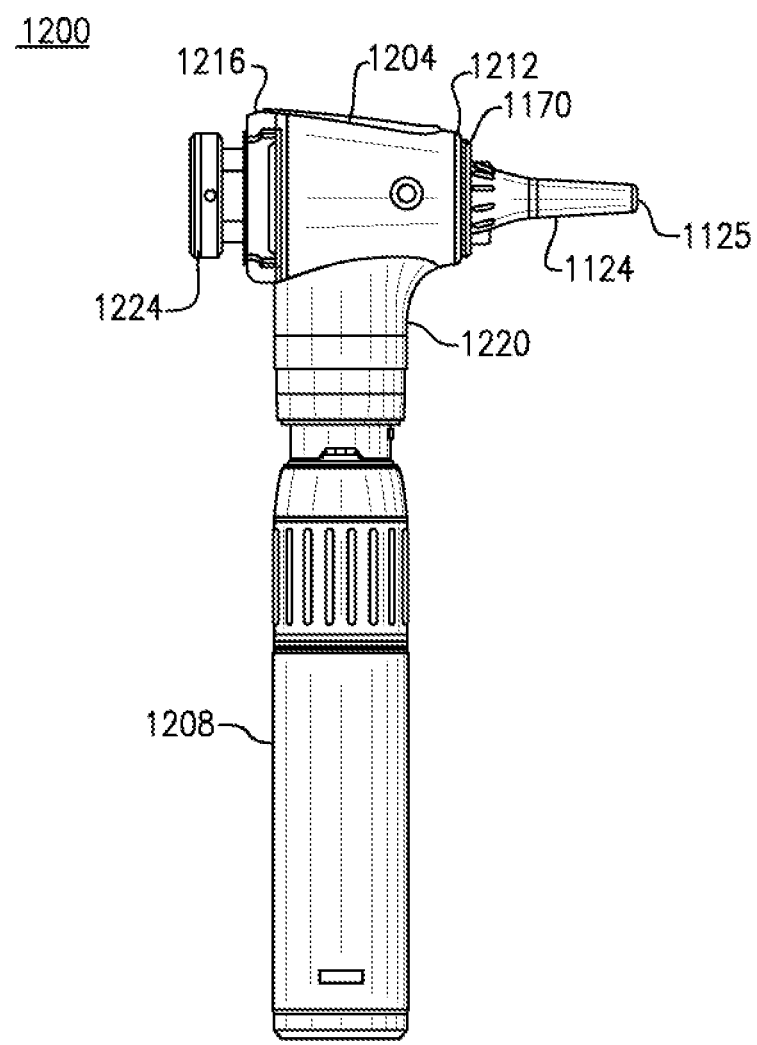
FIG. 22 is a perspective view of a physical assessment device made in accordance with yet another embodiment.
Figure 24A:
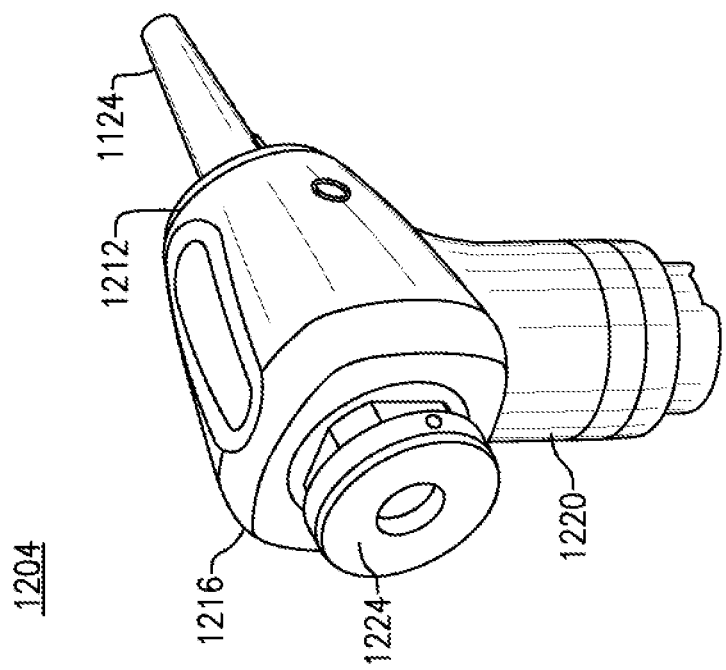
FIG. 24(a) is a perspective view of the instrument head of the physical assessment device of FIG. 22.
Figure 24B:
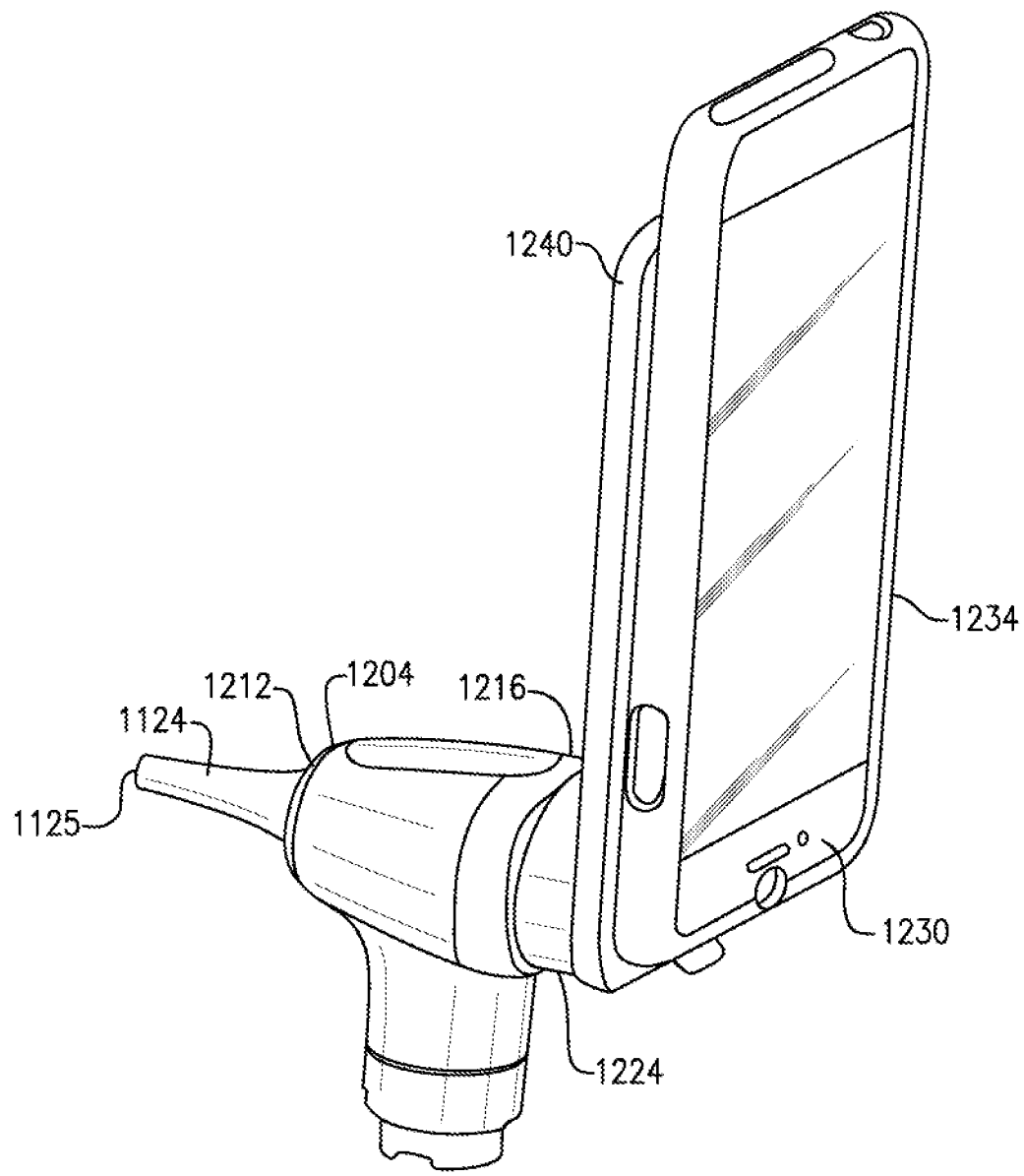
FIG. 24(b) is a rear perspective view of the instrument head of FIG. 24(a), including an attached smart device.

With reference to FIGS. 22 and 24(a), an alternative instrument head 1204 of an otoscope 1200 is similarly defined by a distal end 1212, an opposing proximal end 1216 and a downwardly extending portion 1220. A disposable speculum tip element 1124 is releasably attached to the distal end 1212 of the instrument head 1204 and more specifically a tip retaining member 1170. As shown in FIG. 24(b), a rear mounting member 1224 (also referred to throughout as an adapter interface member) extending from the proximal end 1216 is configured to receive a smart device 1230, such as a smart phone, using an interface member 1240 that aligns the electronic imager of the smart device 1230 with an optical axis of the instrument 1200 to enable digital imaging of the target of interest (e.g. the tympanic membrane) via the display 1234 of the attached smart device 1230.

Assembly of the instrument head 1104 is shown in FIGS. 25(a)-25(d). The instrument head 1104 according to this embodiment includes a pair of housing sections 1134, 1138 (one housing section 1134 being shown as exploded in FIG. 25(a)) that are mated to one another about an innerformer 1140, the latter component creating an interior chamber for the instrument head 1104. An interface stud 1150 extends downwardly from the innerformer 1140 into the downwardly extending portion 1120 of the instrument head 1104 to enable connection to the instrument handle 1108, FIG. 21. A conically-shaped distal insertion portion 1160 is provided at the distal end 1112 of the instrument head 1104 onto which the speculum tip 1124 is placed in overlaying relation and releasably secured to the tip retaining member 1170. A proximal housing member 1180 is secured to the rear end of the innerformer 1140. The proximal housing member 1180 includes a mounting flange 1184 having a pair of spaced slots 1186 that permits the transverse attachment of the optical window 1128. Between the mounted proximal housing member 1180 and the rear of the innerformer 1140 is a groove 1187 that permits the inclusion of a sealing member (not shown). A retaining ring 1190 threadingly attached to the interface stud 1150 secures the housing sections 1134, 1138 together and a cover 1142 attached to the top of the instrument head 1104 covers the mating edges of the housing sections 1134, 1138.

Figure 26B:
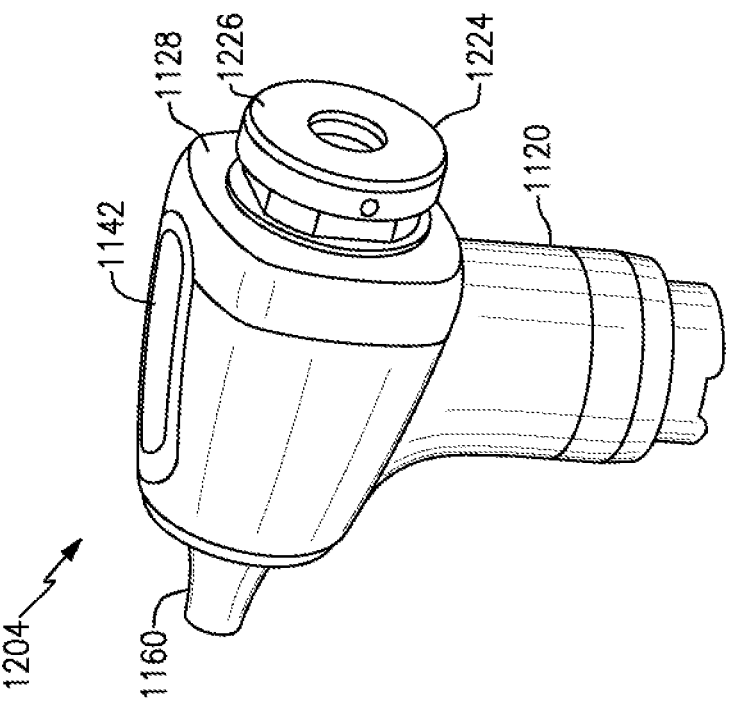
FIGS. 26(a) and 26(b) are partially assembled and assembled views of the instrument head of FIGS. 22 and 24(a)
Figure 26A:
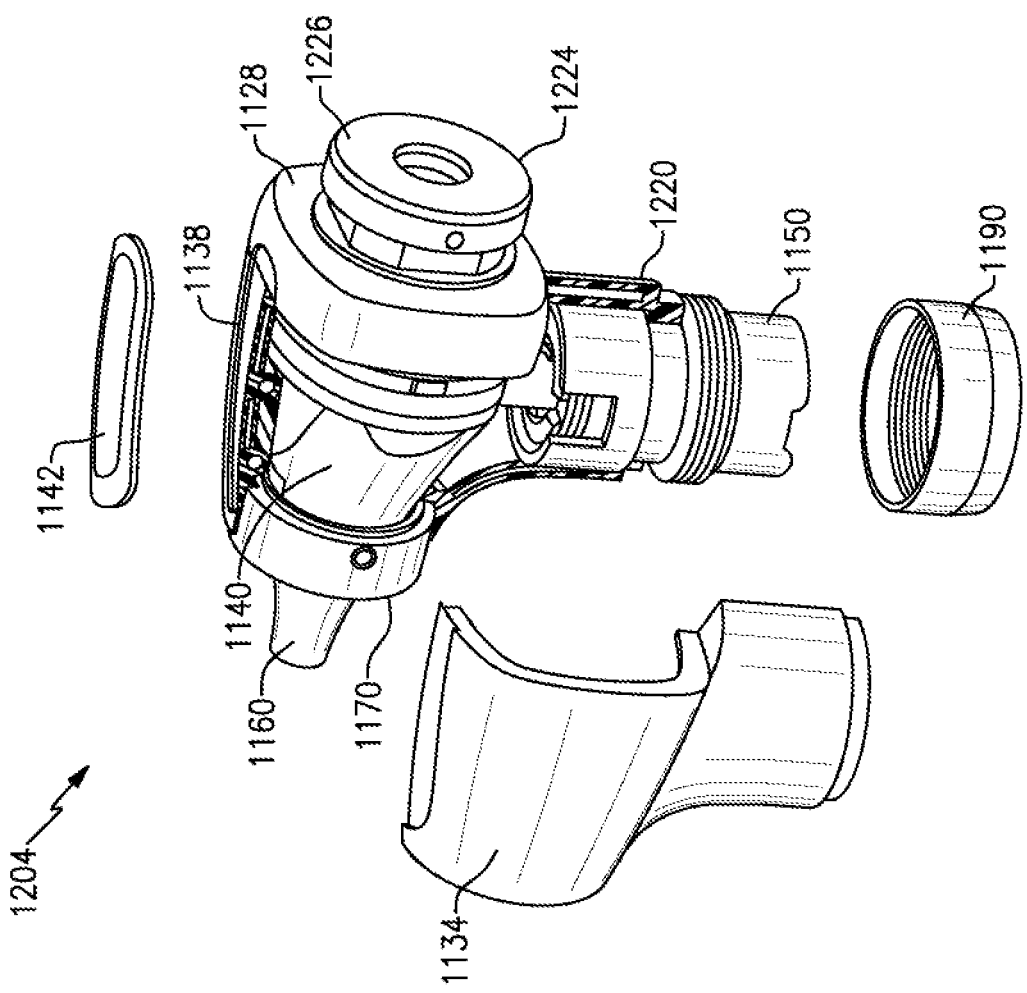

With reference to FIGS. 26(a)-26(b), the assembly of the instrument head 1204 similarly incorporates the housing portions 1134, 1138 that are mated about the innerformer 1150, the latter component forming an interior compartment of the instrument head 1204. Similarly, this assembly incorporates a cover 1142, the distal insertion portion 160 and the tip retaining member 1170 as well as an interface stud 1150 and threadingly retained retaining ring 1190 extending downwardly into the narrowed neck portion 1220. In lieu of the proximal housing member that retains an optical window, the rear mounting (adapter interface) member 1224 is disposed at the proximal end 1218 of the instrument head 1204. According to this embodiment, and similar to the design previously discussed (see 180 at FIG. 1(a)), the rear mounting member 1224 has a defined mounting flange 1226 and an annular slot 1228 that is configured to receive the interface member (smart device adapter) 1240 and attached smart device 1230, as shown in the assembled form previously shown in FIG. 24(b).

Figure 28:
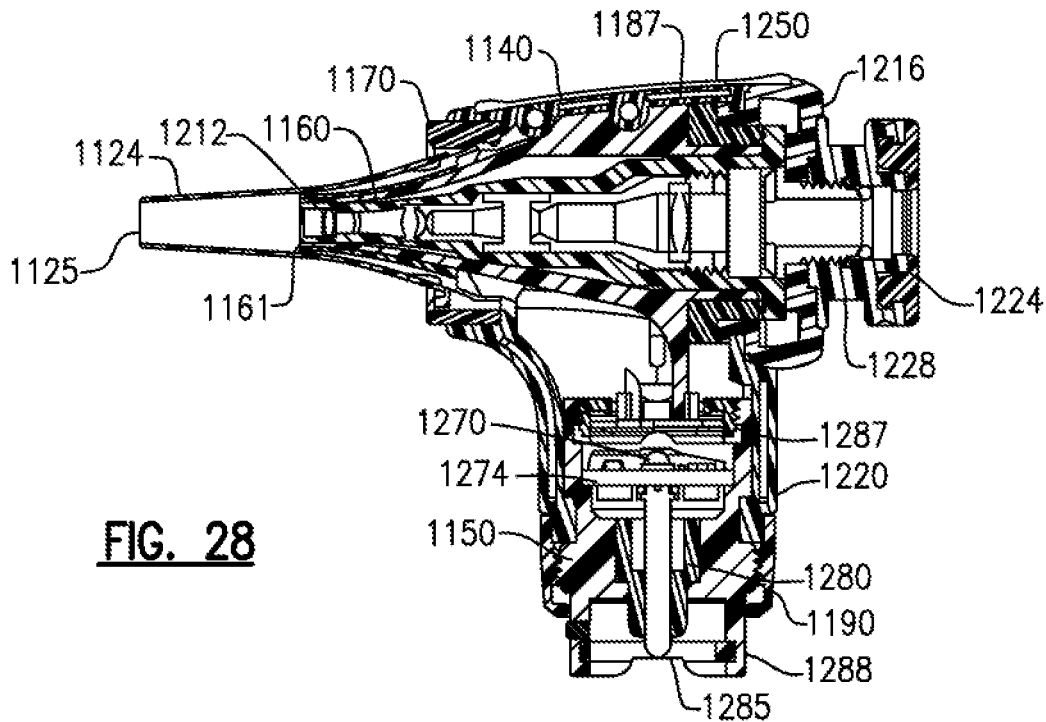
FIG. 28 is a sectioned elevational view of the instrument head of FIGS. 22, 24(a) and 26(a) and 26(b)
Figure 27:
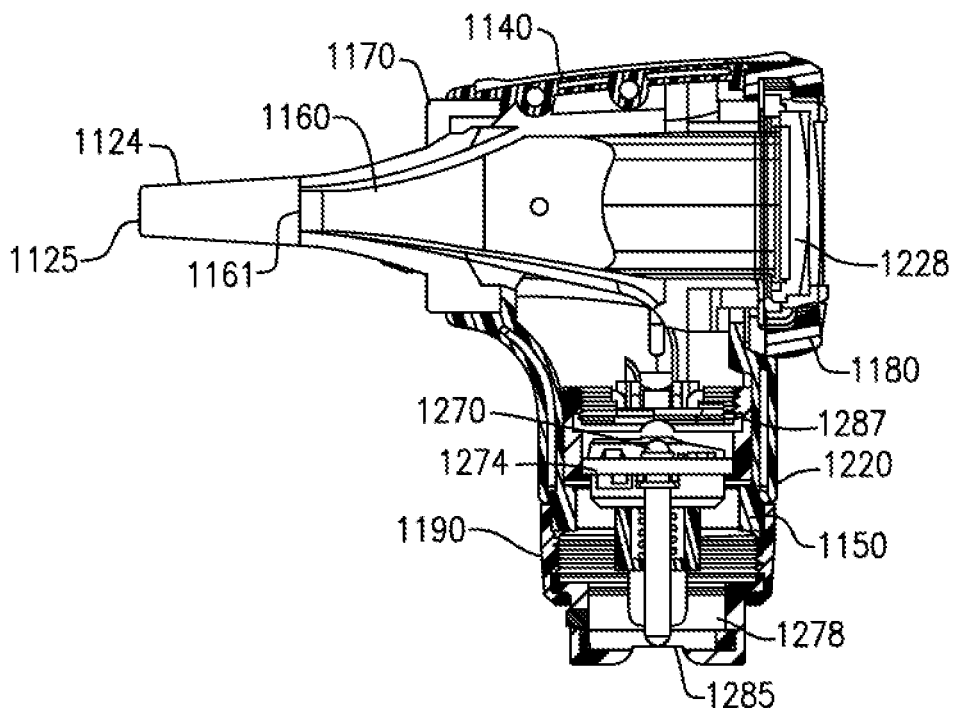
FIG. 27 is a sectioned elevational view of the instrument head of FIGS. 21, 23 and 25(a)-25(d)

Sectioned views of the assembled instrument heads 1104, 1204 are shown in FIGS. 27 and 28. respectively. Referring to FIG. 27, the instrument head 1104 of the otoscope 1100, FIG. 21, enables an image of the medical target (e.g., the tympanic membrane) to be seen through the proximal end 1116 of the instrument head 1104 by viewing through the optical window 1128 as supported by the proximal housing member 1180. This enables viewing of the medical target (e.g. tympanic membrane) through the interior compartment created by the innerformer 1140 and the distal openings 1127, 1161 that are formed in the distal insertion portion 1160 and speculum tip 1124, respectively.

With reference to FIG. 28, an optical assembly is disposed in the interior of the instrument head 1204 of the otoscope 1200 according to this exemplary embodiment. Portions of the optical assembly are retained within a tubular member (also referred to throughout as a lens tube) disposed within the interior compartment created by the innerformer 1140 including a plurality of optical elements, each aligned and disposed along a defined optical or viewing axis of the device 1200 extending between the distal and proximal ends 1212, 1216 of the instrument head 1204. The specifics of the optical assembly are more specifically described in a later portion of this description. As referred to herein, an "optical element" refers to lenses and prisms as well as field stops, aperture stops, polarizers, and any component used to directing or transmitting light along the defined optical or viewing axis. As in the prior described versions of the physical assessment device 100, FIGS. 1(a), 13(b), the optical assembly according to this exemplary embodiment produces an entrance pupil distal relative to the distal most optical element of the optical assembly, creating a field of view that permits the entire tympanic membrane (about 7 mm for an average adult) to be seen all at one time.

A sealing member 1250 is further provided at the rear of the innerformer 1140 as engaged within a formed annular groove 1187. The sealing member 1250 provides an adequate seal to the formed interior compartment of the instrument head 1204 in order to permit insufflation capability (insufflation port not shown in this view) and also preventing fogging of the retained optical elements.

Each of the otoscopic instrument heads 1104, 1204 depicted in FIGS. 27 and 28 commonly include an illumination assembly that is disposed within the downwardly extending portion 1120, 1220 and more specifically the interface stud 1150. The illumination assembly according to this embodiment is more clearly shown in FIG. 33 and includes an LED 1270 as a light source. More specifically, the LED 1270 is disposed upon the upper surface 1272 of a printed circuit board 1274 that is electrically coupled to a downwardly depending electrical contact 1278 biased by a spring 279 disposed within an internal sleeve 1280, the distal end of the electrical contact 1278 extending from an opening of a narrowed portion of the internal sleeve 1280 and proximate an opening 1285 formed in the bottom of the instrument head 1104, 1204. The LED 1270 is disposed in relation to a condensing lens 1290 and the polished proximal end of a fiber optic bundle 1287, the latter of which is advanced upwardly about the innerformer 1140 and extends as a ringlet of optical fibers (not shown) between the distal end of the distal insertion portion 1160 and the innerformer 1140 in order to emit light toward the target of interest.

In each of the above noted devices 1100, 1200 and as described, the pair of housing sections 1134, 1138 can be secured to one another at corresponding mating edges by means of ultrasonic welding with a cover 1142 being introduced at the top of the instrument head 1104, 1204.

Figure 29:
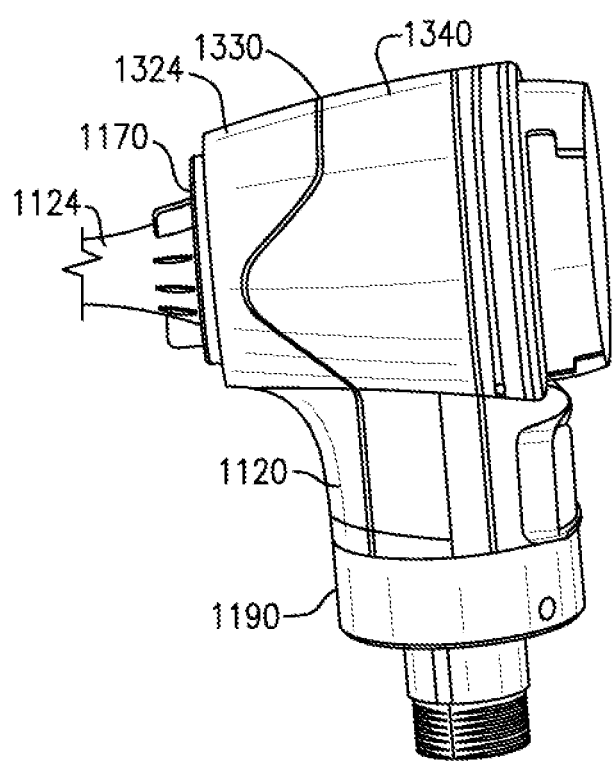
FIG. 29 is a perspective view of an instrument head for a physical assessment device made in accordance with another embodiment.
Figure 30:
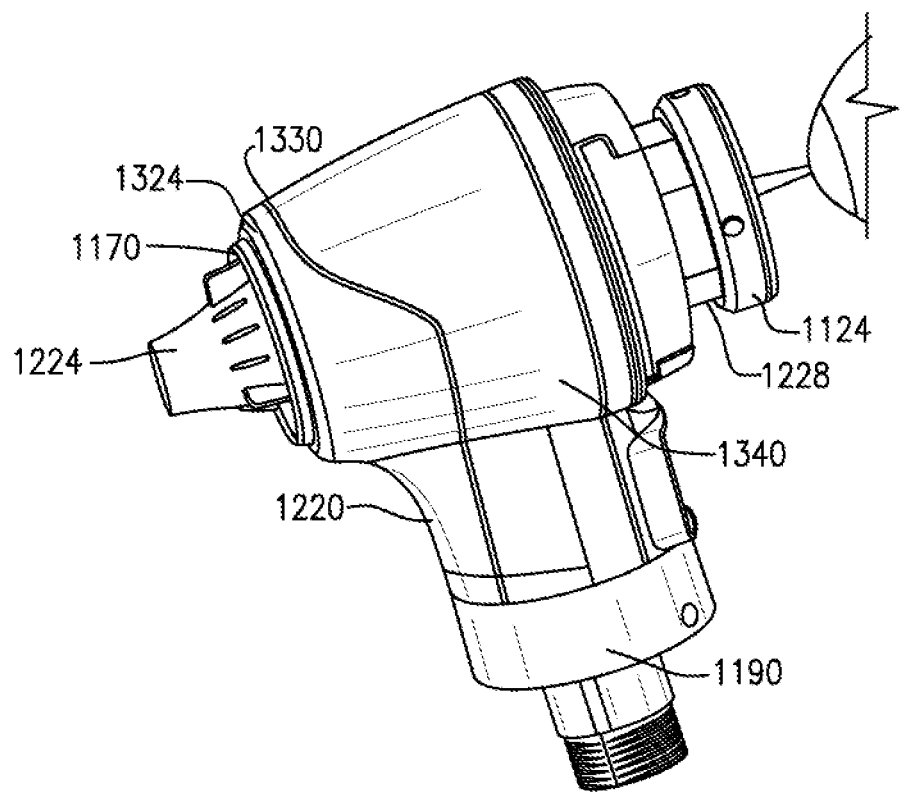
FIG. 30 is a perspective view of an instrument head for a physical assessment device in accordance with yet another embodiment.

With reference to FIGS. 29 and 30 and according to yet another exemplary embodiment, instrument heads 1304, FIG. 29, and 1310, FIG. 30 are shown. Each of these instrument heads 1304, 1310 are similar to instrument heads 1104, 1204. Instrument heads 1304 and 1310 include a pair of mating housing shell sections 1324, 1328 that are attached to one another using an intermediate member, herein referred to as a strap 1340. For purposes of clarity, like structural components are herein labeled with the same reference numerals. The strap 1340 according to this specific embodiment is a singular member made from a flexible, but structural material and having an upper portion 1344 and a lower portion 1348.

Figure 31:
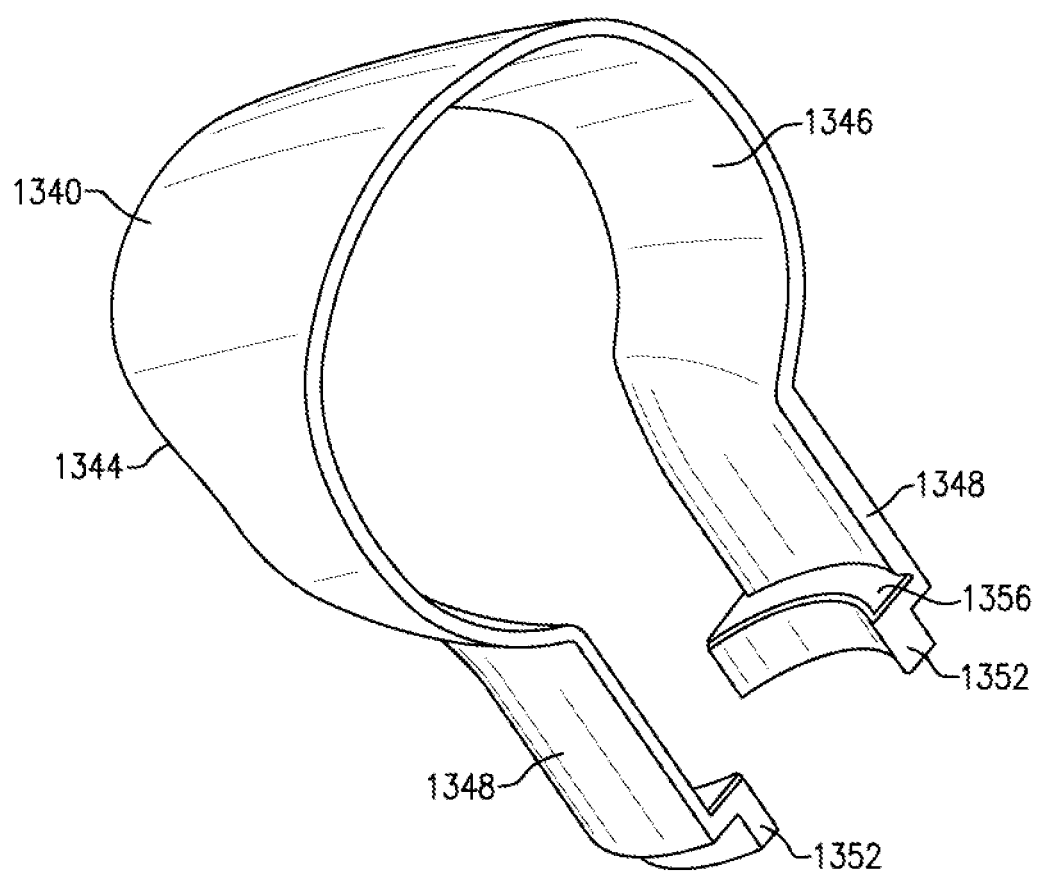
FIG. 31 is a perspective of an intermediate assembly strap used in the instrument heads of FIGS. 29 and 30.

As shown more specifically in FIG. 31, the upper portion 1344 of the strap 1340 is defined by a rounded interior surface 1346 configured and sized to wrap around the exterior of the respective first and second housing shell sections 1324, 1328 after the mating edges of the housing sections 1324, 1328 have been placed in intimate contact with one another. According to this embodiment, the housing shell sections 1324, 1328 define respective halves of the instrument head 1304, 1310. Each of the housing sections 1324, 1328 includes a recess 1330 formed in the exterior surface into which the strap 1340 is received such that the exterior surface of the strap 1340 is substantially coplanar with the exterior surface of the mated housing sections 1324, 1328 when attached.

Figure 32:
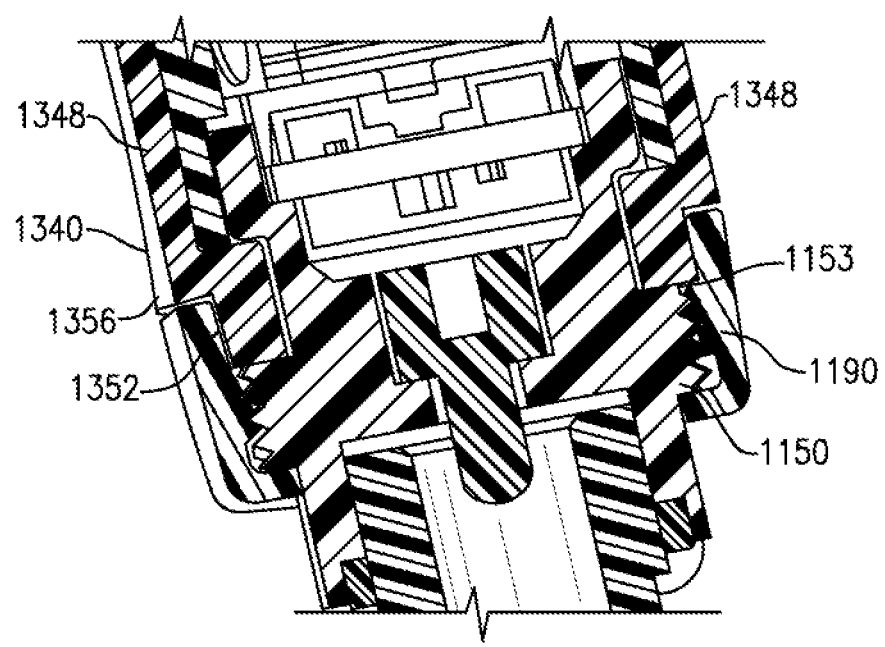
FIG. 32 is a sectioned partial view of the bottom of an instrument head depicting the securement of the intermediate assembly strap of FIG. 31 to an instrument head.

During assembly/manufacture, the inner edges of the pair of housing sections 1324, 1328 are placed in intimate contact and the strap 1340 is snap-fitted into place onto the instrument head 1304 via the recess 1330. As shown in FIGS. 31 and 32, the lower extending portions 1348 of the intermediate strap 1340 each include an annular flange 1352 formed on an inner surface, as well as an annular shoulder 1356 formed at the end of each lower extending section 1348. Referring to FIG. 32, the annular flange 1352 of each lower extending section 1348 is retained within an annular groove 1153 formed in the interface stud 1150 and secured by means of the retaining ring 1190 by threading engagement with the bottom of the interface stud 1150 of the instrument head 1304, the upper end of the retaining ring 1190 engaging the shoulder 1356.

With reference to FIG. 33-36, an illumination assembly is retained within the downwardly extending portion 1120 of the instrument head 1104. According to the depicted embodiment, the illumination assembly includes the LED 1270 attached in a known manner to a top or upper surface 1272 of a printed circuit board 1274. Disposed above the LED 1270 and printed circuit board 1274 is an integrated component 1420 that serves to center and align the LED 1270 and also collimates the light that is emitted from the LED 1270. The outer edges 1275 of the printed circuit board 1274 are retained upon an interior shoulder 1156 of the interface stud 1150. As shown in the sectioned view of FIG. 34, the integrated component 1420 is defined by a cylindrically shaped body 1422 having an upper end 1426, a lower end 1430, and a set of external threads 1434 extending along the length of the integrated component 1420. An interior flange 1438 is disposed at an intermediate distance between the upper and lower ends 1426, 1430 of the integrated component 1420, the flange 1438 having respective and opposing top and bottom surfaces 1442, 1446.

A domed portion 1450, which is provided at the center of the top surface 1442 of the internal flange 1438, is axially aligned with the LED 1270 and acts as a condensing lens. An annular ring 1458 extending downwardly from the bottom surface 1446 of the interior flange 1438 is configured and sized to surround the lens envelope of the LED 1270 and functions to center the domed portion 1450 with the LED 1270, thus minimizing decentration between the LED 1270 and the domed portion 1450 and any associated losses in light transmission. The set of external threads 1434 are configured to mate with corresponding internal threads 1460 that are provided in the interface stud 1150 of the instrument head 1104. Thus mating allows the integrated component 1420 itself to fasten the printed circuit board 1274 into the interface stud 1150 and further ensure a secure electrical contact between the printed circuit board 1274 and the interface stud 1150. This securement further prevents ingress of dirt and debris.

Figure 35:
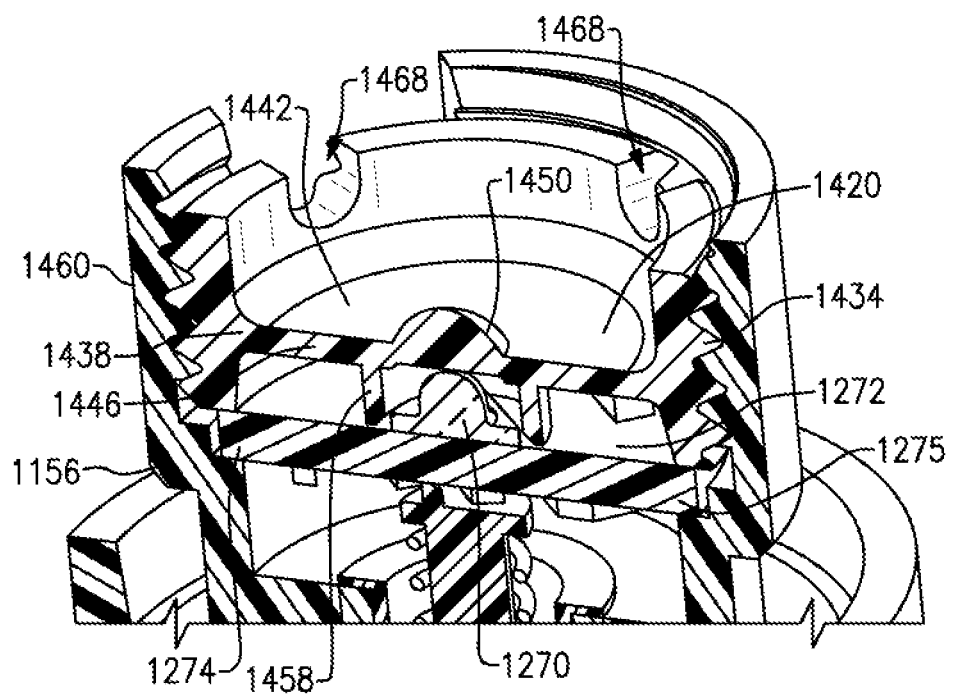
FIG. 35 is a partially cutaway top perspective view depicting the integrated component of FIG. 34 within the instrument head relative to the retained LED.
Figure 36:
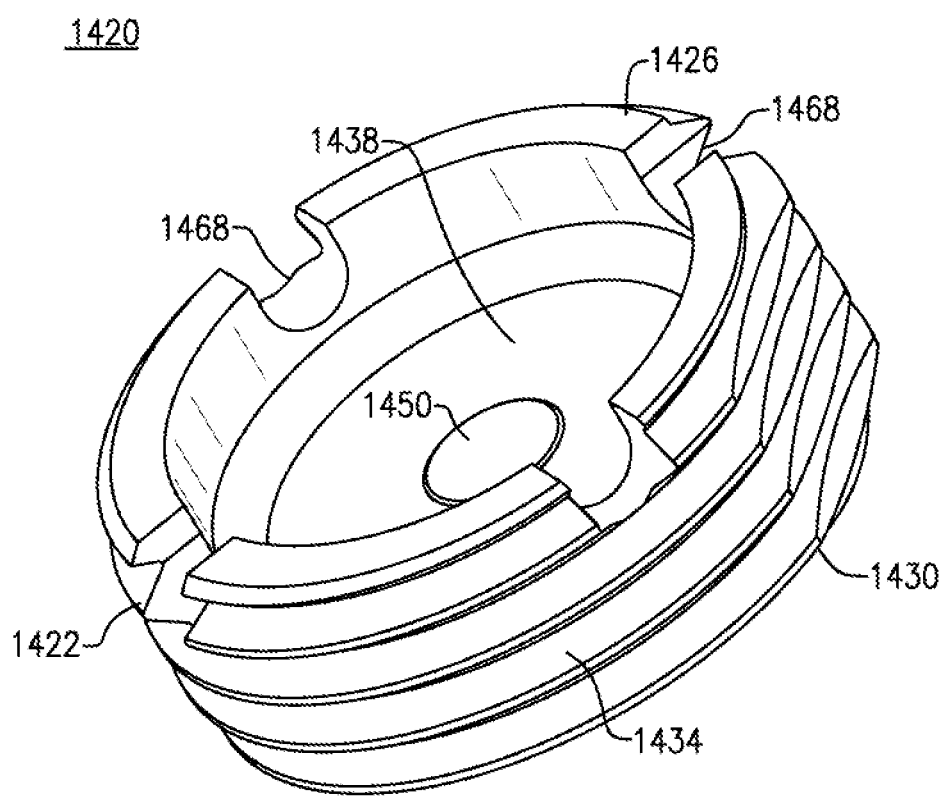
FIG. 36 is a top perspective view of the integrated component of FIGS. 34 and 35.

According to this particular embodiment, a series of notches 1468 are provided in spaced relation along the upper end 1426 of the integrated component 1420, as shown in FIG. 35. The notches 1468 are shaped and configured to accept protrusions provided in a complementary driving or torqueing tool (not shown) for purposes of assembly. The printed circuit board 1274 according to this embodiment further includes an outer ground ring that makes intimate electrical contact with a metal stud. The threaded connection between the integrated component 1420 and the interface stud 1150 of the instrument head insures a secure high pressure mating at this junction. As noted, the domed portion 1450 collimates illumination from the LED 1270. Advantageously, the design of the integrated component 1420 serves to save manufacturing costs and labor and also reduces tolerance build ups, as well as preventing or minimizing ingress of dirt and contaminants.

Figure 37:
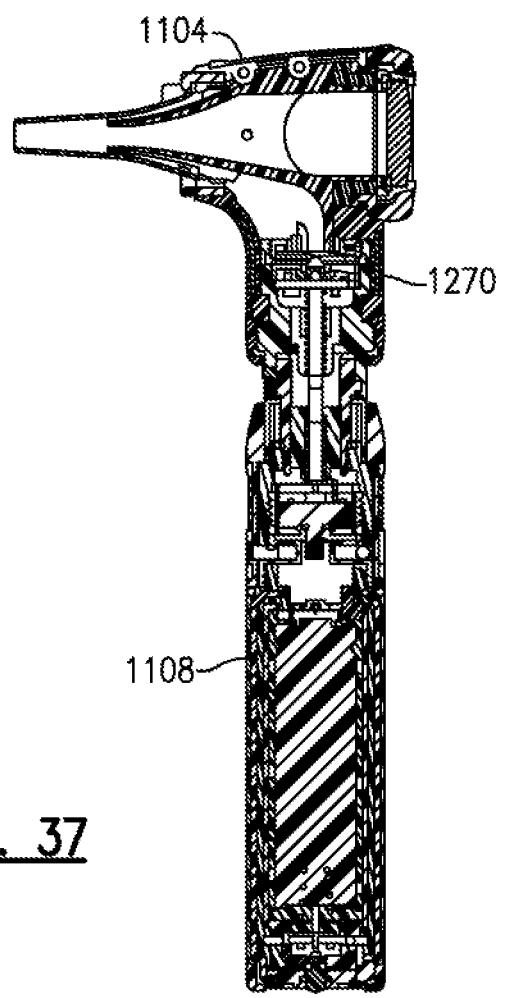
FIG. 37 is an side elevational view in section of the physical assessment device of FIG. 21.

An embodiment depicting the interconnection between an instrument head 1104 and instrument handle 1108 for the physical assessment device 1100 of FIG. 21 is illustrated in the sectioned view of FIG. 37. As shown, the instrument handle 1108 is a substantially cylindrical member having an upper or top end and an opposing lower end, as well as at least one interior compartment that is sized and configured to retain at least one battery for powering the contained light source in the instrument head 1104. It should be noted that similar connections are provided for the instrument heads previously described in this application.

Each of the instrument heads 1104, 1204 such as those shown in FIGS. 27 and 28 and having an LED 1270 as a contained light source can be interchangeably attached to the instrument handle 1108 by means of a bayonet connection between the top end of the instrument handle 1108 and the narrowed neck portion of the instrument head 1104. Known physical assessment devices, such as those commercially sold by Welch Allyn, Inc provide a bayonet connection between the instrument head and the instrument handle. More specifically, a set of spaced lugs are provided on the top of the instrument handle that engage a corresponding slot formed in the lower end of the instrument head when the instrument head is twisted in a predetermined direction.

As noted, each of the previously described instrument heads, including instrument heads 1104, 1204 or 104, FIG. 13(*b*), 104A, FIG. 5(*a*), include an LED as a light source for the contained illumination assembly.

There is a need with the evolution of LEDs as light sources in physical assessment devices to prevent instrument handles, especially those wired to wall mounted systems that will not power instrument heads equipped with halogen lamps. Halogen lamps draw large currents and the associated voltage drop through wall unit power cords. This voltage drop makes compliance with safety standards difficult and forces the further inclusion of expensive electronics. LED systems, on the other hand, draw relatively small currents and do not have this drawback. As instrument heads evolve and utilize LED as illumination sources, it is anticipated these instrument heads can be used with existing instrument handles. However and as wall mounted systems also evolve, it is a desire to prevent the use of existing instrument heads having halogen lamp light sources.

Figure 38:
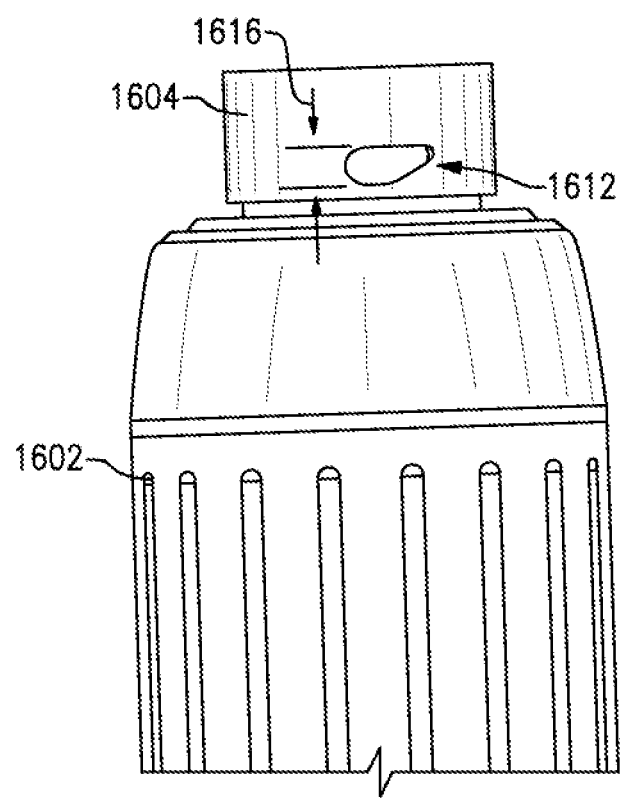
FIG. 38 is an enlarged elevational view of the top of an instrument handle of a physical assessment device in accordance with an embodiment.

With reference to FIGS. 37-43, an embodiment is herein described to enable an instrument handle to be incompatible with certain instrument heads (i.e. those having halogen lamps). With reference to FIG. 38, an instrument handle 1602 includes a top portion 1604. A pair of equally spaced male lugs 1612 are provided on the exterior of the top portion 1604 of the instrument handle 1602. Each lug 1612 according to this embodiment is defined by a width dimension denoted by arrows 1616 that enables the lug 1612 to be fitted within a defined bayonet slot of a mated instrument head.

Figure 39:
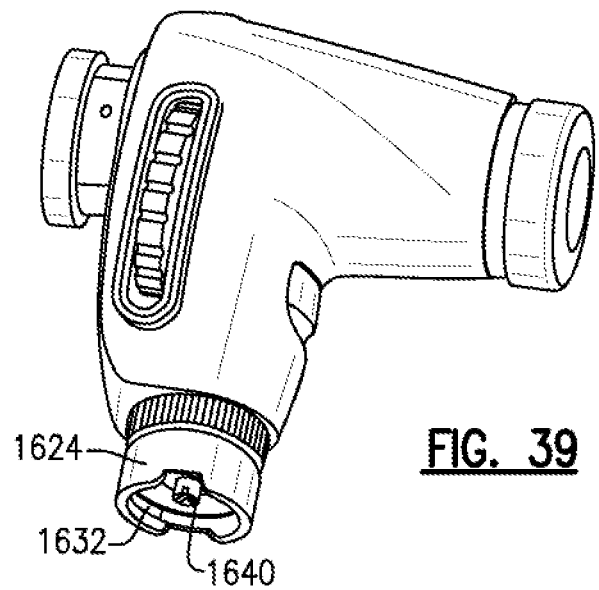
FIG. 39 is a bottom perspective view of an instrument head configured to engage the instrument handle of FIG. 38.
Figure 40:
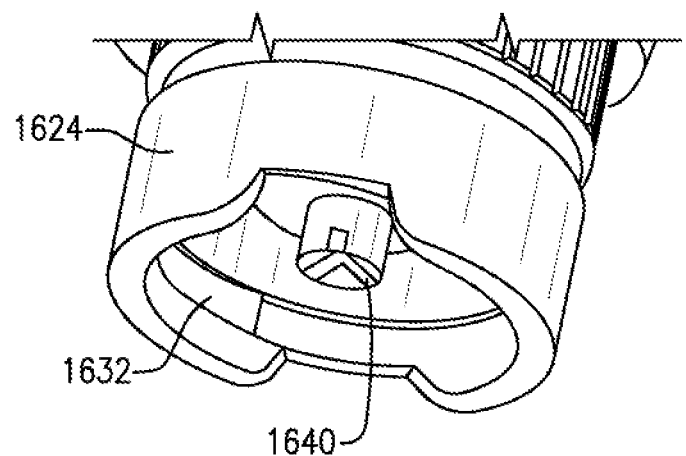
FIG. 40 is an enlarged portion of the instrument head of FIG. 39.

An instrument head 1620 is shown in FIGS. 39 and 40. In this instance, the physical assessment device is an ophthalmoscope, but the principle is common to other physical assessment devices, such as the previously described otoscopes. The mating connection is provided at the bottom of the instrument head 1620 and includes an interface stud 1624 whose bottom end 1628 is defined with a contoured slot 1632 to provide a secure locking engagement when the instrument head 1620 is rotated relative to the instrument handle 1602 by means of a bayonet connection.

Figure 41:
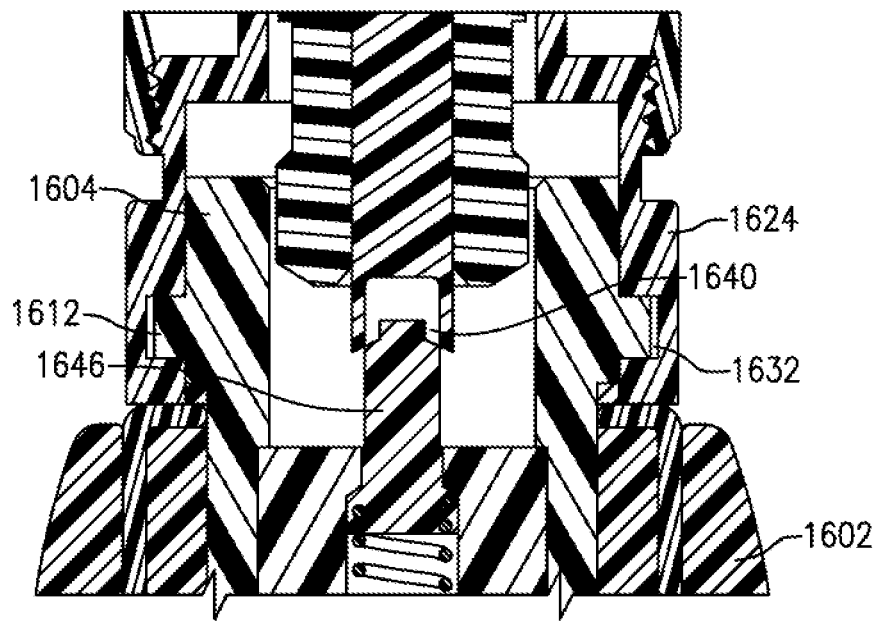
FIG. 41 is a partial sectioned view of the physical assessment device of FIG. 37, depicting the engagement between the instrument head and instrument handle.
Figure 42:
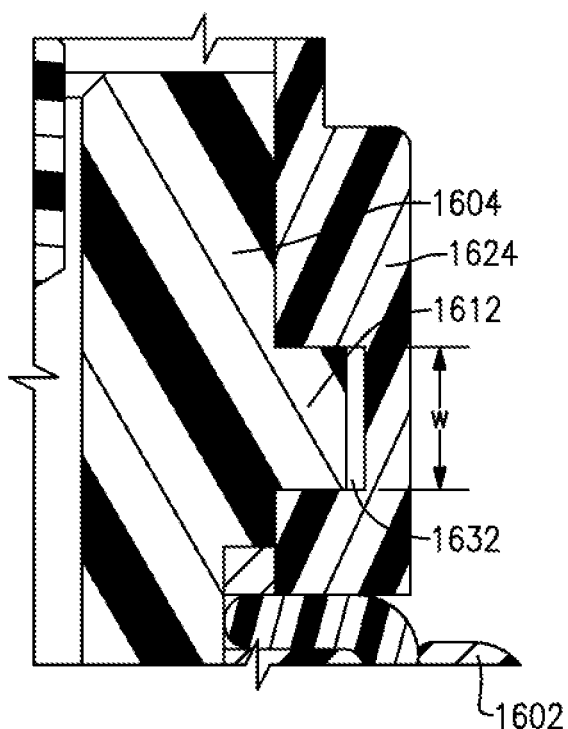
FIG. 42 is an enlarged view of a portion of FIG. 41.
Figure 43:
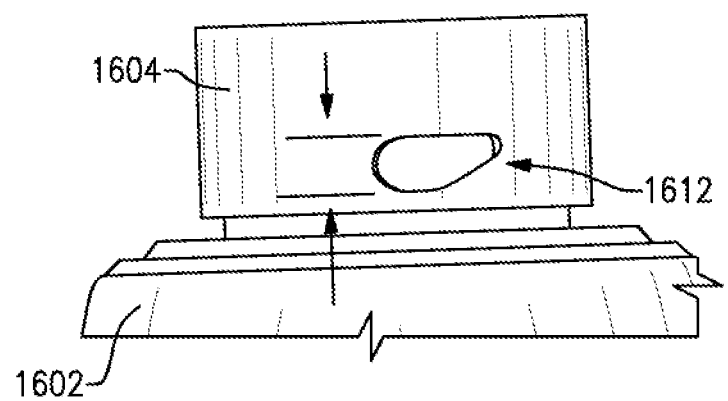
FIG. 43 is an enlarged portion of the instrument handle of FIG. 38.

The assembled interface is shown more clearly in FIGS. 41 and 42 with each of the spaced lugs 1612 of the instrument handle 1602 engaged within the contoured mating slot 1632 of the instrument head 1620. In this mounted position, the electrical contacts 1640, 1646 of the instrument head 1620 and the instrument handle 1602 are positioned into contact with one another. For purposes of this embodiment and referring to FIG. 42, the width dimension of the contoured mating slot 1632 is increased enabling interchangeability between various instrument heads and handles. With reference to FIG. 43, the width dimension of the mating lugs 1612 of the instrument handle 1602 can be increased such that the lugs 1612 will not fit within the mating slot (not shown) of an already existing ophthalmic instrument head having a halogen light source.

Figure 33:
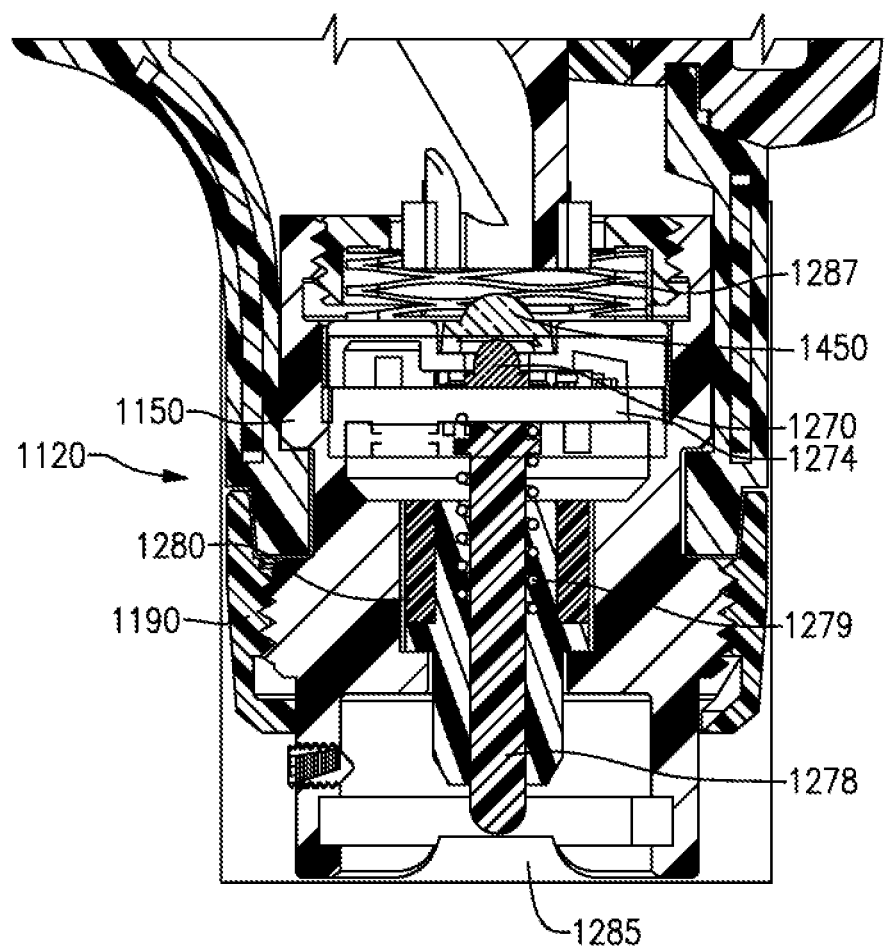
FIG. 33 is a sectioned partial view of an instrument head of a physical assessment device in accordance with an embodiment.
Figure 34:
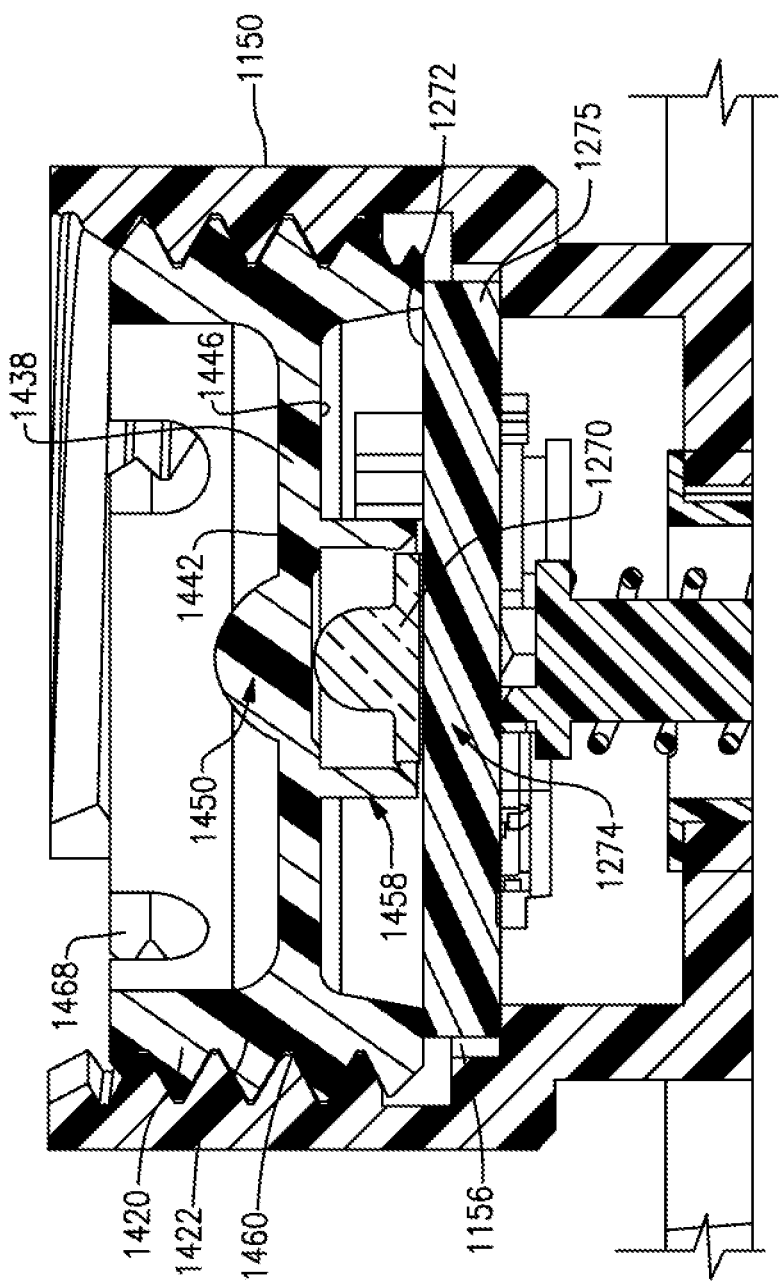
FIG. 34 is an enlarged sectioned view of a portion of the instrument head of FIG. 33, including an integrated component of the illumination assembly used for centering a contained LED and collimating light emitted from the LED.
Figure 44:
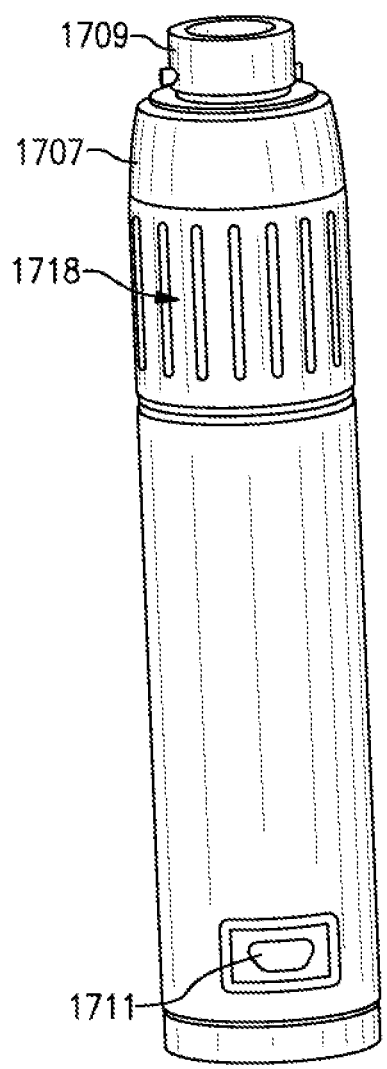
FIG. 44 is an elevational view of an instrument handle for a physical assessment device in accordance with an embodiment.
Figure 45:
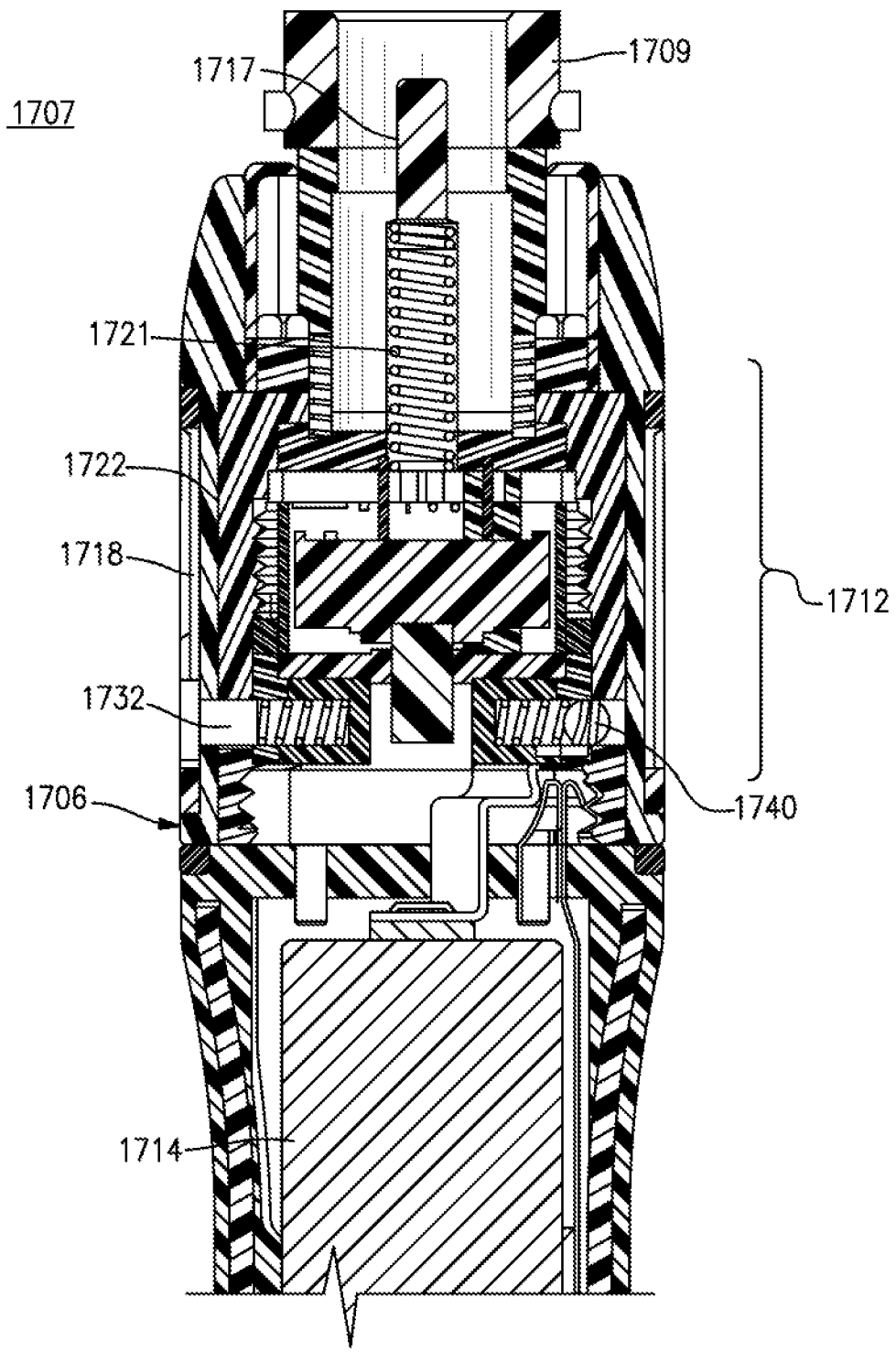
FIG. 45 is a sectioned partial view of the top of the instrument handle of FIGS. 37 and 38.
Figure 46:
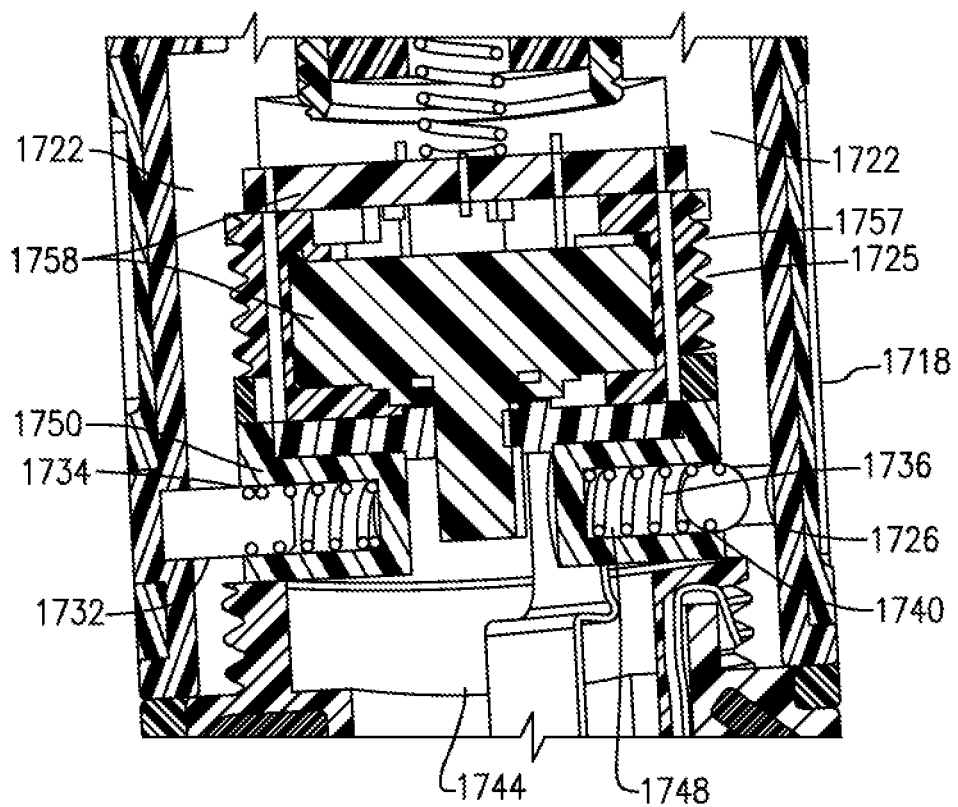
FIG. 46 is a partial sectioned view of the instrument handle of FIGS. 37 and 45, depicting aspects of a rheostat assembly in accordance with an embodiment.
Figure 47:
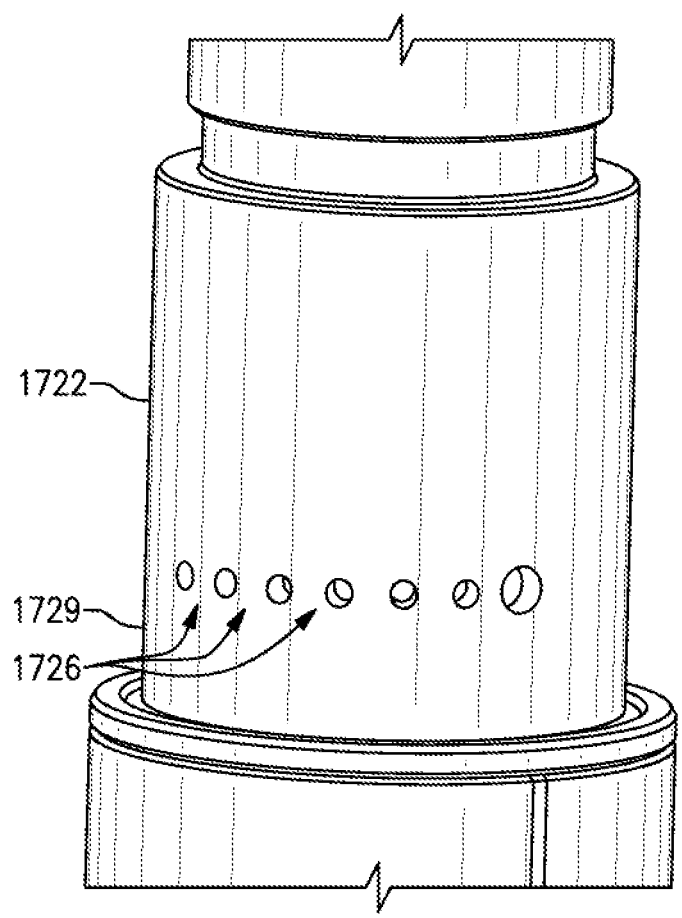
FIG. 47 is a perspective view of a detent ring member of the rheostat assembly of FIG. 46.

Referring to FIG. 44, an exemplary instrument handle 1706 is shown having a upper end 1707 including a top portion 1709 and an opposing bottom end 1711. A partially sectioned view of the upper end 1707 of the instrument handle 1706 is further depicted in FIG. 45. More specifically, the upper end 1707 includes a rheostat assembly 1712 that selectively adjusts the level of illumination of the retained light source, such as the at least one LED 1270, FIG. 33, when the instrument head (not shown) is attached to the instrument handle 1706. This connection is made using bayonet engagement features provided on each of the mated components such as those previously discussed. When connected, the LED 1270, FIG. 33, is powered through coupling between the retained battery 1714 (partially shown in FIG. 45), the rheostat assembly 1712, the electrical contact 1717 biased by spring 1721 and the electrical contact 1640, FIG. 40, in order to electrically couple the LED 1270, FIG. 33, with the battery 1714.

Referring to FIGS. 45-48 and according to one embodiment, the rheostat assembly 1704 includes a twistable grip section 1718 that is provided on the exterior of the instrument handle 1706. The twistable grip section 1718 is disposed over a cylindrically shaped detent ring member 1722 having a series of holes 1726 arranged along its periphery proximate a lower end 729 of the detent ring member 1722, as shown more clearly in FIG. 47. A pin member 1732 extends within an annular recess 1734 formed in the detent ring member 1722 and is biasedly retained within a recess 1736 formed in an internal sleeve 1750. A ball 1740 is also biasedly retained in an opening formed in the internal sleeve 1750 which is diametrically opposite that of the pin member 1732. The ball 1740 is configured to rotate with the twistable grip section 1718 and is caused to extend into one of the holes 1726 in the detent ring member 1732, the latter being stationary to create an audible and tactile sensation for the user. Each of the ball 1740 and the pin member 1732 are biased by springs 1744, 1748 which are disposed within the diametrically opposed openings in the internal sleeve 1750 extending in a direction that is transverse to a primary axis of the instrument handle 1706. The detent ring member 1732 includes the set of interior threads 1725 that engage a corresponding set of external threads 1757 provided on a rheostat housing 1758.

In operation, the twistable grip section 1718 rotates around the stationary detent ring member 1722. The pin member 1732 keys into the twistable grip section 1718 and rotates with the grip section 1718 when twisted by a user. The spring-loaded ball 1740 also rotates with the twistable grip section 1718 and depending on the rotational position of the grip section 1718 detents into one of the series of holes 1726 provided in the stationary detent ring member 1722. Attributes of the spring 1748 biasing the ball 1740 can be suitably varied as needed in order to provide a desired detent release force. The foregoing provides audible and tactile feedback about the location of the rheostat. This feature allows a user of the instrument to create a preferred setting which can repeated to obtain a consistent amount of light with each use. The detent positions and size and configuration of the detent stops can be altered in order to provide a different sound or release strength at different or selected positions, such as the zero position or other rheostat position.

Figure 48:
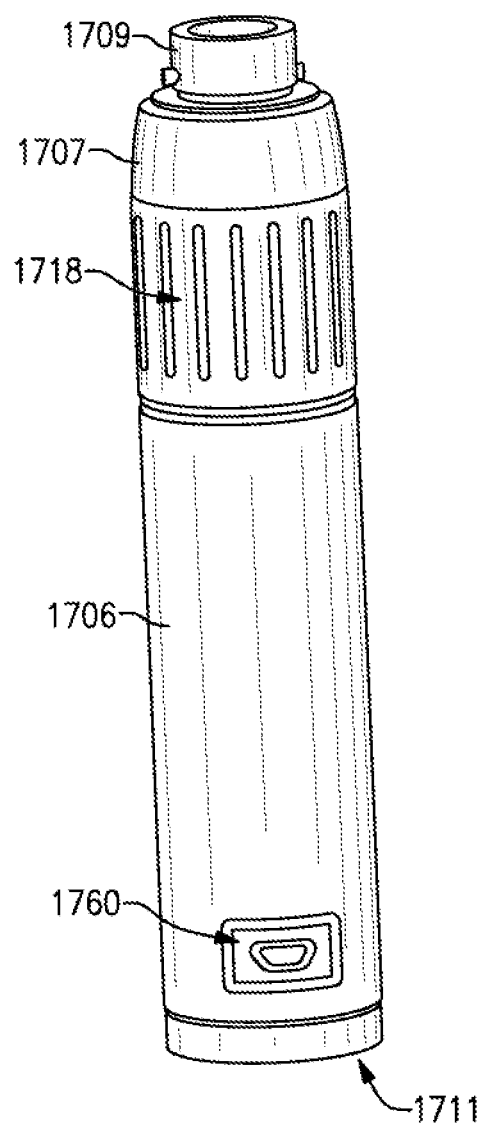
FIG. 48 is a perspective view of an instrument handle made in accordance with another embodiment.
Figure 49:
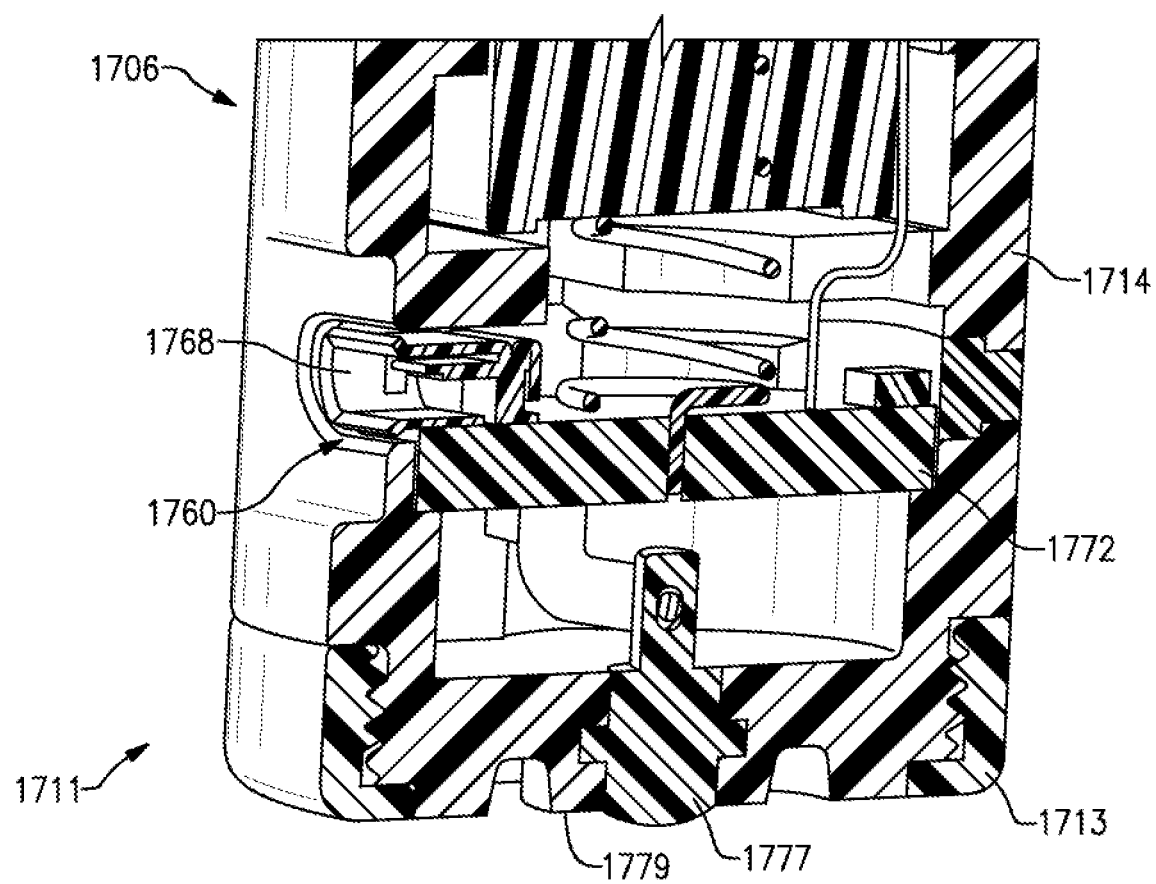
FIG. 49 is a partial sectioned view of the instrument handle of FIG. 48, depicting a USB charging port.

With reference to FIGS. 48 and 49, the instrument handle 1706 can be equipped with a USB charging or power boosting port 1760. According to this embodiment, the USB port 1760 is provided on the exterior of the instrument handle 1706 and proximate the bottom or lower end 1711. It will be understood, however, that the location of this port 1760 can be suitably varied relative to the instrument handle 1706. With reference to the sectioned view of FIG. 49 and according to this embodiment, the charging port 1760 extends to a USB connector 1768 mounted to the top surface of a printed circuit board 1772 that is disposed within the interior of the instrument handle 1706 in which contacts extend to the contained battery 1714 (partially shown in this view). According to this embodiment, a set of electrical charging contacts axially extend from the lower end 1709 of the instrument handle 1706 enabling the instrument to be used in conjunction with a charging base or cradle 1800, FIG. 52, that enables the at least one contained battery 1714 to be recharged.

Figure 50:
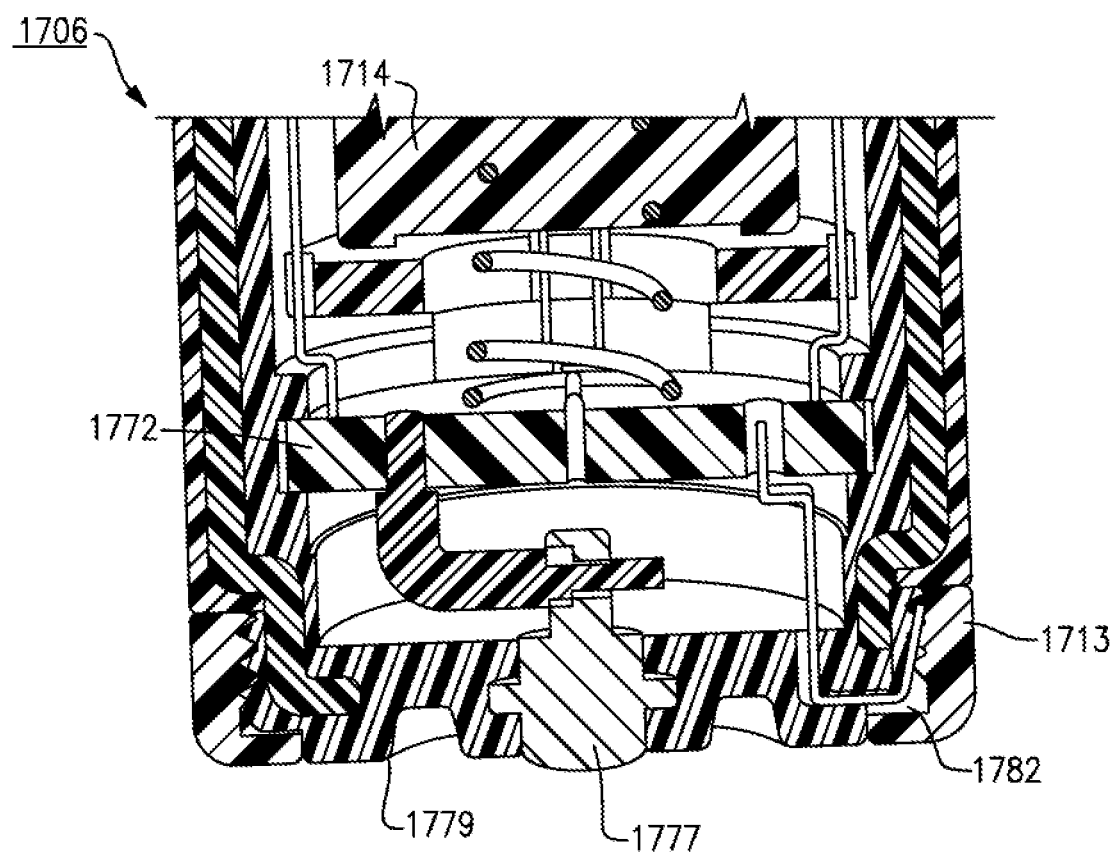
FIG. 50 is a sectioned view of the instrument handle of FIGS. 48 and 49, illustrating battery charging contacts.

According to this embodiment and with reference to FIGS. 49 and 50, a positive contact 1777 extending from the lower end 1709 of the instrument handle 1706 is soldered to the printed circuit board 1772 via a connection 1779 and a conductive spring clip 1782 is provided to serve as a negative contact connecting an outer ring 1713 at the bottom end 1711 of the instrument handle 1706 with the printed circuit board 1772, the latter being electrically coupled to the lower contact end of the battery 1714. As such, the herein described instrument handle 1706 can be configured with dual charging modes.

The norm in the medical industry is to charge the instrument handle (power source) through either a desk charger or more recently using USB. With reference to FIG. 50, a circuit is depicted that allows one or more instrument handles to be charged through a desk charger, such as base 1800, or the USB charging port 1760. This charging circuit uses a charging IC and accepts power from either a USB input or via positive and negative contact pins.

Figure 51:
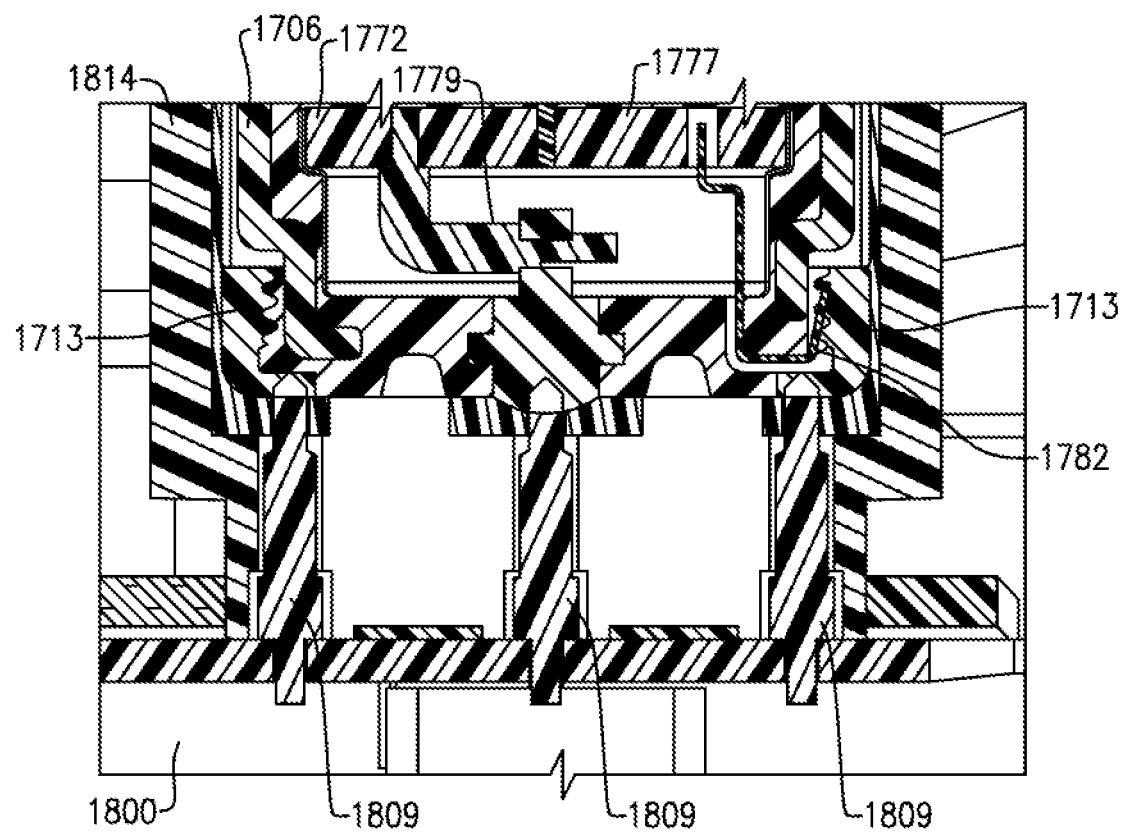
FIG. 51 is the sectioned view of FIG. 50, illustrating the engagement of the instrument handle with a charging base or cradle.

FIG. 51 illustrates a sectioned view of the alternative charging mode with the electrical contacts 1777 and 1782 being coupled to respective charging pins 1809 that are provided within a charging well 1814 of the charging base 1800, which is only partially shown in this view.

Figure 52:
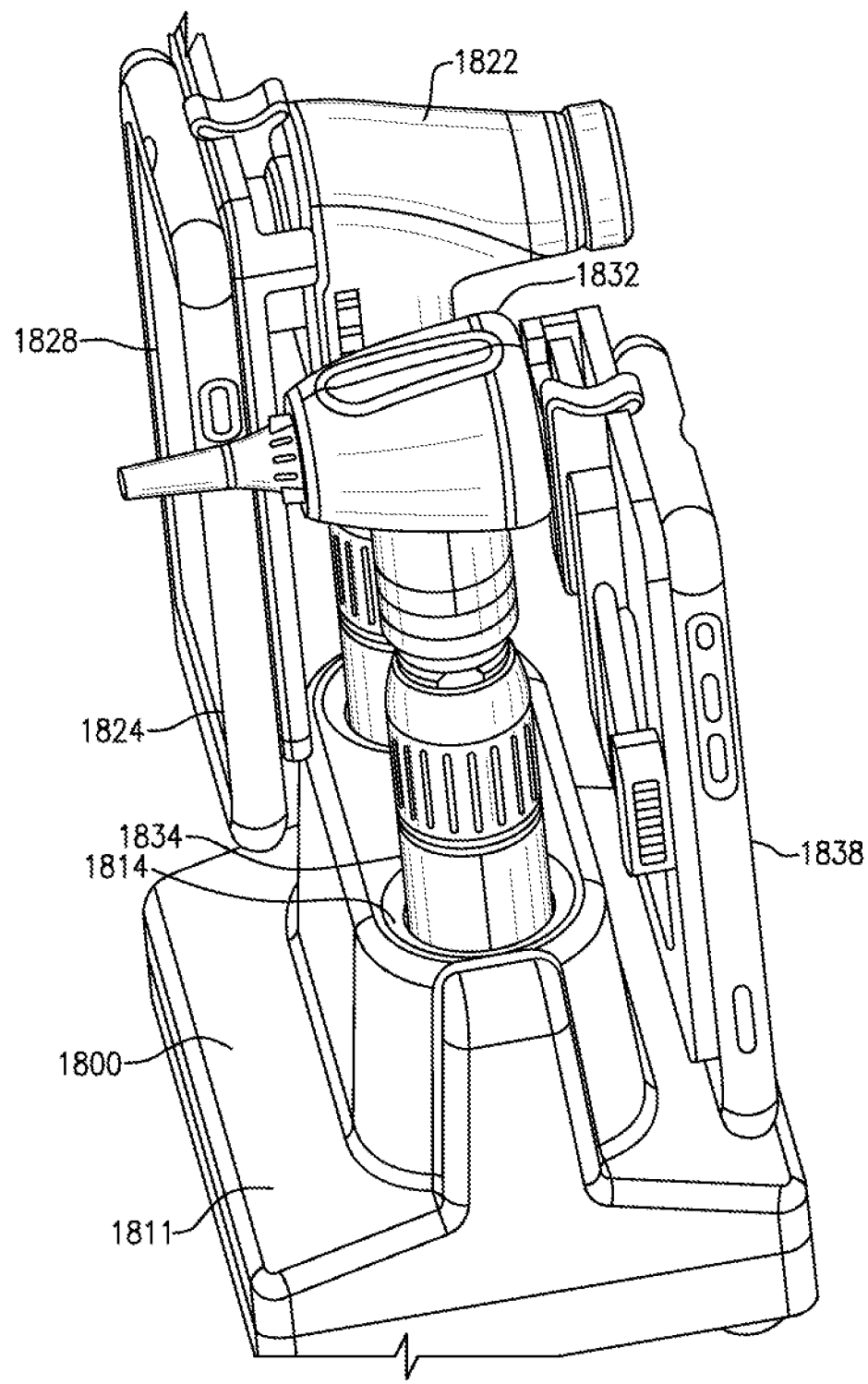
FIG. 52 is a perspective view of a charging base or cradle having a pair of physical assessment devices attached thereto.

FIG. 52 provides a perspective view of a charging base 1800 made in accordance with an embodiment and including a pair of charging wells 1814 extending from a top surface 1811. Each of the charging wells 1814 are sized to receive an instrument handle 1822, 1832 of a physical assessment device 1820, 1830 and provide a stable base, the charging wells 1814 having a defined height that creates a stable base for the retained physical assessment devices 1820, 1830. With continued reference to FIG. 52, a pair of physical assessment devices 1820, 1830 and more specifically, an ophthalmoscope and an otoscope are commonly retained in separate charging wells 1814 of the charging base 1800 in which each of the retained devices 1820, 1830 includes an attached smart device 1828, 1838, such as a smart phone. The two physical assessment devices 1820, 1830 are mounted at the same time, as shown, with the respective instrument handles 1824, 1834 being inserted into the charging wells 1814 such that the retained smart devices 1828, 1838 are opposed to one another. In this mounted position, there is with no interference between the mounted devices or between either retained physical assessment device 1820, 1830 and the charging base 1800.

Figure 53:
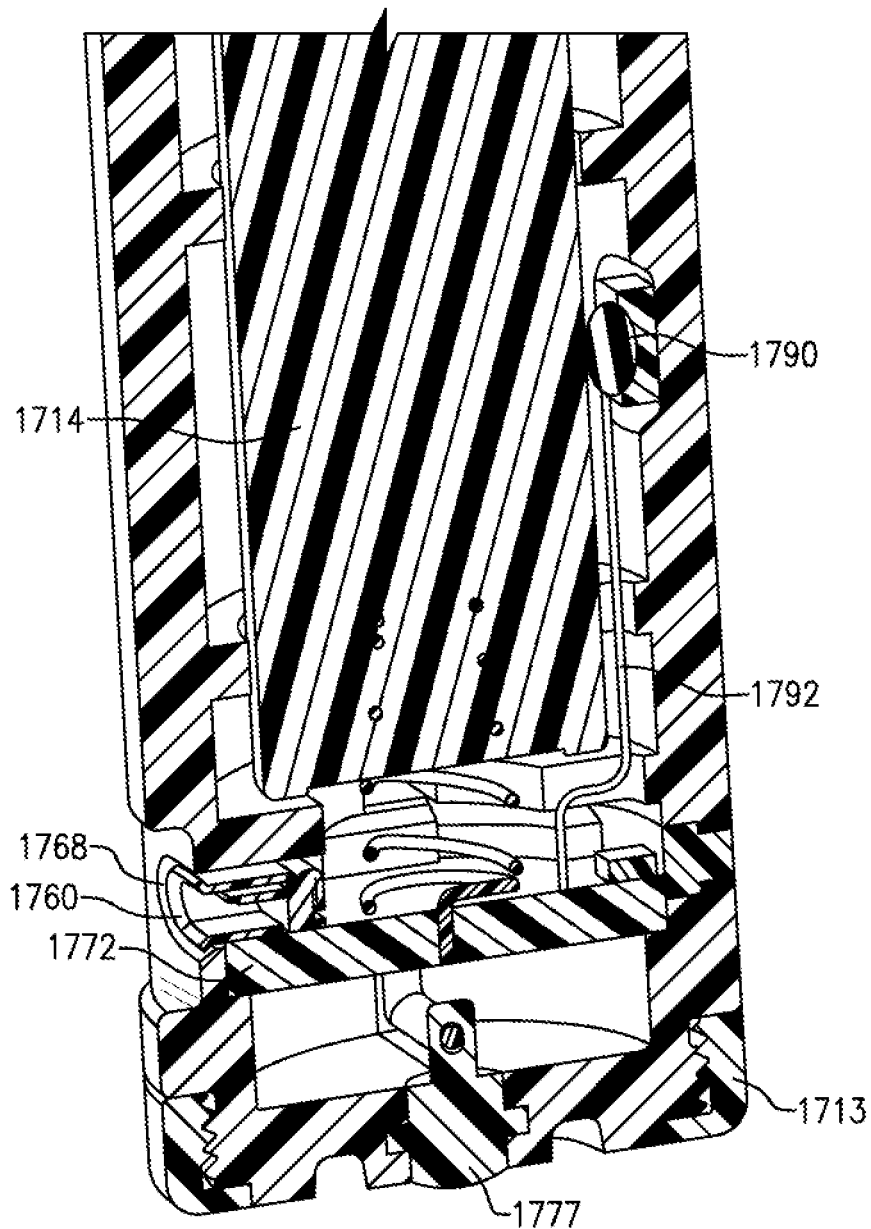
FIG. 53 is a sectioned view of an instrument handle including a feature for detecting overheating of a contained battery.

According to one version and as shown in FIG. 53, a thermistor, thermocouple 1790 or other temperature determining apparatus can extend from the printed circuit board 1772 within the instrument handle 1706 by connection 1792 and be disposed in relation with the contained battery 1714. The output of the thermistor 1790 provides direct battery temperature measurement during charging and discharging of the battery 1714 which can further be coupled to an indicator (not shown) on the charging base 1800, FIG. 52, or the instrument handle 1706. As such, potential overheating of a contained battery, such as an alkaline battery, can be monitored.

Due to the fact that both halogen lamp based and LED-based instrument heads may be used interchangeably, instrument handles should be designed so as to prevent overheating of a contained alkaline battery, especially if a halogen-based instrument head is attached.

An example of an electrical circuit intended to solve this problem is depicted in FIG. 53, preventing overheating of a contained battery. The electrical circuit employs a voltage boost design with input current limit (such as Texas Instruments TPS 61251). With this circuit's design, a current limit can be set on the voltage boost IC so that if a halogen based lamp is connected to the instrument handle having an alkaline battery, the current will be limited and not exceed the battery's limit that would cause overheating.

In addition, this voltage boost IC will enable improved performance of an instrument head that is equipped with an LED as a light source and subsequent use of LED replacement lamps.

As discussed, the interior of at least one of the herein described instrument heads 104, FIG. 2(*b*), FIGS. 13(*b*) and 1204, FIG. 28, can retain an optical system or assembly that includes a plurality of components aligned along an optical or viewing axis extending through the distal end opening 124, 1125 of the hollow speculum tip element 120, 1124, which is releasably attached to the instrument head 104, 1204 and continuing through the interior of the instrument head 104, 1204, passing through the proximal end 1014, 1216 thereof.

Reference is herein made to FIG. 54(*a*), which depicts a ray trace of the optical system or assembly 1900 of the physical assessment device 100, FIGS. 2(*b*) and 13(*b*) and FIG. 54(*b*), providing a comparison between three (3) additional optical assemblies 1910, 1940 and 1950 for an exemplary instrument head, including that of instrument head 1204. The bottommost optical assembly 1910 depicted is representative of a known optical assembly which is fully described in U.S. Pat. No. 7,399,275, and incorporated herein by reference in its entirety.

First and with reference to FIG. 54(*b*), the known optical assembly 1910 includes a distal objective lens doublet 1914 that would be disposed proximate the distal opening of the distal insertion portion 1160, FIG. 28, of the instrument head 1204 having an attached speculum tip element 1124. A pair of aligned relay lenses 1919, 1922 are disposed proximally to the objective lens doublet 1914, as well as an aperture plate 1920 disposed between the pair of relay lenses 1919, 1922. A set of eyepiece lenses 1930 is disposed proximally from the second relay lens 1922, each aligned along a defined optical axis. This optical assembly 1910 produces an entrance pupil (shown as 1934) that is proximate to, but distal relative to the objective lens doublet 1914, and creating a field of view that enables the entire tympanic membrane to be viewed all at one time at the image plane of the clinician's eye, if viewed optically, or the image plane of an attached digital imager (not shown). More specifically, this optical assembly 1910 produces a field of view of about 9 mm at a working distance (distance between the distalmost optic and the patient) of about 33 mm, which allows the entire tympanic membrane (about 7 mm) to be viewed all at one time. Though this optical assembly 1910 is highly effective due to the increased field of view, the resulting image is influenced by the attached speculum tip 1124, as shown in the top illustration of FIG. 55.

Figure 54B:
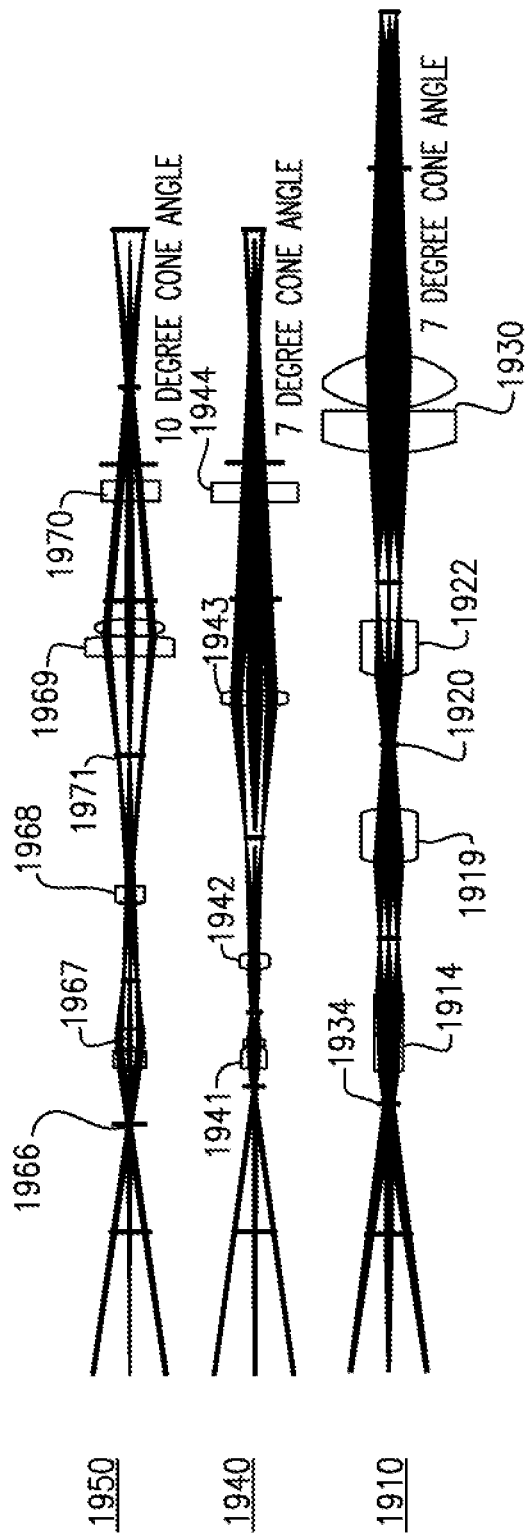
FIG. 54(b) depicts a comparison of layouts between an optical assembly of a known physical assessment device with other versions in accordance with various embodiments of the invention.

Referring to FIG. 54(b), two other optical assemblies 1940 and 1950 are shown and compared to optical assembly 1910 as well as FIG. 54(a), which illustrates the optical assembly 1900 of instrument head 100, FIG. 2(b), FIG. 13(b). More specifically, the optical assembly 1940 includes in order and arranged from distalmost to proximalmost: an objective lens 1941, relay lens 1942, field stop 1945, imaging lens 1943 and a plano window 1944. The optical assembly 1950 is similarly defined starting from the distal end and moving toward the proximal end by an objective lens 1967, relay lens 1968, a field stop 1971, an imaging lens doublet 1969 and a plano window 1970. The optical assembly 1900, FIG. 54(a) is similar to the optical assembly 1950 and is defined by the following elements from distalmost to proximalmost: an optical window 161 disposed distally relative to an objective lens 160 separated by a field stop 164, FIG. 4, that reduces light scatter, a relay lens 166, an aperture plate 167, FIG. 4, a field stop 170, FIG. 4, an imaging lens 169 and a window 189 provided at the proximal end of the assembly 1900.

The optical components of each of these optical assemblies 1900, 1940, 1950 are also configured to create an entrance pupil that is distal from the distalmost optical element 160/161, 1941, 1967, respectively.

Figure 55:
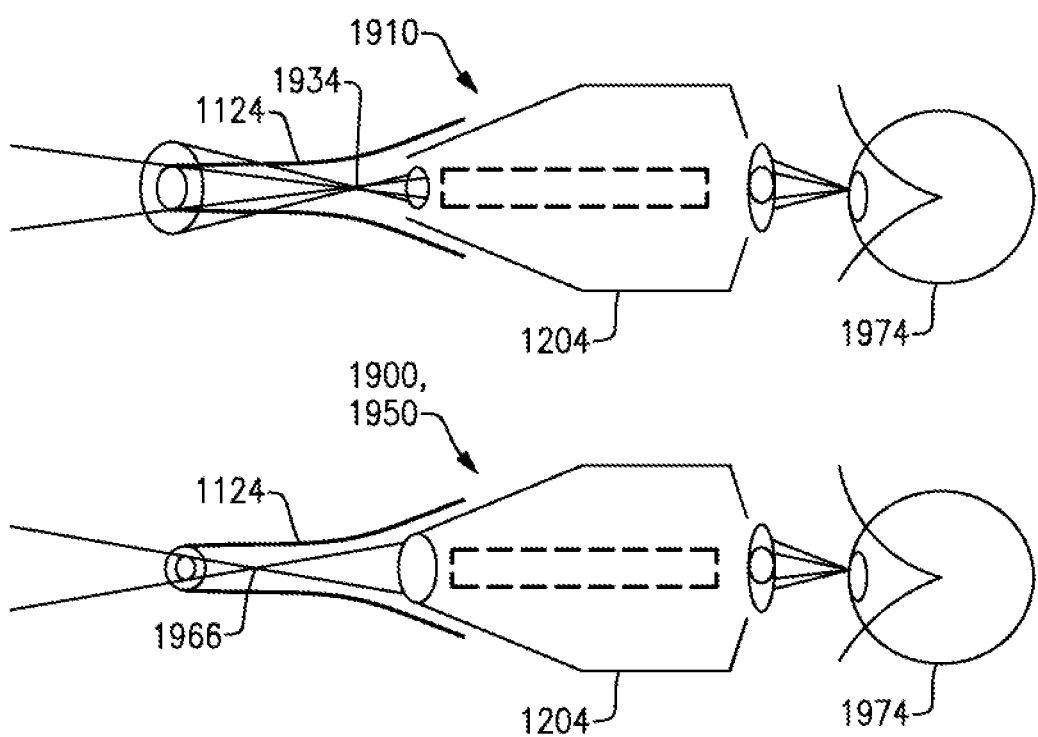
FIG. 55 illustrates the advantageous effect of the inventive optical assemblies of FIGS. 54(a) and 54(b) relative to an attached accessory of the physical assessment device, as compared to an existing optical assembly.

The overall effect is shown in the schematic comparative view depicted in FIG. 55, contrasting the known optical system 1910 with optical assemblies 1900 and 1950 in which each optical assembly is disposed within the instrument head 1204 for purposes of comparison. A similar field of view is created by each of the optical assemblies 1900, 1950, but the distal entrance pupil 1966 created by each of the latter optical assemblies 1900, 1950 is moved distally toward the patient, as compared with that of the distal entrance pupil 1934. Consequently, the cone of light rays does not chop the attached speculum tip element 1124 and enabling the tympanic membrane to still be viewed all at one time by the caregiver, but without any portion of the speculum tip element 1124 being in the resulting image.

Surprisingly and resulting from the above optical system, Applicants have further discovered that the attached speculum tip element can be made optically clear, as opposed to the typical black opaque versions of these elements. The resulting light spot produced is clear, crisp and well defined without edge effects.

Figure 56:
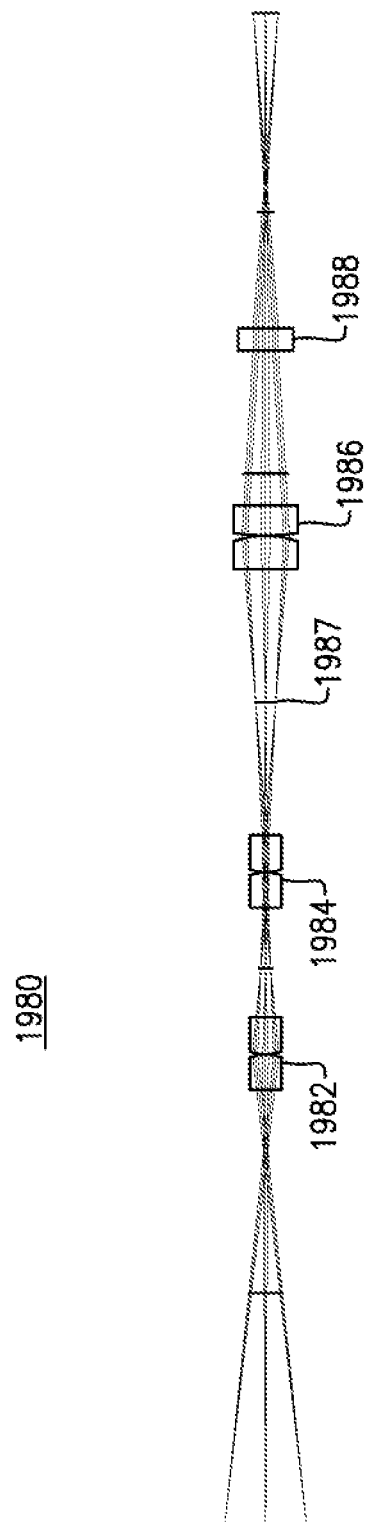
FIG. 56 is a layout of an alternative optical system, which is defined having glass components in lieu of plastically molded components.

Another alternative optical assembly 1980 is depicted schematically in FIG. 56 based on a change in materials that produces a similar overall effect (distal entrance pupil 1966, FIG. 55) upon a resulting image of the medical target. In the optical assemblies 1900 and 1950, each of the optical elements are made from a moldable plastic, while the optical elements according to this latter optical assembly 1980 are made from glass. More specifically, two (2) glass lenses are used in place of a plastic aspheric lens for each of the objective lens 1982, relay lens 1984 and eyepiece lens 1986 wherein the two glass lenses achieve image quality by two facing plano-convex lenses of high index of refraction (greater than 1.80) and abbe value greater than 35. The optical assembly 1980 further includes a plano window 1988. It will be understood that similar configurations are possible.

Ophthalmoscope

The following portion of the description relates to the design of another physical assessment device that is made in accordance with various exemplary embodiments. More specifically, the physical assessment device is an ophthalmic device that is configured for examining the eyes of a patient. It will be understood, however, to those in the field that certain of the inventive aspects described herein can be applied to various other medical examination or diagnostic devices.

Figure 57A:
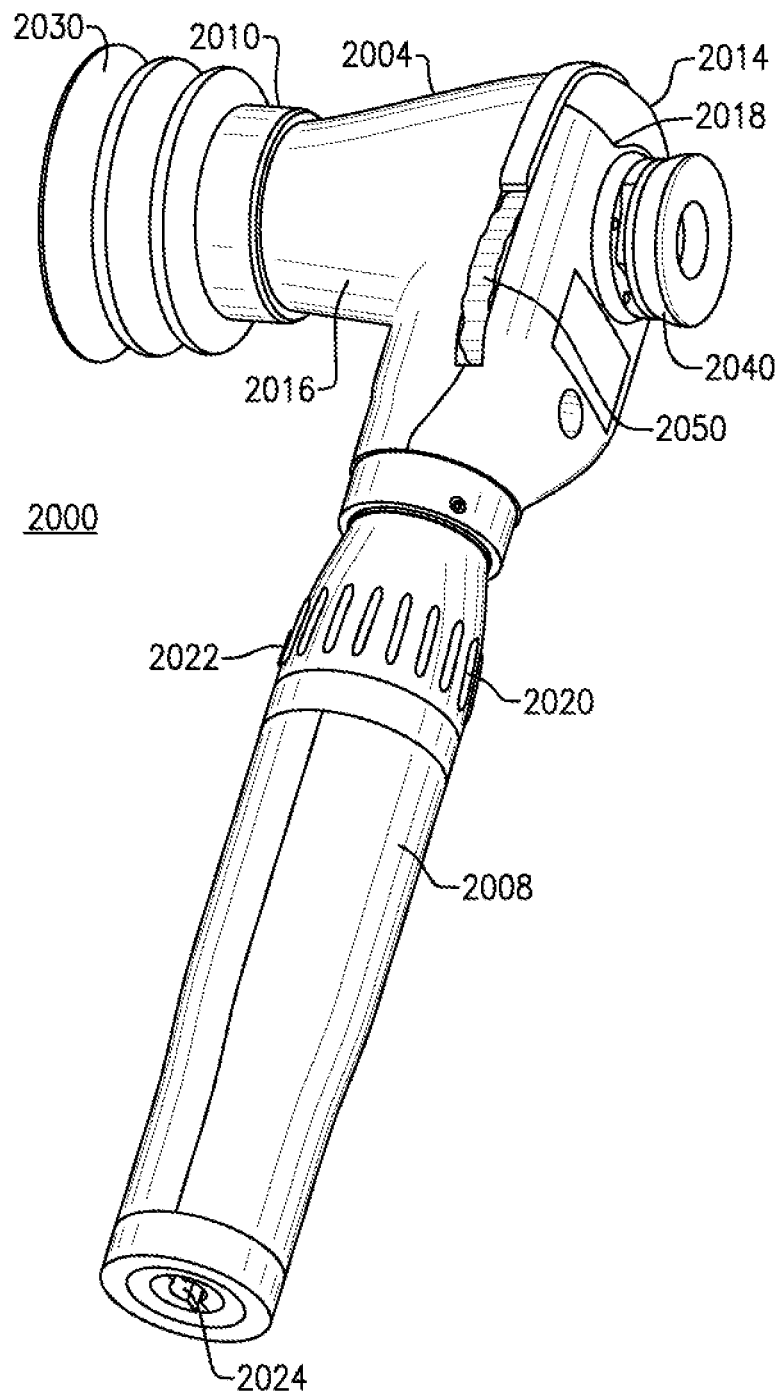
FIGS. 57(a) and 57(b) are side perspective views of a physical assessment device made in accordance with another embodiment.
Figure 57B:
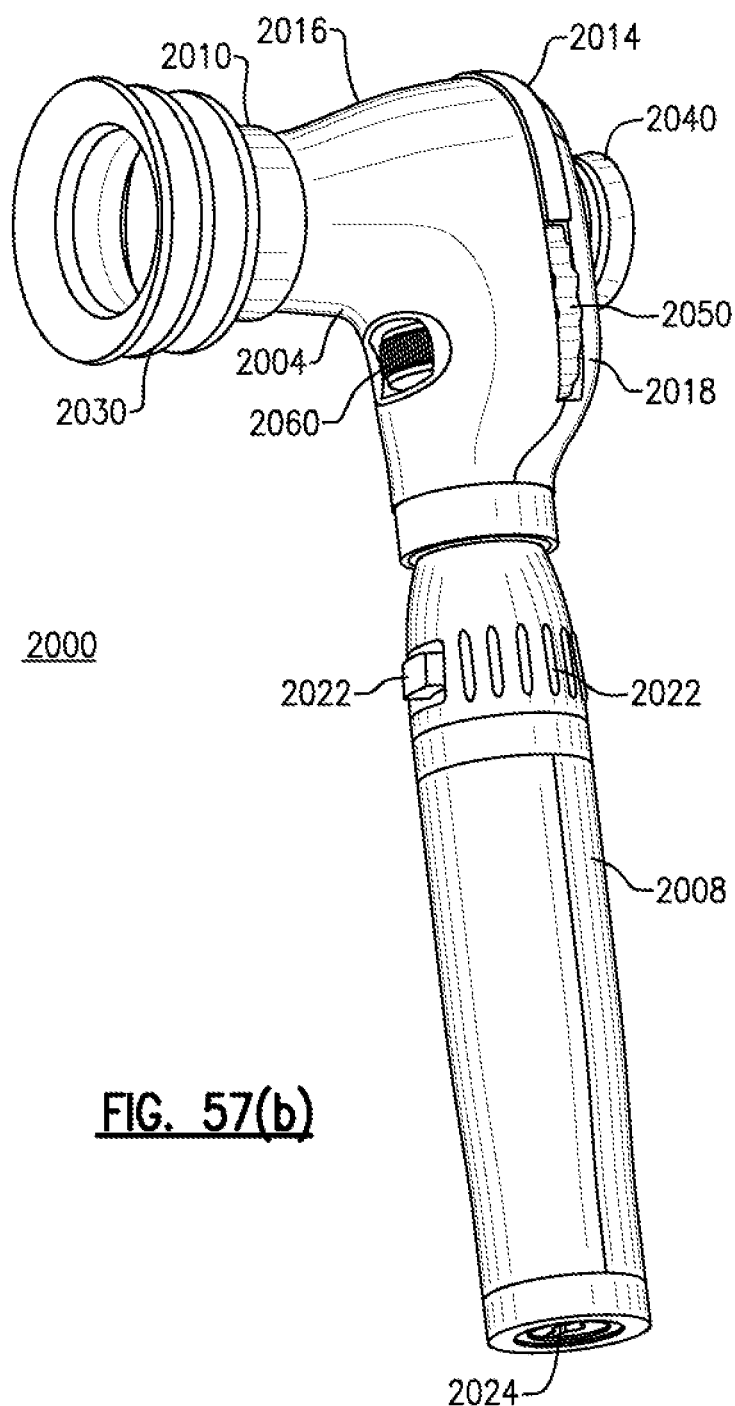

With reference to FIGS. 57(a) and 57(b), the ophthalmoscope 2000 includes an instrument head 2004 that is releasably supported to the upper end of a handle or handle portion 2008 using a bayonet or similar connection, the handle portion 2008 enabling the instrument 2000 to be portable and configured for hand-held use. The handle portion 2008 includes at least one contained battery (not shown) for powering a light source (i.e., an LED—not shown) provided in the instrument head 2004. In addition, a rheostat 2020, which includes a rotatable portion of the handle portion 2008 is configured to control the amount of illumination of the light source, as well as a depressible on-off button 2022. The contained battery is preferably rechargeable, wherein the lower portion of the handle portion 2008 includes a charging port 2024.

The instrument head 2004 is defined by a distal (patient) end 2010 and an opposing proximal (caregiver) end 2014, and further defined by an interior that is sized and configured to retain a plurality of components. As described in greater detail below, the distal end 2010 of the instrument head 2004 receives a deformable eye cup 2030, while the proximal end 2014 of the instrument head 2004 includes an adapter interface member 2040, similar to the adapter interface member 180, FIG. 2(a), and 1224, FIG. 30, to enable releasable attachment of a smart device adapter 300, FIGS. 6-13(b). The instrument 2000 further includes a rotatable diopter wheel 2050 supported between mating front and rear housing sections 2210 and 2214, as well as an rotatable aperture wheel 2060, the latter being disposed in a lower portion of the instrument head 2004 and having a portion of the aperture wheel 2050 extending outwardly from a formed slot that is provided in the front housing section 2210.

An optical assembly and an illumination assembly are commonly retained within the interior of the instrument head 2004. According to this exemplary embodiment and with reference to FIGS. 58, 59(a) and 59(b), the distal most component of the optical assembly is an objective lens 2240, which is mounted adjacent the distal end 2010 of the instrument head 2004. The rear peripheral edge 2242 of the objective lens 2240 is secured against an annular shoulder 2245 formed in the instrument head 2004 and held in position by means of an end cap 2248 that is threadingly positioned onto the distal end of the front housing section 2016, the latter having a corresponding set of threads 2249. When secured, the end cap 2248 also is configured to retain a fixation target retainer 2254, the latter of which is peripherally disposed about the objective lens 2240. An O-ring 2260 creates a seal between the objective lens 2240 and the fixation target retainer 2254.

Angled slots are provided on a front facing surface of the fixation target retainer 2254 that receive polarizer windows 2256, (shown only in the exploded FIG. 58) which according to this embodiment can be formed of different colors (i.e., blue, red) for directing a pair of fixation targets to the patient. The polarizer windows 2256 are positioned at the distal (objective) end 2010 of the instrument head 2004 with slots being disposed on diametrically opposite (left/right) sides of the objective lens 2240 where the fixation illumination targets are located. When the patient looks at the fixation target in the opposite direction relative to the eye being examined (that is, the right eye looking at the left target or the left eye looking at the right target), the patient's eye will align at approximately 17 degrees positioning their optic disc near the center of the view. According to this embodiment, a set of optical fibers (not shown), preferably having polished ends, extend from a contained LED 2356 of the illumination assembly of the ophthalmoscope 2000 to each of the fixation targets. More specifically, the polished distal end of the optical fibers are placed in contact with the polarizer windows 2256, with the fibers being routed through the interior of the instrument head 2004 upwardly from the LED 2356, the latter of which is retained in the lower portion of the instrument head 2004. According to this embodiment, the proximal end of the fixation target fibers are disposed on lateral sides of the LED 2356, although other suitable configurations can be utilized to direct the required illumination efficiently to the distally disposed fixation targets.

The proximal end of the eye cup 2030 is disposed over the distal end 2010 of the instrument head 2204 and about the contained objective lens 2240 to create the proper working distance between the physical assessment device 2000 and the eye of the patient, which according to this embodiment is approximately 25 mm. The eye cup 2030 is made from an elastomeric material and is shaped and configured to allow the distal end of the eye cup to be placed over the eye of the patient. The proximal end of the eye cup 2030 includes at least one internal engagement feature and is shaped to be releasably and securely attached to the end cap 2248, the latter also being suitably shaped and configured for this engagement.

At the proximal end 2014 of the instrument head 2004, the contained optical assembly includes an eyepiece holder 2270 projecting outwardly (proximally) from the instrument head 2004 and contained within the adapter interface member 2040. According to this embodiment, the eyepiece holder 2270 is defined by an open-ended structure that retains a pair of eyepiece lenses 2280, 2284 each separated an appropriate distance by an intermediate eyepiece spacer 2288. The eyepiece lenses 2280, 2284 are retained proximally relative to a field stop holder 2290 in which the eyepiece holder 2270 is threadingly engaged within an opening formed in the adapter interface member 2040. A field stop 2297 is retained within a narrowed portion 2299 of the field stop holder 2290, which is aligned with the eyepiece lenses 2280, 2284 and the objective lens 2240 along a defined optical axis of the device 2000.

Disposed between the proximal and distal ends 2010, 2014 of the herein described physical assessment device 2200 is a relay lens 2286 that is aligned along the defined viewing axis, as well as an aperture stop 2291, each of the foregoing optical components being intermediately disposed within the interior of the instrument head 2004 as part of the optical assembly. The relay lens 2286 is retained within a relay lens holder 2287 and more specifically within an aperture that is sized to retain the relay lens 2286 and aligned with the remaining optical components along the defined optical axis. A polarizer window is disposed immediately distal to the supported relay lens 2286. The relay lens holder 2287 is attached to a proximal end of a top optical base member 2426.

Figure 58:
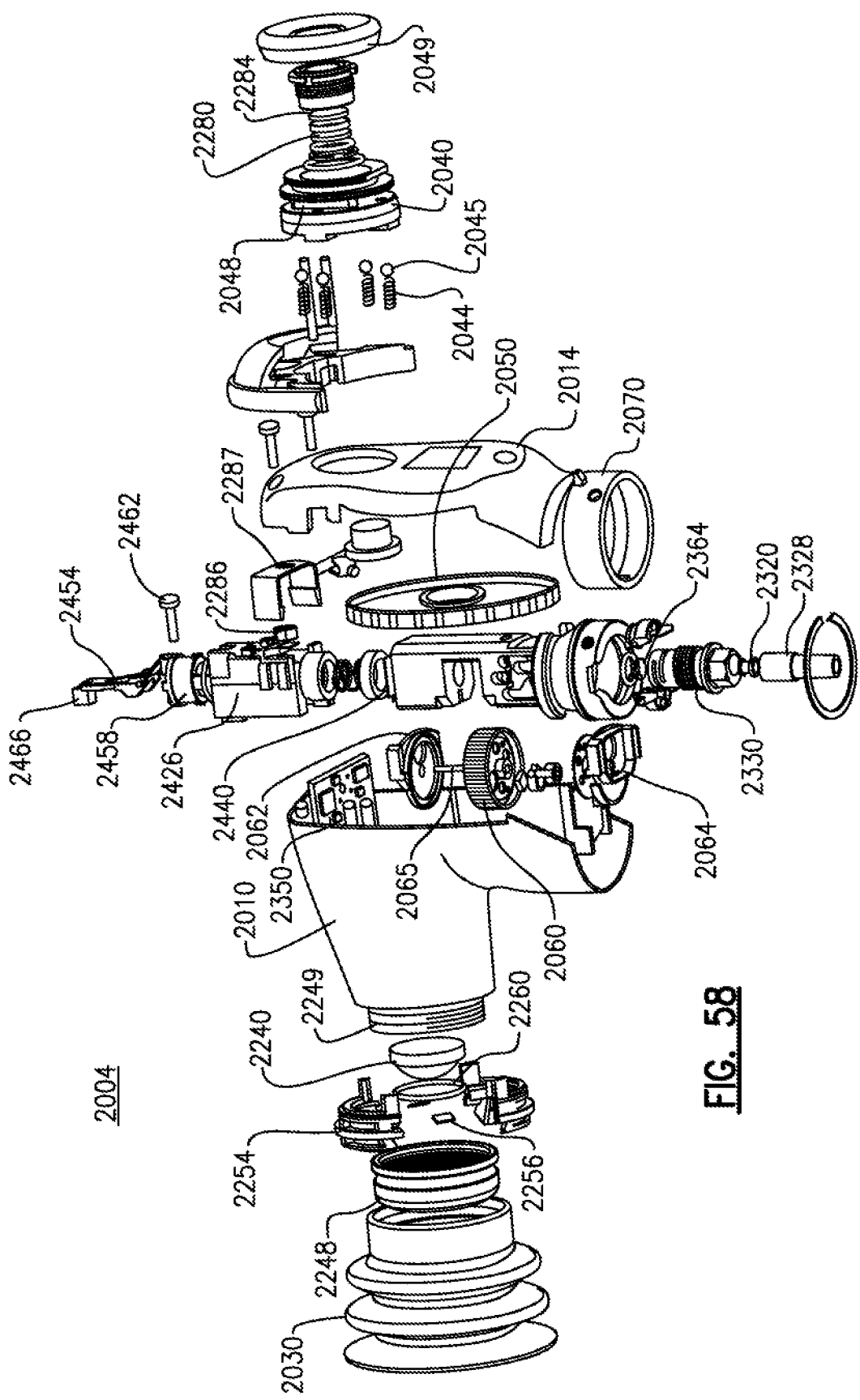
FIG. 58 is an exploded view of the instrument head of the physical assessment device of FIGS. 57(a) and 57(b)

Regarding the illumination assembly and with reference to FIGS. 58, 59(*a*) and 59(*b*), the instrument head 2004 further retains a plurality of components configured for illuminating the patient's eye. An electrical contact pin 2320 is disposed within a hollow plastic insulator 2328, the latter having an upper portion which is sized and configured to retain a coil spring 2332 for biasing the contact pin 2320. The coil spring 2332 is preferably disposed between a top or upper end of the contact pin 2320 and a shoulder formed in an upper portion of the insulator 2328.

When a lowermost end of the contact pin 2320 is engaged with electrical contacts (not shown) in the handle (not shown) of the physical assessment device 2000, the top end of the contact pin 2320 is pressed into contact with a lower surface of a printed circuit board 2350 for an LED 2356 that is disposed on the upper surface of the circuit board 2350. The circuit board 2350 is positioned in place onto a circuit board retainer 2330 that further retains the insulator 2328 and contact pin 2320, the circuit board retainer 2330 having a set of external threads 2331 that engage a set of corresponding threads that are provided within an optical base member 2390. As discussed herein, the circuit board 2350 can be configured with an LED drive circuit that is compatable with different instrument handles, including those typically configured for driving incandescent light sources. This circuitry is described in a later portion of this application.

For purposes of this embodiment, the LED 2356 is aligned with a condenser lens 2364 along a defined illumination axis, the condenser lens 2364 being retained within a lens holder 2380 that is snapfitted in a manner that creates alignment with the LED 2356. Each of these latter components are further retained within the optical base member 2390, in which the optical base member 2390 is fitted within a lower necked portion of the instrument head 2004.

According to this embodiment, the aperture wheel 2060 is disposed above the condenser lens 2364 and supported for rotation by the optical base member 2390. A slot is provided in the front housing section 2016 to permit access to the aperture wheel 2060, which is configured for rotational movement in order to selectively position each of a series of circumferentially spaced apertures formed on an aperture plate 2404 into alignment with the LED 2356 and condenser lens 2364 along the defined illumination axis. A pair of cover sections 2062, 2064 retain the rotatable aperture wheel 2060 within a recessed portion of the optical base member 2390. The cover portions 2062, 2064 retain ends of an axle 2065 that extends through the center of the aperture wheel 2060 and the aperture plate 2404, enabling rotation. More specifically, a plurality of windows are circumferentially disposed on the aperture wheel 2060 that may include a red free filter, a blue filter, as well as varying sized apertures. Various other configurations can easily be realized.

Above the aperture wheel 2060 and the optical base member 2390, the illumination assembly further includes a relay lens 2420, which according to this exemplary embodiment is retained within the upper end of the optical base member 2390 and aligned with the condenser lens 2364, the rotatable aperture wheel 2060, and the LED 2356 along the defined illumination axis.

A polarizer window 2440 is retained at the top surface of the optical base member 2390 above and distally relative to the relay lens 2420 and in relation to a mirror 2450, the latter being supported by a mirror mount assembly 2453. A compression spring 2395, FIG. 60(*a*), provided between the top optical base member 2426 and the upper portion of the optical base member 2390 maintains pressure against the polarizer window 2440 and relay lens 2420 of the illumination assembly in which the lower end of the optical base member 2426 is accommodated, but not secured, within an upper portion of the optical base member 2390. The foregoing arrangement further maintains the alignment of the relay lens 2286 and relay lens holder 2287 of the optical assembly of the herein described device 2000, each of which are retained within the top optical base member 2426 as previously discussed.

With reference to FIGS. 58, 59(b), and 60(a)-60(d), the mirror mount assembly 2453 includes a elongate mirror mount 2454 having an upper end 2455 and a lower end 2456. The lower end 2456 of the mirror mount 2454 retains the mirror 2450 along an inclined support surface 2451. The mirror mount 2454 is pivotally supported within an enclosure 2458 that is provided within the top optical base member 2426. An adjustment member 2462, such as a threaded fastener, extends into a formed slot in the rear housing section 2018 of the instrument head 2004 and further extends into an upper section of 2459 of the enclosure 2458. The distal end of the adjustment member 2462 is configured to engage a rear facing surface 2457 at the top of the mirror mount 2454 in order to cause the mirror mount 2454 to pivot and enable the angle of the supported mirror 2450 to be adjusted to direct light from the LED 2356, FIG. 59(b), toward the distal end of the instrument head 2004.

Figure 60A:
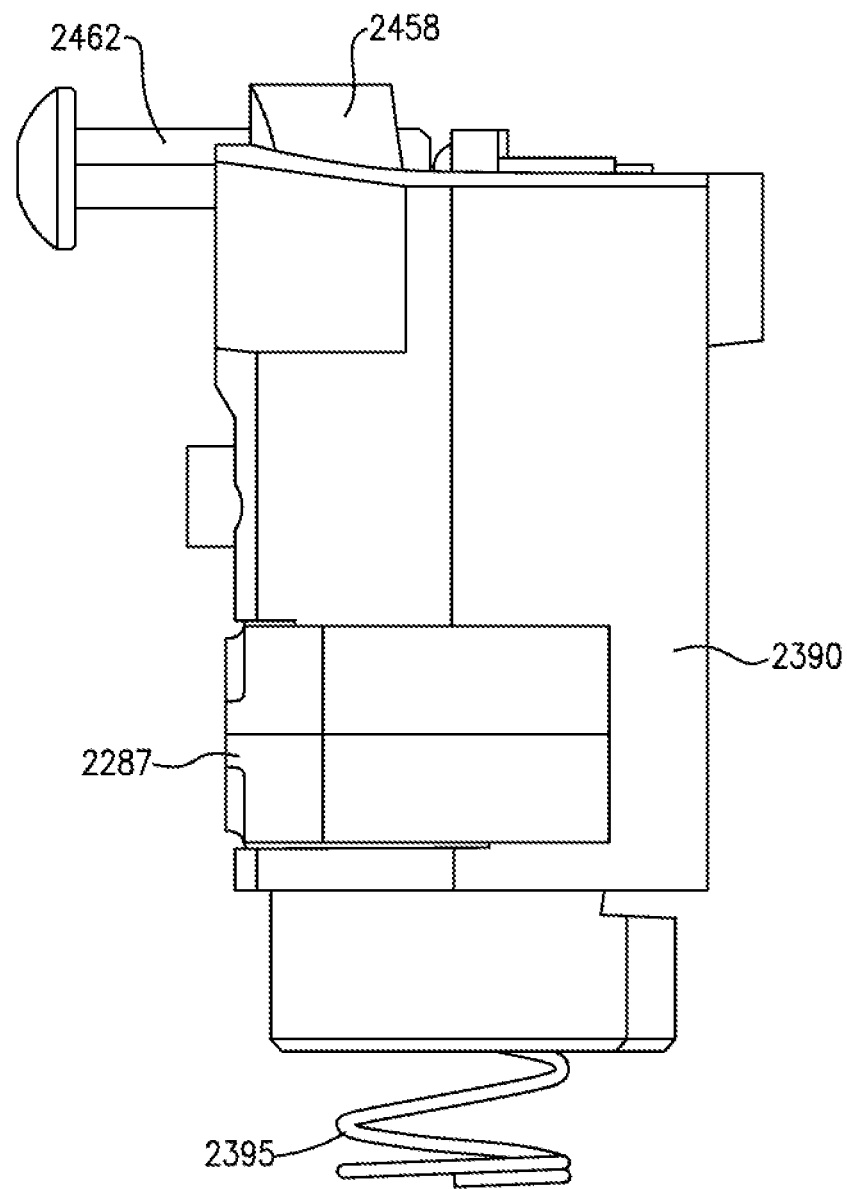
FIG. 60(a)-60(d) are various views of an adjustable mirror mount assembly of the instrument head of FIGS. 58-59(b)
Figure 60B:
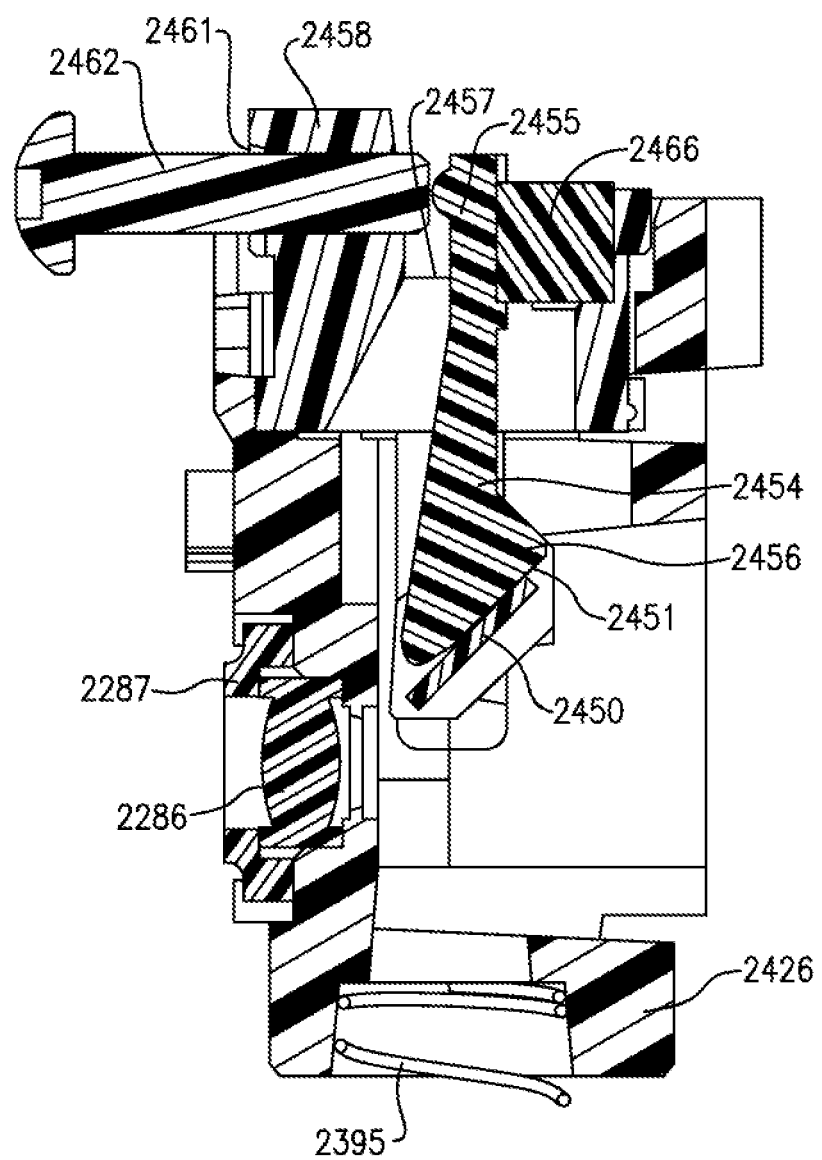
Figure 60C:
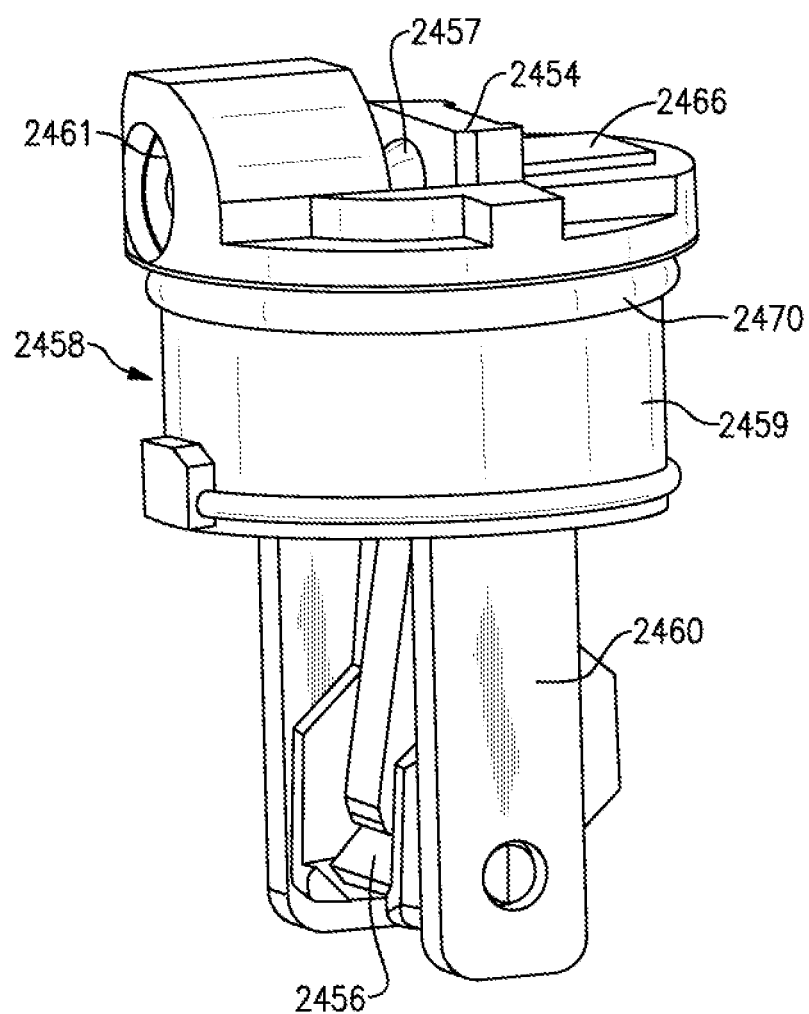
Figure 60D:
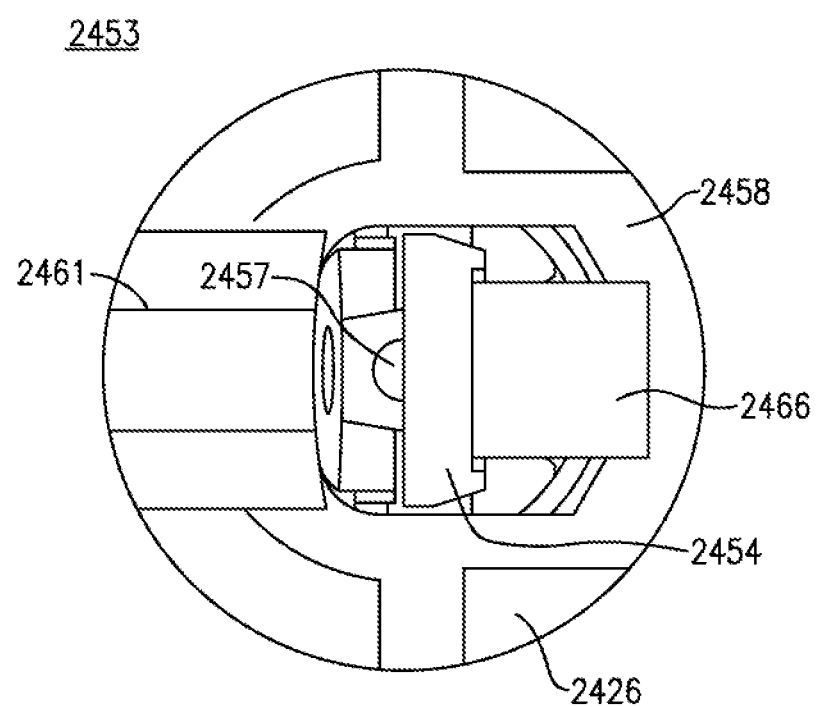

A block 2466 of a elastomeric material, such as poron, is also fitted within the top of the enclosure 2458 immediately adjacent a front facing surface of the mirror mount 2454 against which the adjustment member 2462 engages. With reference to FIG. 60(c), the enclosure 2458 according to this embodiment is defined by a substantially cylindrical upper portion 2459 and a pair of lower extending legs 2460, the latter which retain the lower end 2456 of the mirror mount 2454 through a pinned connection. The upper end 2459 of the enclosure 2458 includes a threaded sleeve 2461 aligned with the rear facing surface 2457 of the top of the mirror mount 2454 that receives the adjustment member 2462. The enclosure 2458 according to this embodiment is supported within the top optical base member 2426 along with a sealing member, such as an O-ring 2470. According to this embodiment, the adjustment member 2462 further permits lateral adjustments of the retained mirror 2450 in addition to angular (pivotal) adjustments of the mirror mount 2454, wherein the O-ring 2470 contacting the inner surface of the optical base member 2426 provides sufficient resistance to maintain the lateral adjustment of the supported mirror 2450.

Figure 59A:
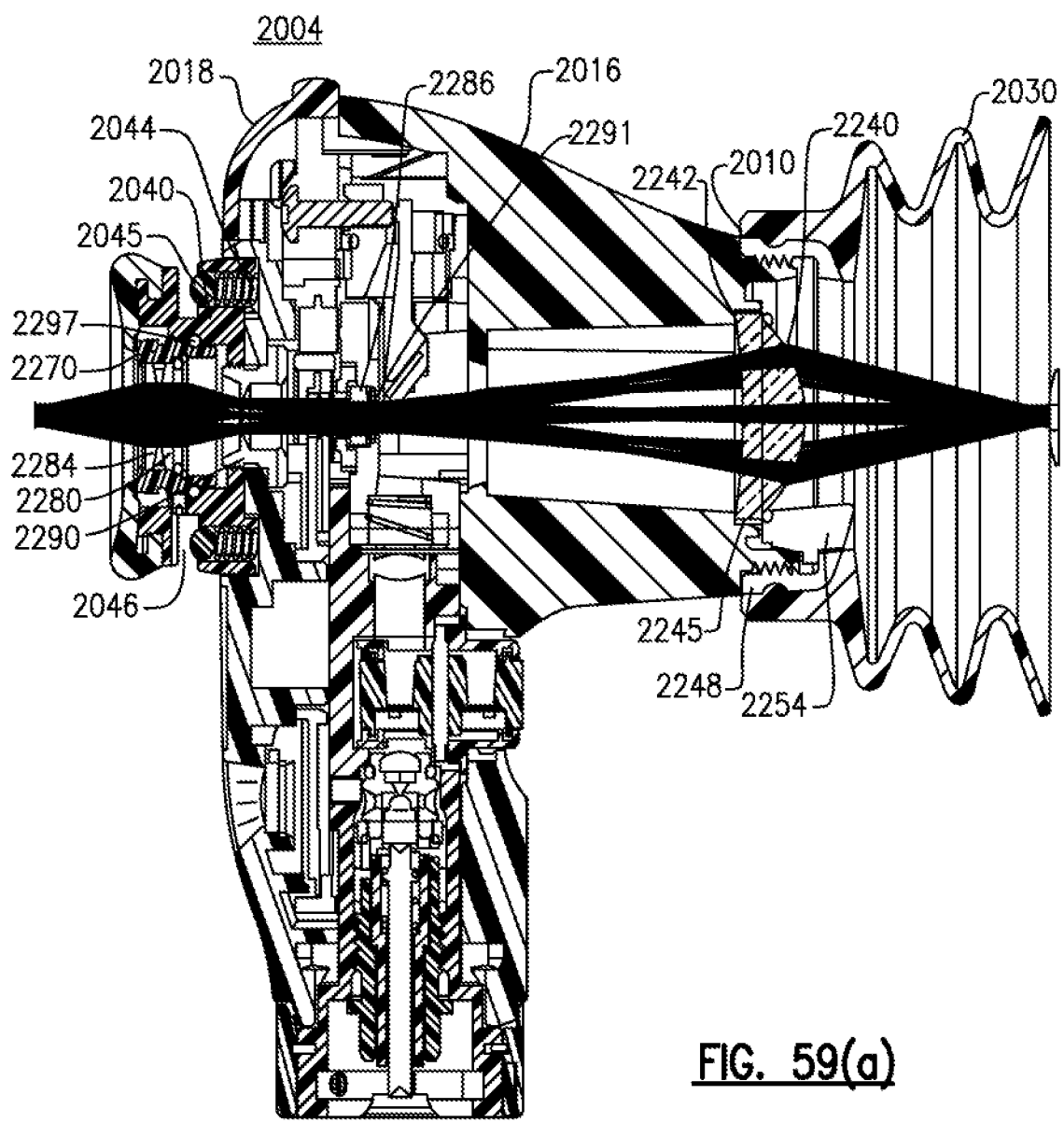
FIG. 59(a) is a side elevation view in section of the instrument head of FIG. 58, further depicting a ray trace of a contained optical assembly.
Figure 59B:
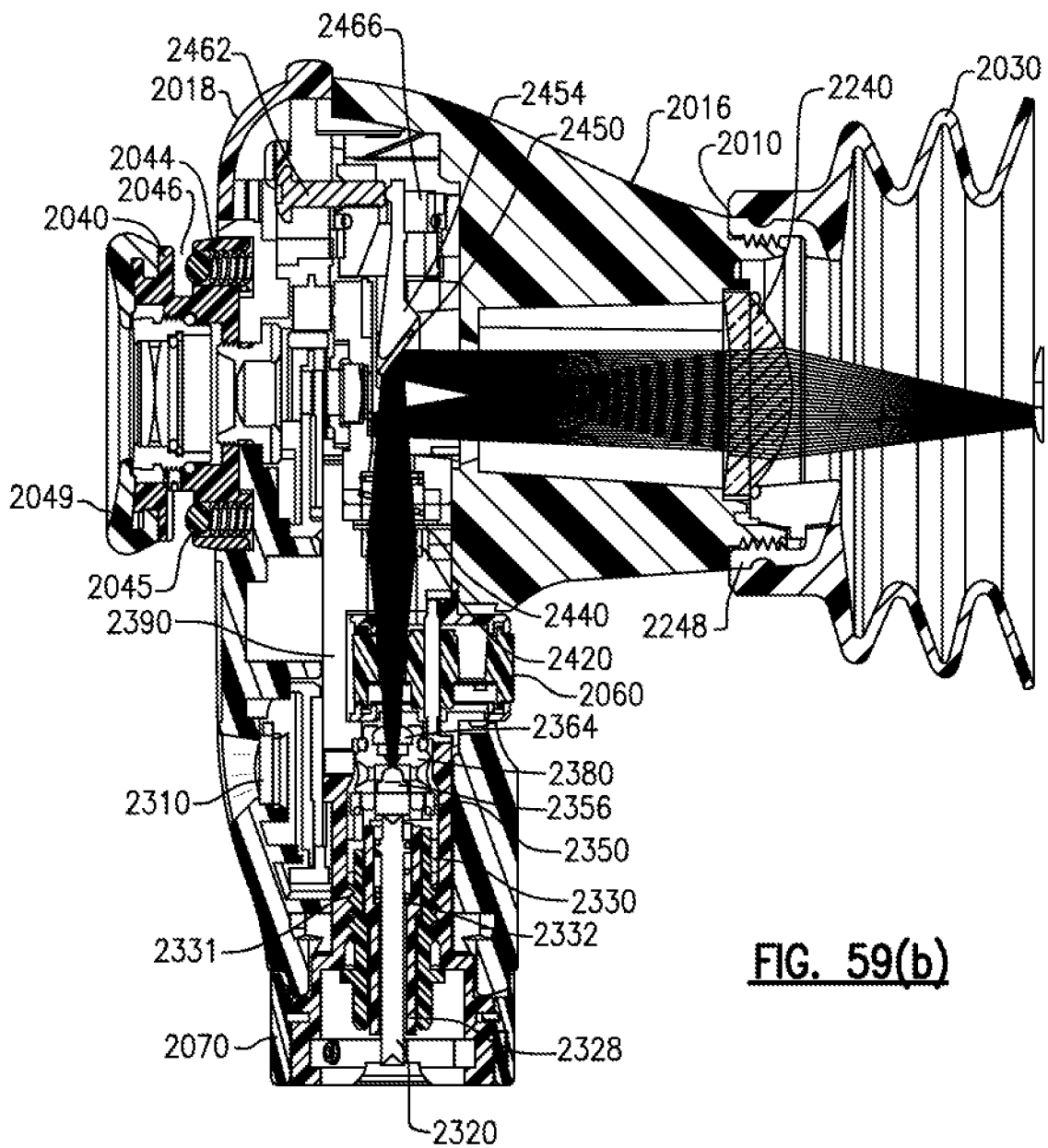
FIG. 59(b) is the side elevation view in section of the instrument head of FIG. 59(a), further depicting a ray trace of a contained illumination assembly.

Referring to FIG. 59(b), the illumination assembly allows light from the contained LED 2356 to be directed through the aligned condenser lens 2364, the aperture wheel 2060, the relay lens 2420 and the polarizer window 2440 to the supported mirror 2450 along the defined illumination axis. A reticle (not shown) can further be provided as part of the aperture wheel or otherwise within the optical base member. The light is then further directed toward the distal end 2012 of the instrument head 2004 and more specifically through the objective lens 2240 and in which the light is focused at the edge of the pupil of the patient's eye. The position of the objective lens 2240 can be suitably adjusted at the time of manufacture to further offset any tolerancing mismatches in addition to the adjustment of the supported mirror via the mirror mount assembly.

Referring to FIG. 59(a), light reflected from the back of the patient's eye is directed into the distal end of the ophthalmoscope 2000 through the objective lens 2240 in which the light is then focused onto the relay lens 2286, which directs the light through the field stop 2297 and the imaging lenses 2280, 2284 to the clinician's eye (not shown) or to an attached smart device attached to the adapter interface member 2040. The adapter interface member 2040 according to this embodiment is structurally similar to the adapter interface member 180, FIGS. 6-13(b), and does not require additional discussion.

Variations—Ophthalmoscope

Figure 61:
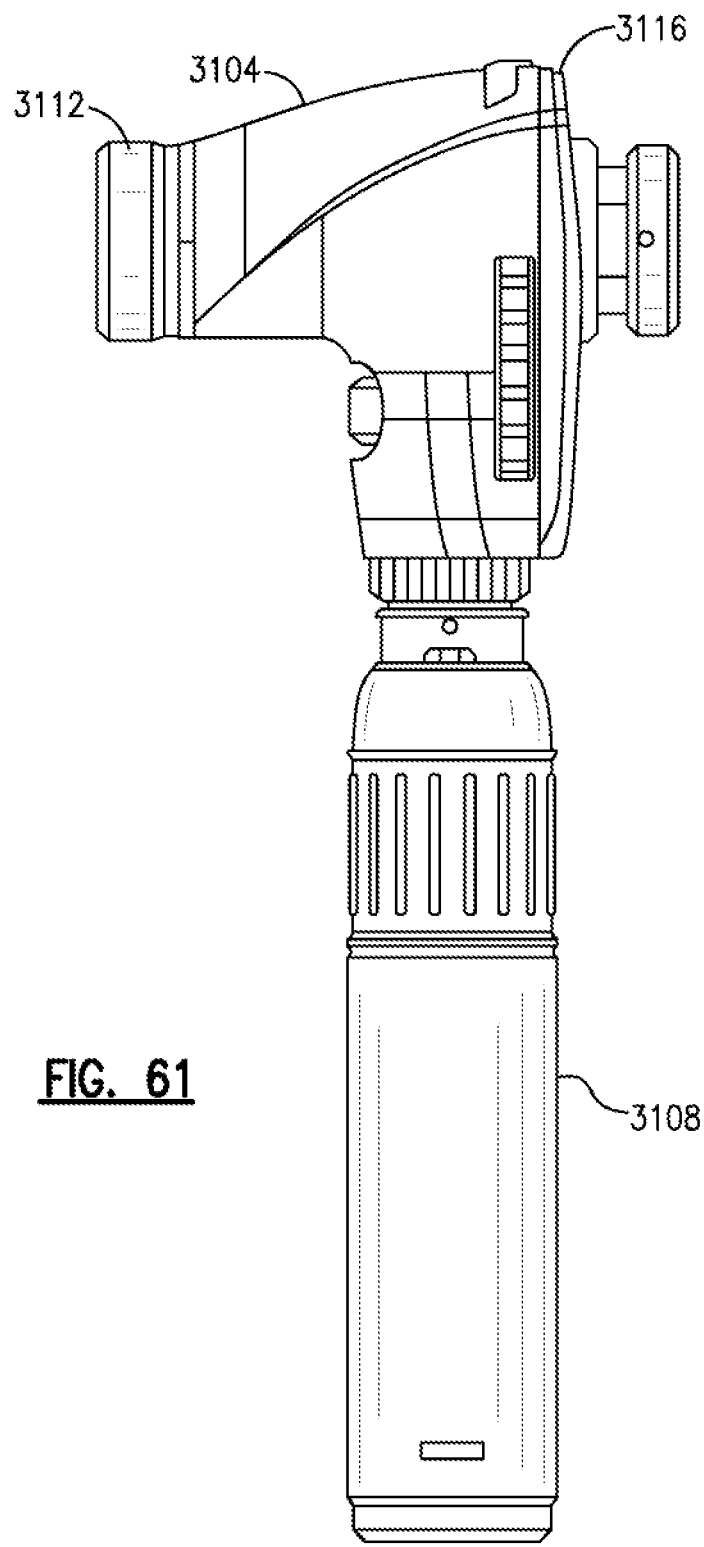
FIG. 61 is a side elevational view of a physical assessment device made in accordance with another embodiment.

As shown in FIG. 61, an ophthalmoscope 3100 made in accordance with another exemplary embodiment is herein described. As discussed herein and shown in FIG. 65, the ophthalmoscope 3100 includes an instrument head 3104 that is releasably attached to the upper end of a handle portion 3108. The instrument head 3104 is defined by a distal (patient) end 3112 and an opposing proximal (caregiver) end 3116. The interior 3105 of the instrument head 3104 is sized and configured for retaining an illumination assembly 3101 and an optical assembly 3102.

Figure 62:
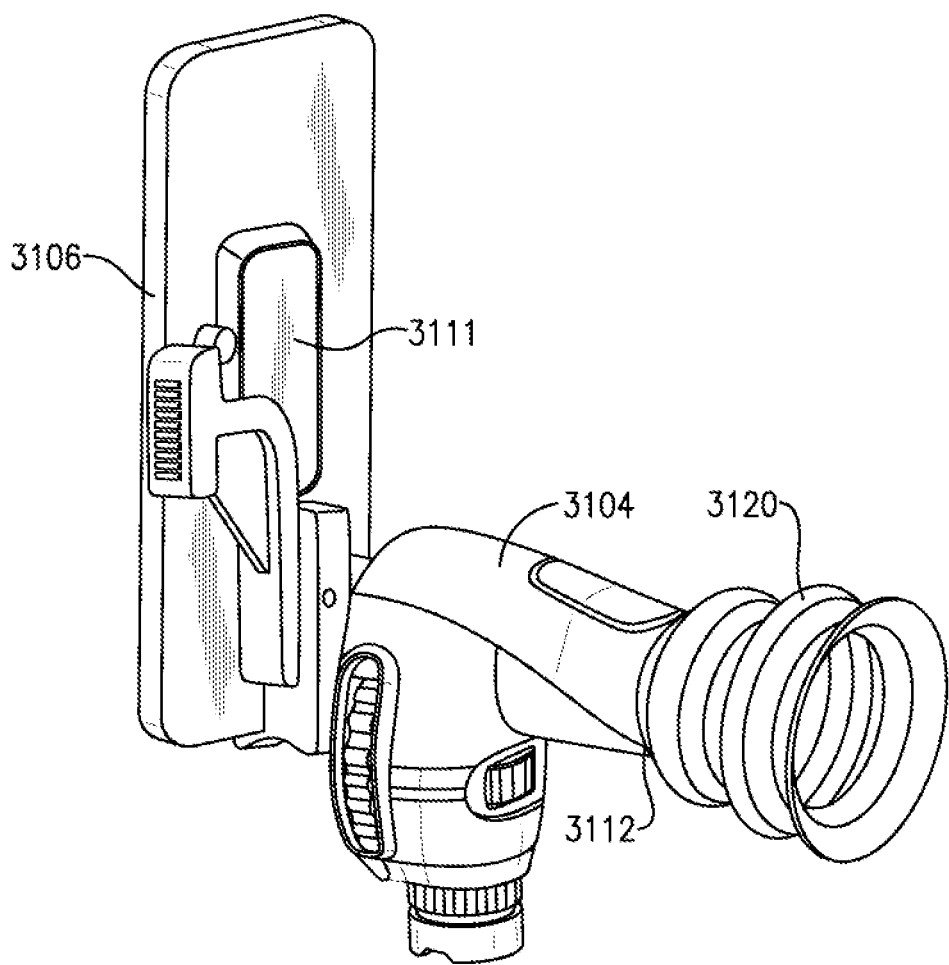
FIG. 62 is a partial front perspective view of a physical assessment device having an attached smart device.
Figure 63:
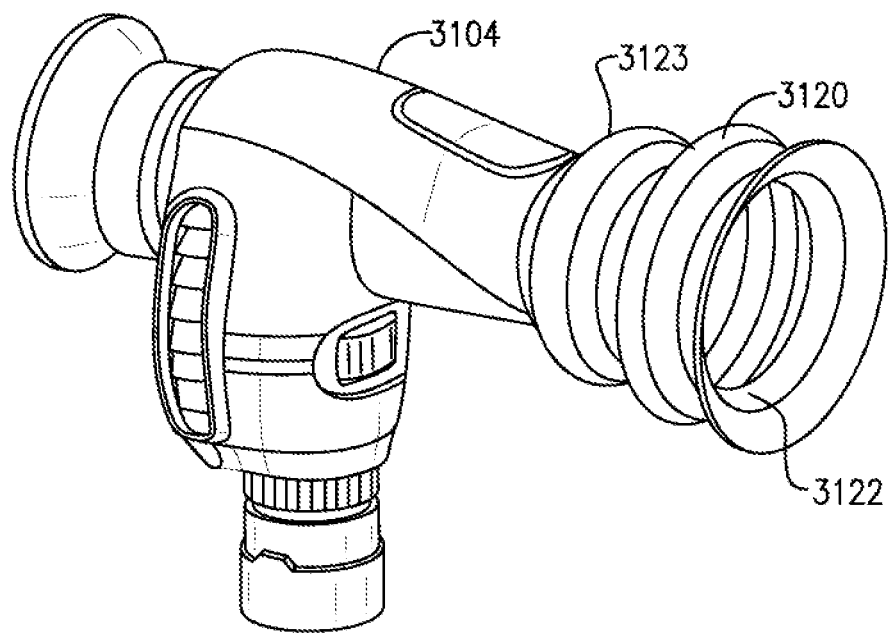
FIG. 63 is a front perspective view of an instrument head of the physical assessment device of FIG. 62, including an attached eye cup.

According to this version and as shown in FIGS. 62 and 63, an eye cup 3120 is attached to the distal end 3112 of the instrument head 3104. According to this embodiment, the eye cup 3120 is a flexible component, preferably made from an elastomeric material that is designed for direct engagement with the patient. When attached, the eye cup 3120 establishes a working distance between the patient's eye and a first distalmost lens component of a contained optical assembly.

The eye cup 3120 according to this embodiment is defined by a solid contiguous member. In an alternative embodiment, the eye cup can include one or a plurality of slits or openings (not shown) that do not sacrifice structural integrity for purposes of patient alignment.

Figure 64A:
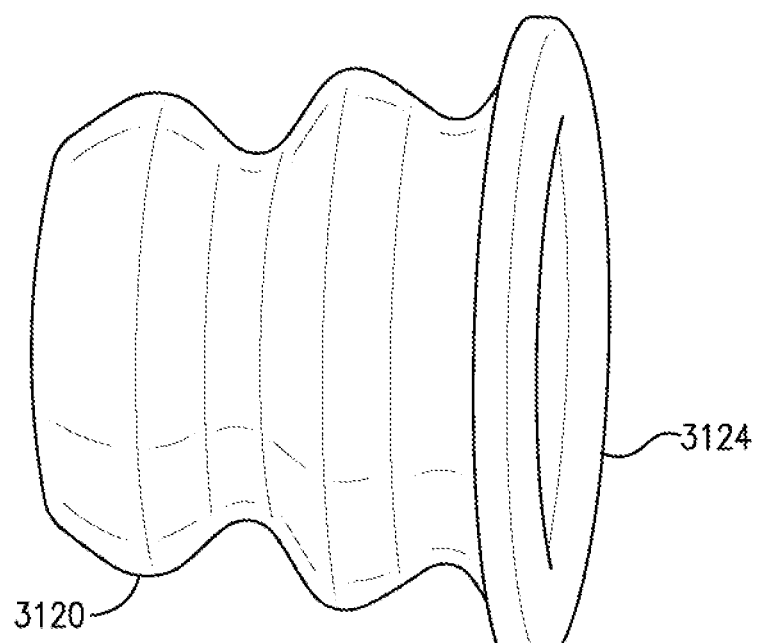
FIGS. 64(a) and 64(b) are side elevation view, one in section of the eye cup of FIG. 63 having a disposable ring member in accordance with an embodiment.
Figure 64B:
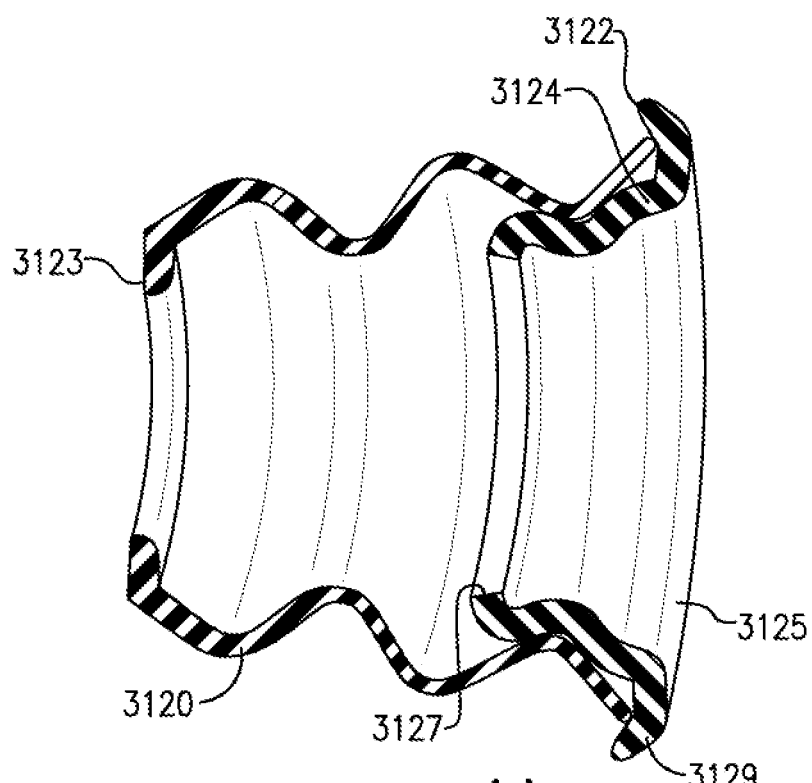

In accordance with an embodiment and as shown in FIGS. 64(a) and 64(b), a disposable ring member 3124 can be provided which is configured and sized to fit within the distal end opening 3122 of the eye cup 3120. More specifically, the disposable ring member 3124 is defined by a flexible material, such as, for example, a foam material or polypropylene and defined by opposing distal and proximal end openings 3125, 3127 in which the distal end opening 3125 includes an annular outer flange 3129. When attached, the disposable ring member 3124 can be inserted into the distal end opening 3125 of the eye cup 3120 with the annular outer flange 3129 of the disposable ring member 3124 creating a stop.

According to one embodiment, a user can load the disposable ring member 3124 from a stacked set of rings (not shown) in a container (not shown) having an open top and engaging the distal end of the eye cup 3120 with the disposable ring member 3124 until the distal end of the eye cup 3120 engages the annular outer flange 3129 of the disposable ring member 3124. Compression of the eye cup 3120 creates positive engagement between the inner portions of the eye cup 3120 and the outer surface of the disposable ring member 3124, allowing the disposable ring member 3124 to remain attached to the eye cup 3120 when the eye cup 3120 is removed from the container. Advantageously, the disposable ring member 3124 can be attached without having to touch the ring member 3124 and wherein the disposable ring member 3124 permits reuse of the eye cup 3120 as shown. The disposable ring member 3124 also serves as a stop, preventing eye cup 3120 from fully compressing against a patient's eye.

Figure 65:
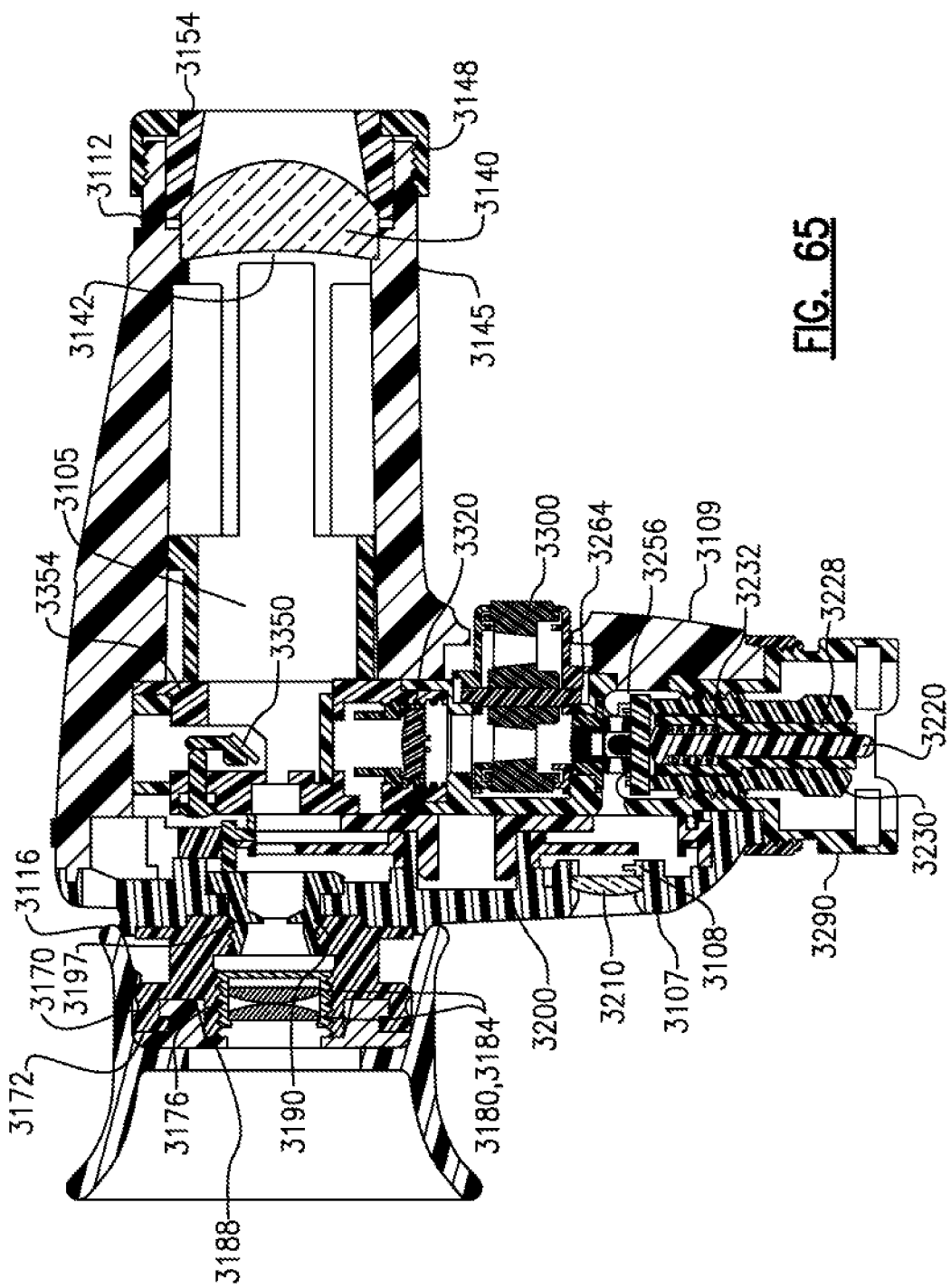
FIG. 65 is a sectioned view of the instrument head of a physical assessment device in accordance with another embodiment.

With reference to the sectioned view of FIG. 65, the instrument head 3104 according to this embodiment is manufactured using a two-part housing made up of a front housing section 3109 and a rear housing section 3110 that are mated together. The instrument head 3104 is defined by an interior 3105 that is sized and configured for retaining a plurality of components, including an optical assembly 3101 and an illumination assembly 3102. As shown schematically according to FIGS. 66-68, the optical assembly 3101 includes a plurality of optical components or elements disposed and aligned along a defined viewing or optical axis 3132 that extends through the eye 3130 of the patient, as well as the distal and proximal ends 3112, 3116 of the device 3100. As previously referred to herein, an "optical component" or "optical element" refers to lenses and prisms as well as field stops, aperture stops, polarizers, and any component used to directing or transmitting light along a defined optical or viewing axis.

According to this embodiment, the distal most component of the optical assembly is an objective lens 3140, which is mounted adjacent the distal end 3112 of the instrument head 3104. As shown in FIG. 65, the rear peripheral edge 3142 of the objective lens 3140 is secured against an annular shoulder 3145 formed in the instrument head 3104 and held in position by means of an end cap 3148 that is threadingly positioned to the distal end 3112 of the instrument head 3104. When secured, the end cap 3148 also is configured to retain a fixation target retainer 3154, the latter of which is peripherally disposed about the objective lens 3140 and as further shown in FIG. 69. Angled slots are provided on a front facing surface of the fixation target retainer 3154 that receive polarizer windows which according to this embodiment can be formed of different colors (i.e., blue, red) for directing a pair of fixation targets to the patient.

Figure 69:
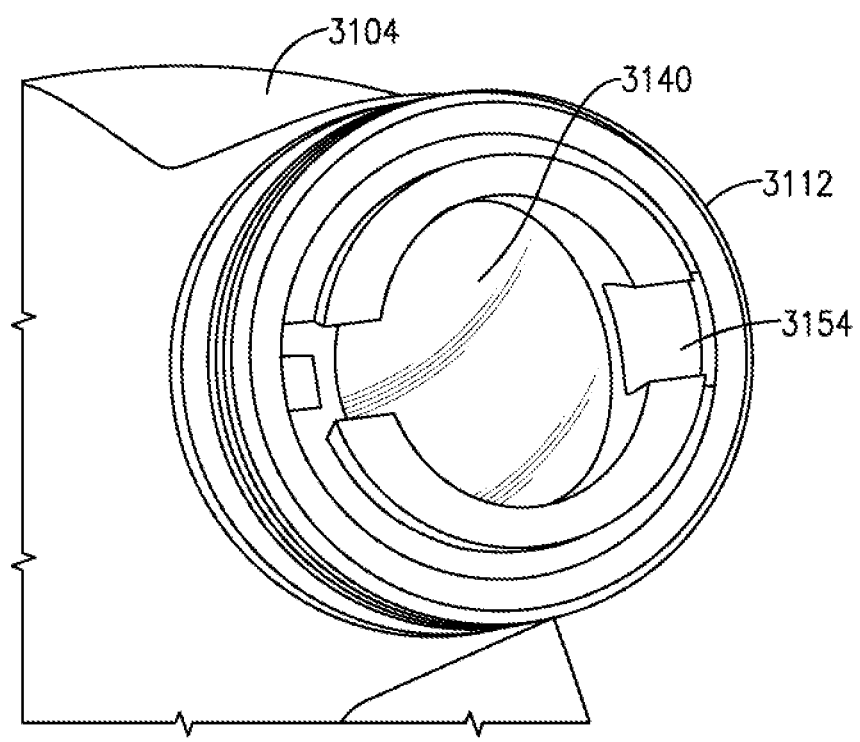
FIG. 69 is a front view of the distal end of the instrument head of FIG. 65, depicting a pair of spaced fixation target illuminators.

As shown in FIG. 69, the objective end of the instrument head 3104 is shown with two slots on each side (left/right) of the lens 3140 where the fixation illumination targets are located. When the patient looks at the target in the opposite direction relative to the eye being examined (that is, the right eye looking at the left target or the left eye looking at the right target), the patient's eye will align at approximately 17 degrees positioning their optic disc near the center of the view. According to this embodiment, a set of optical fibers, preferably having polished ends, extend from the contained LED to each of the fixation targets. More specifically, the polished distal end of the optical fibers are placed in contact with the polarizer windows, with the fibers being routed through the interior of the instrument head and downwardly to the contained LED. According to this embodiment, the proximal end of the fixation target fibers are disposed on lateral sides of the LED, although other configurations can be utilized.

Figure 66:
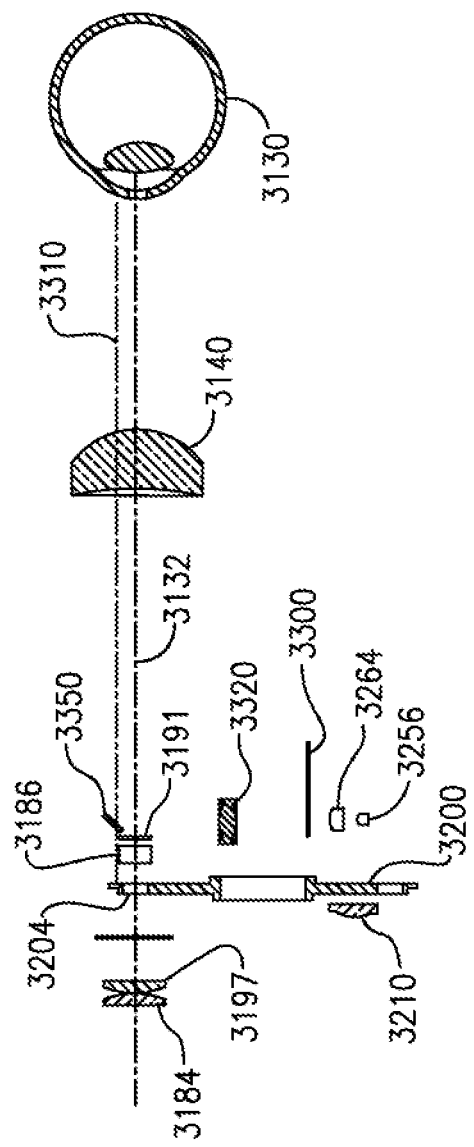
FIG. 66 is an overall schematic view of the optical and illumination assemblies of the physical assessment device of FIG. 65.

The proximal end of the eye cup 3120 is disposed over the distal end 3112 of the instrument head 3104 and about the contained objective lens 3140 to create the proper working distance between the device 3100 and the patient, schematically shown in FIG. 66, which according to this embodiment is approximately 25 mm.

The proximal end 3116 of the instrument head 3104 includes an eyepiece holder 3170 projecting outwardly (proximally) from the instrument head 3104. According to this embodiment, the eyepiece holder 3170 is defined by an open-ended structure including an annular shoulder 3172 formed on an outward (proximal) facing side, which is sized and configured to retain a brow rest 3176 for use by the clinician. The eyepiece holder 3170 retains a pair of eyepiece lenses 3180, 3184 that are separated an appropriate distance by an eyepiece spacer 3188. The eyepiece lenses 3180, 3184 are retained in a field stop holder 3190 that is threadingly engaged within an opening formed in the eyepiece holder 3170 and the instrument head 3104. A field stop 3197 is retained within a narrowed portion 3199 of the field stop holder 3190 and aligned with the eyepiece lenses 3180, 3184 and the objective lens 3140 along the defined optical axis.

Disposed between the proximal and distal ends 3112, 3116 of the device 3100 and referring to FIGS. 65-68, the herein described optical assembly 3101 further includes a relay lens 3186 that is aligned along the defined viewing axis 3132, as well as an aperture stop 3191, each intermediately disposed within the interior 3105 of the instrument head 3104.

Figure 67:
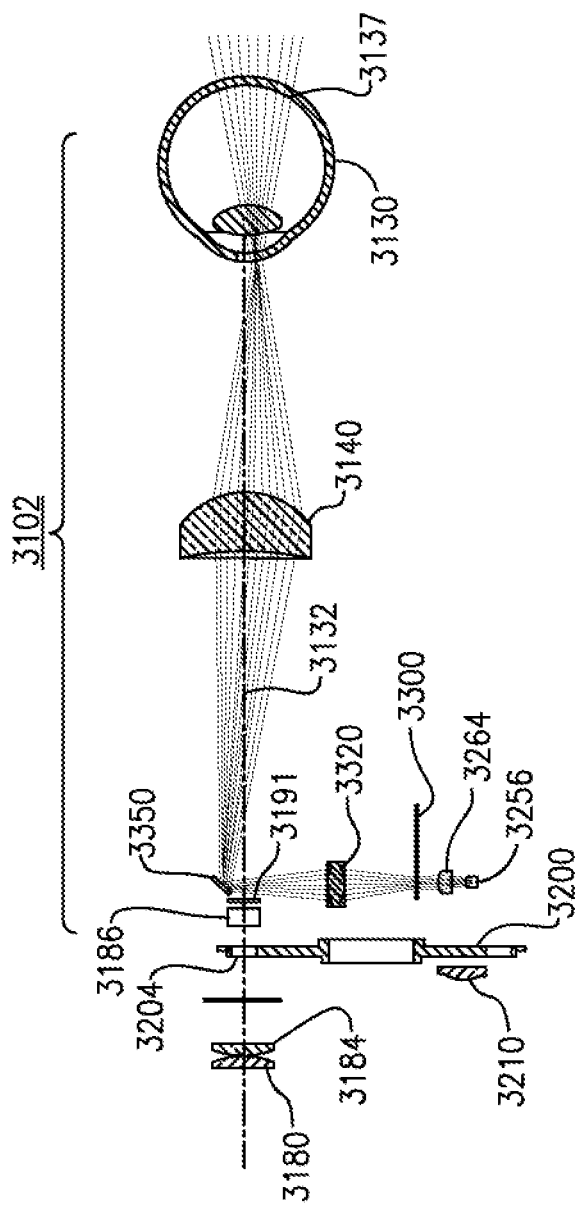
FIG. 67 is a ray trace diagram of the illumination assembly of the physical assessment device of FIGS. 65 and 66.
Figure 68:
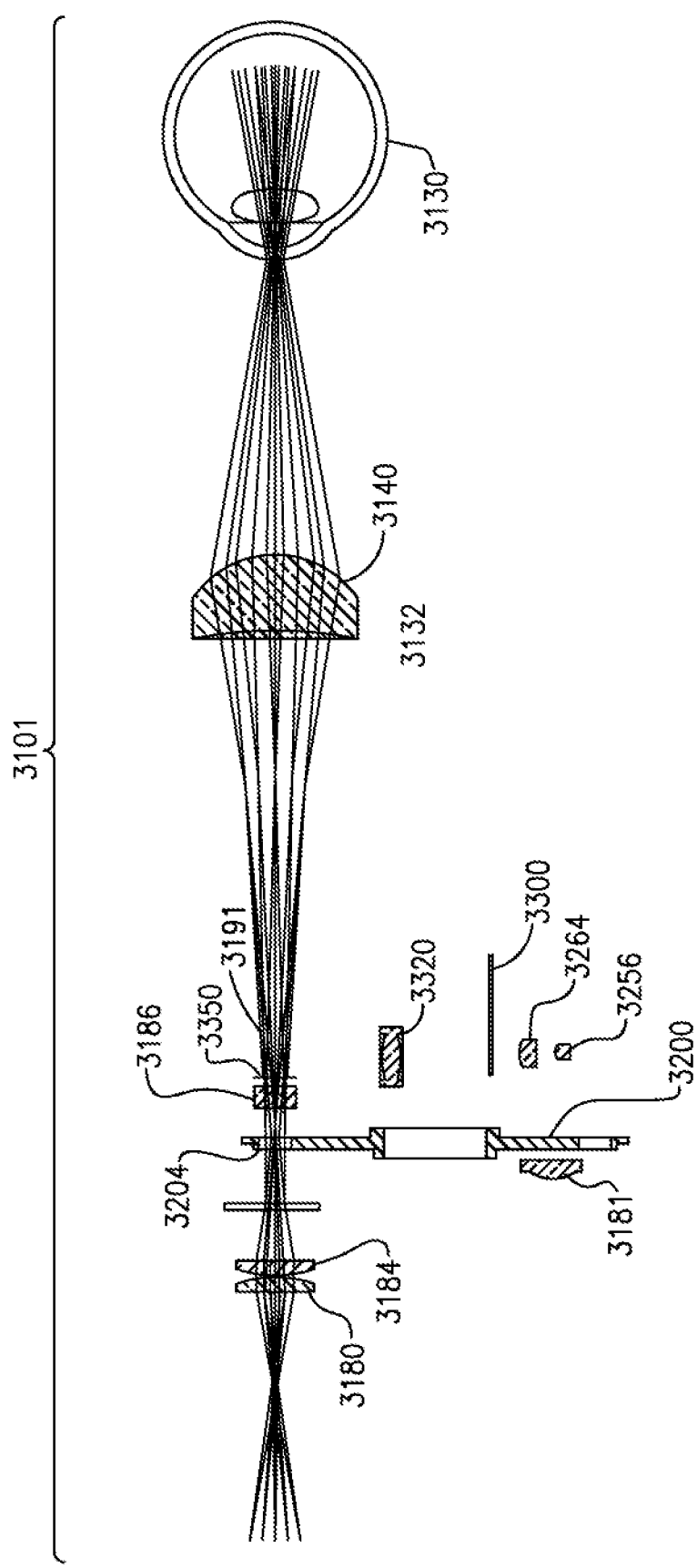
FIG. 68 is a ray trace diagram of the optical assembly of the physical assessment device of FIGS. 65-67.

The components of the optical assembly 3101 are shown in respective layouts presented according to FIG. 66-68, which includes the objective lens 3140, the aperture stop 3191, relay lens 3186, field stop 3197 and eyepiece lenses 3180 and 3184, each aligned along the viewing axis 3132 relative to the clinician's eye (not shown) as brought to the brow rest 3176 or as shown in FIG. 62, relative to the interface and imaging aperture of an attached smart device 3106.

Figure 70:
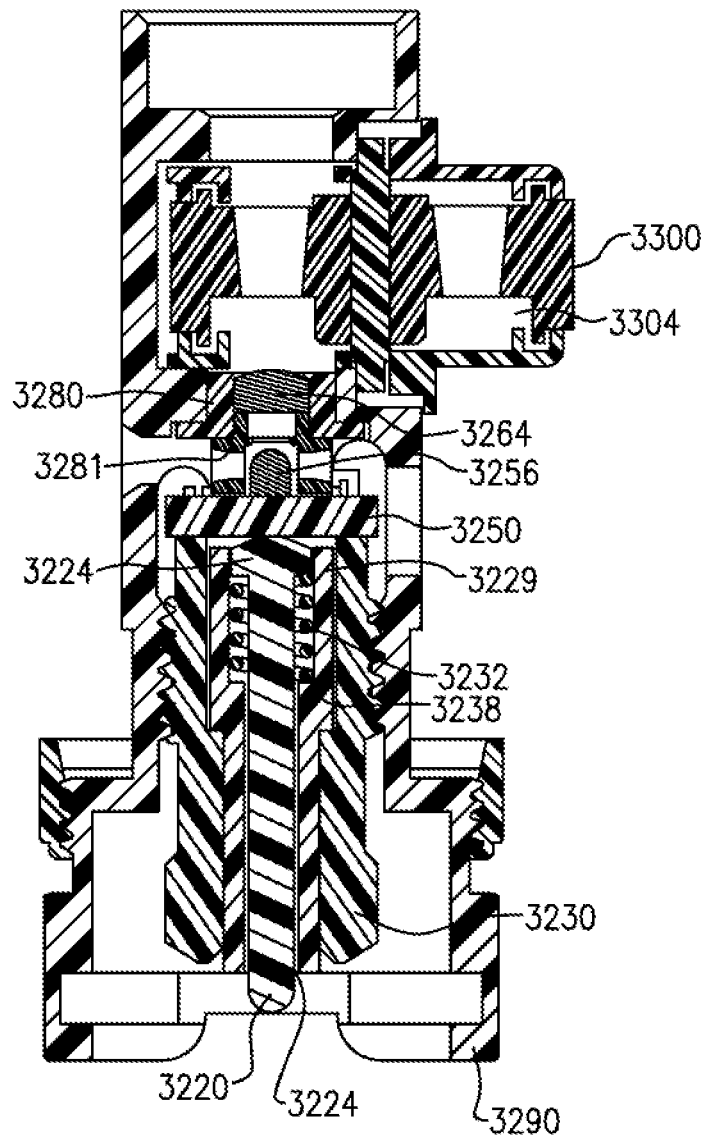
FIG. 70 is an enlarged sectioned view of the lower portion of the instrument head of FIG. 65.

Regarding the illumination assembly 3102 and with reference to FIG. 70, the lower necked portion 3107 of the instrument head 3104 includes a plurality of components configured for illuminating the target (eye) of interest. An electrical contact pin 3220 is disposed within an opening 3224 formed in a plastic insulator 3228, the latter having an upper portion 3229 that retains a coil spring 3232 for biasing the contact pin 3220. The spring 3232 is disposed between a top or upper end 3224 of the contact pin 3220 and a shoulder 3238 formed in the upper portion 3229 of the insulator 3228.

When a lowermost end of the contact pin 3220 is engaged with electrical contacts (not shown) in the handle (not shown) of the physical assessment device 3100, the top end 3224 of the contact pin 3220 is pressed into contact with a lower surface of a printed circuit board 3250 for an LED 3256 that is disposed on the upper surface of the circuit board 3250, shown most clearly in FIG. 70. The circuit board 3250 is positioned in place onto a circuit board retainer 3230 that further retains the insulator 3224 and contact pin 3220, the retainer 3230 having a set of external threads that engage corresponding threads provided within an assembly support member 3290.

The LED 3256 is aligned with a condenser lens 3264 along an illumination axis 3310, FIG. 66, the condenser lens 3264 being retained within a lens holder 3280 that further retains a centering ring 3281 aligned with the LED 3256. Each of these latter components are further retained within the assembly support member 3290, the assembly support member 3290 being fitted within the lower necked portion 3107, FIGS. 65, 70, of the instrument head 3104.

Referring to FIGS. 65 and 70, an aperture wheel 3300 is disposed above the condenser lens 3264. The aperture wheel 3300 is supported by the assembly support member 3290 and configured for rotational movement so as to selectively locate and position each of a series of circumferentially spaced apertures formed on an aperture plate 3304 into alignment with the LED 3256 and condenser lens 3264 along the defined illumination axis 3310, FIG. 67. More specifically, a plurality of windows 3304 are circumferentially disposed on the aperture wheel 3300 that include a red free filter, a blue filter, as well as varying sized apertures. It will be readily apparent that various other configurations can easily be realized. Additional details relating to the assembly support member 3290 and retention of the illumination assembly components are provided in U.S. Pat. No. 9,629,544, the entire contents of which are herein incorporated by reference.

With reference to FIGS. 65 and 67 and above the aperture wheel 3300 and the assembly support member 3290, the illumination assembly further includes a relay lens 3320 which according to this embodiment is retained in a holder 3326. According to this embodiment, the relay lens holder 3326 is threadingly secured to an upper portion of the assembly support member 3290 and aligned with the condenser lens 3264, aperture wheel 3300, and the LED 3256 along the defined illumination axis 3310.

With reference to FIGS. 66-68, the optical and illumination assembly components of this physical assessment instrument are illustrated in schematic form for the sake of clarity. As noted, the optical assembly 3101 includes the objective lens 3140 aligned with eyepiece lenses 3180, 3184 and the field stop 3197, as well as the relay lens 3186 and the aperture stop 3191, each of which are aligned along the defined optical axis 3132. In addition, a diopter wheel 3200 supports a plurality of optical elements 3204 of varying power (concave/convex). The diopter wheel 3200 is rotatably movable into and out of the defined viewing axis 3132 for purposes of establishing the focus of the patient's eye 3130.

Still referring to FIG. 67, the illumination assembly 3102 comprises the LED 3256 aligned along the defined illumination axis with the condenser lens 3264 and the rotatable aperture wheel 3300, as well as the illumination relay lens 3320, each disposed in alignment with an angled mirror 3350, the latter being offset relative to the imaging axis 3132.

Figure 71B:
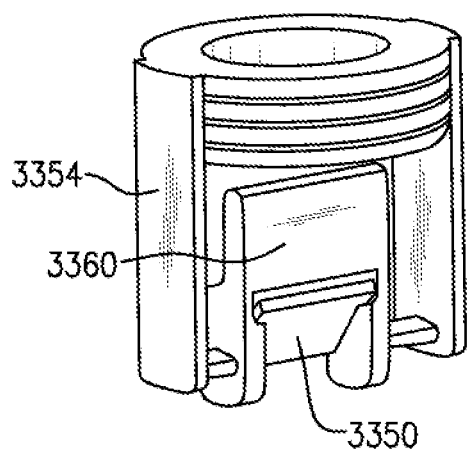
FIG. 71(b) is a perspective view of the mirror support member of FIG. 71(a)
Figure 71A:
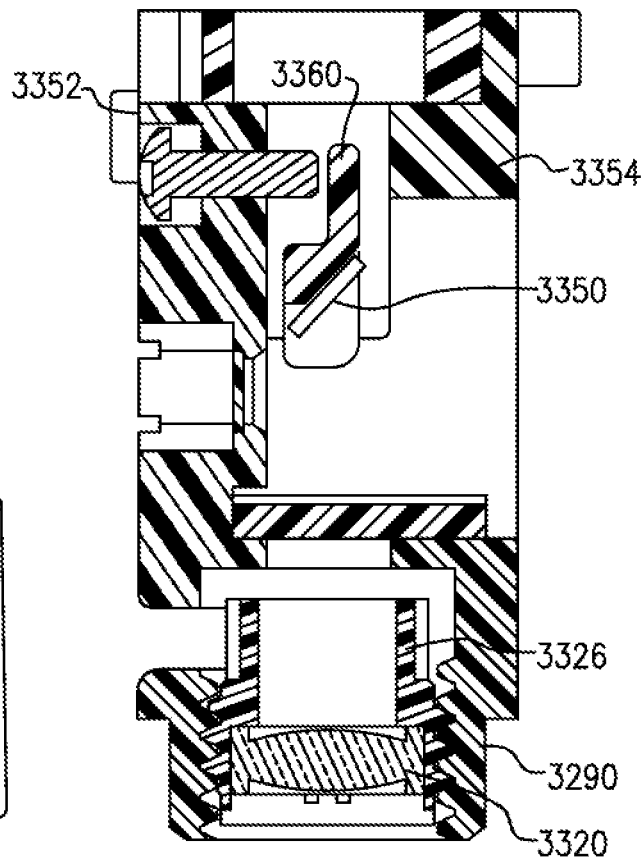
FIG. 71(a) is an enlarged sectioned view of a portion of FIG. 65.
Figure 72A:
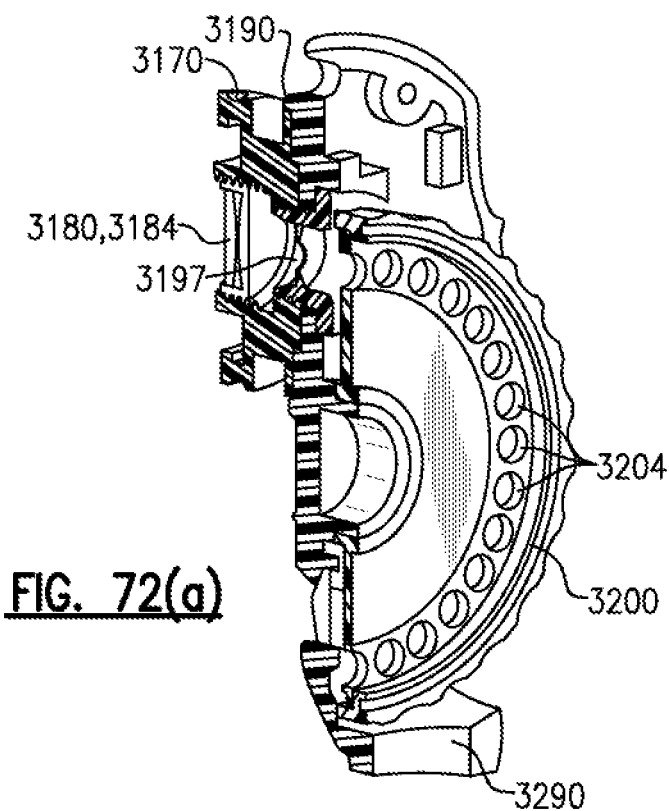
FIGS. 72(a) and 72(b) are partial perspective views, partially in section, of a portion of the optical assembly, including the rotatable diopter wheel of the instrument head of FIGS. 65-67.
Figure 72B:
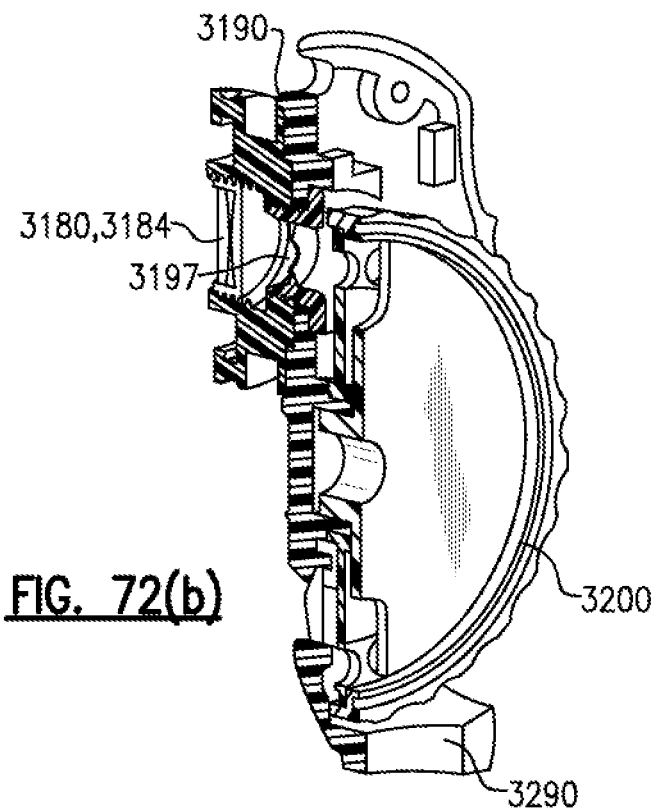

In accordance with this embodiment and referring to FIGS. 71(*a*) and 71(*b*), the mirror support member 3354 can be threadingly fitted into a formed port at the top of the instrument head 3104. A mirror 3350 is attached to a pivotable portion 3360 which can be accessed and enables adjustment during the time of manufacture. According to one version, the mirror 3350 can be adjusted using and adjustment member 3352 that is accessible through a port formed in the rear of the instrument head 3104. The mirror 3350 is further attached to a movable member that enables additional adjustment of the supported mirror 3350, as needed. The mirror mount assembly described is exemplary. For example, the mirror mount assembly 2453 described in the prior embodiment (see FIGS. 60(*a*)-60(*f*)) can be substituted for this version.

For purposes of this embodiment, the illumination assembly 3101 utilizes a single LED 3256, though the number and color temperature of the LED can be suitably varied. According to this embodiment, a magnification lens 3210 is provided adjacent a window of the necked portion 3107 in order to permit a caregiver to more easily read the diopter wheel setting of the herein described ophthalmic device 3100.

FIG. 67 illustrates an illumination ray trace of the herein described instrument 3100. According to this embodiment and upon engagement between the lower end of the contact pin with the contained battery (not shown) in the instrument handle (not shown), the contained LED 3256 is energized. The output of the LED 3256 is directed through the centering ring 3251, the condenser lens 3260 and the aperture wheel 3300 along the defined illumination axis 3310 in which the beam passes through the relay lens 3320 and a polarizer 3340 and is directed against the folded mirror 3350, whose position is adjusted at the time of manufacture within the mirror mount by accessing a threaded adjustment member.

Though the imaging elements of the assembly are also shown in this view, the light does not cross the imaging axis 3132. In addition and also not shown, a portion of the emitted light is directed through a set of optical fibers (not shown) through the instrument head 3104 and to the fixation targets positioned at the distal end 3112.

Still referring to FIG. 67, the emitted light from the LED 3256 is reflected from the angled mirror 3350, the latter having an angled surface that directs the light toward the distal end 3112 of the instrument head 3104 and more specifically through the objective lens 3140. The reflected light passes through the objective lens 3140 and is then focused onto the eye 3130 of the patient. According to this embodiment, the focal point of the reflected light is off center relative to the front of the eye 3130 of the patient and more specifically the pupil serving as the image plane wherein the light is then spread outward onto the back of the eye and more specifically the retina 3137. As shown and described herein, the focused spot is off-line relative to the optical axis 3132 of the device 3100.

With reference to FIGS. 66 and 68, the imaging of the target (i.e., the retina 3137) is reflected from the back of the eye 3130 to the objective lens 3140 in which the light is further directed along the defined optical axis 3132 through the image aperture plate 3188 in which an inverted image is passed. The light is then directed to the relay lens 3186, field stop 3197 and through the eyepiece lenses 3180, 3184, respectively, wherein the light is focused onto the eye (not shown) of the caregiver as an erect image.

Alternatively and in lieu of the eyepiece, the light can be directed through the aperture of a smart device 3106, FIG. 62, such as a smart phone, which is attached to the proximal end 3116 of the device 3100 and aligned in relation to the optical axis 3132. This attachment can be done in the manner previously described according to FIGS. 6-13(*b*) or the alternative techniques described in FIGS. 14-20.

Figure 73:
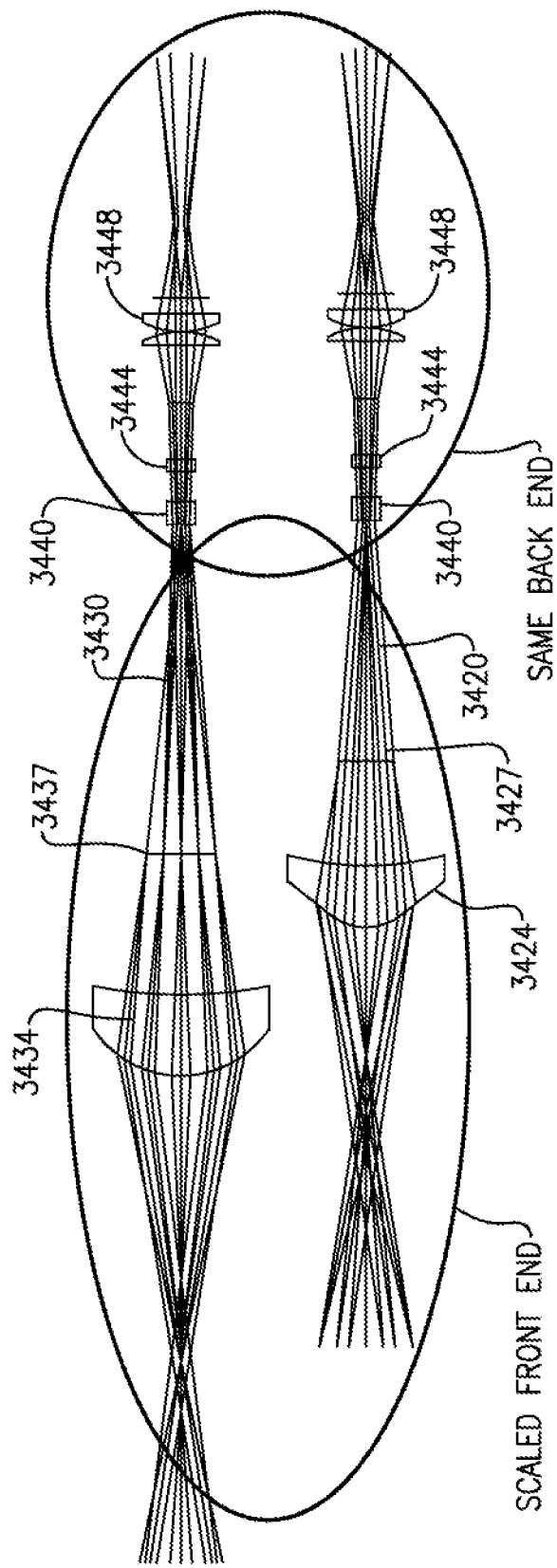
FIG. 73 depicts a comparative layout of a pair of optical assemblies for a physical assessment device.

FIG. 73 illustrates an optical layout illustrating scaling for instrument heads 3404, 3414, such as shown in FIG. 74. More specifically, the instrument heads 3404, 3414 can include scaled optical assemblies maintaining back ends that commonly include relay lenses 3440, 3444 and eyepiece lenses 3448, while axially adjusting the position and dimensionally scaling the objective lens 3424, 3434 and aperture plate 3427, 3437, the latter enabling common interfaces for various physical assessment devices.

A benefit of the optics of the illumination assembly is depicted in FIG. 75. At the top of the figure is a known ophthalmic illumination assembly in which the positioning of the condensing lens in which the focus distance creates a potential issue in which dirt or debris on the condensing lens can interfere with the resulting examination. The lower portion of the figure indicates a point focus relative to the front and back surface of the condensing lens that effectively removes this issue, while maintaining a reticle plan focus at infinity.

Figure 76A:
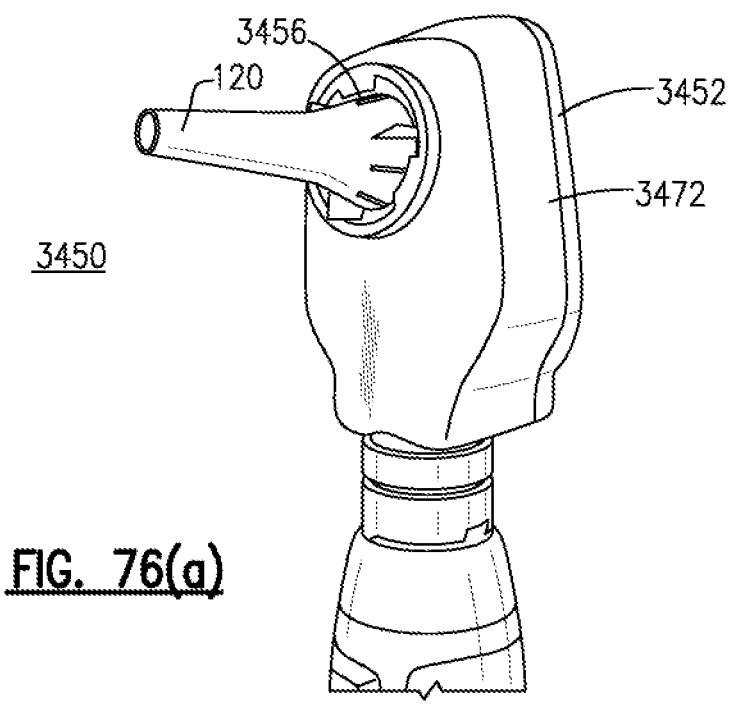
FIGS. 76(a) and 76(b) depict instrument heads typically used for ophthalmic examinations in which the instrument heads can be configured for otological examinations in accordance with exemplary embodiments.
Figure 76B:
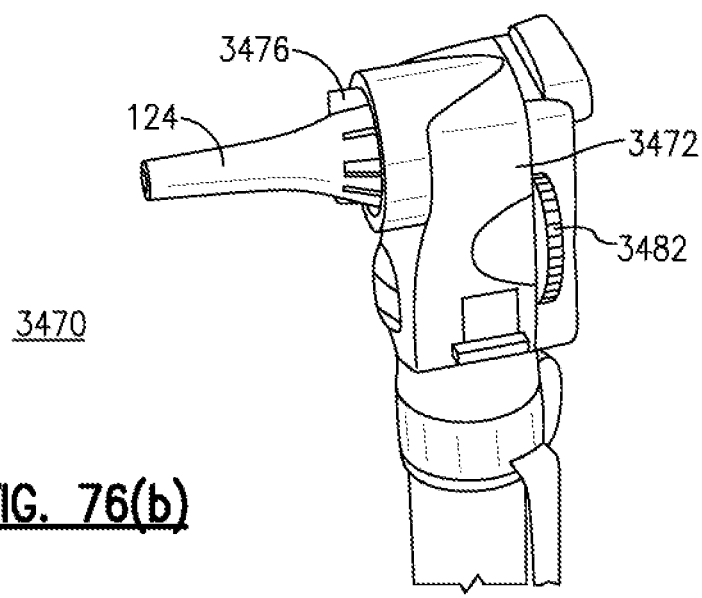

A general need in the field of diagnostic medicine is that of enhancing versatility and interchangeability between physical assessment devices, such as, for example, otoscopes and ophthalmoscopes. According to one example, depicted in FIGS. 76(*a*) and 76(*b*), ophthalmoscopes can be reconfigured in order to permit examinations of eye of a patient. The depicted ophthalmoscopes 3450, 3470 in these figures are those of Model 117 Ophthalmoscope and Model 12800 Pocket Ophthalmoscopes, respectively, each commercially sold by Welch Allyn, Inc of Skaneateles Falls, N.Y. In accordance with this exemplary embodiment, each of the instrument heads 3454, 3474 are configured to permit otoscopic examinations. More specifically, a tip attaching and releasing mechanism is fitted into the distal end 3456, 3476 of each ophthalmoscope 3450, 3470 to enable the releasable retention of a disposable speculum tip element 120 at the distal end as a patient interface, in lieu of an eye cup. For purposes of this conversion, each existing instrument head 3450, 3470 can be configured with a distal insertion portion and distal ring member similar to that included in the previously described otoscope 100, FIG. 2(b).

In use and for purposes of close-up viewing, the existing diopter wheel 3462, 3482 of each ophthalmoscope 3450, 3470 can be used to provide accommodation at a setting of approximately 10-15 diopters, based on the caregiver's personal vision and the application/use. Each are accomplished using the rotatable diopter wheel common to the known ophthalmoscopes.

According to a further version, the speculum tip attachment mechanism can be installed onto the distal end 3456, 3476 of the instrument head 3452, 3472 in order to preset the angle of the attached tip element 120 relative to the contained light source. Advantageously, this preset positioning of the attached speculum tip can optimize uniformity and concentricity of the illuminated light from the contained light source in the handle portion of each of the depicted instruments 3450, 3470.

LED Drive Circuitry

Current instrument heads, such as those commercially sold by Welch Allyn, Inc. are wholly halogen lamp based. Electrically, the lamp filament is a piece of wire whose resistance increases with temperature. So, for any given input voltage, the filament heats up which increases its resistance until the drive circuit reaches a natural equilibrium (heat/light/resistance/current for the given input voltage). When the input voltage is raised, the lamp filament becomes brighter and when the input voltage is lowered the lamp filament dims.

Contrasting, all known LED controller ICs in the electronics industry are designed to ignore its input voltage. This is done for a number of valid reasons, but the crucial point is that by definition, a system that varies voltage as a way of controlling light output is categorically incompatible with LED technology. Therefore, it is not recommended to vary/dim LED brightness by changing its input voltage. With the incorporation of both light sources into instrument heads, a solution is needed for driving and dimming both halogen lamps and LEDs.

Accordingly, FIGS. 77-81 describe an exemplary embodiment of circuitry for controlling LED lighting in an instrument head. The embodiments disclosed herein provide numerous enhancements over conventional lighting control circuits. For instance, typical instrument heads are only compatible with specific instrument handles, because the instrument handles provide electrical power to the instrument head, and must provide that electrical power in a very specific profile of voltage and current. Thus, instrument heads are not typically usable with different instrument handles, requiring a proliferation of instrument heads and designs.

For instance, different types of lighting have different electrical properties. For example, LED light dimming may be achieved by constant voltage, and thus a constant current, that is pulse-width modulated to reduce the duty time that the LED is on, whereas incandescent light dimming may be achieved by changing voltages. In addition, traditional instrument heads may include alternating current (AC) power sources, and may only be compatible with lighting that can use AC power, such as incandescent or halogen lighting. Further, different instrument handles may be wired with different polarities, requiring the instrument heads to be hardwired to accept the specific polarity. And LEDs and LED drive circuits have strict requirements for polarity. Current instrument handles have multiple polarities (+/−, −/+ and a variation of AC), and therefore the input power must be rectified to a single polarity before an LED in the instrument head can be driven.

Advantageously, the circuits disclosed herein are designed to solve these problems by allowing compatibility between different instrument heads and instrument handles.

Figure 77:
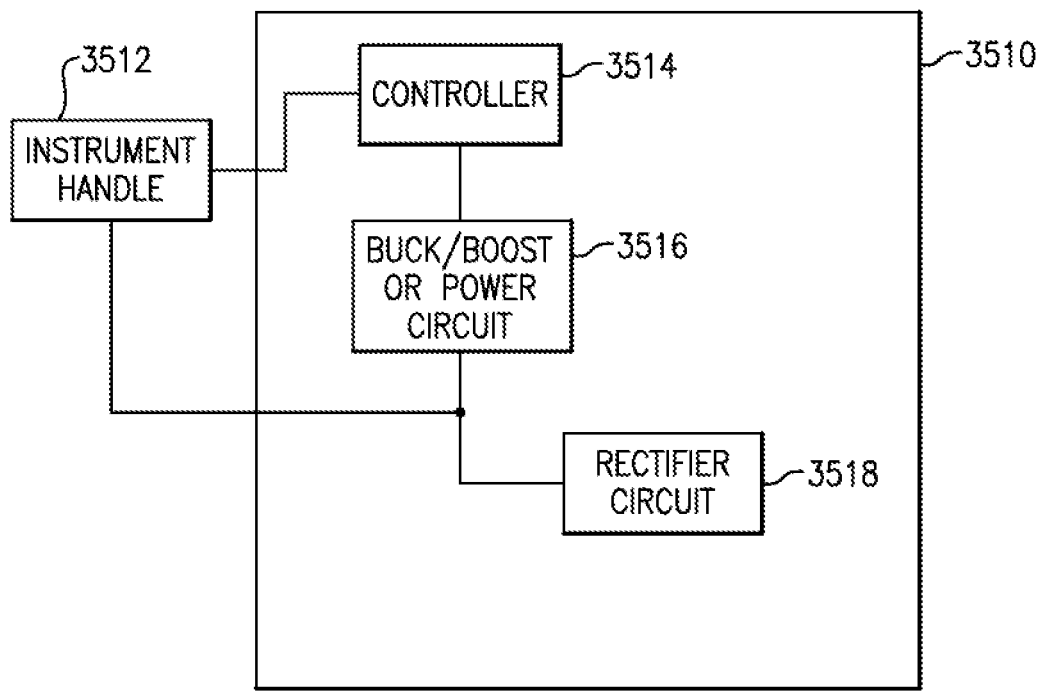
FIG. 77 is a block diagram of a circuit for controlling LED lighting in an instrument head in accordance with an embodiment.

FIG. 77 depicts a block diagram of a circuit 3510 for controlling or driving LED lighting. The circuit 3510 may be disposed within an instrument head, such as the instrument head 104 of the otoscope of FIGS. 1(a)-5 or the instrument head 2004 of the ophthalmoscope of FIG. 59(b), which provides power and has buttons for controlling the lighting, including turning on or off, dimming, brightening, etc. The circuit 3510 includes a controller 3514, a buck/boost or power circuit 3516, and a rectifier circuit 3518. The circuit 3510 may be connected to an instrument handle 3512, and such connection may be through a 2-wire connection, 3-wire connection, or any other suitable connection having multiple wires for voltages and/or signals. Working examples of specific implementations of the controller 3514, the power circuit 3516, and the rectifier circuit 3518 are discussed below with respect to FIGS. 79-81.

Figure 78:
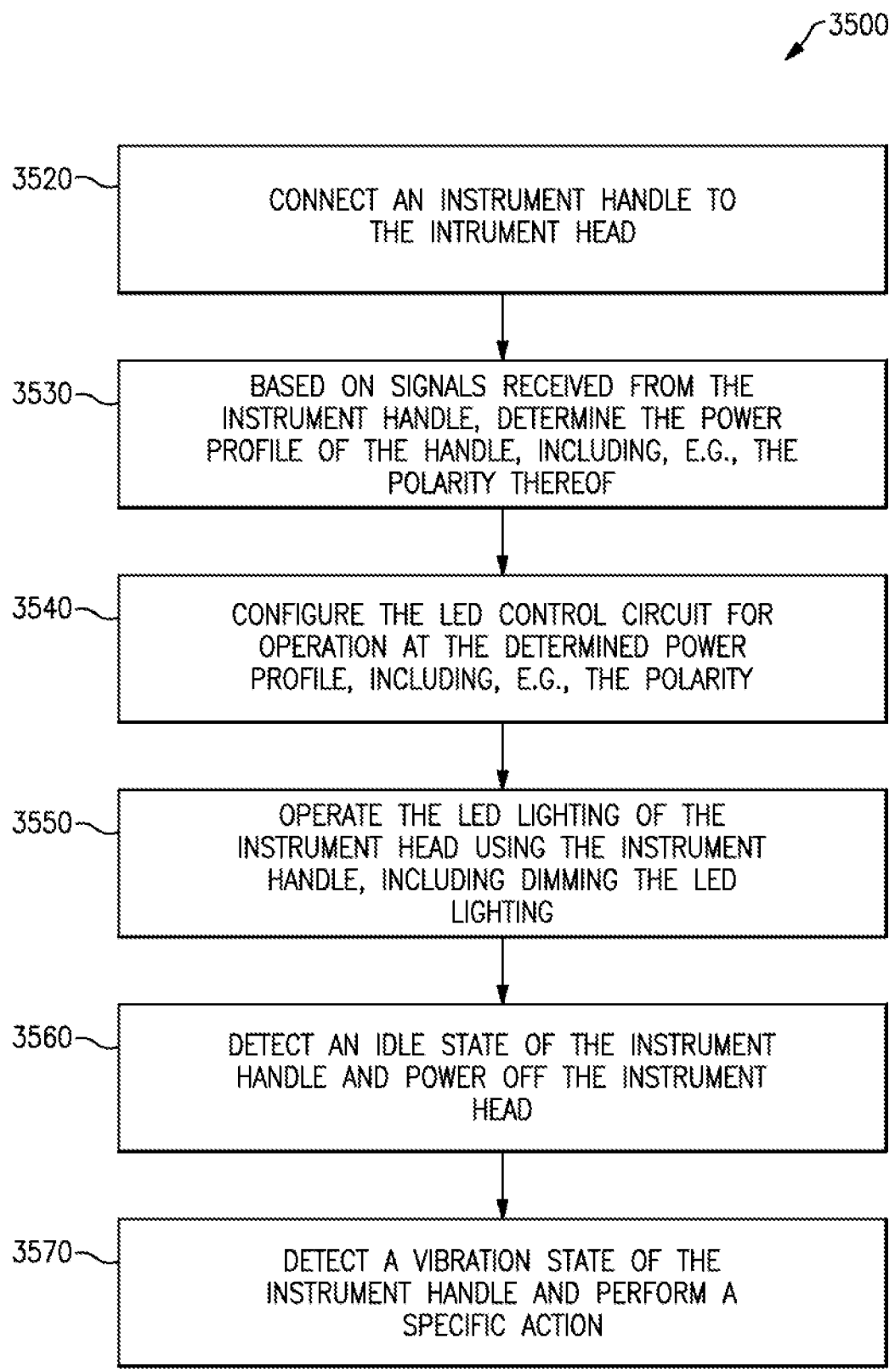
FIG. 78 is a flowchart depicting a method for controlling LED lighting in an instrument head in accordance with an embodiment.

FIG. 78 is a flowchart depicting a method 3500 for controlling LED lighting in an instrument head, by using the circuit 3510 of FIG. 77. With reference to FIGS. 77-78, in one example, at block 3520 an instrument handle 3512 may be connected to an instrument head, such as the instrument head 104 of the otoscope of FIGS. 1(a)-5 or the instrument head 2004 of the ophthalmoscope of FIG. 59(b), where the instrument head includes the circuit 3510. This connection may be through a 2-wire, 3-wire, or other suitable connection. In one example, simple 2-wire connection would only allow the instrument handle 3512 to provide electrical power (e.g., at specific voltages and currents) to the circuit 3510. In another example, the instrument head may include one or more wires with a control signal, such as a serial port, for sending control signals from the instrument handle 3512 to the circuit 3510. The signals received by the circuit 3510 from the instrument handle 3512 may be an AC voltage or a DC voltage signal having varying levels of voltage and/or current.

Based on the signals received by the circuit 3510 from the instrument handle 3512, at block 3530 the power profile of the instrument handle 3512 may be determined. For instance, the controller 3514 of the circuit 3510 may be programmed to sense the voltage, current, polarity, and other signals from the instrument handle 3512, and use this information to determine what type of instrument handle is in fact connected.

For example, conventional instrument handles may be designed to use voltage change to control dimming of halogen or other incandescent lamps. In such a case, electrically, the lamp filament is a piece of wire whose resistance increases with temperature. So, for any given input voltage, the filament heats up which increases its resistance until the drive circuit reaches a natural equilibrium (heat/light/resistance/current for the given input voltage). When the input voltage is raised, the lamp filament becomes brighter and when the input voltage is lowered the lamp filament dims. Contrasting, all LED controller ICs in the electronics industry are designed to ignore its input voltage. This is done for a number of valid reasons, but the crucial point is that by definition, a system that varies voltage as a way of controlling light output is incompatible with LED technology. Therefore, it is not recommended to vary/dim LED brightness by changing its input voltage. With the incorporation of both light sources into instrument heads, the present circuit 3510 allows for driving both LED and incandescent light sources from a single instrument handle 3512. Thus, the controller 3514 could sense the properties described above and make a determination that the instrument handle connected is of a type typically used to drive halogen or other incandescent lamps, but that this instrument handle now needs to drive LED lighting.

Continuing with method 3500 of FIG. 78, at block 3540, the circuit 3510 may be configured for operation at the power profile determined at block 3530. This configuration may include configuring the controller 3514 and/or the power circuit 3516, as explained in further detail below with respect to FIGS. 79-81.

Advantageously, configuring the circuit 3510 for operation with the instrument handle 3512, based upon auto-detection of the handle profile, allows any number of different instrument handles that have been deployed in the field to be used with the new instrument heads described herein. Thus, the benefits of the features, such as LED lighting, may be realized even without replacing these previously deployed instrument handles. This auto-detection and configuration of instrument heads for use with instrument handles represent improves the field of medical scopes, because the technique allows mixing and matching of different handles and heads by the medical user, increasing efficiency with which patients may be treated.

Next, at block 3550, the LED lighting of the instrument handle, which is driven by the power circuit 3516, may be operated and controlled using the instrument handle 3512. In order to facilitate operating and controlling the LED lighting with different instrument handles 3512 that may have very different electrical profiles, the power circuit 3516 includes buck-boost voltage conversion that allow variable input voltages to be converted into a specified output voltage, where the input voltages may be above or below the specified output voltages. The buck portion of power circuit 3516 decreases a higher input voltage to meet the requirements of a lower specified output voltage, and the boost portion of power circuit 3516 increases a lower input voltage to meet the requirements of a higher specified output voltage. Specific details of this power circuit 3516 is set forth with respect to FIG. 80. In addition, operating and controlling (at block 3550) the LED lighting with the instrument handle 3512 is also achieved by converting changes in voltage to changes in current, as will be described in more detail with respect to FIGS. 79-81.

Further, at block 3560 of the method 3500, the controller 3514 can detect an idle state of the instrument handle. Upon detection of an idle state, the instrument head can be powered off. And, at block 3570, the controller 3514 can detect a vibration state of the instrument handle, and can perform a specific action based on that state, such as powering off the instrument head.

Another problem identified with portable physical assessment devices is that of theft of the instrument handles from the charging base. Using the controller 3514 to detect state changes, a theft deterrent mechanism that could be included. For example, an audible alarm could be set off from the charging base if the instrument handle is not returned in a predetermined time interval. In addition, an LED indicator can also be provided on the charging base when the alarm feature is enabled.

An electrical circuit design can provide a controller that generates an audible alarm if the instrument handle is not returned to the charging base, such as base 1800, FIG. 52, in a defined amount of time.

In another embodiment, an auto-off feature will turn off the instrument after a predetermined time period of inactivity. In such an example, the controller is programmed with a timer. If a motion sensor subsystem that is connected to the controller fails to report any motion during the time period, as counted by the timer, the system will turn off the instrument.

Figure 79:
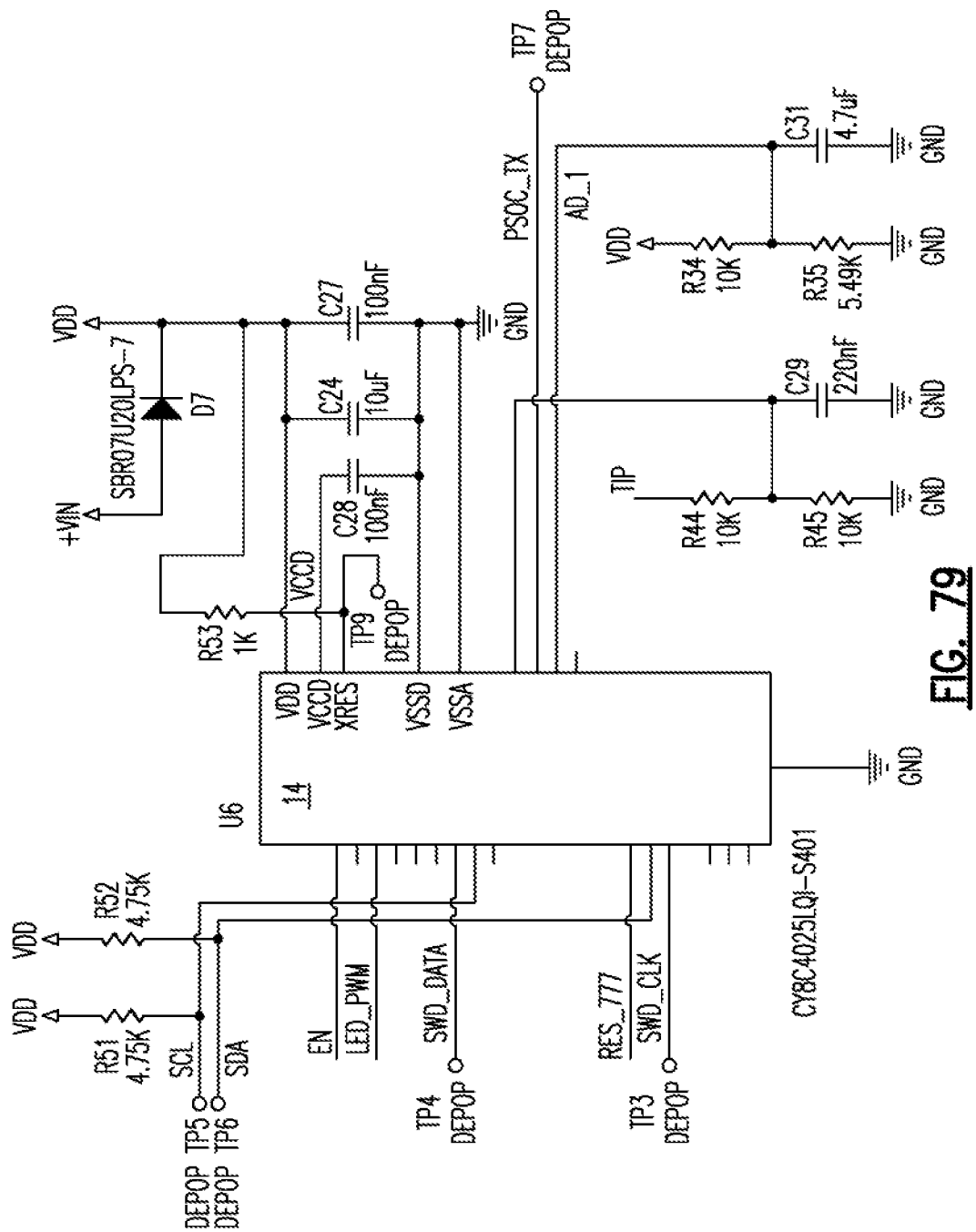
FIG. 79 is a circuit diagram of the controller of FIG. 77.

FIG. 79 is a circuit diagram of the controller 3514 and affiliated circuitry. In the embodiment of FIG. 79 the controller 3514 may be a model CY8C4025LQI-S401 microcontroller available from Cypress Semiconductor Corporation, of San Jose, Calif., USA. In other embodiments, discrete logic elements may be employed instead of a microcontroller.

Figure 81:
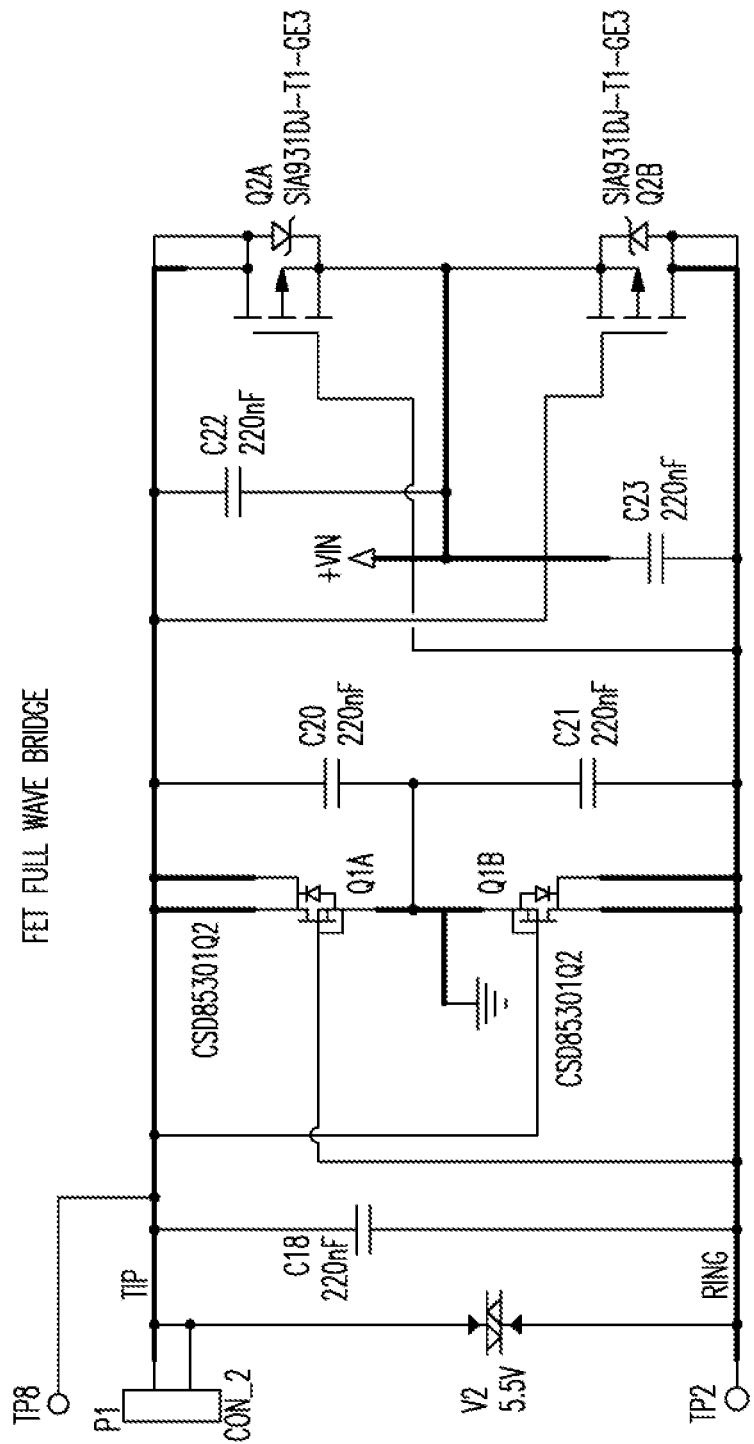
FIG. 81 is a circuit diagram of the FET full-wave bridge circuit of FIG. 77.

As shown in FIG. 79, the controller 3514 is connected to the input voltage that has passed through the rectifier of FIG. 81. The rectifier is needed because the LEDs may be powered by direct current rather than alternating current. The rectified voltage then is input into the controller 3514, which then outputs a pulse width modulation signal LED_PWM. The LED_PWM signal is input into the buck/boost or power circuit 3516, as depicted in FIG. 81. Any of a number of PWM algorithms may be used with the circuit. For instance, in traditional voltage based dimming, a voltage vs. brightness curve may be described that relates a given voltage to a given brightness. A linear relation would mean that if the voltage is reduced by 50% from a nominal high voltage, the brightness would reduce by 50%. In order to translate this into dimming an LED, a PWM signal that is on for 50% of the time would power an LED half the time and thus achieve 50% brightness.

In other embodiments, a non-linear relationship between the voltage an brightness may be observed. In one example, a calibration of a legacy handle and legacy incandescent head can be carried out, so that the legacy handle can later be used with a new head of the present disclosure. For example, the calibration process could use the legacy handle connected to the legacy incandescent head, and the legacy handle's voltage may be varied from maximum to minimum while measuring the brightness percentage as a function of voltage. The resulting calibration data set relates voltage to expected brightness percentage for the legacy handle. This calibration curve can be loaded into the controller on an instrument head of the present disclosure so that the brightness control of the legacy handle will have the same effective result when using the new instrument head.

The controller would achieve this by detecting the input voltage from the handle, and using a lookup table containing the calibration data set to find the appropriate desired brightness percentage. Then, instead of applying the input voltage to the LED, the input voltage would be buck/boost converted to yield a constant LED current. The brightness would be controlled by a PWM signal that turned on and off the LED such that the LED was on for the desired brightness percentage of the time, and off the rest of the time. In such a manner, numerous different legacy handles with different voltages can be profiled to find calibration data for use in the instrument head described herein.

In an embodiment, the controller 3514 receives the input voltage VIN from the instrument handle and determines its polarity. Depending on the polarity of the voltage VIN received from the instrument handle, and potentially other indicia such as power on signals, initial voltage, etc., the controller can determine the power profile for that specific instrument handle, e.g., by using a lookup table that lists all the known instrument handles and their known polarities, initial voltages, power on signals, etc. In such a case, the controller can determine what type of instrument handle has been attached, and then can access the voltage calibration curve of the instrument handle, which relates the voltage to the output illumination level of the LED as explained above. The LED_PWM signal from the controller may the appropriately drive a PWM signal of the correct duty cycle (e.g., percentage on to off) to achieve the brightness of the LED that corresponds to the brightness that an incandescent instrument head would output if the same instrument head were connected to it and directly driven using the voltages. In such a manner, the input voltages changes have been converted to PWM signals of specific duty cycles of a constant current that can be used to power and dim an LED. In another example, specific pins on the instrument handle may carry identification or handshake data that tells the instrument head which handle has been connected, allowing the controller to lookup a pre-loaded power profile for that handle.

In an embodiment, the controller 3514 may also determine vibration/motion or idle states of the instrument head and/or handle, and perform appropriate actions as described with respect to method 3500 above. In one example, idle states can be determined by a lack of motion sensor indicated activity during a predetermined time period, and the action can be to shut off the instrument. In another example, motion of the instrument can be detected by the motion sensor, and an idle timer can be reset, or other subsystems may be turned on.

Figure 80:
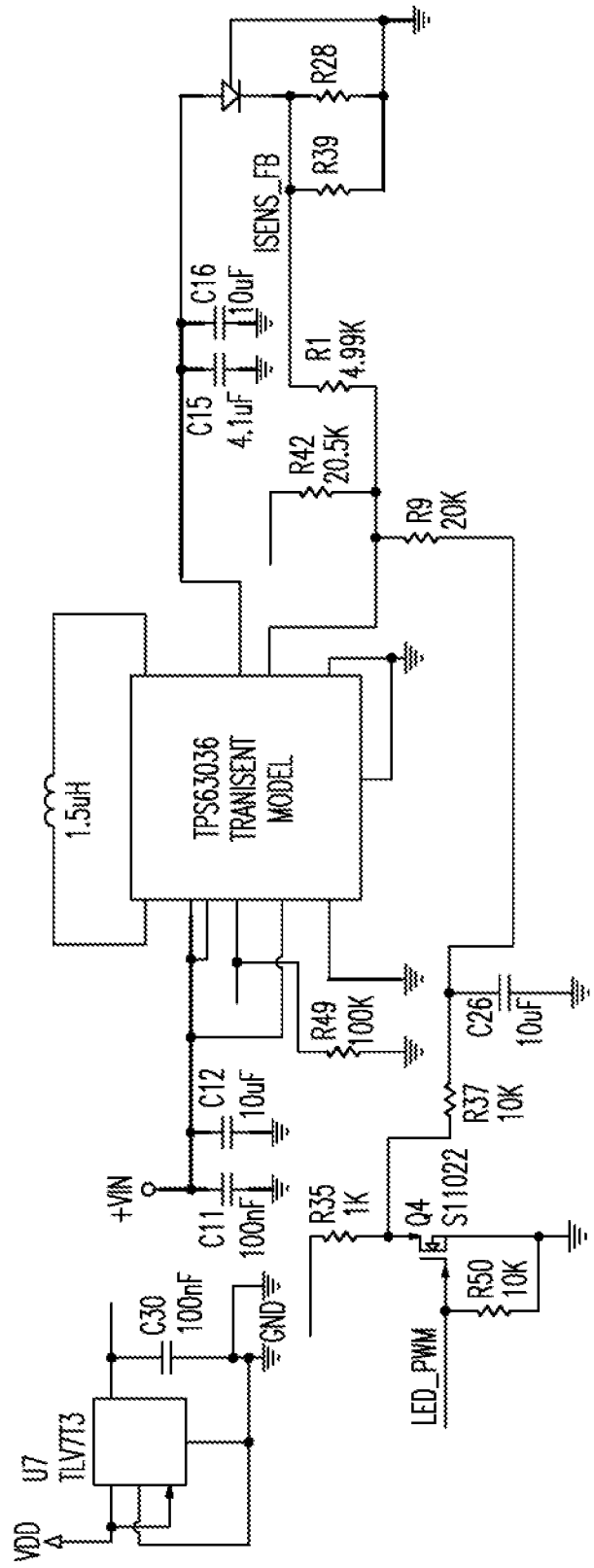
FIG. 80 is a circuit diagram of the power conversion circuit of FIG. 77.

FIG. 80 is a circuit diagram of the buck/boost or power circuit 3516. In the example of FIG. 80, the power circuit 3516 is based on a TPS63036 Buck/Boost converter U5 with support for receiving the LED_PWM signals from the controller as described above. The TPS63036 is available from Texas Instruments Inc., Dallas, Tex., USA. In the circuit diagram of FIG. 80, we see that the input voltage is fed into the converter U5, which is also controlled using the EN and PWM_LED signal from the controller 3514, in order to apply the PWM profile to dim the LED lighting as noted above with respect to FIG. 79.

In operation, the buck/boost or power circuit 3516 may receive the input voltage VIN and provide an output voltage VOUT that generates a fixed or constant current for powering the LED lights. The output voltage VOUT may be tuned by appropriately setting resistors R1 and R2, in the specific example using a TPS63036 converter. Once set up, the buck/boost or power circuit 3516 would output the fixed or constant current for powering the LEDS, and the PWM_LED wire from the controller 3514 would be used to provide the PWM signal with the appropriate duty cycle for achieving a specific brightness. In other examples, the buck and boost portions of the circuit may be implemented separately using discrete components instead of a single buck/boost converter. In such a case, the circuit would boost a VIN that was less than VOUT through a boosting sub-circuit, and decrease or buck a VIN that was greater than VOUT through a buck sub-circuit.

FIG. 81 is a circuit diagram of the FET full-wave bridge circuit 3518. Rectification to a single polarity is typically done with a diode Full Wave Bridge (FWB). Diode FWB's typically lose between 1V and 1.4V in the rectification process. This is a considerable proportion of the LED voltage, which is typically 2.7V. That ratio approximates the loss of energy from the battery never to produce light. In order to minimize losses associated with a diode full-wave-bridge, a FET full-wave-bridge is introduced, as shown in FIG. 81. The FET FWB design only loses about 50 mV, depending upon the current and FETs selected. The energy not lost means energy available to produce light and increasing overall battery life of the device.

The FET FWB circuit design is made up of two NFETs, two PFETs, and the necessary capacitors. The FET full-wave-bridge has considerable ESD protection, mostly realized in capacitors across the gate-source for each FET.

Figure 82:
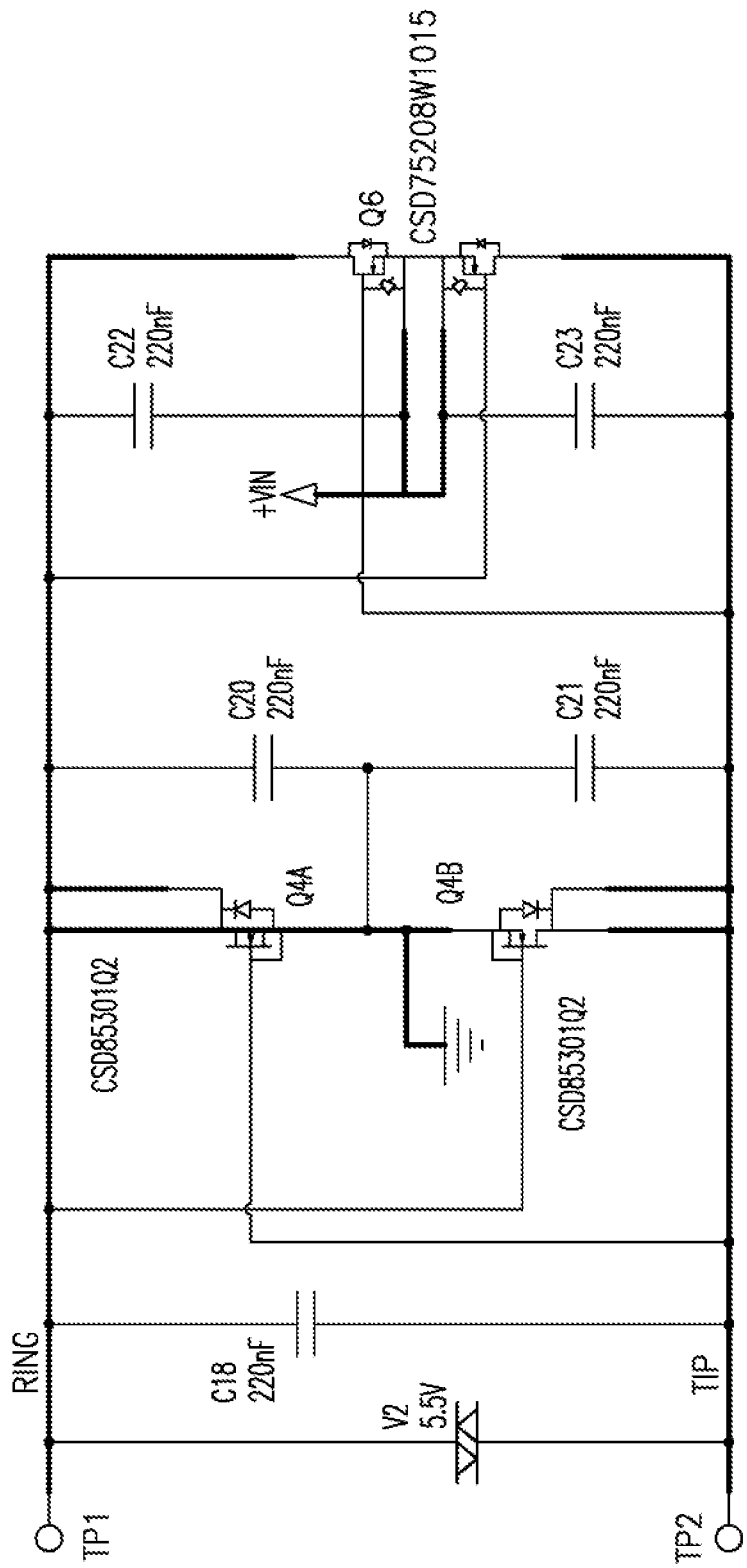
FIG. 82 illustrates an electrical circuit diagram of a field-effect transistor (FET) rectifier/bridge in accordance with another exemplary embodiment.

In accordance with another embodiment and with reference to FIG. 82, an instrument head for a physical assessment device is configured with a buck convertor head design, which is an LED controller circuit design that will drive an LED effectively and without risk of instability (LED Flicker) with a PWM(Bang-Bang) power source.

For the power source, a traditional RC hysteretic oscillator (nicknamed bang-bang in the electronics world) will be used. This power source will drive both a halogen lamp head and the LED instrument head having the buck converter. For the buck converter LED driver head, and while the input voltage is sufficient, there is controlled brightness. For output voltage varying power sources (as the drive voltage lowers (dimming)), the buck converter eventually runs out of headroom and the LED is driven directly by the driving voltage (in series with the parasitic resistances of the controller and the mechanical system). This occurs when $V_{in}$ approaches the LED's VF plus the controller's sense voltage plus the parasitic IR losses. For a PWM power source, as long as the output voltage is greater than the LED's VF, the bang-bang dimming will dim the LED effectively and without instability (flicker). For purposes of this specific embodiment, the circuit is the PAM2804 IC LED driver applied as the manufacturer recommends. The PAM2804 is a suitable example of an LED Driver IC since it will run down to the appropriate voltage of 2.5V. This is an anomaly because no high brightness LED has a forward voltage of 2.5V. The 2.5V capable DC-DC converter IC, PAM2312-ADJ, can be repurposed for LED drive by lowering its reference voltage from 0.6V to 0.1V.

An alternative drive circuit is shown in FIG. 83 in which R25, R26 and R27 are additionally provided to enable fine tuning in order to adjust the LED effective forward voltage. This capability enables a number of LEDs to operate in a representative manner across instrument heads and handles.

LED's and LED drive circuits have strict requirements for polarity. Current instrument handles have multiple polarities (+/−, −/+ and a variation of AC), and therefore the input power must be rectified to a single polarity before an LED in the instrument head can be driven.

Rectification to a single polarity is typically done with a diode Full Wave Bridge (FWB). Diode FWB's typically lose between 1V and 1.4V in the rectification process. This is a considerable proportion of the LED voltage, which is typically 2.7V. That ratio approximates the loss of energy from the battery never to produce light. In order to minimize losses associated with a diode full-wave-bridge, a FET full-wave-bridge is introduced, as shown in FIG. 82. The FET FWB design only loses about 50 mV, depending upon the current and FETs selected. The energy not lost means energy available to produce light and increasing overall battery life of the device.

The FET FWB circuit design is made up of two NFETs, two PFETs, and the necessary capacitors. The FET full-wave-bridge has considerable ESD protection, mostly realized in capacitors across the gate-source for each FET.

While a 2-wire voltage varying input is the standard method for adjusting brightness for a halogen or incandescent lamp, it's problematic for LED circuits as has happened in the commercial and residential lighting industry. The most significant issue is loop stability going unstable, causing LED's to blink. This can be a serious problem in physical assessment devices such as ophthalmoscopes, otoscopes, etc. Industry LED circuits rely upon pulse width modulation for dimming LEDs. In order to drive both an LED and halogen based lamp from a single voltage varying power source an electrical solution must be designed.

Figure 83A:
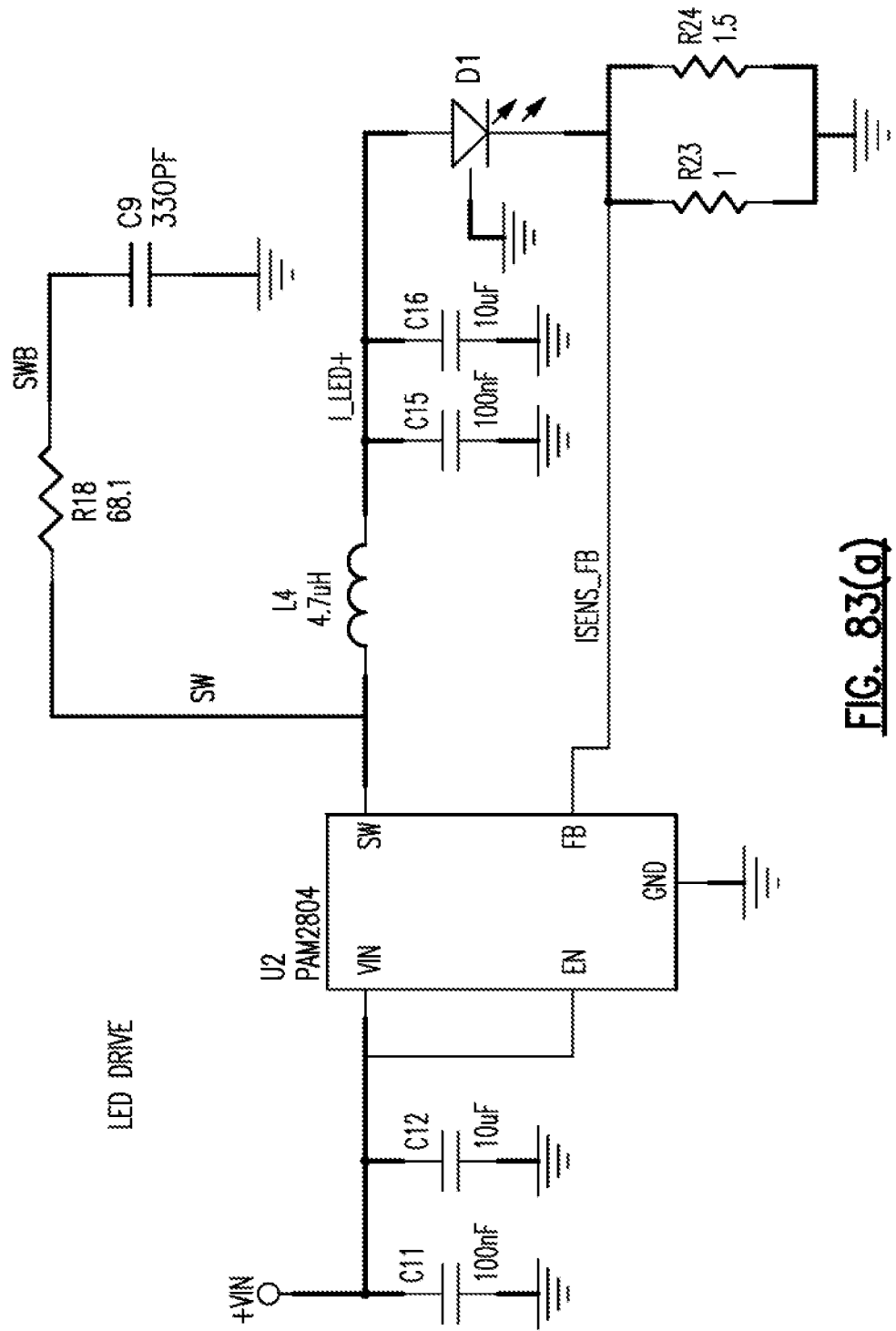
FIGS. 83(a) and 83(b) illustrates a diagram of an LED drive circuit in accordance with another exemplary embodiment.
Figure 83B:
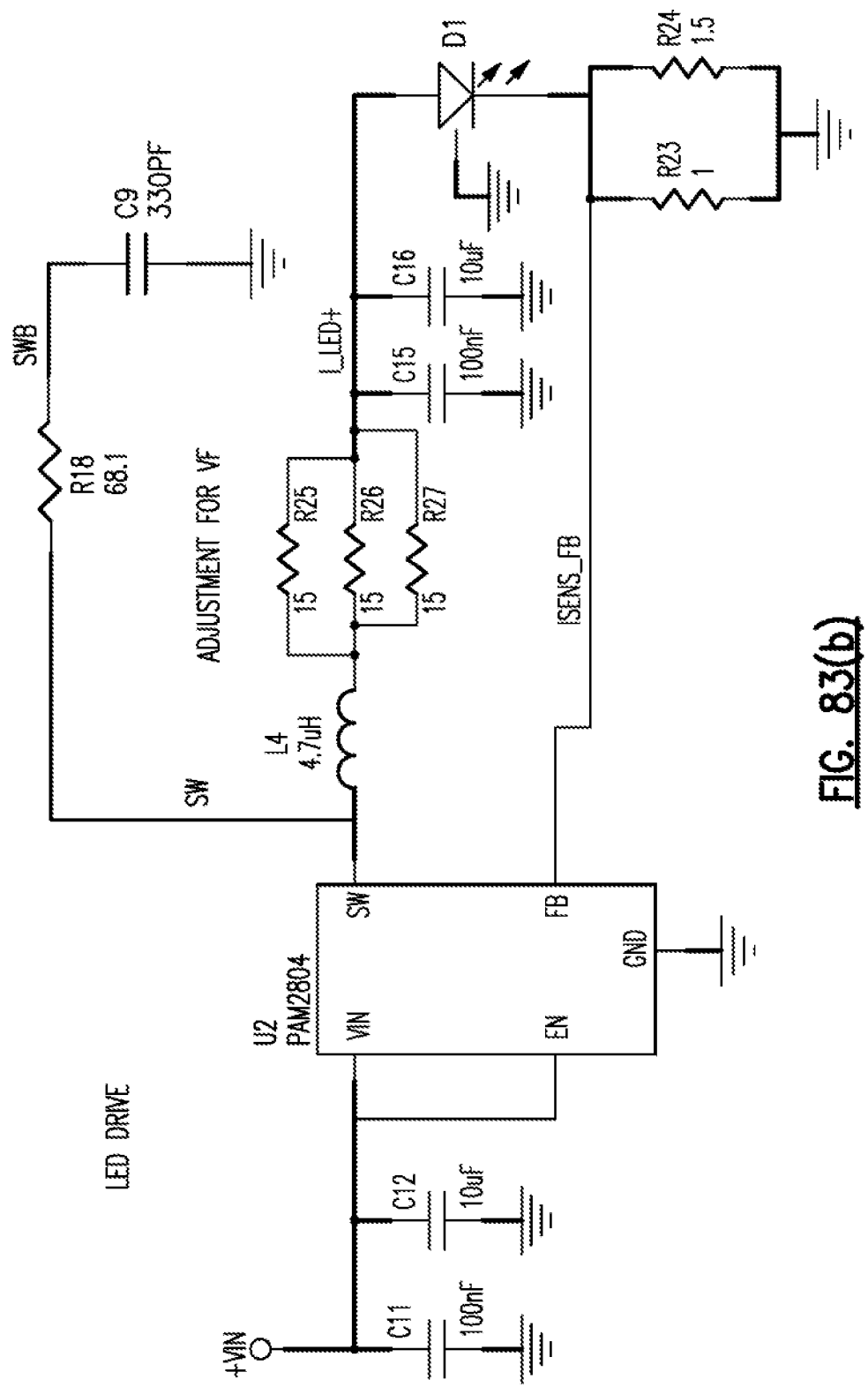
Figure 84:
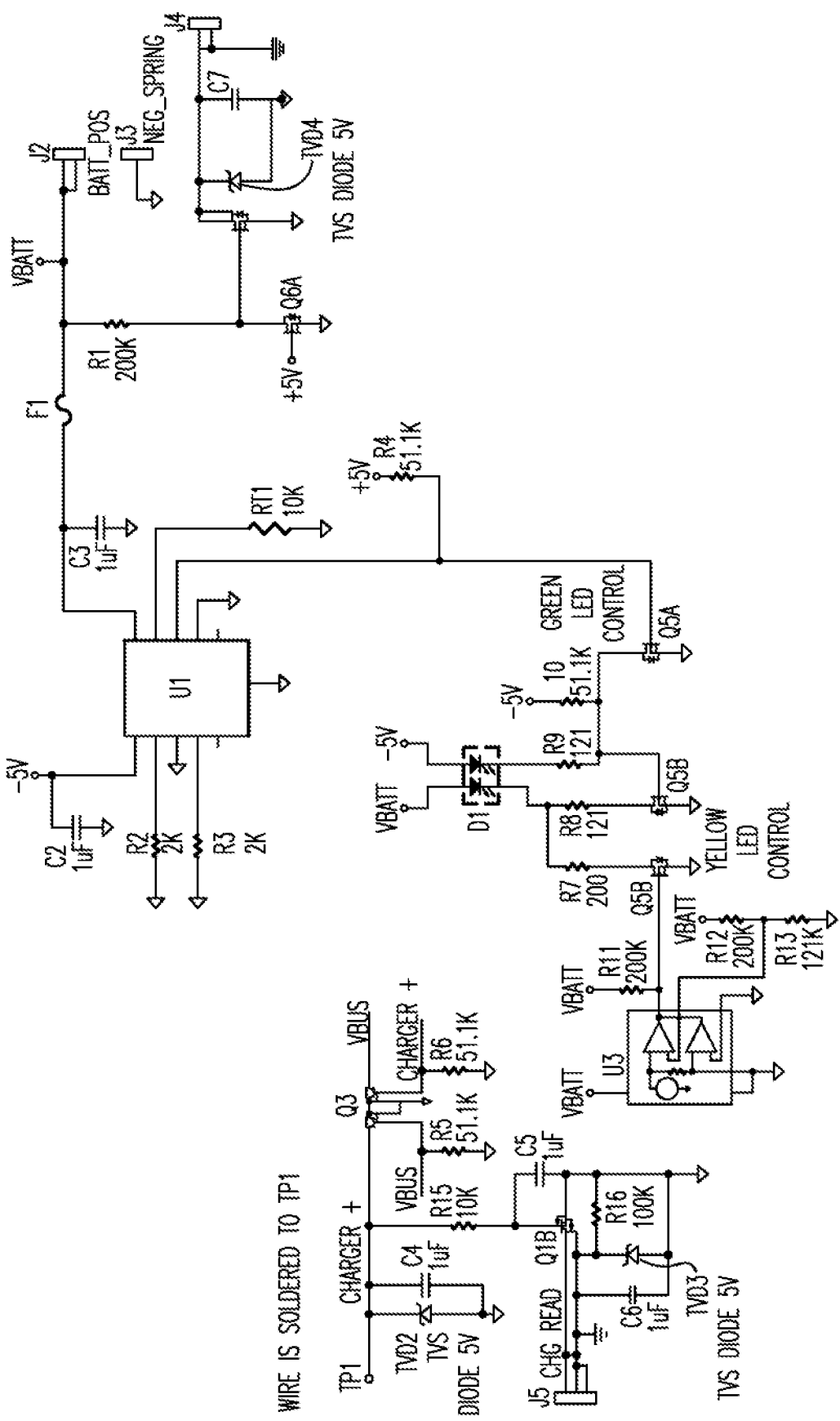

The herein described electrical circuit design shown in FIGS. 83(a), 83(b) will drive both an LED and halogen based lamp from a single varying power source and maintain loop stability so that there is no risk of blinking LEDs.

This electrical circuit design works when first energized, the output of the comparator is low, turning on the PFET. Assuming the LED voltage to approximate a constant, the voltage across the Power Inductor will approximate a constant. As such, current will rise at a linear rate. This causes a positive slope voltage ramp across the sense resistor. For purposes of this circuit, this sense voltage is "faked" low at the positive input of the comparator by the voltage divider (ratio Hyst Res/(hyst Res×FeedBack Res). When this comparator positive input voltage reaches VREF, the comparator output goes high, turning off the PFET. This is called the "Upper Threshold" of the hysteresis circuit. This output swing instantaneously reverses the voltage divider, faking the sense current high instead of low at the positive input to the comparator. As such, the current must go to the Lower Threshold of a hysteresis circuit before it crosses +VREF before the output will again go low. While the PFET is turned off (comparator output high), current continues to flow through the inductor, through the catch diode, causing a negative slope across the sense resistor.

When the current reaches the lower threshold, the output goes low, turning on the FET and the cycle continues. Since the sense voltage ramp is nearly linear both up and down, the average current will be the +VREF/SENSE RESISTOR. In other words, given a triangle wave, there will be half the area above and below its average. The circuit is regulated and controlled. The only drawback is high ripple current, but this doesn't matter for a LED, especially since practical frequencies are far above what the human eye can detect. More so, increasing the output capacitor (C17) of the hysteretic current source will reduce the ripple current and make the slopes more linear. Of more importance though, is that there is no high gain closed loop most often used in power supply control circuits, including LED drivers. Since the oscillation is no more than an inductor being charged and discharged while banging into two predictable thresholds, the instability of the oscillator cycle eliminates the chance of subharmonic oscillations that traditional controllers are prone to. In other words, the connected LEDs will not be prone to blinking.

This described circuit is stable. This circuit also does not dim with input voltage so no advantage is otherwise over traditional LED driver circuits. However, and if the reference voltage is varied as a function of input voltage (something that cannot be done with traditional power supply—including LED controllers—control loops without risking instability), the LED current will vary as a function of input voltage. Unlike high-gain control loops which vary many of their stability parameters with input voltage and reference voltage changes, the hysteretic controller continues to bang between the upper and lower thresholds and the average is the reference voltage. The addition of a voltage divider to create +VREF and the LED voltage will vary proportionally to +VIN.

As previously discussed, another problem identified with portable physical assessment devices that require base charging is that of theft of the instrument handles from the charging base. Another object of the herein described invention is to provide a theft deterrent mechanism that would be included in the charging base.

Such theft detection could include an audible alarm from the charging base if the instrument handle is not returned in a predetermined time interval. In addition, an LED indicator can also be provided on the charging base when the alarm feature is enabled.

An electrical circuit design can provide a controller that generates an audible alarm if the instrument handle is not returned to the charging base, such as base 1800, FIG. 52, in a defined amount of time. According to one version, there are four (4) pogo pins provided in the charging base; a positive contact, two negative contacts, and one contact for instrument handle detection. This handle detection contact would be what triggers the time period once the instrument handle is removed and stop the timer once the handle is placed back into the charging base. In addition, an LED indicator on the charging base can be illuminated to alert individuals that the theft alarm is enabled. This LED indicator would flash/blink when the audible alarm is sounded. A switch can be provided on the bottom or otherwise upon the charging base to enable/disable the alarm feature. This switch could be recessed in the housing of the charging base and be made only accessible by a specialized tool or other access feature, such as small piece of metal (e.g., a paper clip). There may also be some other type of switch to set the defined time for the alarm to enable once the handle is removed.

PARTS LIST FOR FIGS. 1(a)-86

100 otoscope
104 instrument head
104A instrument head
108 handle portion
112 distal or patient end, instrument head
114 access opening, instrument head
116 proximal or caregiver end, instrument head
117 rheostat
118 on-off button
119 charging port
120 speculum tip element
124 distal tip opening, tip element
125 distal entrance pupil
128 proximal opening, tip element
130 front housing section
131 lower end, front housing section
134 rear housing section
134A rear housing section
135 lower end, rear housing section
136 fasteners
137 bumper, peripheral
138 innerformer
139 conical distal portion, innerformer
140 distal insertion portion
141 lower portion, innerformer
142 sealing member
144 sleeve
146 distal ring member
152 lens tube, hollow
154 distal end, lens tube
155 intermediate axial portion
156 proximal end, lens tube
157 proximal threaded portion
160 objective lens
161 optical window
163 spacer, cylindrical
164 field stop
166 relay lens 167 aperture plate
169 imaging lens
170 field stop
172 coiled spring
175 retaining cap, threaded
180 adapter interface member
182 distal portion, adapter interface member
183 axial openings
184 recess
185 spring, coiled compression
186 machined flats
187 balls
188 proximal portion, adapter interface member
189 window
190 intermediate plate
194 cap or browrest
196 eyepiece optical window
198 cover portion
220 electrical contact
224 insulator member
240 printed circuit board
244 LED
248 lens retainer
250 condensing lens
254 biasing spring
270 handle stud base member
273 recessed portion, intermediate
280 securing ring
281 aperture, securing ring
300 adapter, smart device
304 housing or body
308 front housing section, adapter
309 front facing surface
312 rear housing section
313 interior surface, rear housing section
314 exterior surface, rear housing section
315 mounting holes
316 slot
317 fasteners
320 lower portion, front housing section
322 semicircular slot, front housing section
324 interior ridge, rear housing section
326 peripheral border, rear housing section
327 through opening, rear housing section
328 device engagement portion
330 engagement surface, device
332 engagement surface, device
335 recess, front housing portion
340 protruding portion
346 compression spring
350 slider member
352 upper plate, slider member
353 lower portion, slider member
354 edge surface, slider member
355 tracks
356 slider retainer
358 fastener(s)
359 rails
360 device engagement member
361 front facing side or surface, device engagement member
362 rear facing side or surface, device engagement member
363 adhesive strip
366 recess, device engagement member
367 transverse groove, device engagement member
370 detent cover
371 front facing surface, detent cover
372 rear facing side, detent cover
373 molded projecting portion, detent cover
375 spaced slots, detent cover
376 recess, detent cover
384 detent member
389 ears, projecting portion
391 detent, projecting
394 detent spring
395 strip of insulating material
400 adapter, smart device
420 flexible arm
424 distal end, flexible arm
428 ring-shaped portion
429 proximal end, flexible arm
433 opening
450 physical assessment device
454 instrument head
456 distal end
459 proximal end
480 smart device
500 adapter, smart device
504 base or support plate
508 upper portion, base plate
512 lower portion, base plate
520 hollow projection
522 flexible engagement portion
524 C-shaped engagement end
550 physical assessment device
554 instrument head
556 distal end
558 handle portion, physical assessment device
559 proximal end
562 focusing wheel
563 eyepiece
1100 otoscope
1104 instrument head
1108 instrument handle
1112 distal end
1116 proximal end
1120 downwardly extending portion
1124 speculum tip
1125 distal opening, speculum tip
1128 optical window
1134 housing section
1138 housing section
1140 innerformer
1142 cover
1150 interface stud
1153 groove, interface stud
1156 interior shoulder, interface stud
1160 distal insertion portion
1161 distal opening, distal insertion portion
1170 tip retaining member
1180 proximal housing member
1184 mounting flange
1186 slots, mounting flange
1187 groove (for sealing member)
1190 retaining ring
1200 otoscope
1204 instrument head
1208 instrument handle
1212 distal end
1216 proximal end
1220 downwardly extending portion
1224 rear mounting member (adapter interface member)
1226 mounting flange, rear mounting member
1228 annular slot
1230 smart device 1234 display, smart device
1240 interface member
1250 sealing member
1270 LED
1272 upper or top surface, printed circuit board
1274 printed circuit board
1275 outer edge, printed circuit board
1278 downwardly depending electrical contact
1279 spring
1280 internal sleeve
1285 opening
1287 fiber optic bundle
1290 condensing lens
1304 instrument head
1308 instrument head
1324 housing section
1328 housing section
1330 recess
1340 strap
1344 upper portion
1346 rounded interior surface
1348 lower extending portion
1352 annular flange
1356 annular shoulder
1420 integrated component
1422 body, integrated component
1426 upper end, integrated component
1430 bottom or lower end, integrated component
1434 external threads, integrated component
1438 internal flange, integrated component
1442 top surface, internal flange
1446 bottom surface, internal flange
1450 domed portion
1458 annular ring
1460 internal threads, interface stud
1468 notches, integrated component
1602 instrument handle
1604 top portion, instrument handle
1612 spaced male lugs
1616 arrows
1620 instrument head
1624 interface stud
1628 bottom end, instrument head
1632 contoured mating slot
1640 electrical contact, instrument head
1646 electrical contact, instrument handle
1706 instrument handle
1707 upper end, instrument handle
1709 top section, instrument handle
1711 bottom end, instrument handle
1712 rheostat assembly
1713 outer ring
1714 battery
1717 electrical contact, instrument handle
1718 twistable grip section
1721 spring, biasing
1722 detent ring member
1725 internal threads, detent ring member
1726 holes, detent ring member
1729 lower end, detent ring member
1732 pin member
1734 annular recess, detent ring member
1736 recess
1738 internal threads, detent ring member
1740 ball
1744 spring, biasing
1748 spring, spring
1750 internal sleeve
1757 external threads, rheostat housing
1758 rheostat housing
1760 USB charging or power boost port
1768 USB connector
1772 printed circuit board
1777 positive contact
1779 connection
1782 conductive spring clip
1790 temperature measuring apparatus
1792 connection
1800 charging cradle or base
1809 charging pins
1811 top surface, charging base
1814 charging well
1820 physical assessment device
1822 instrument head
1824 instrument handle
1828 smart device
1830 physical assessment device
1832 instrument head
1834 instrument handle
1838 smart device
1900 optical assembly or system
1910 optical assembly
1914 objective lens doublet
1919 relay lens
1920 aperture plate
1922 relay lens
1930 eyepiece lenses
1934 distal entrance pupil
1940 optical assembly
1941 objective lens doublet
1942 relay lens
1943 imaging lens
1944 plano window
1945 field stop
1950 optical assembly
1966 distal entrance pupil
1967 objective lens doublet
1968 relay lens
1969 imaging doublet
1970 plano window
1971 field stop
1974 clinician's eye
1980 optical assembly
1982 objective lens doublet
1984 relay lenses
1986 eyepiece lenses
1988 plano window
2000 ophthalmoscope
2004 instrument head
2008 handle portion or handle
2010 distal end, instrument head
2014 proximal end, instrument head
2016 front housing section, instrument head
2017 cover
2018 rear housing section, instrument head
2019 fasteners
2020 rheostat
2022 on-off button
2024 charging port
2030 eye cup
2040 interface member, adapter
2041 distal portion, adapter
2042 proximal portion, adapter
2043 openings, axial 2044 springs
2045 balls
2046 recess
2048 machined flats
2049 browrest or cap
2050 diopter wheel
2060 aperture wheel
2062 aperture wheel cover
2064 aperture wheel cover
2065 axle
2070 retaining ring
2072 locking pin
2240 objective lens
2242 rear peripheral edge
2245 annular shoulder
2248 end cap
2249 threads
2254 fixation target retainer
2256 polarizer windows
2260 O ring
2264 O ring
2270 eyepiece holder
2272 annular shoulder
2280 eyepiece lens
2284 eyepiece lens
2286 relay lens
2287 relay lens holder
2288 eyepiece spacer
2289 polarizer window
2290 field stop holder
2291 aperture stop/plate
2297 field stop
2299 narrowed portion
2310 magnification lens
2320 contact pin, electrical
2328 plastic insulator, hollow
2330 printed circuit board retainer
2331 threads
2332 coil spring
2350 printed circuit board
2356 LED
2364 condenser lens
2380 lens holder
2390 optical base member
2394 shoulder, optical base member
2395 compression spring
2404 aperture plate
2420 illumination relay lens
2426 top optical base member
2440 polarizer
2450 mirror
2451 support surface
2453 mirror support assembly
2454 mirror mount
2455 upper end, mirror mount
2456 lower end, mirror mount
2457 rear facing side, mirror mount (top)
2458 mirror support assembly enclosure
2459 upper portion, enclosure
2460 lower legs, enclosure
2461 threaded sleeve
2462 mirror adjustment member
2466 block of insulating material
2470 O-ring
3100 ophthalmoscope
3101 optical assembly
3102 illumination assembly
3104 instrument head
3105 interior
3106 smart device
3107 lower neck portion, instrument head
3108 instrument handle or handle portion
3109 front housing section
3110 rear housing section
3111 interface member
3112 distal end, instrument head
3116 proximal end, instrument head
3120 eye cup
3122 distal end opening, eye cup
3123 proximal end opening, eye cup
3124 disposable ring member
3125 distal end opening, ring member
3127 proximal end opening, ring member
3129 annular outer flange, ring member
3130 patient's eye
3132 optical axis
3137 retina
3140 objective lens
3142 rear peripheral edge
3145 annular shoulder
3148 end cap
3154 fixation target retainer
3170 eyepiece holder
3172 annular shoulder
3176 brow rest
3180 eyepiece lens
3184 eyepiece lens
3186 relay lens
3188 eyepiece spacer
3190 field stop holder
3191 aperture stop/plate
3197 field stop
3199 narrowed portion
3200 diopter wheel
3204 lenses of varying optical power
3210 magnification lens
3220 contact pin
3224 top or upper end, contact pin
3228 plastic insulator
3229 upper portion, insulator
3230 printed circuit board retainer
3232 coil spring
3238 shoulder
3250 printed circuit board
3256 LED
3264 condenser lens
3280 lens holder
3281 centering ring
3290 assembly support member
3300 aperture wheel
3304 aperture plate
3310 illumination axis
3320 illumination relay lens
3340 polarizer
3326 relay lens holder
3350 mirror
3352 adjustment member
3354 mirror support member
3360 pivoting portion, mirror support member
3404 instrument head
3414 instrument head
3420 optical assembly
3424 objective lens
3427 aperture plate

3430 optical assembly
3434 objective lens
3437 aperture plate
3440 relay lens
3444 relay lens
3448 eyepiece lenses
3450 physical assessment device
3452 instrument head
3456 distal end
3462 diopter wheel
3470 physical assessment device
3472 instrument head
3476 distal end
3482 diopter wheel
3500 method for controlling LED lighting
3510 LED drive circuit
3512 instrument handle
3514 controller
3516 buck/boost or power circuit
3520 method block for connecting an instrument head
3530 method block for determining a power profile
3540 method block for configuring an LED control or drive circuit
3550 method block for operating LED lighting including dimming
3560 method block for detecting an idle state
3570 method block for detecting a vibration state Additional variations and modifications of the inventive concepts which are described herein will be readily apparent based on the above description and further in accordance with the following claims.

APPENDIX

The following material relates to additional views of medical devices that are made in accordance with embodiments of the invention, as follows:

FIG. A-1 is a perspective view of a medical device in accordance with another embodiment;

FIG. A-2 is another perspective view of the medical device of FIG. A-1;

FIG. A-3 is a left side perspective view of the medical device of FIG. A-1 – FIG. A-2;

FIG. A-4 is a right side elevation view of the medical device of FIG. A-1 – FIG. A-3;

FIG. A-5 is a front elevation view of the medical device of FIG. A-1 – FIG. A-4;

FIG. A-6 is a rear elevation view of the medical device of FIG. A-1 – FIG. A-5;

FIG. A-7 is a top plan view of the medical device of FIG. A-1 – FIG. A-6;

FIG. A-8 is a bottom plan view of the medical device of FIG. A-1 – FIG. A-7;

FIG. A-9 is another perspective view of the medical device of FIG. A-1 – FIG. A-8 with an attached handle;

FIG. A-10 is a perspective view of a medical device made in accordance with another embodiment;

FIG. A-11 is another perspective view of the medical device of FIG. A-10;

FIG. A-12 is a left side elevation view of the medical device of FIG. A-10 and FIG. A-11;

FIG. A-13 is a right side elevation view of the medical device of FIG. A-10 – FIG. A-12;

FIG. A-14 is a front elevation view of the medical device of FIG. A-10 – FIG. A-13;

FIG. A-15 is a rear elevation view of the medical device of FIG. A-10 – FIG. A-14;

FIG. A-16 is a top plan view of the medical device of FIG. A-10 – FIG. A-15;

FIG. A-17 is a bottom plan view of the medical device of FIG. A-10 – FIG. A-16;

FIG. A-18 is another perspective view of the medical device of FIG. A-10 – FIG. A-17, with an attached handle;

FIG. B-1 is a perspective view of a medical device made in accordance with another embodiment;

FIG. B-2 is another perspective view of the medical device of FIG. B-1;

FIG. B-3 is a left side view of the medical device of FIG. B-1 and FIG. B-2;

FIG. B-4 is a right side view of the medical device of FIG. B-1 – FIG. B-3;

FIG. B-5 is a front elevation view of the medical device of FIG. B-1 – FIG. B-4;

FIG. B-6 is a rear elevation view of the medical device of FIG. B-1 – FIG. B-5;

FIG. B-7 is a top plan view of the medical device of FIG. B-1 – FIG. B-6;

FIG. B-8 is a bottom plan view of the medical device of FIG. B-1 – FIG. B-7;

FIG. B-9 is perspective view of the medical device of FIG. B-1 – B-8, including an instrument handle;

FIG. B-10 is a side elevation view of the medical device of FIG. B-1 – FIG. B-9, including instrument handle;

FIG. B-11 is a perspective view of a medical device made in accordance with another embodiment;

FIG. B-12 is another perspective view of the medical device of FIG. B-11;

FIG. B-13 is a left side view of the medical device of FIG. B-11 and FIG. B-12;

FIG. B-14 is a right side view of the medical device of FIG. B-11 – FIG. B-13;

FIG. B-15 is a front elevation view of the medical device of FIG. B-11 – FIG. B-14;

FIG. B-16 is a rear elevation view of the medical device of FIG. B-11 – FIG. B-15;

FIG. B-17 is a top plan view of the medical device of FIG. B-11 – FIG. B-16;

FIG. B-18 is a bottom plan view of the medical device of FIG. B-11 – FIG. B-17;

FIG. B-19 is perspective view of the medical device of FIG. B-11 – B-18, including an instrument handle;

FIG. B-20 is a side elevation view of the medical device of FIG. B-11 – FIG. B-19, including the instrument handle;

FIG. B-21 is a perspective view of a medical device made in accordance with another embodiment;

FIG. B-22 is another perspective view of the medical device of FIG. B-21;

FIG. B-23 is a left side view of the medical device of FIG. B-21 and FIG. B-22;

FIG. B-24 is a right side view of the medical device of FIG. B-21 – FIG. B-23;

FIG. B-25 is a front elevation view of the medical device of FIG. B-21 – FIG. B-24;

FIG. B-26 is a rear elevation view of the medical device of FIG. B-21 – FIG. B-25;

FIG. B-27 is a top plan view of the medical device of FIG. B-21 – FIG. B-26;

FIG. B-28 is a bottom plan view of the medical device of FIG. B-21 – FIG. B-27;

FIG. B-29 is perspective view of the medical device of FIG. B-21 – B-28, including an instrument handle; and
FIG. B-30 is a side elevation view of the medical device of FIG. B-21 – FIG. B-29, including the instrument handle.
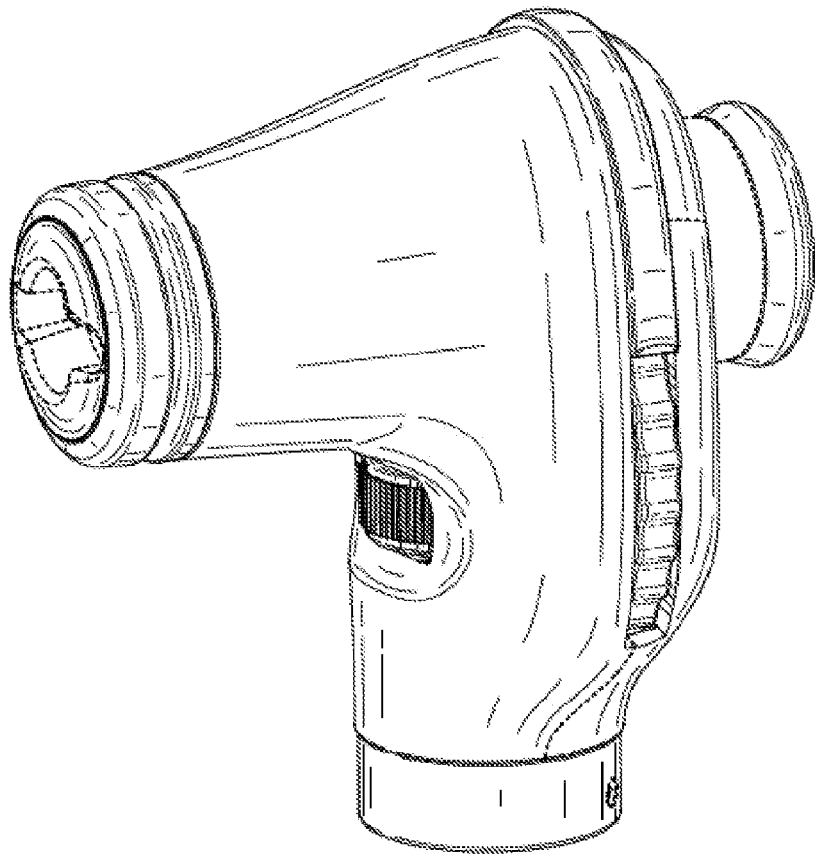
FIG. A-1

61 62
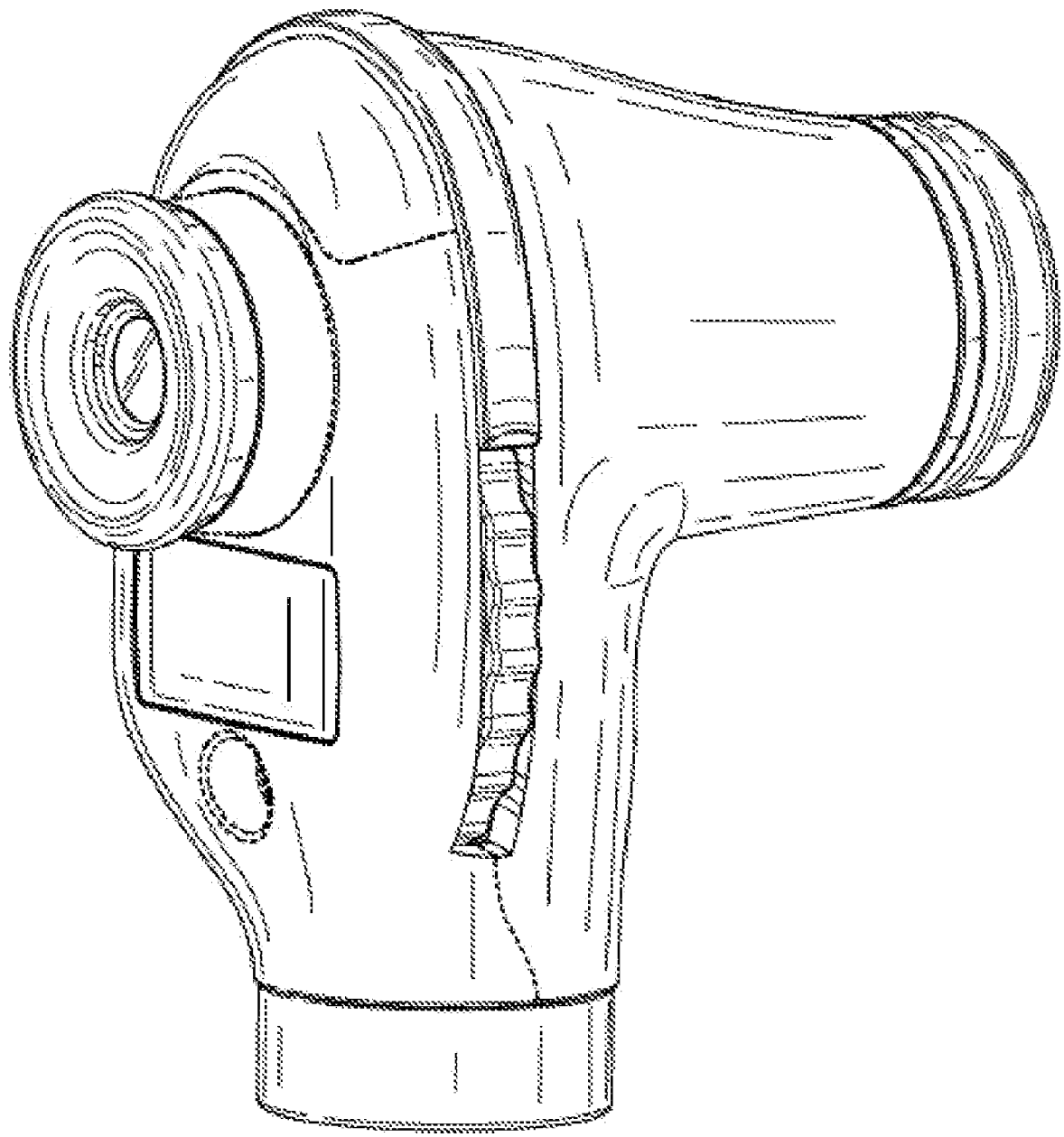
FIG. A-2

63 64
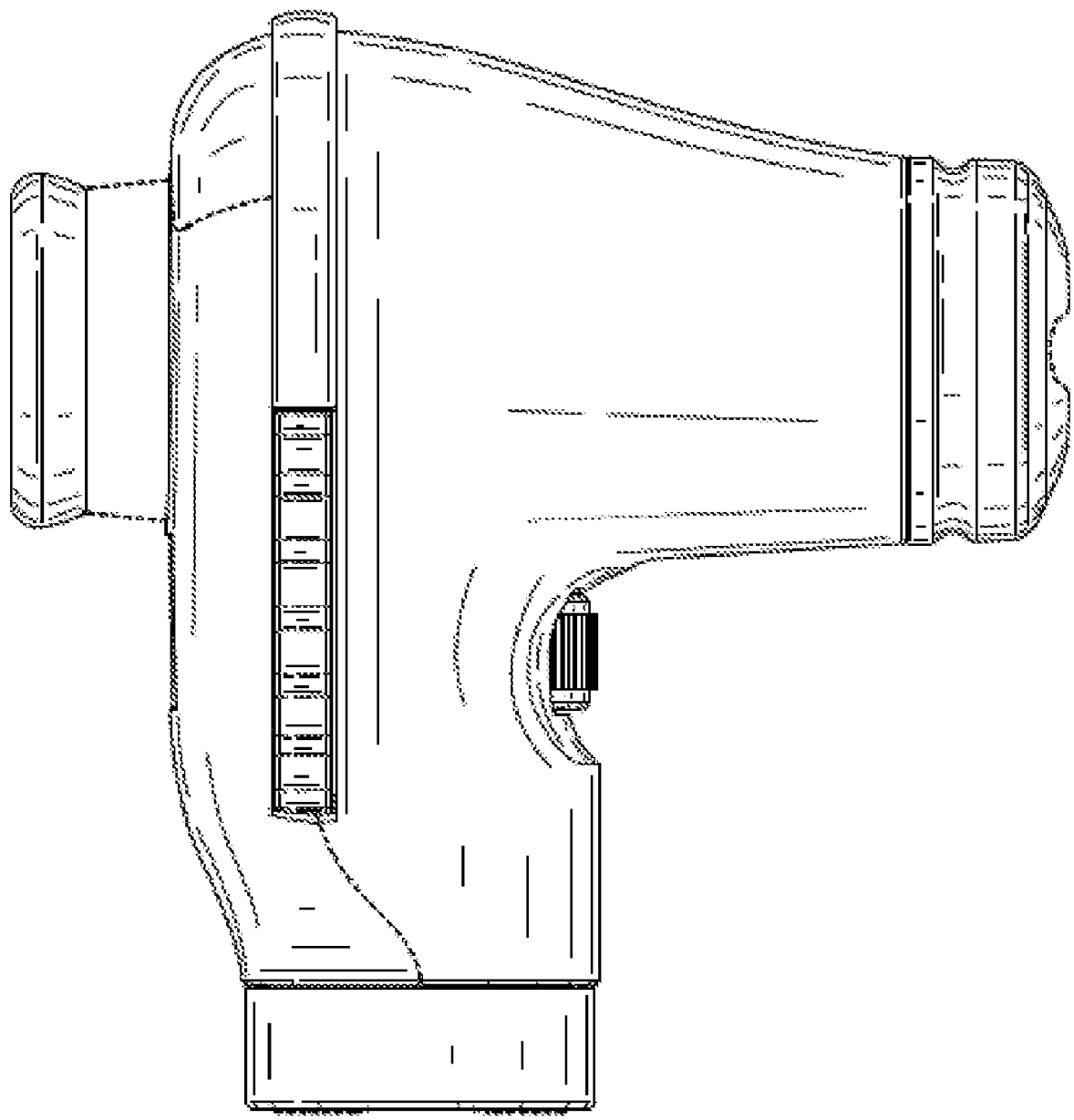
FIG. A-3

65 66
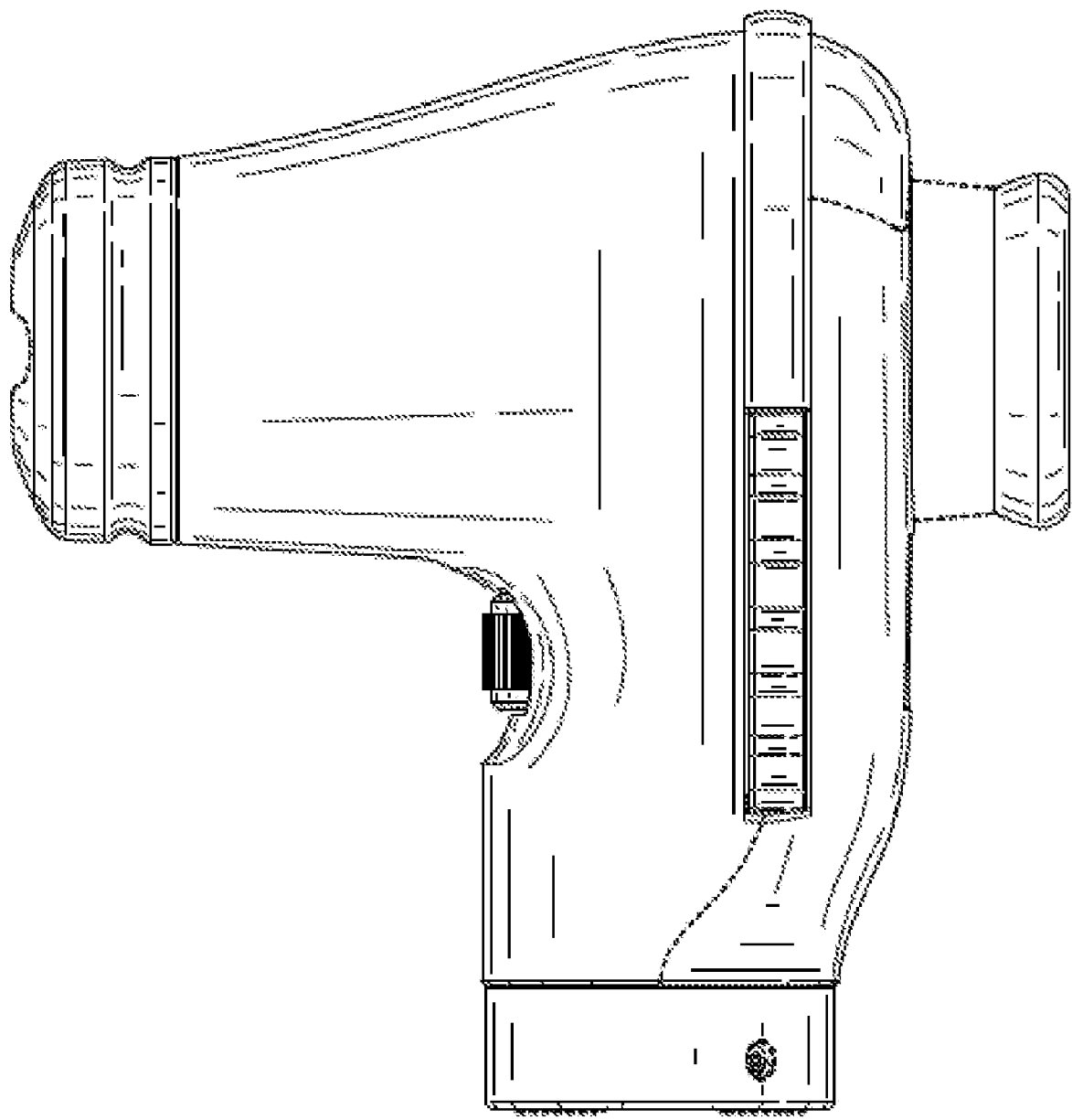
FIG. A-4

67 68
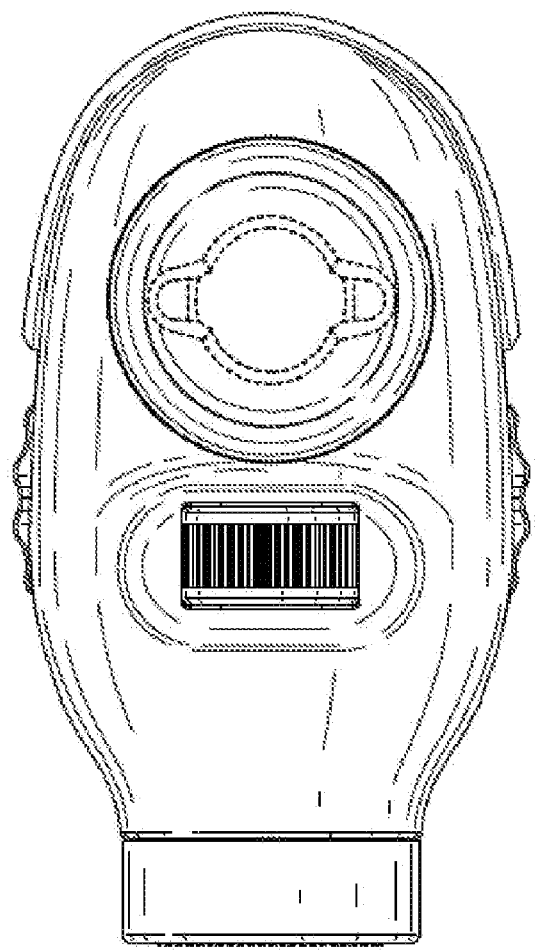
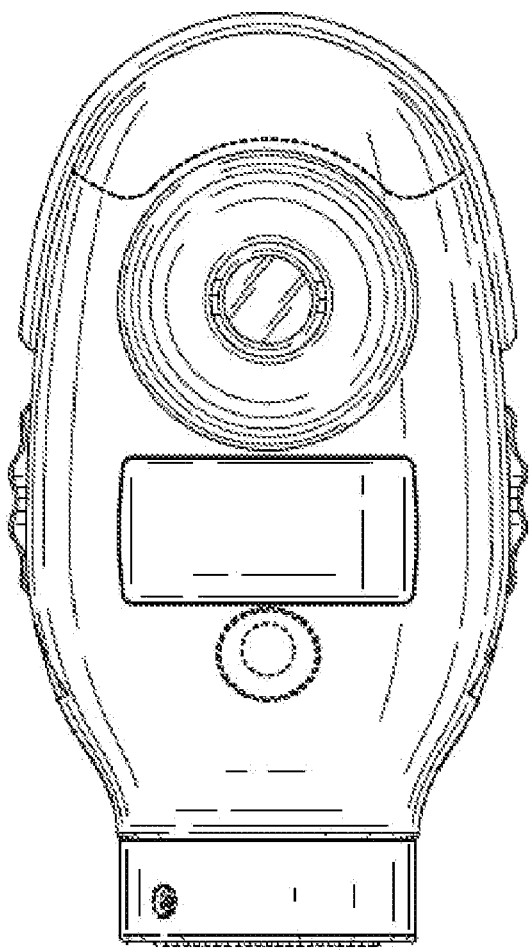
FIG. A-5
FIG. A-6

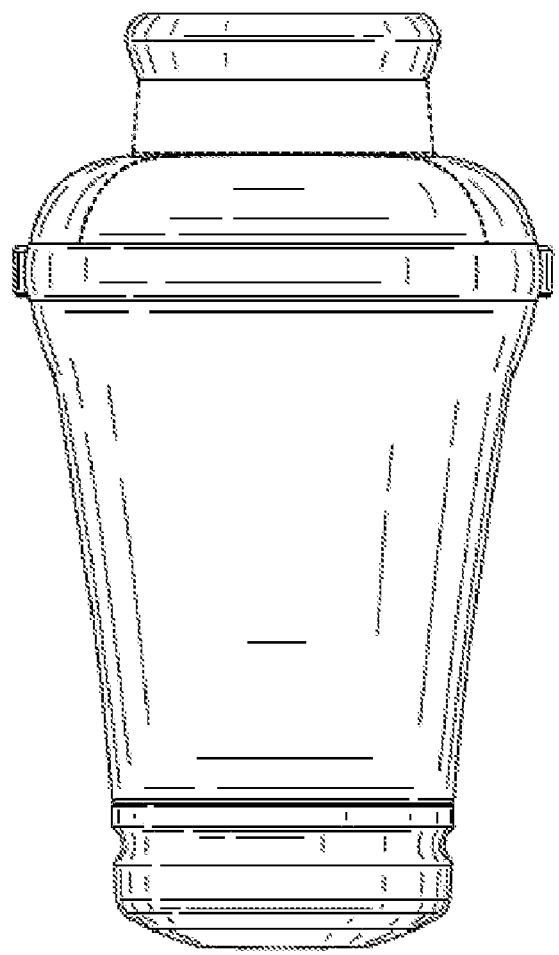
FIG. A-7
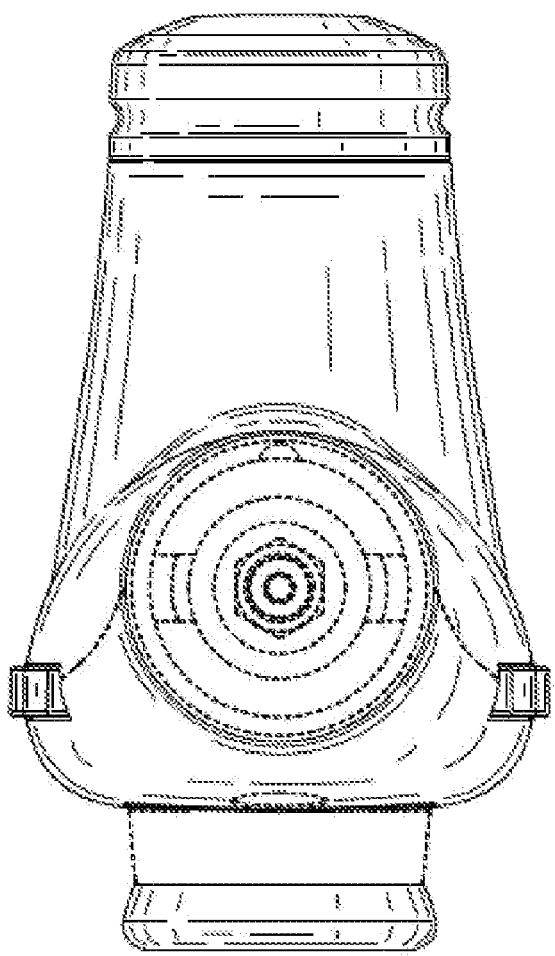
FIG. A-8

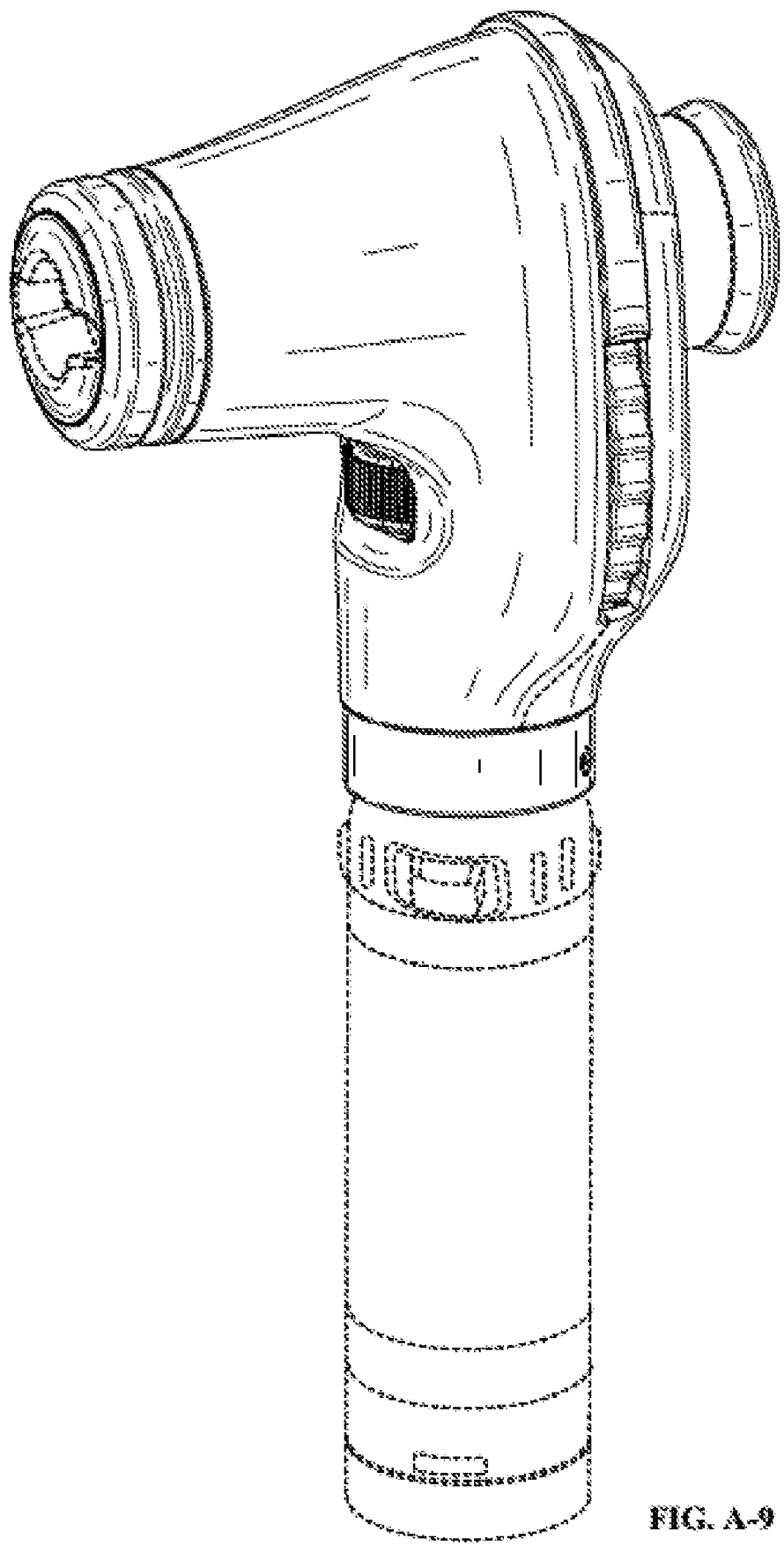
FIG. A-9

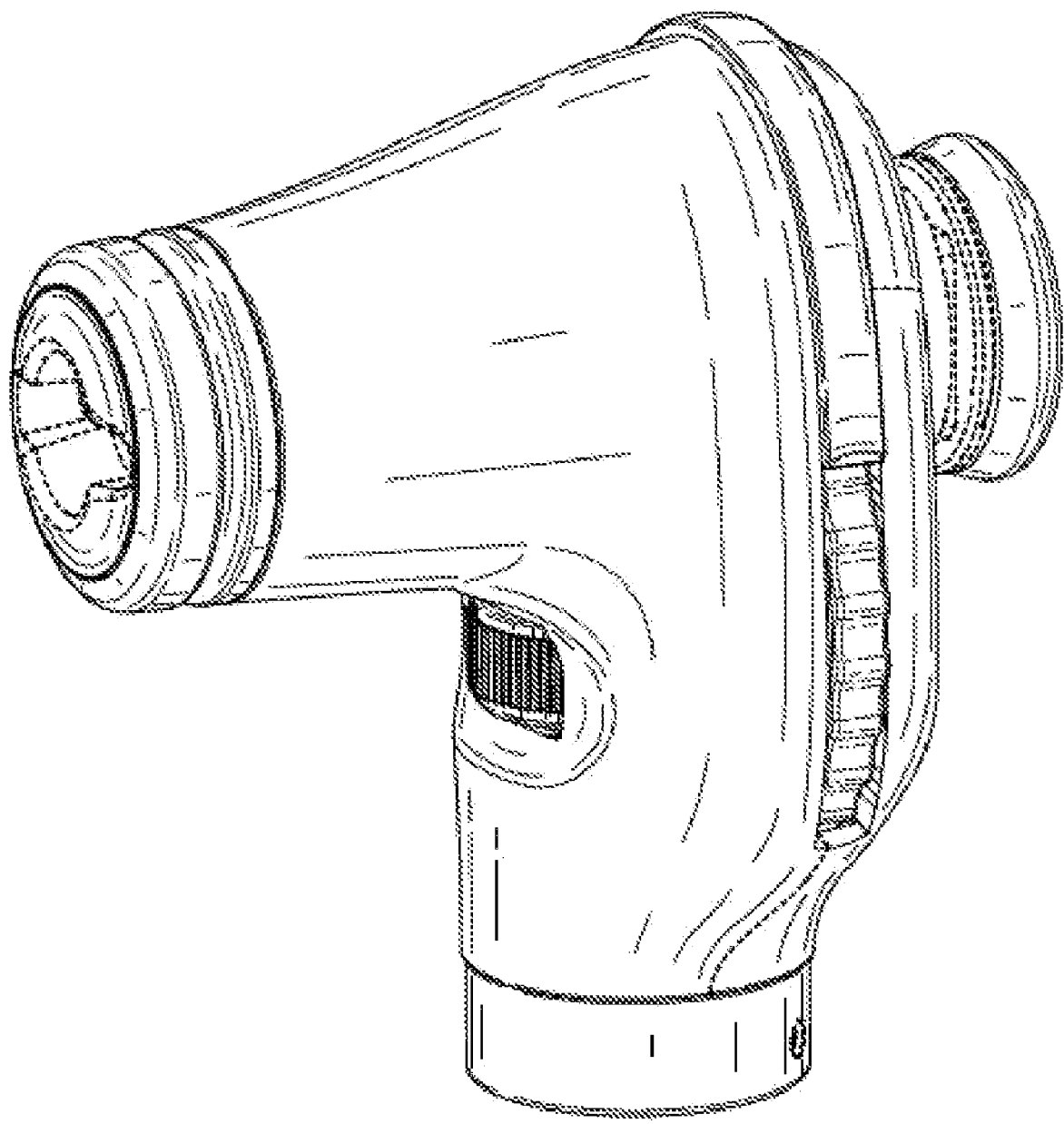
FIG. A-10

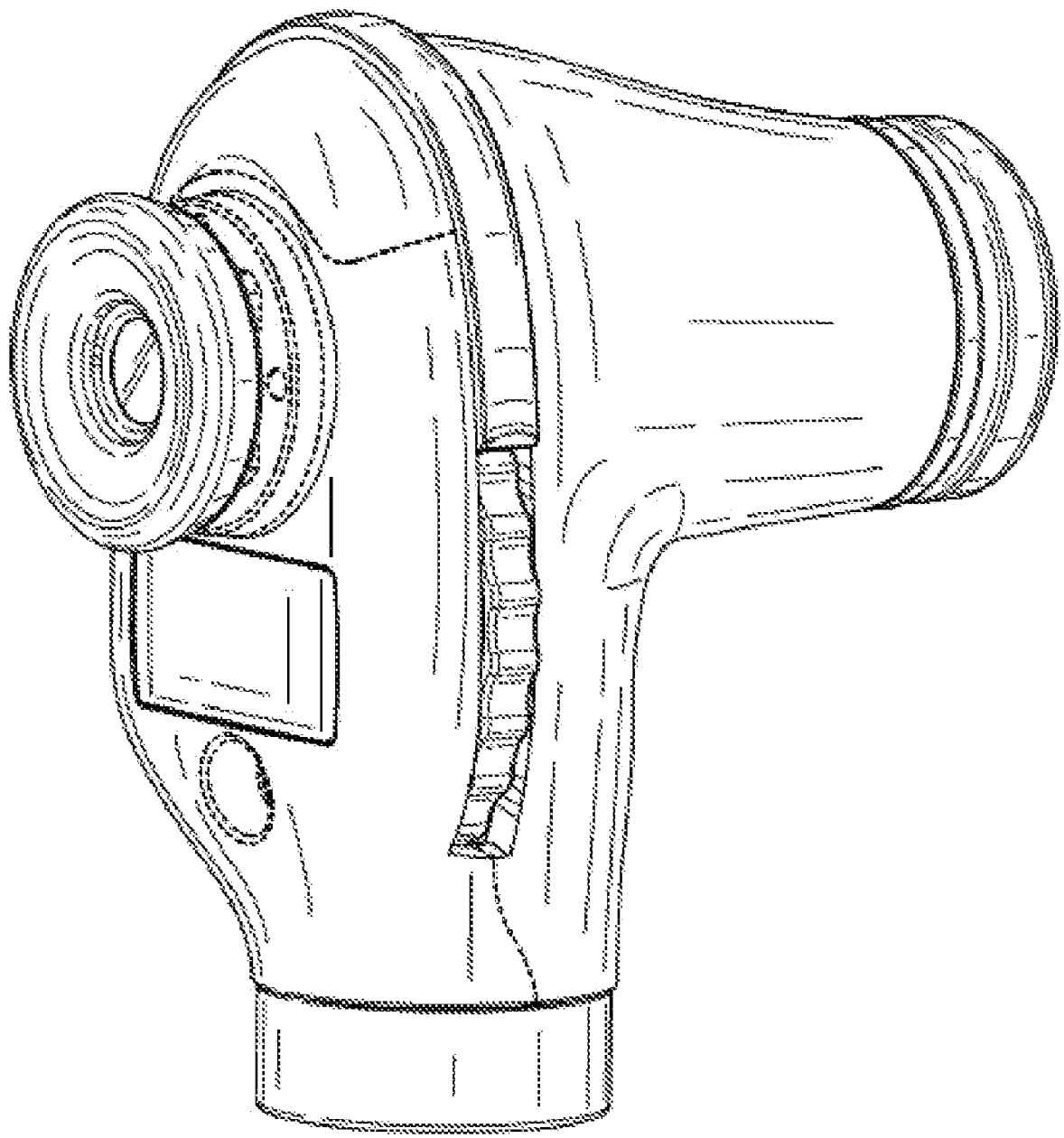
FIG. A-11

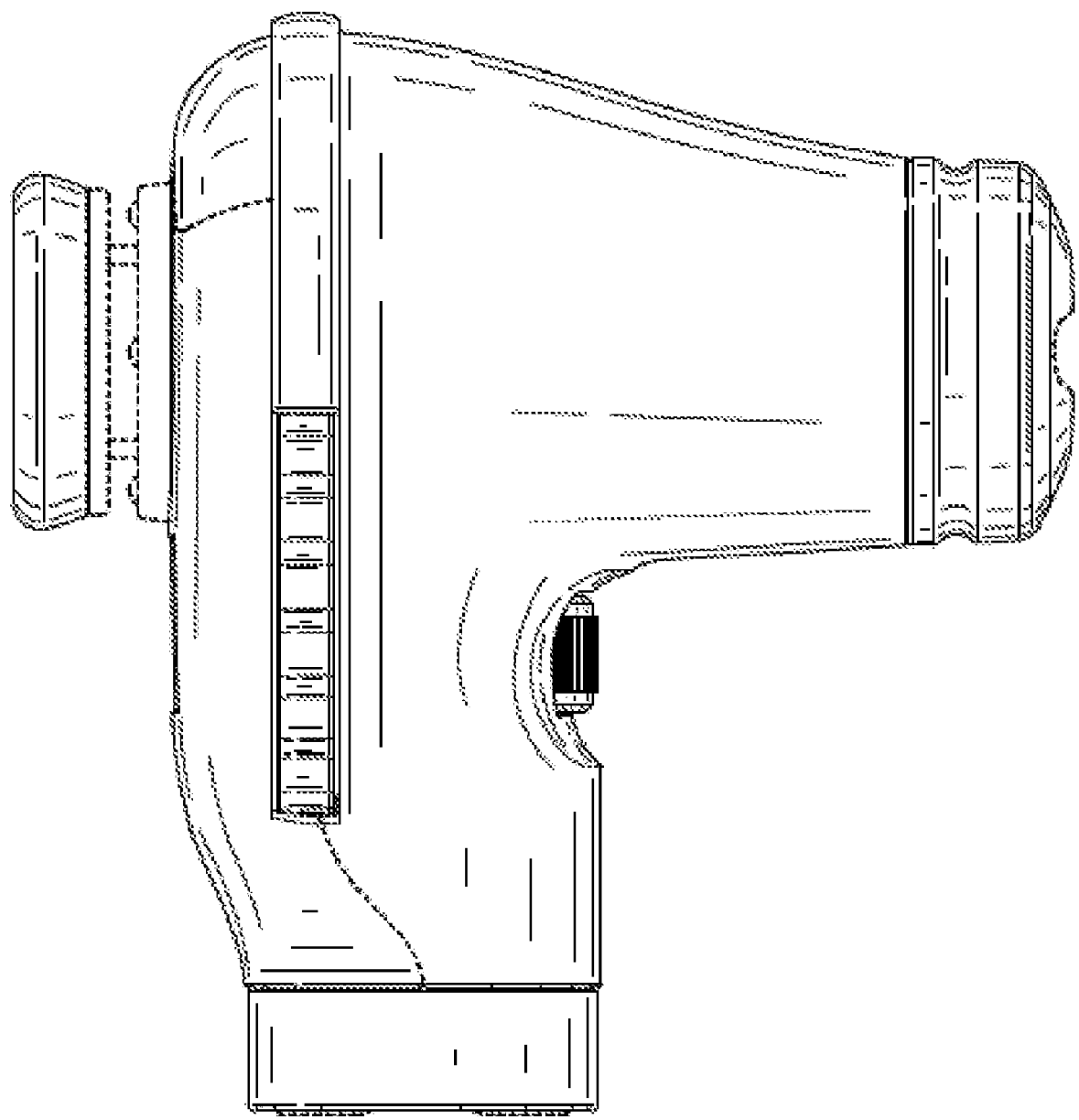
FIG. A-12

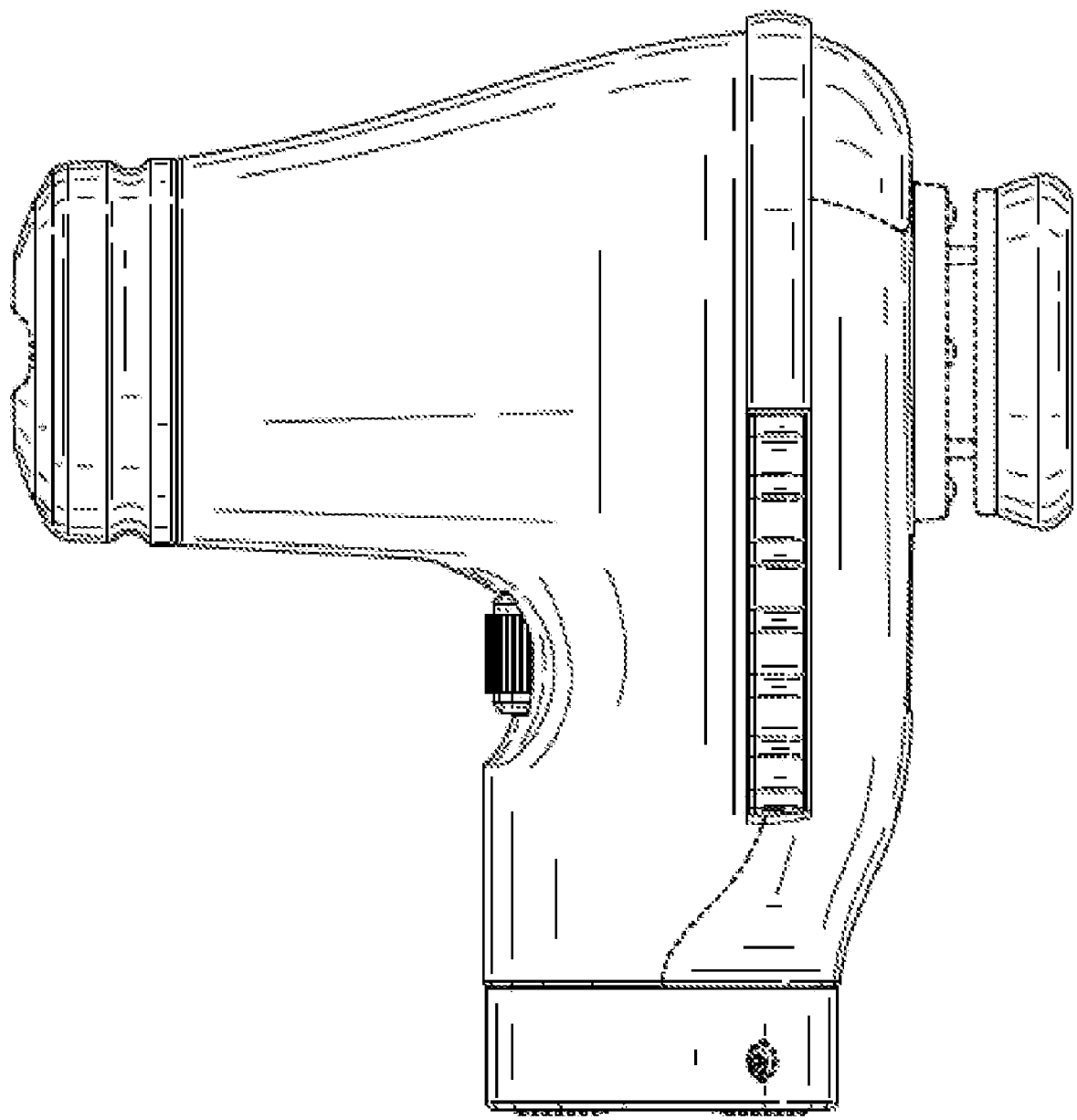
FIG. A-13

81 82
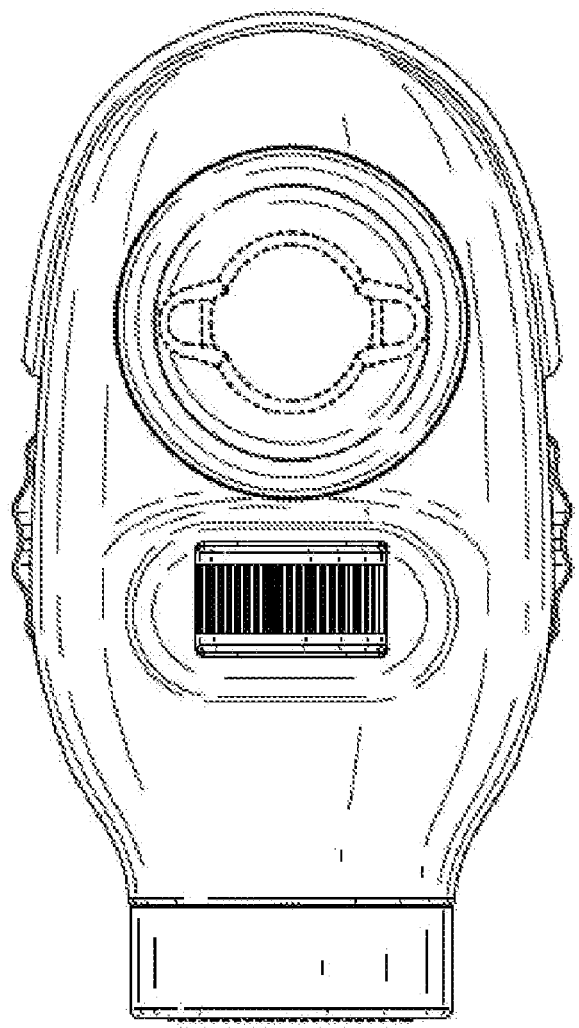
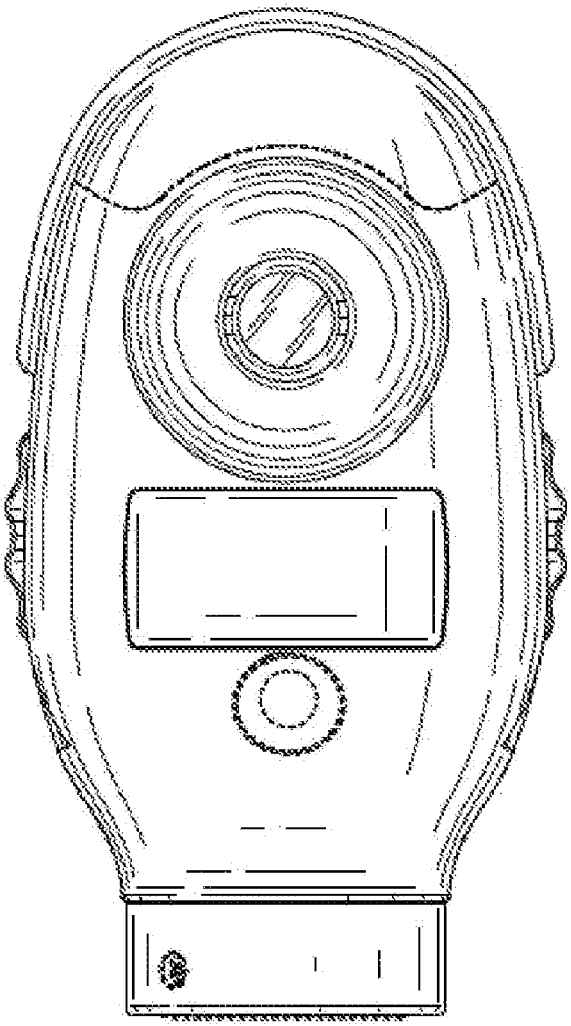
FIG. A-14　　　　　　　　FIG. A-15

83
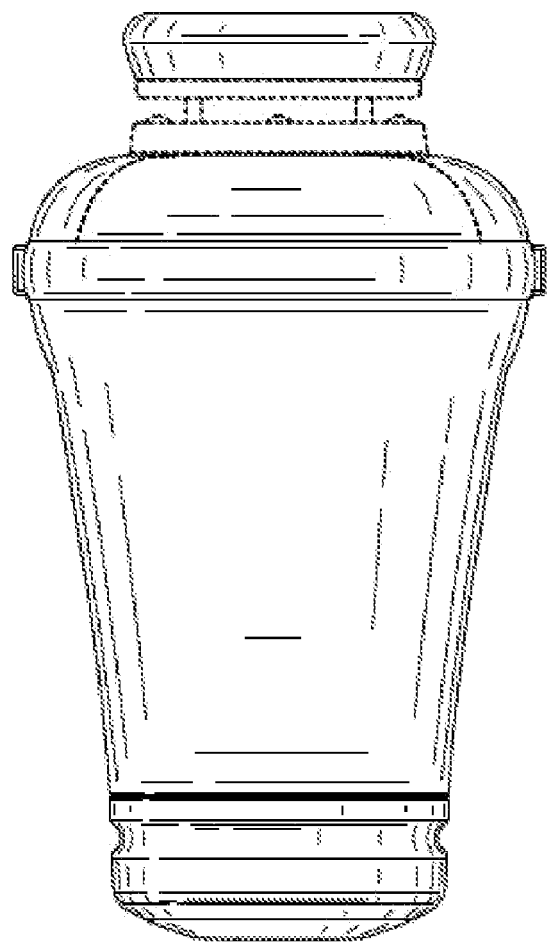
FIG. A-16
84
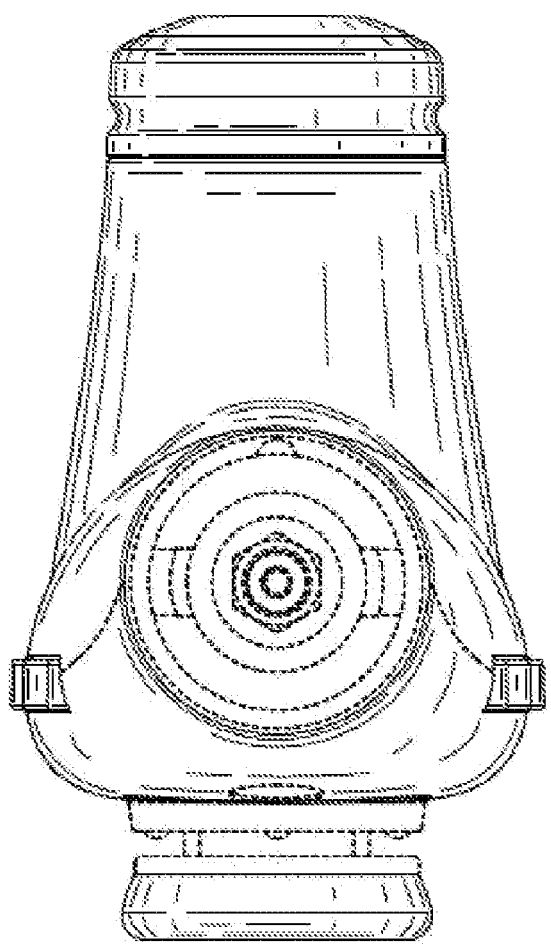
FIG. A-17

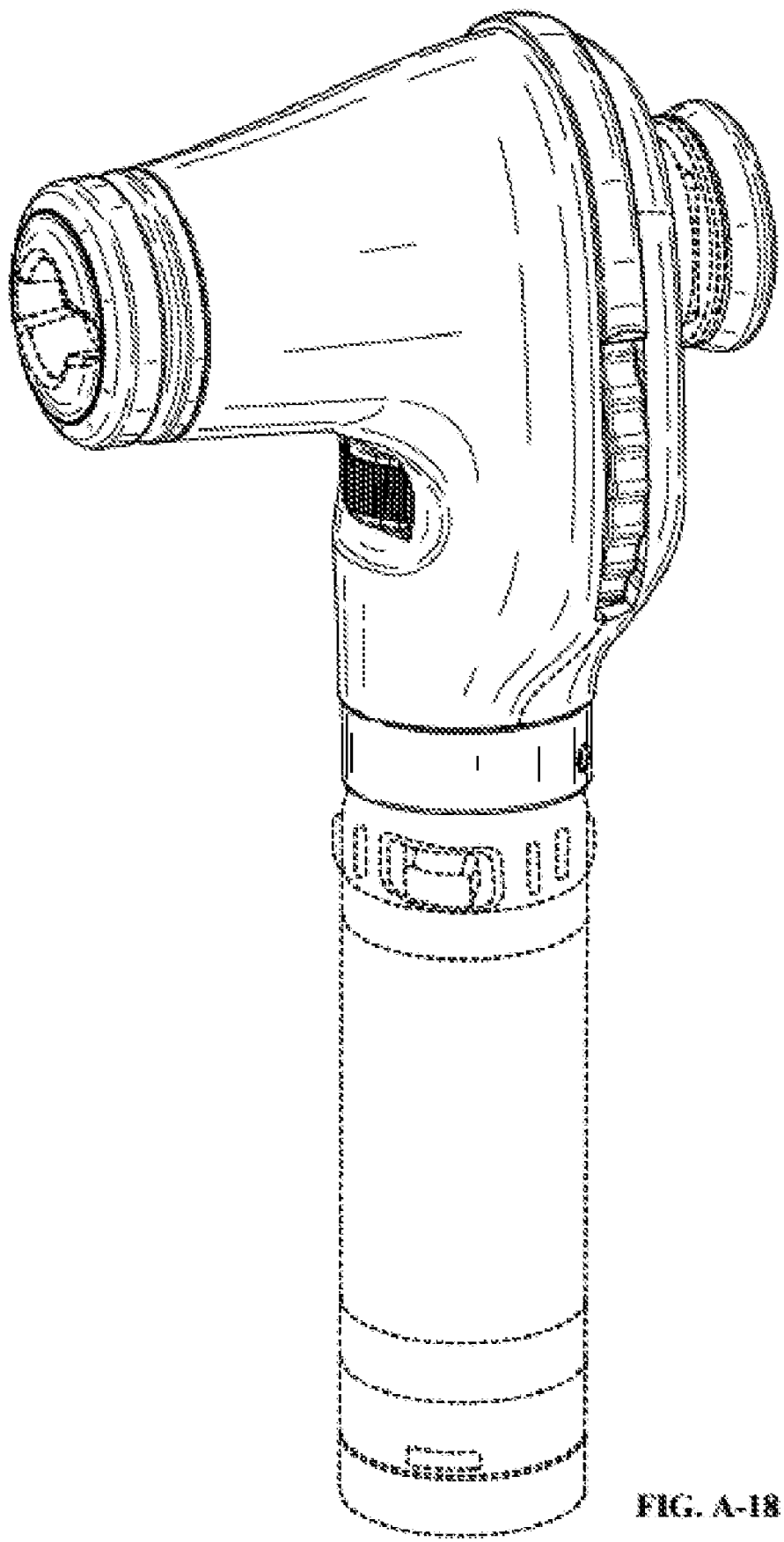
FIG. A-18

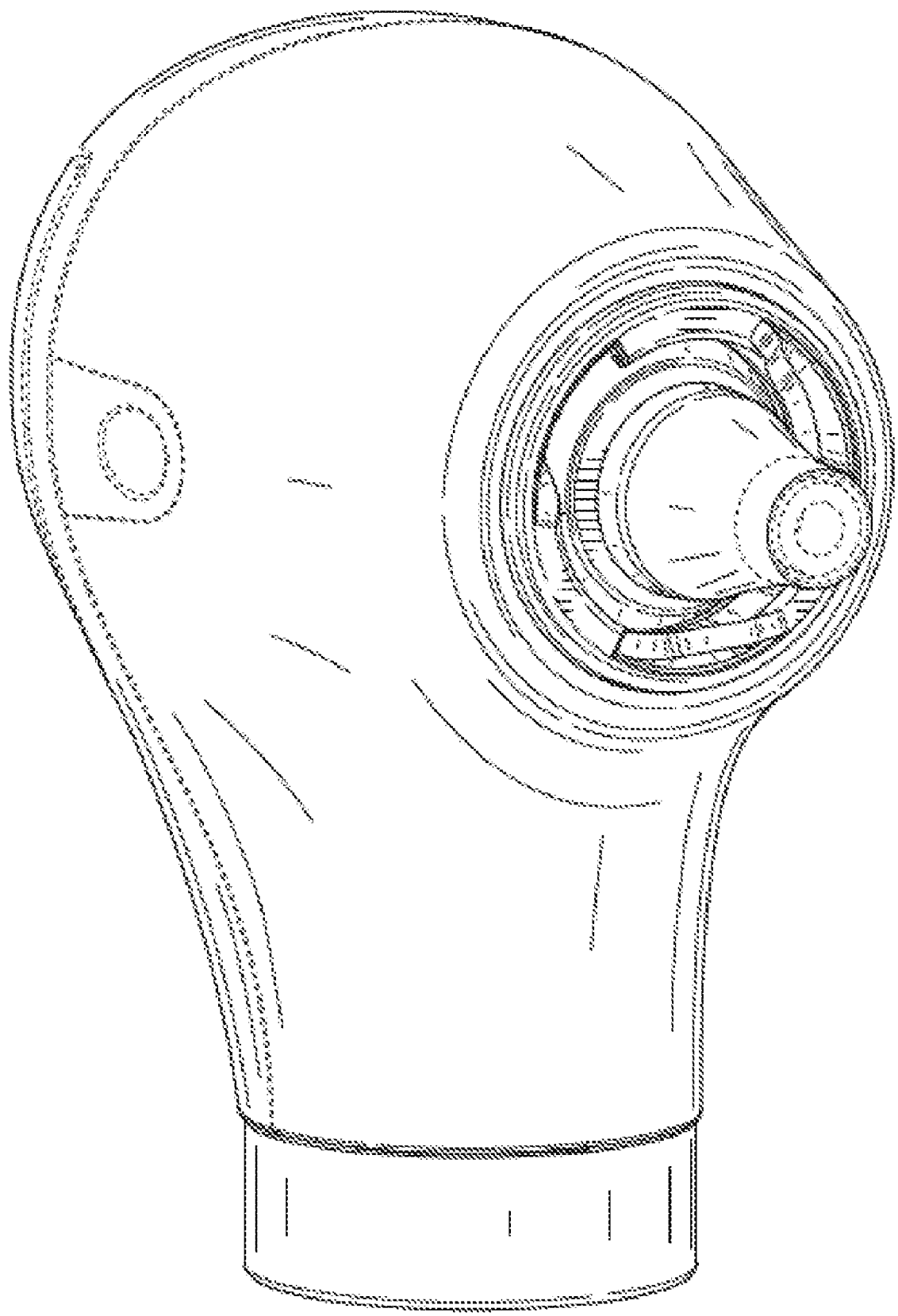
FIG. B-1

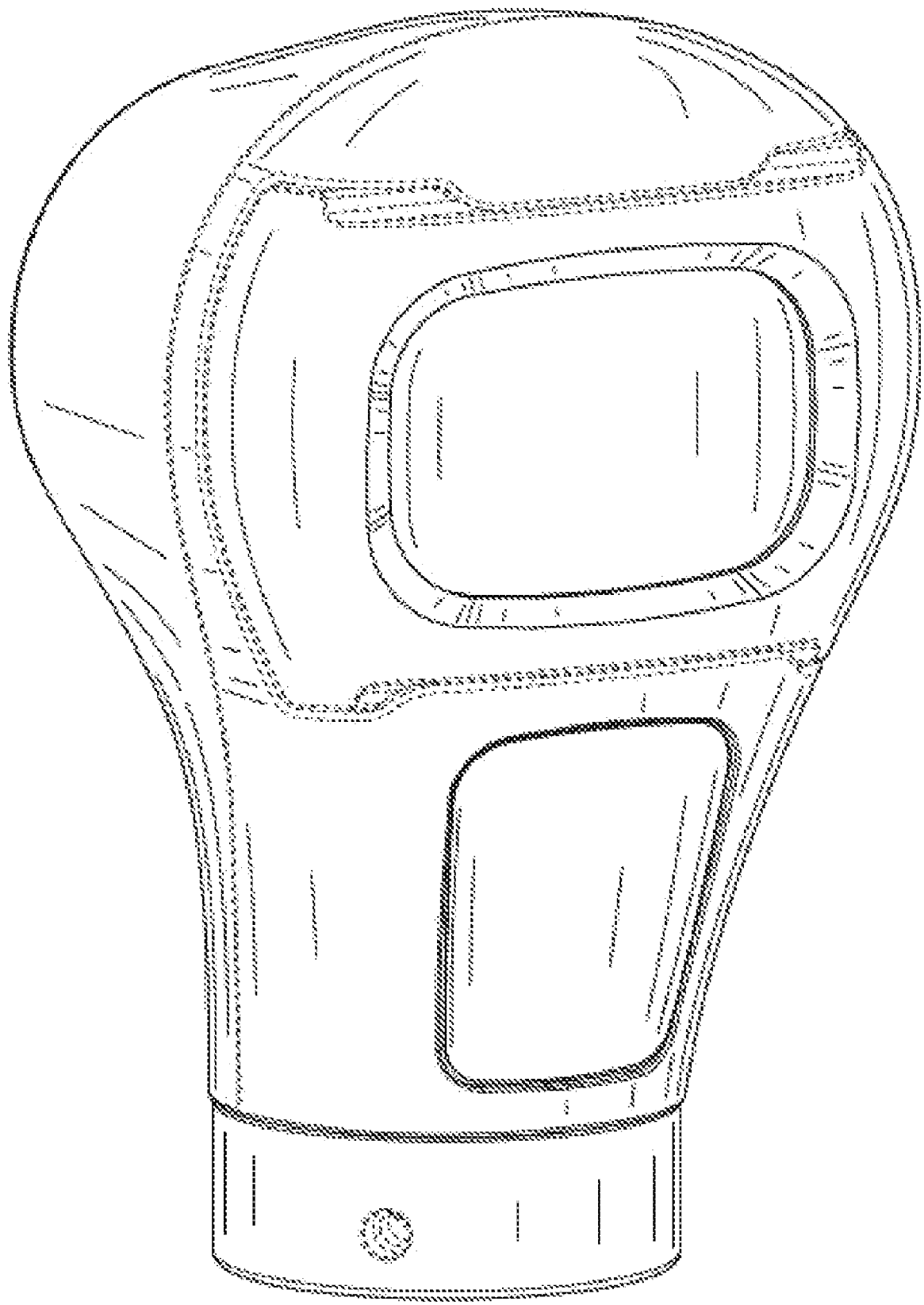
FIG. B-2

91 92
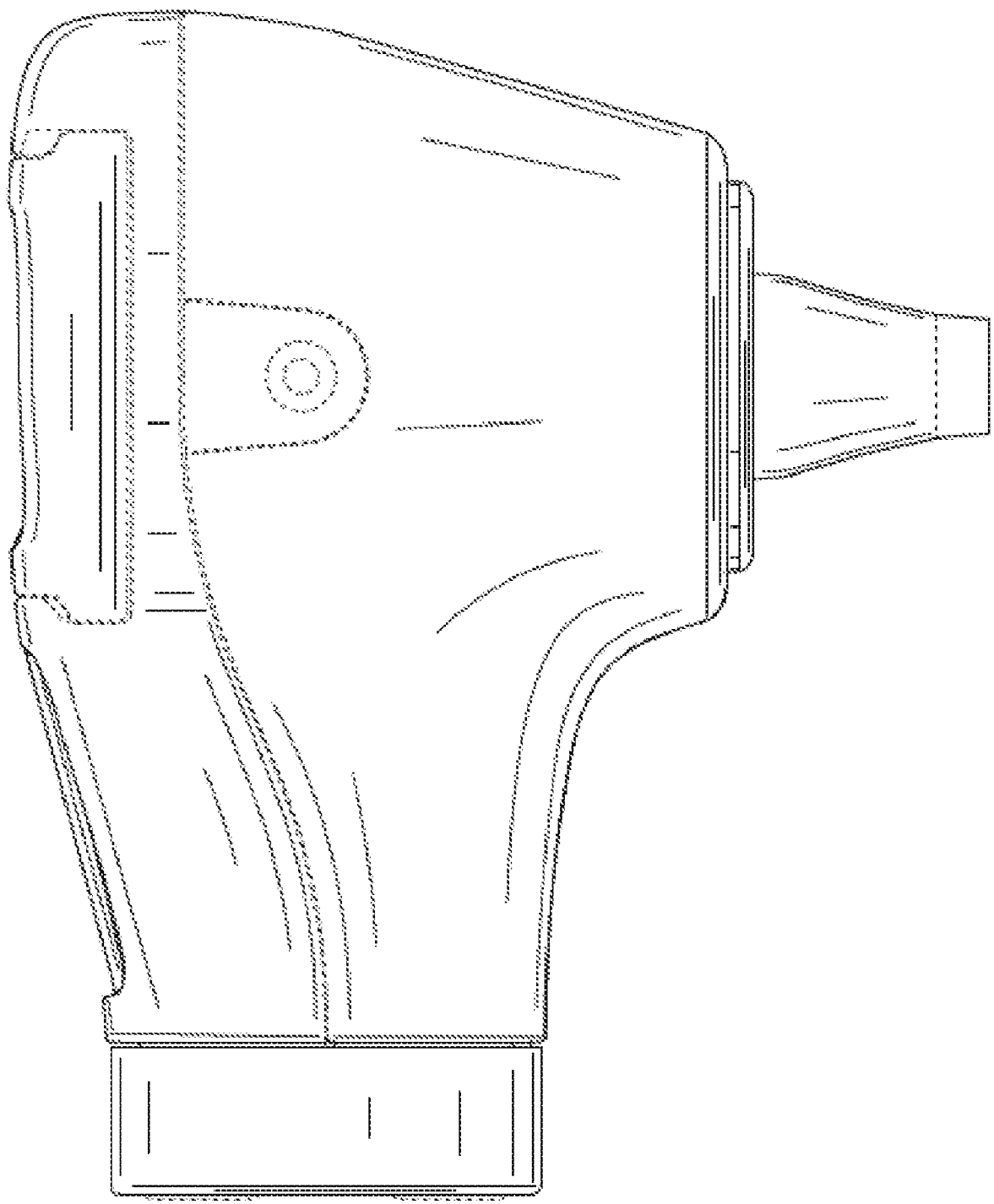
FIG. B-3

93 94
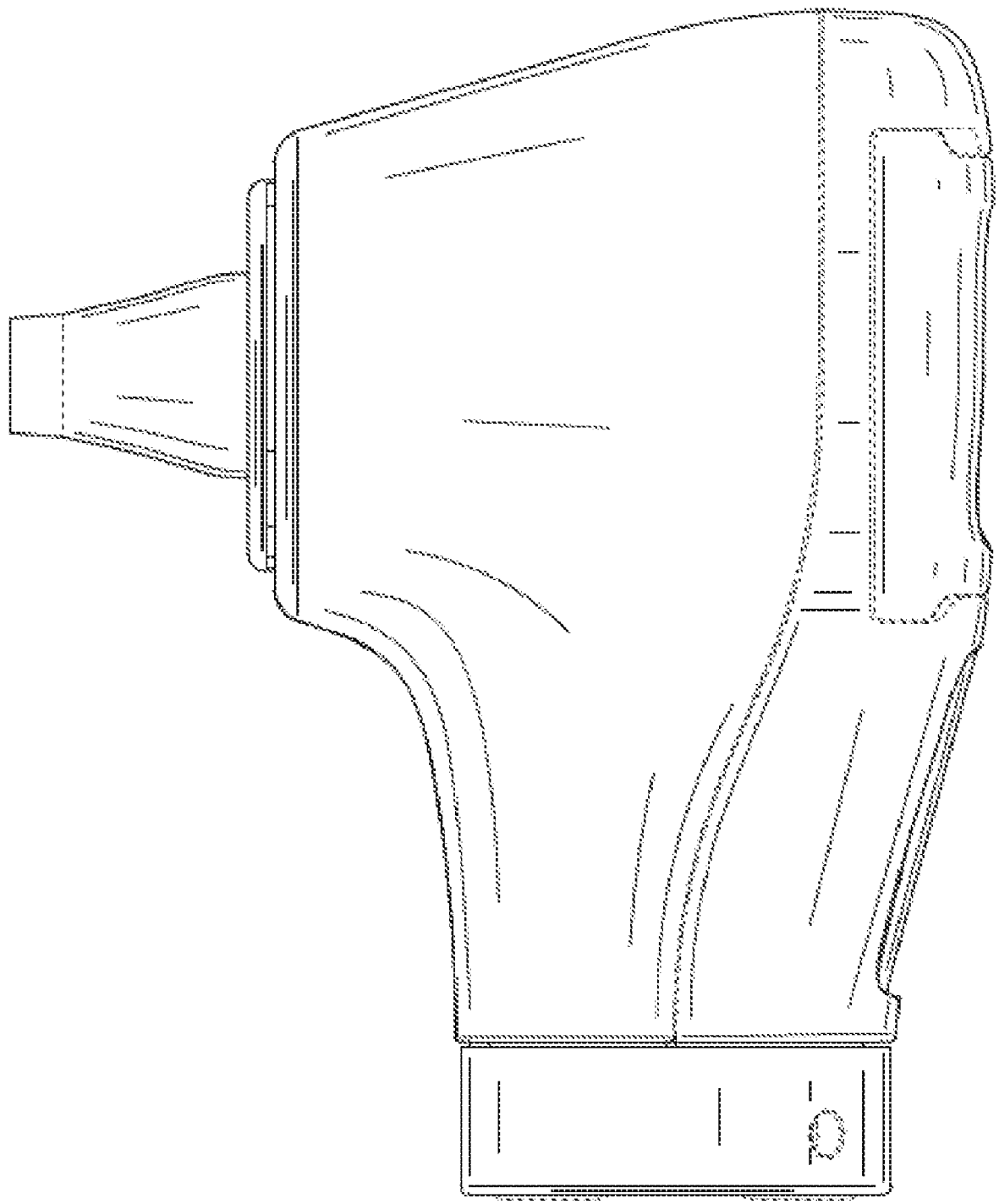
FIG. B-4

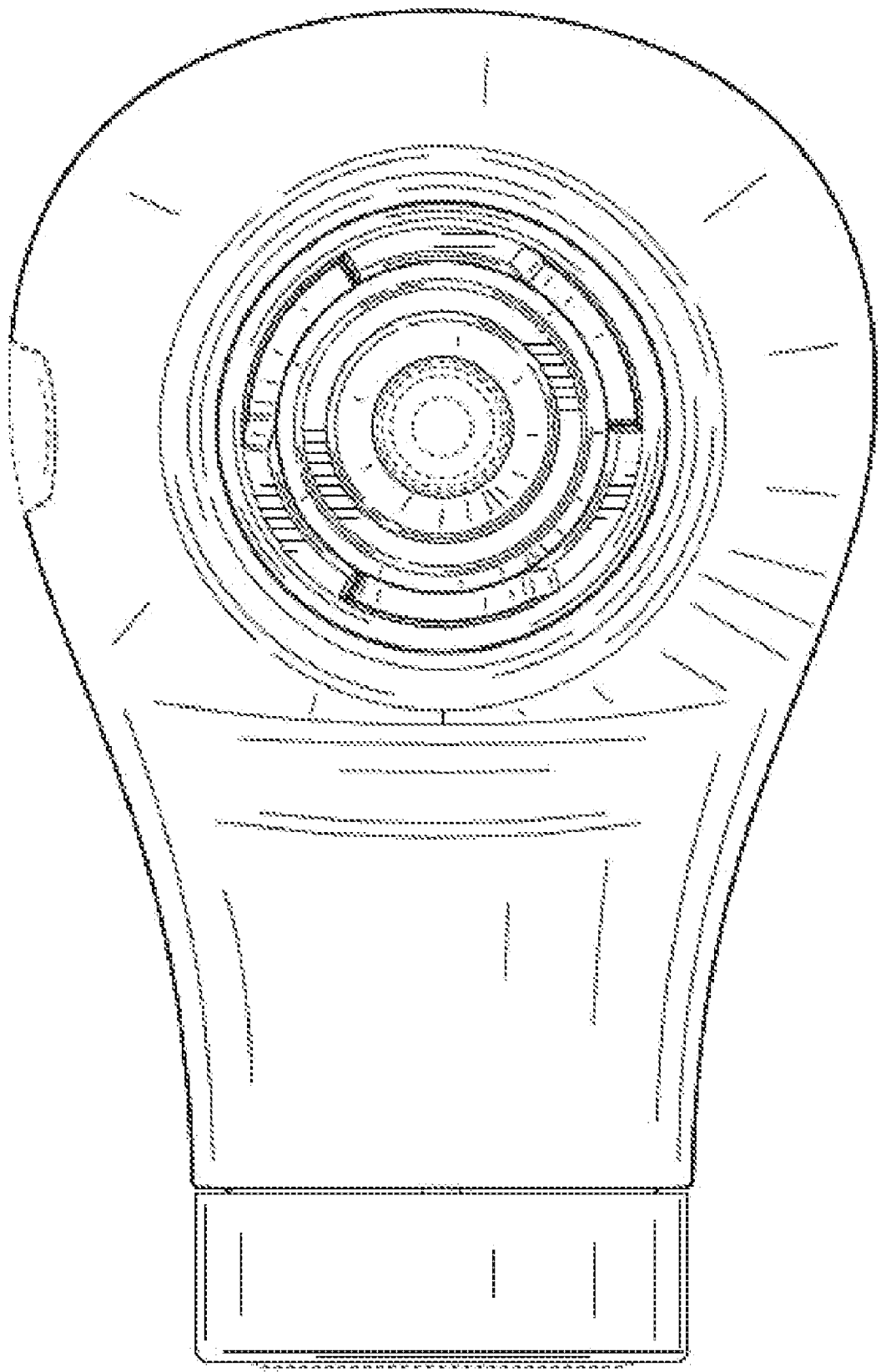
FIG. B-S

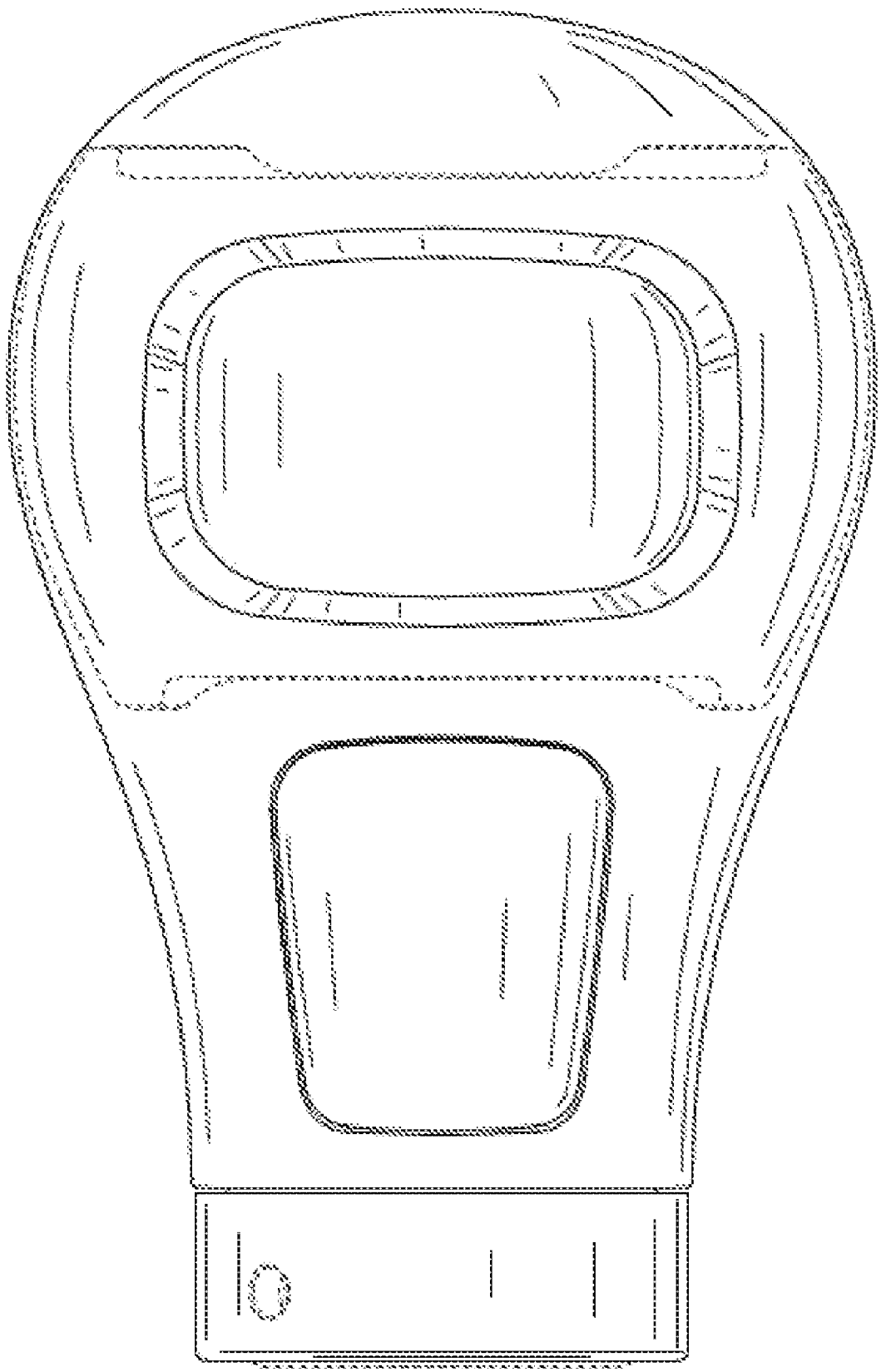
FIG. B-6

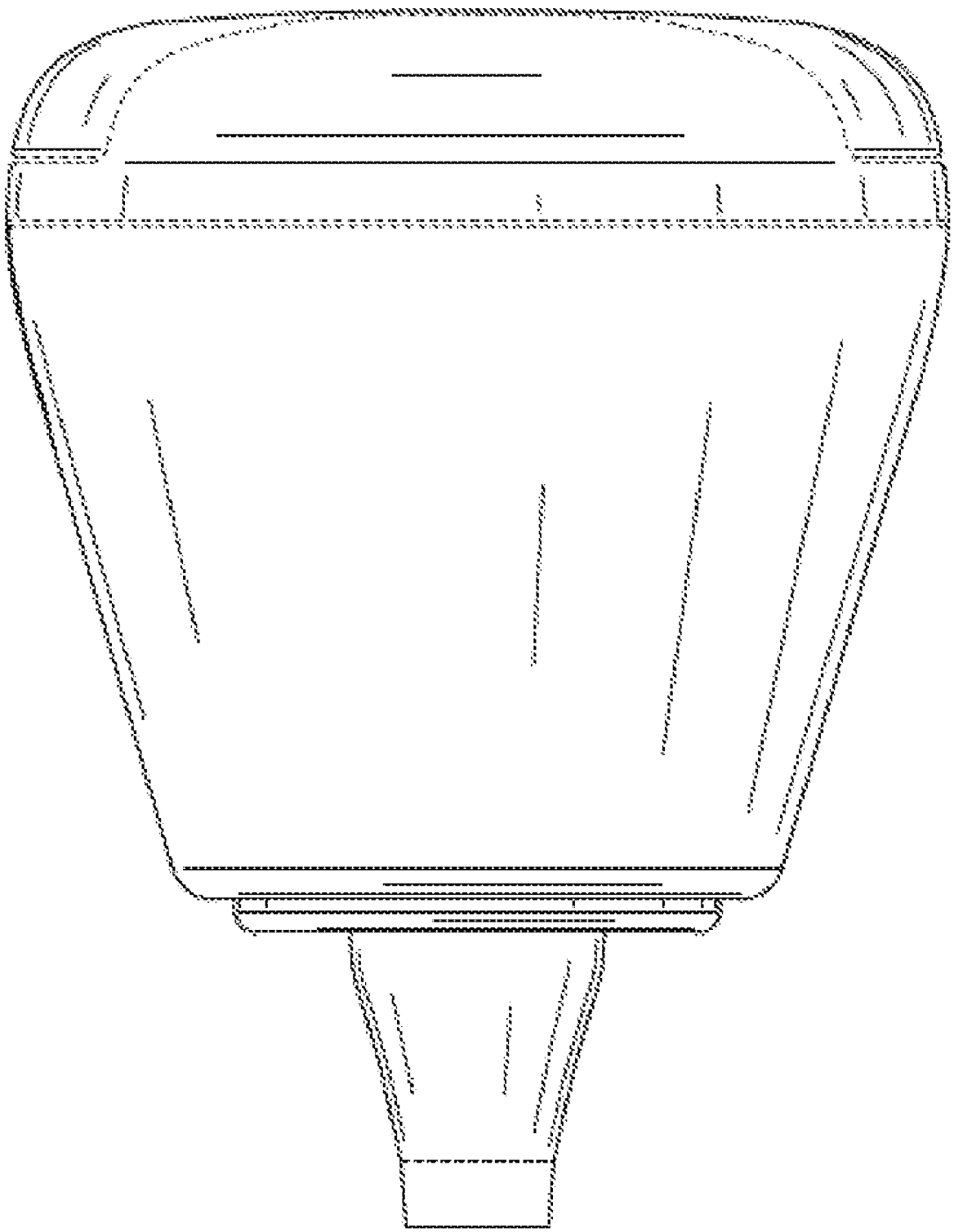
FIG. B-7

101  102
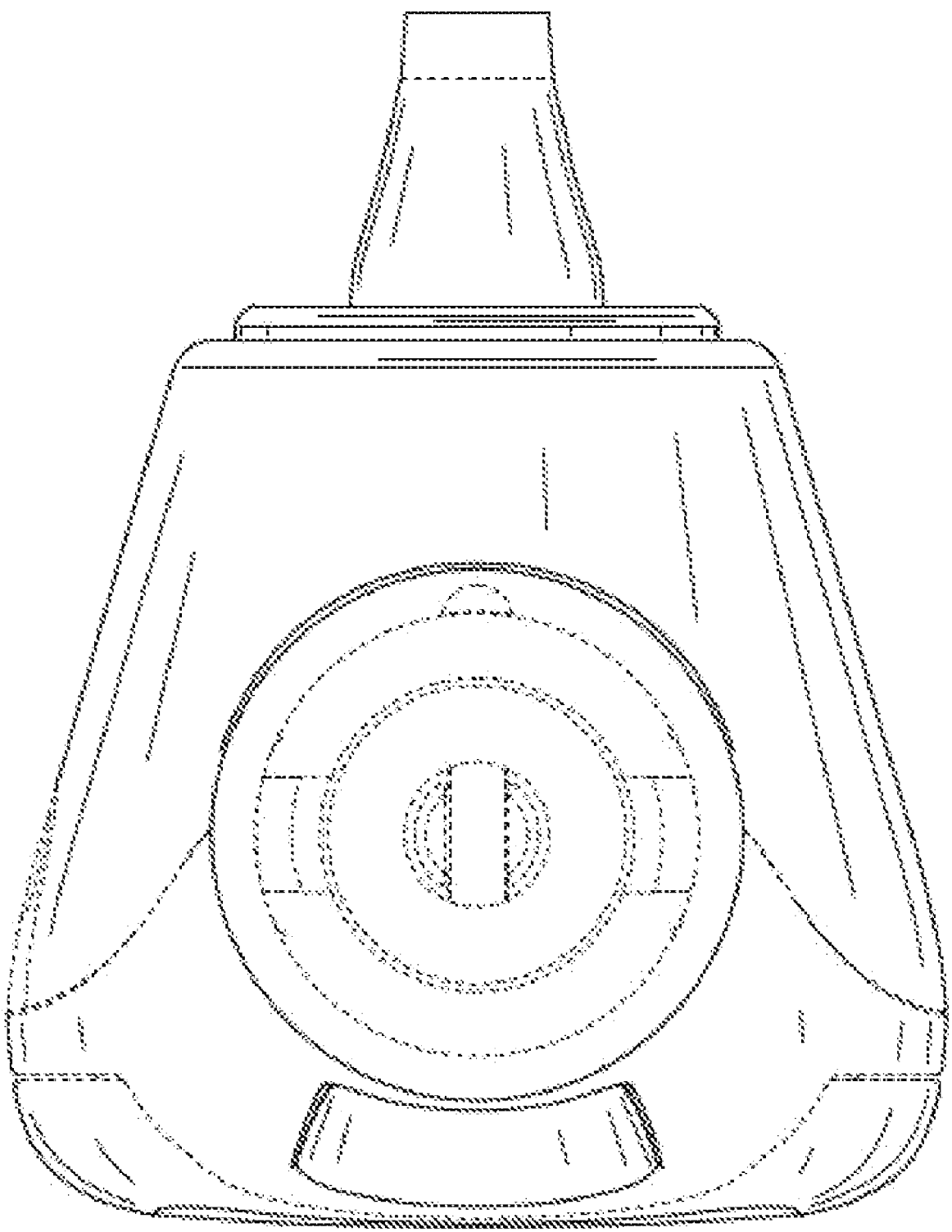
FIG. B-8

103
104
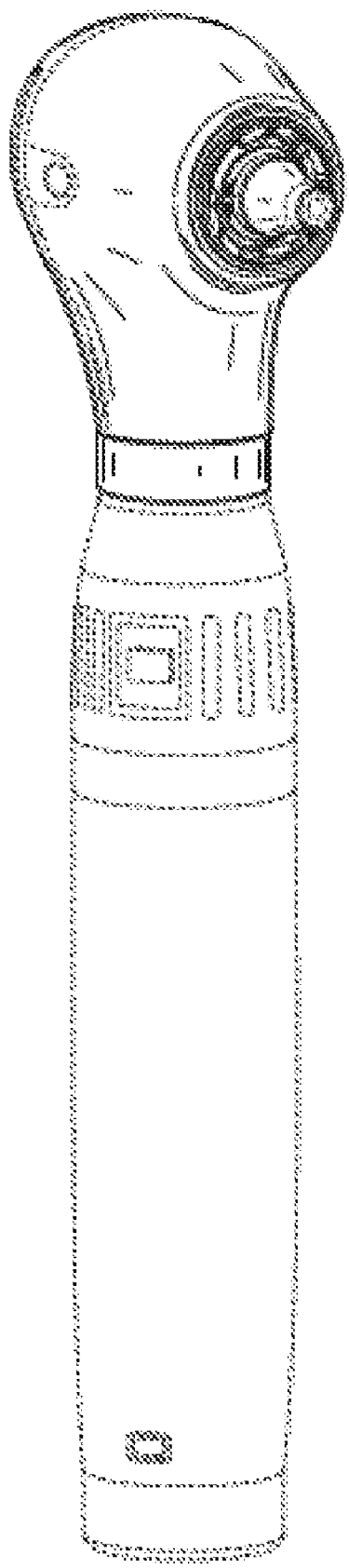
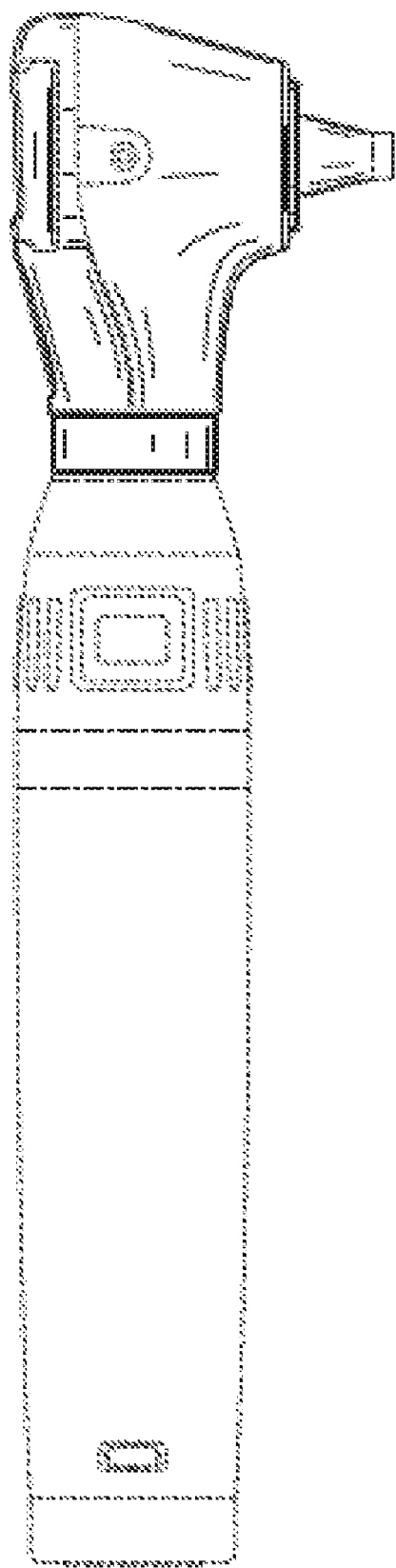
FIG. B-9
FIG. B-10

105 106
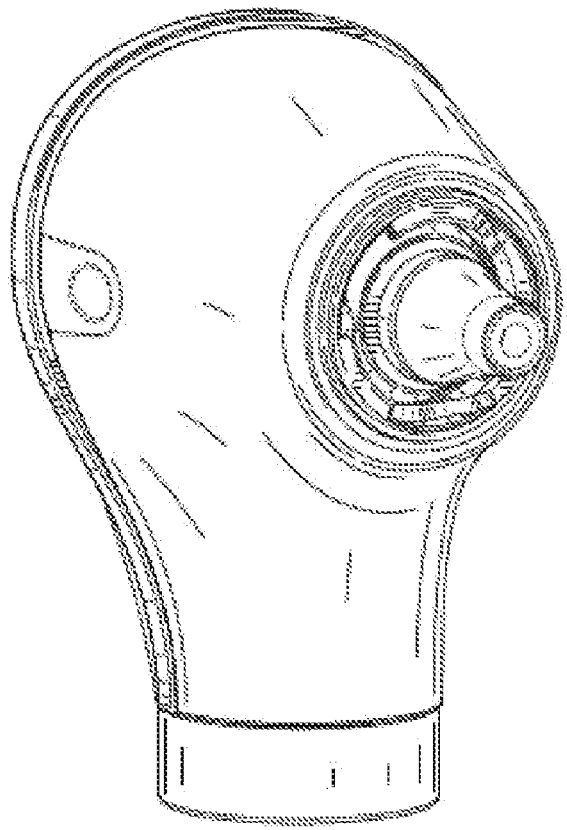
FIG. B-11
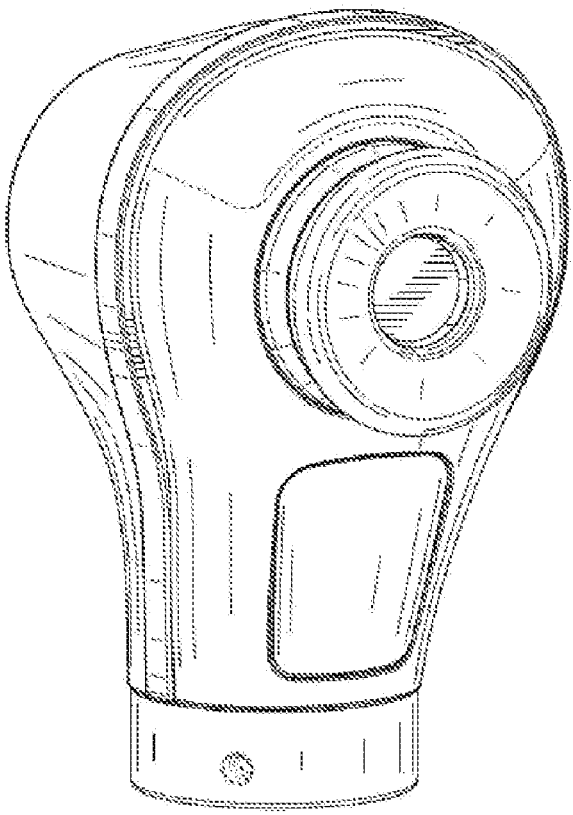
FIG. B-12

107 108
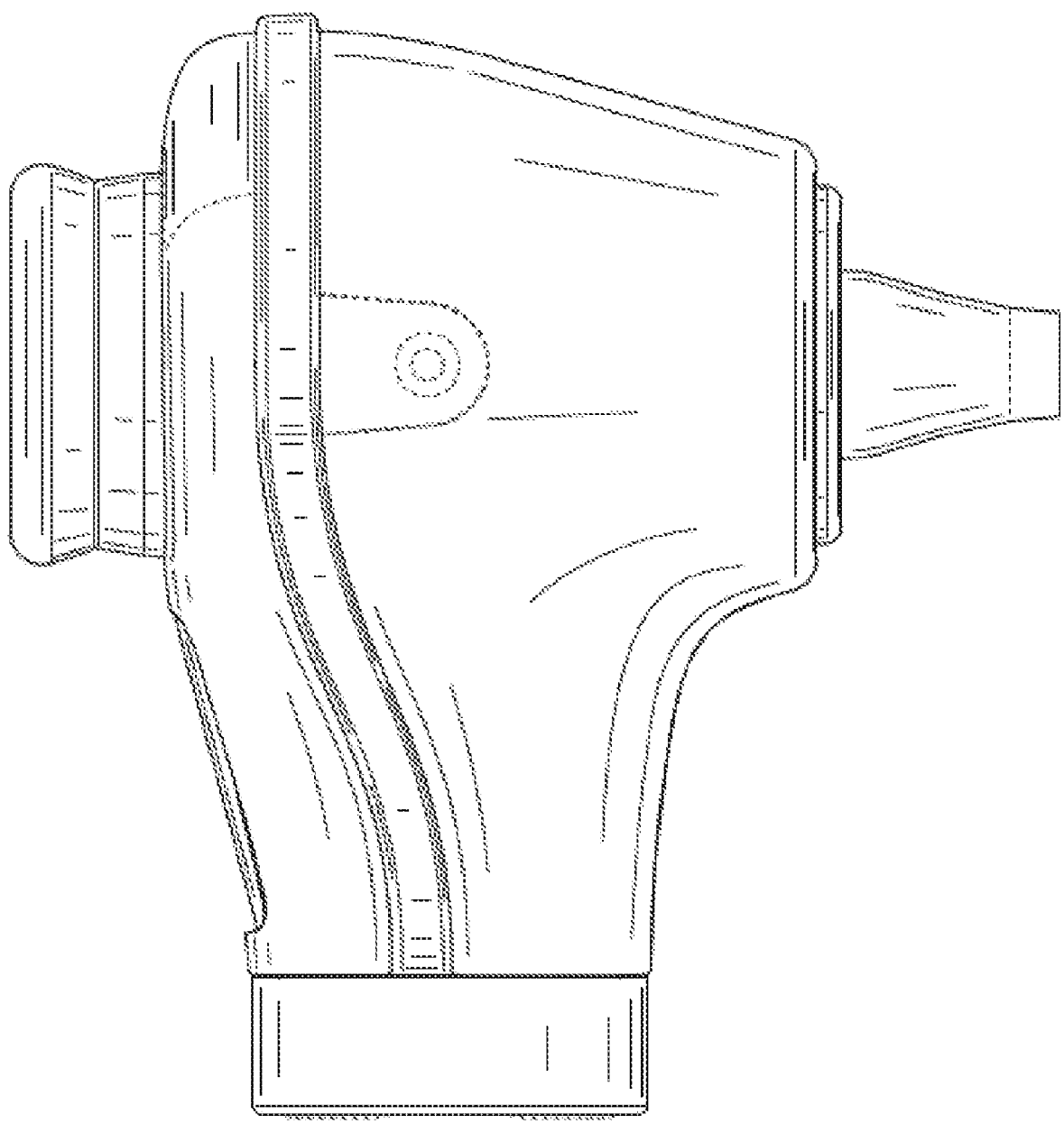
FIG. B-13

109 110
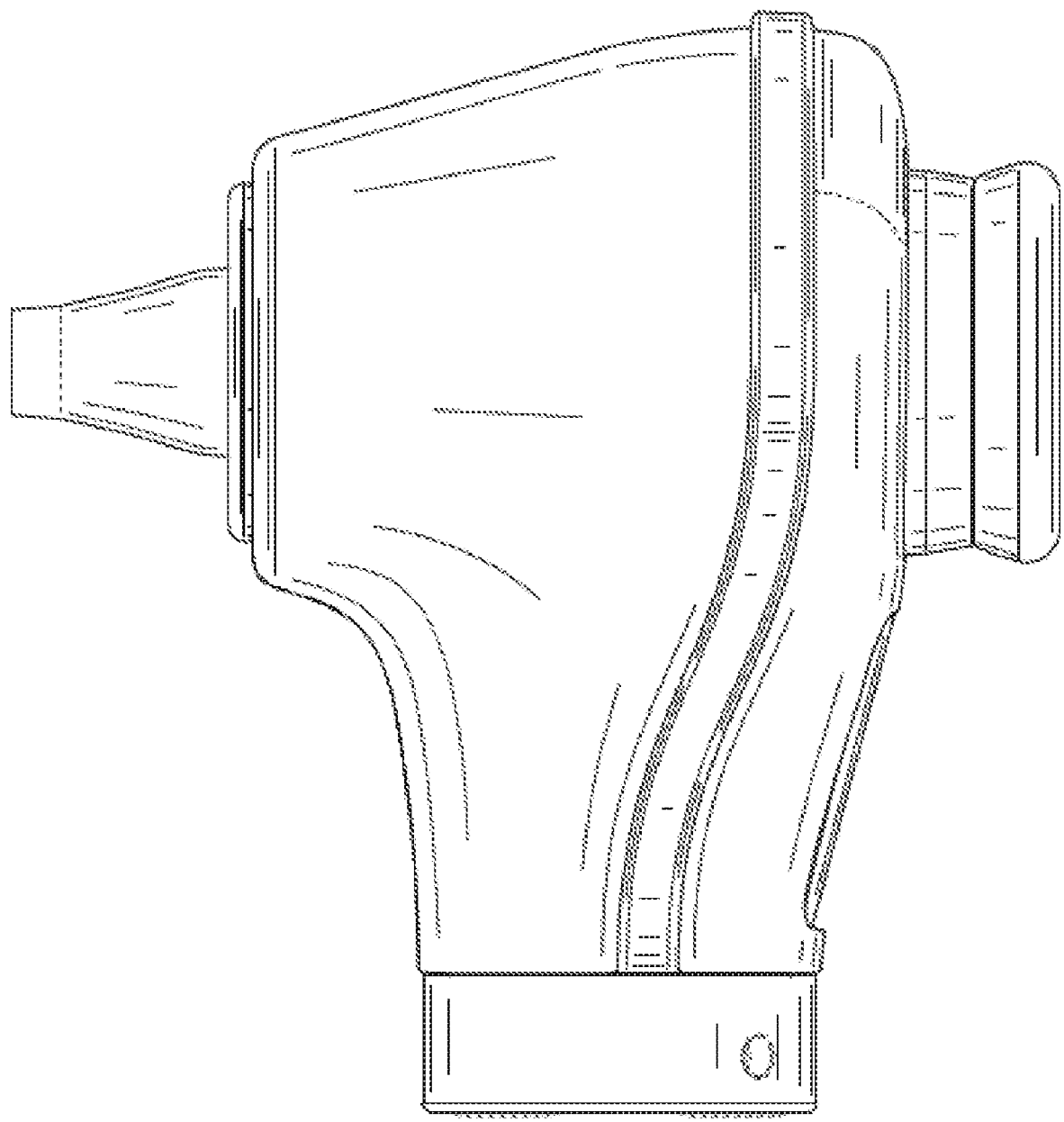
FIG. B-14

111   112
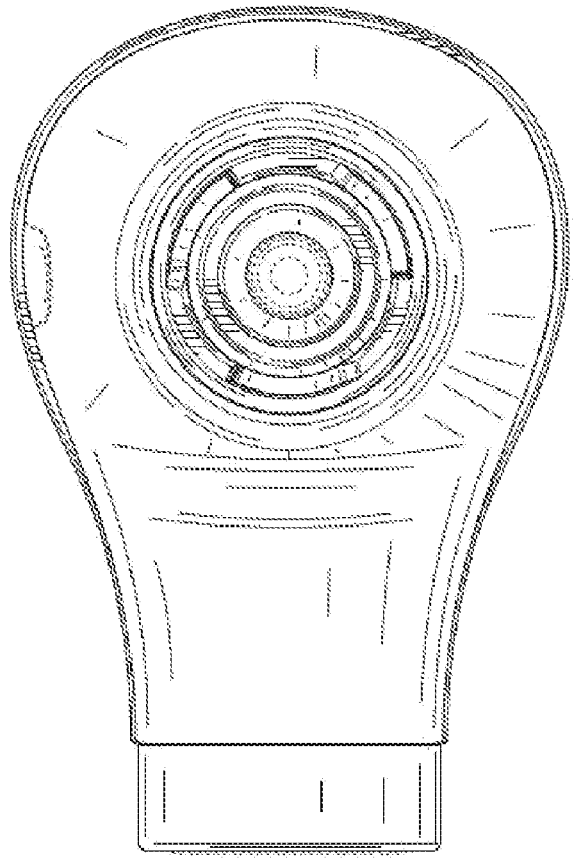
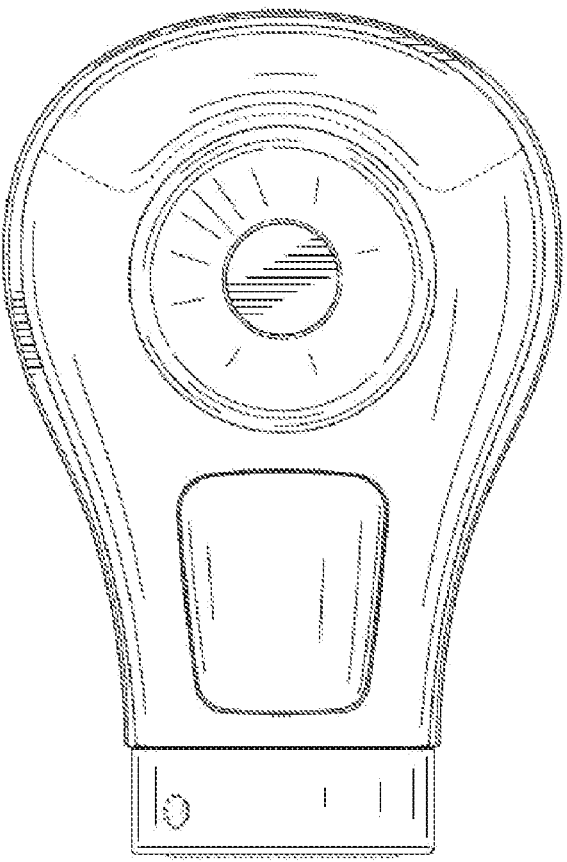
FIG. B-15   FIG. B-16

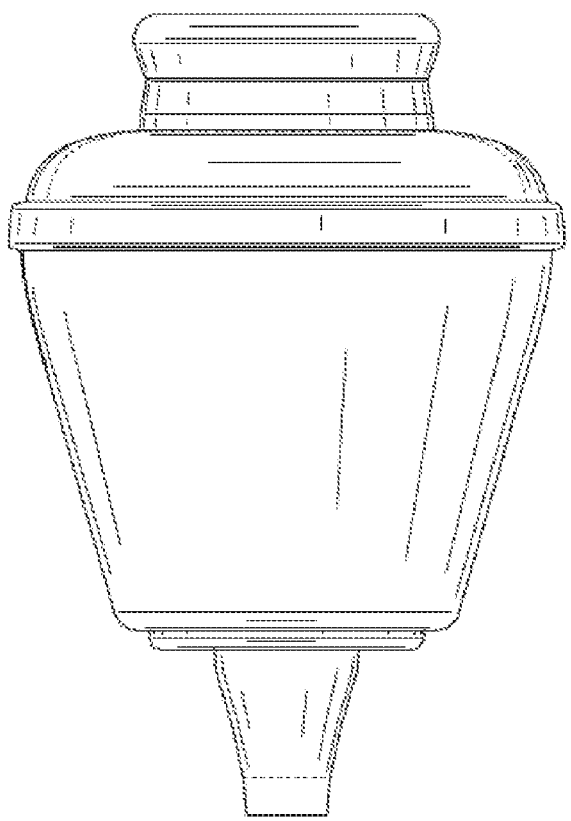
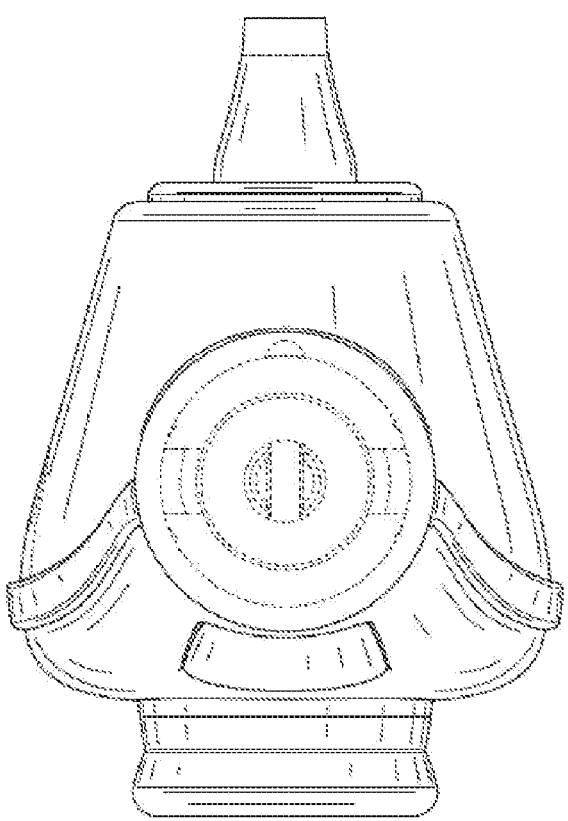
FIG. B-17
FIG. B-18

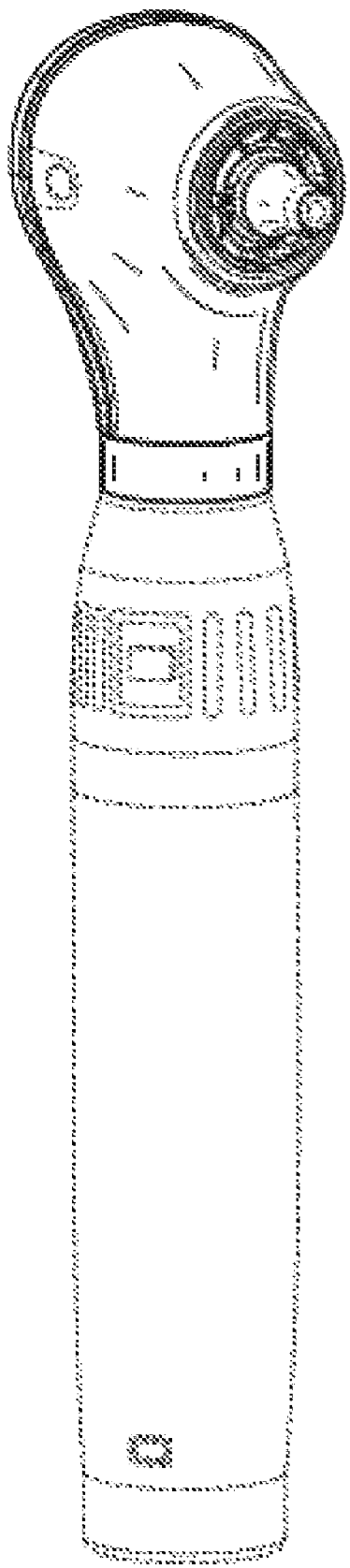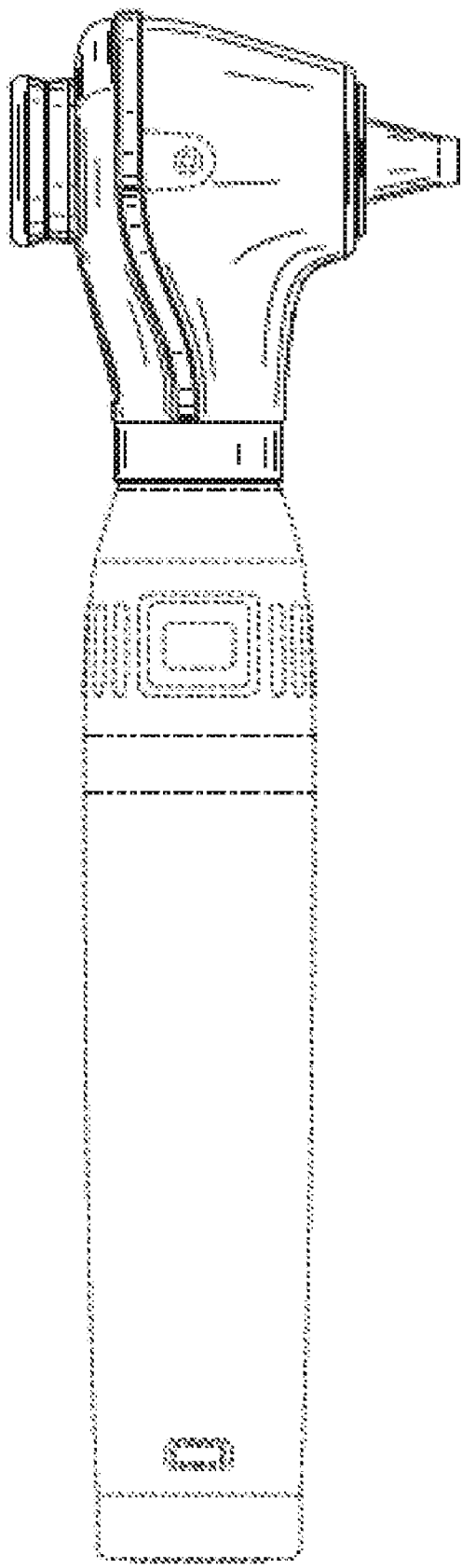
FIG. B-19    FIG. B-20

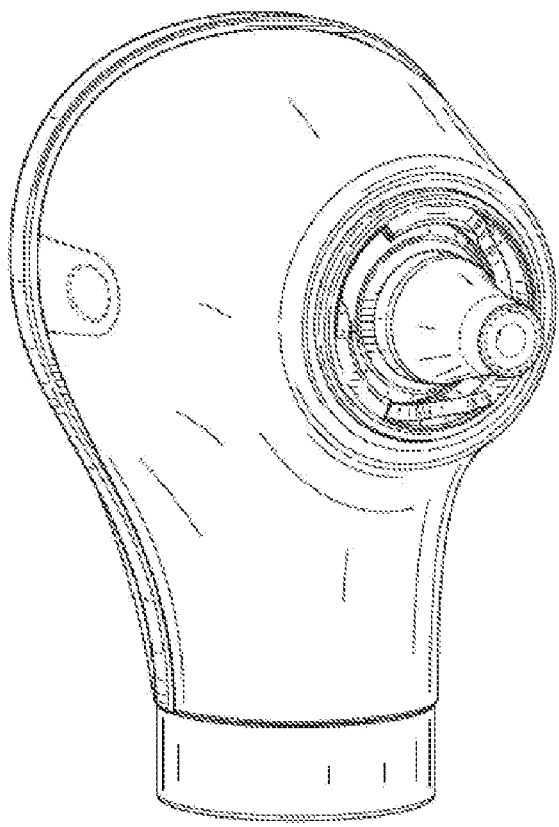
FIG. B-21
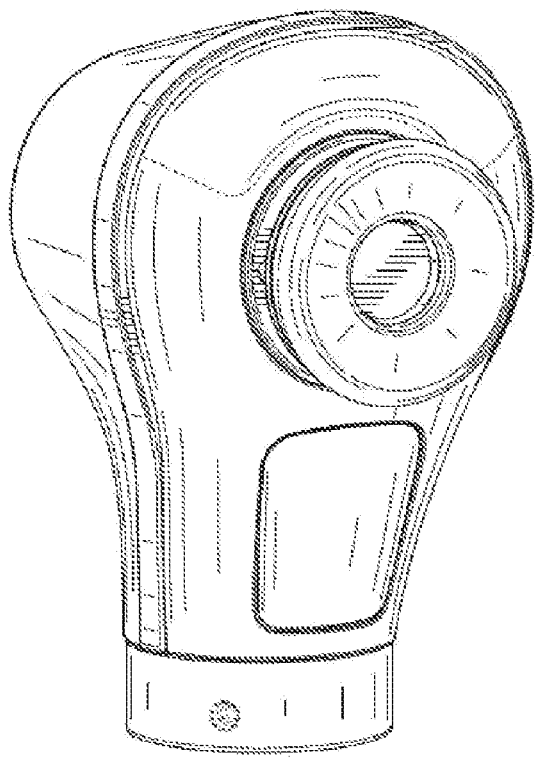
FIG. B-22

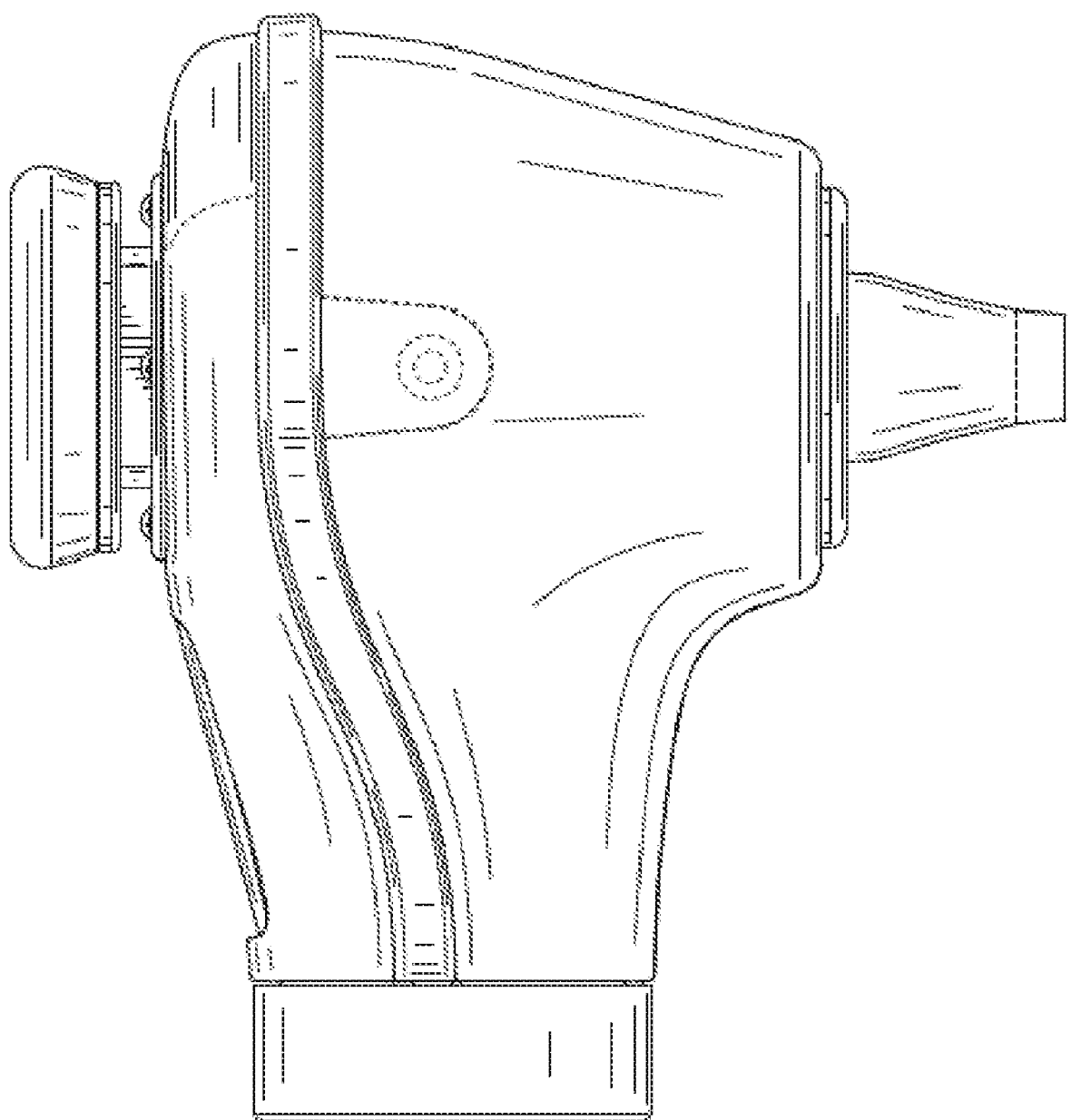
FIG. B-23

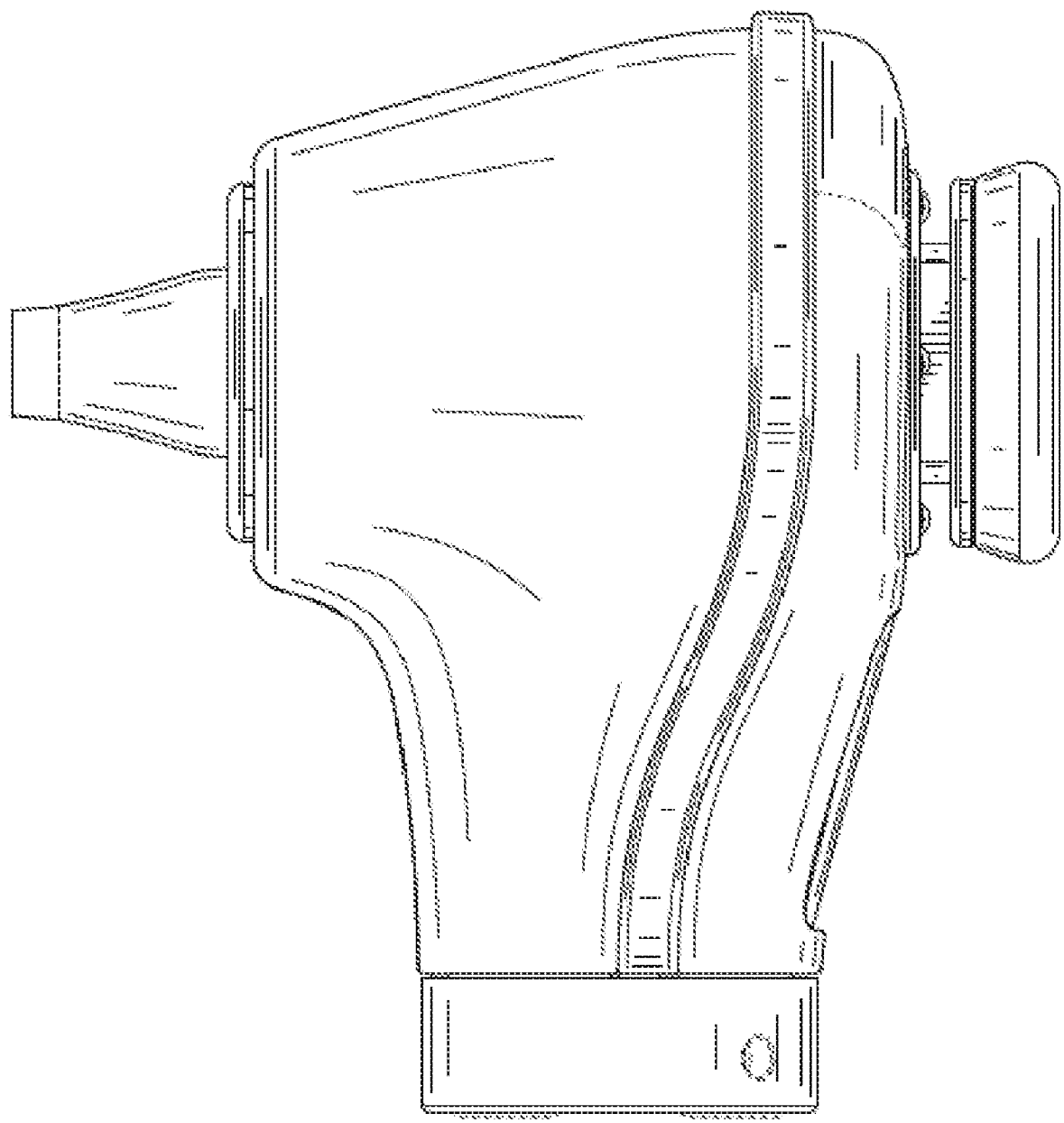
FIG. B-24

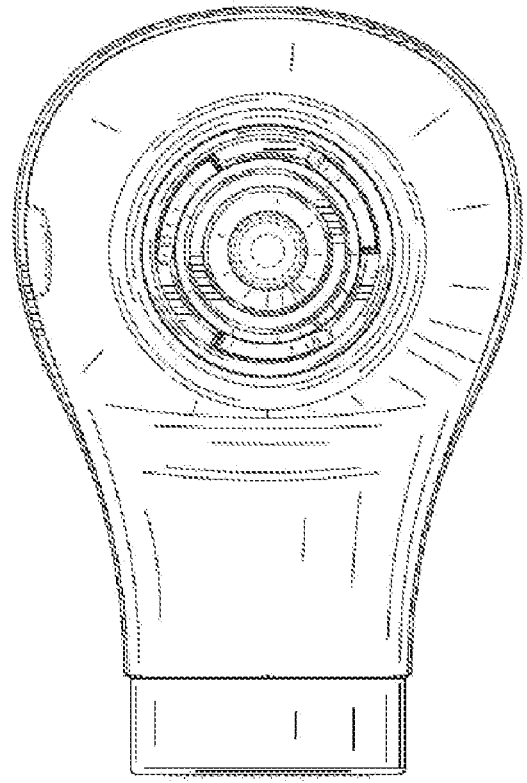
FIG. B-25
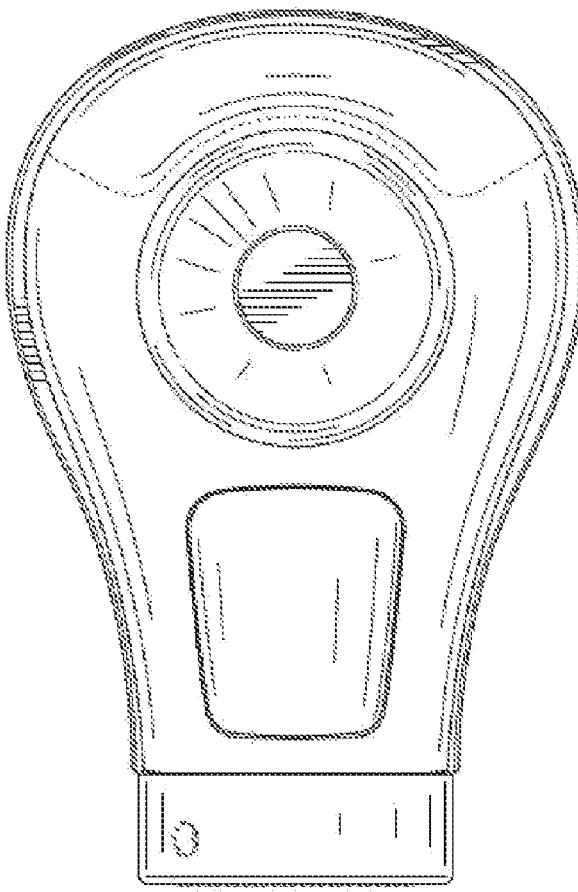
FIG. B-26

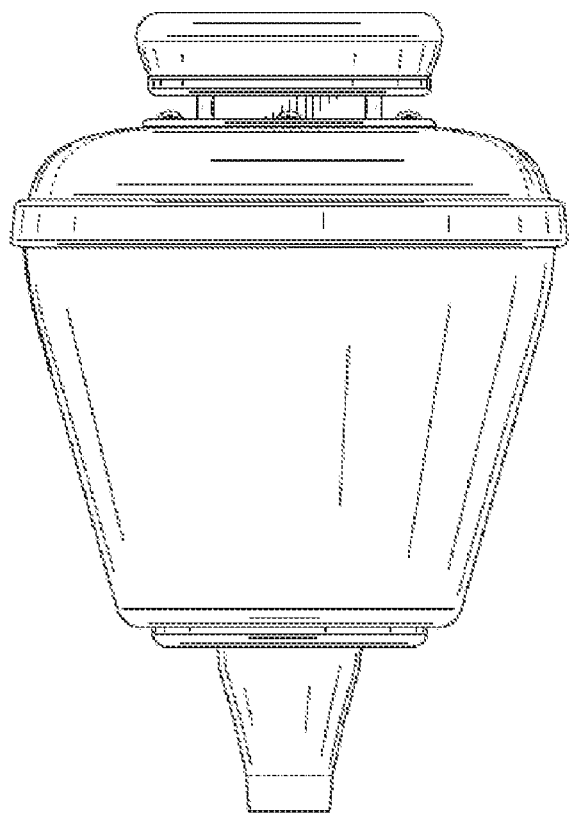
FIG. B-27
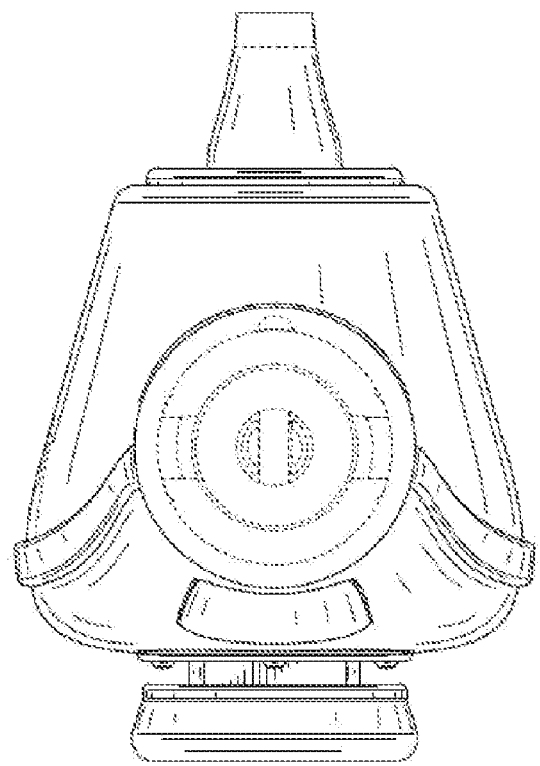
FIG. B-28

127 128
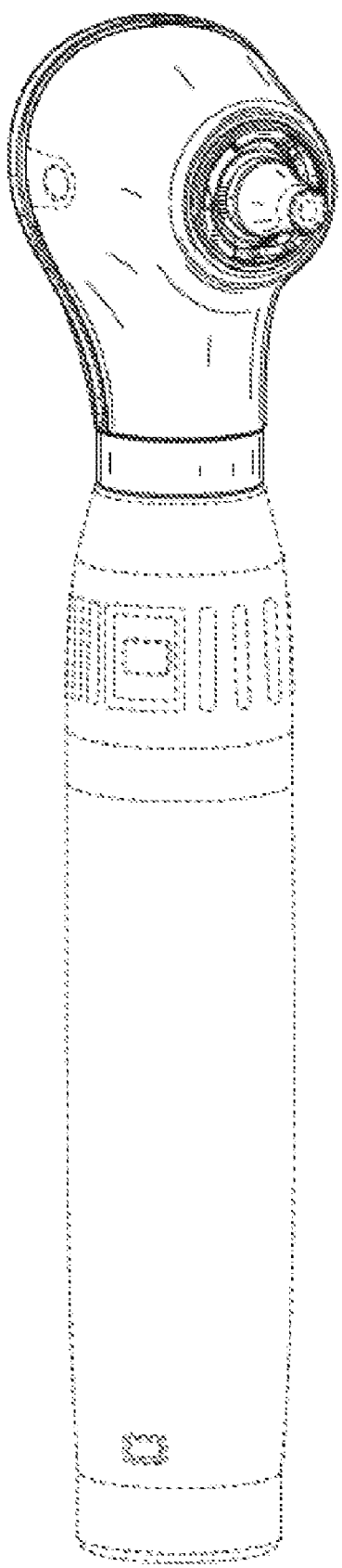
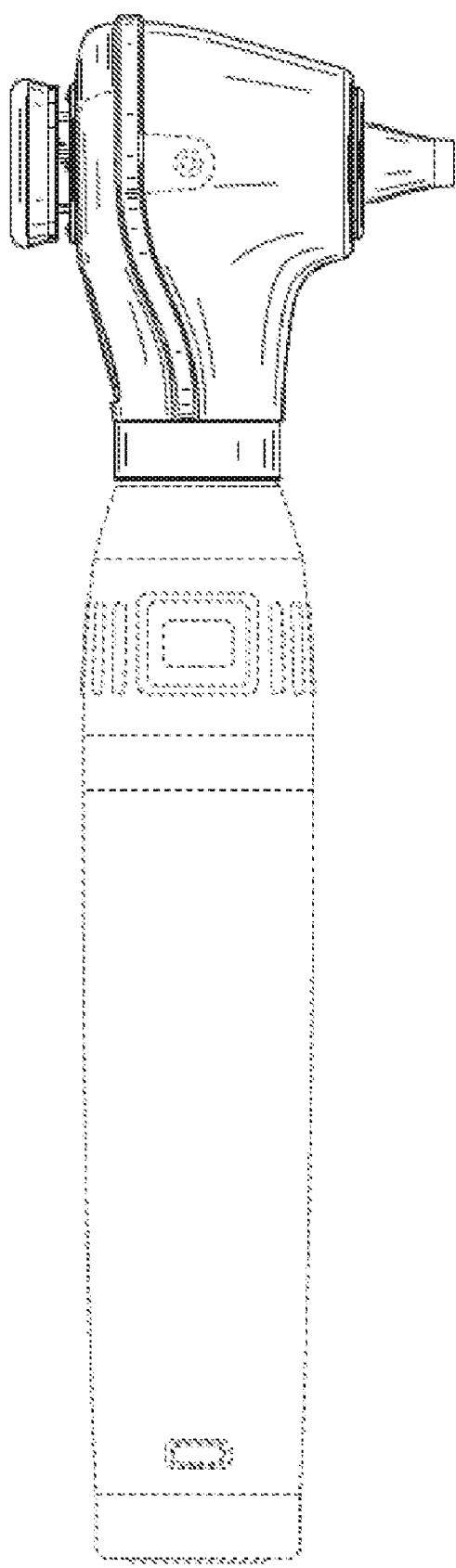
FIG. B-29  FIG. B-30

The invention claimed is:

1. An instrument head for attachment to a plurality of instrument handles having different power profiles, the instrument head comprising:
an illumination assembly including at least one LED; and
a drive circuit comprising a controller, the controller being configured to:
detect power up signals from an attached instrument handle of a specific type;
determine a power profile of the attached instrument handle based on the detected power up signals, the power profile including a voltage calibration curve; and
convert variable voltages received from the attached instrument handle to a constant current for powering the at least one LED based on the voltage calibration curve of the power profile to illuminate the at least one LED with a specific brightness.

2. The instrument head of claim 1, wherein the drive circuit outputs a pulse width modulation (PWM) of the constant current to illuminate the at least one LED, wherein dimming of the at least one LED is achieved by varying a duty cycle of the PWM of the constant current responsive to changes in the variable voltages received from the attached instrument handle.

3. The instrument head of claim 2, wherein the drive circuit outputs the PWM of the constant current to power the LED at a given illumination level when connected to either a first of the plurality of instrument handles with a first power profile and first variable voltages or a second of the plurality of instrument handles with a second power profile and second variable voltages, wherein the first and second power profiles are different power profiles.

4. The instrument head of claim 1, wherein the drive circuit comprises a buck/boost circuit, the buck/boost circuit outputting a constant voltage notwithstanding an input voltage from the instrument handle being above or below the constant voltage.

5. The instrument head of claim 1, wherein the drive circuit comprises a rectifier, the rectifier comprising field effect transistors (FETs) for converting an alternating current input from the instrument handle to a direct current for powering the at least one LED.

6. The instrument head of claim 1, wherein the controller further detects a polarity of the instrument handle attached to the instrument head.

7. The instrument head of claim 6, wherein the drive circuit comprises a buck/boost circuit, the buck/boost circuit outputting a constant current notwithstanding an input voltage from the instrument handle being above or below the constant voltage, and the controller further controls the buck/boost circuit to output the constant current with a pulse width modulation (PWM) at a duty cycle selected to illuminate the at least one LED at a specific brightness.

8. The instrument head of claim 6, wherein the controller detects a vibration or idle state of the instrument head and responsive thereto powers up or powers down the instrument head.

9. The instrument head of claim 6, wherein the controller uses a lookup table to determine the power profile of the attached instrument handle based on the power up signals received when attached.

10. The instrument head of claim 1 in which the instrument head is part of a physical assessment device.

11. The instrument head of claim 10, in which the physical assessment device is an otoscope or an ophthalmoscope and in which at least one of the instrument handles used with the instrument head are typically configured only for use with an incandescent light source.

* * * * *